(12) United States Patent
Cheng et al.

(10) Patent No.: US 11,981,712 B2
(45) Date of Patent: *May 14, 2024

(54) POLYPEPTIDES CAPABLE OF PRODUCING GLUCANS HAVING ALPHA (1-->2) LINKAGES AND USE OF THE SAME

(71) Applicant: NUTRITION & BIOSCIENCES USA 4, INC., Rochester, NY (US)

(72) Inventors: Qiong Cheng, Wilmington, DE (US); Robert Dicosimo, Chadds Ford, PA (US); Jahnavi Chandra Prasad, Wilmington, DE (US); Zhenghong Zhang, Shanghai (CN)

(73) Assignee: NUTRITION & BIOSCIENCES USA 4, INC., Rochester, NY (US)

(*) Notice: Subject to any disclaimer, the term of this patent is extended or adjusted under 35 U.S.C. 154(b) by 467 days.

This patent is subject to a terminal disclaimer.

(21) Appl. No.: 17/084,945

(22) Filed: Oct. 30, 2020

(65) Prior Publication Data

US 2021/0206819 A1 Jul. 8, 2021

Related U.S. Application Data

(63) Continuation of application No. 15/767,689, filed as application No. PCT/US2016/063233 on Nov. 22, 2016, now Pat. No. 10,822,383.

(30) Foreign Application Priority Data

Nov. 26, 2015 (WO) ................. PCT/CN2015/095687
Jun. 13, 2016 (WO) ................. PCT/CN2016/085547

(51) Int. Cl.
| | | |
|---|---|---|
| C07K 14/47 | (2006.01) |
| A23L 33/10 | (2016.01) |
| A23L 33/135 | (2016.01) |
| A23L 33/21 | (2016.01) |
| A61K 8/60 | (2006.01) |
| A61K 8/64 | (2006.01) |
| A61K 8/73 | (2006.01) |
| A61K 31/716 | (2006.01) |
| A61Q 19/00 | (2006.01) |
| C08B 37/00 | (2006.01) |
| C08L 5/00 | (2006.01) |
| C08L 5/02 | (2006.01) |
| C12N 9/10 | (2006.01) |
| C12P 19/04 | (2006.01) |
| C12P 19/18 | (2006.01) |
| C11D 3/22 | (2006.01) |

(52) U.S. Cl.
CPC .......... *C07K 14/4725* (2013.01); *A23L 33/10* (2016.08); *A23L 33/135* (2016.08); *A23L 33/21* (2016.08); *A61K 8/60* (2013.01); *A61K 8/64* (2013.01); *A61K 8/73* (2013.01); *A61K 31/716* (2013.01); *A61Q 19/00* (2013.01); *C08B 37/0009* (2013.01); *C08L 5/00* (2013.01); *C08L 5/02* (2013.01); *C12N 9/1051* (2013.01); *C12P 19/04* (2013.01); *C12P 19/18* (2013.01); *C12Y 204/00* (2013.01); *C12Y 204/01* (2013.01); *C12Y 204/01005* (2013.01); *C12Y 302/01* (2013.01); *A23V 2002/00* (2013.01); *A23V 2200/00* (2013.01); *A61K 2800/10* (2013.01); *C11D 3/22* (2013.01)

(58) Field of Classification Search
None
See application file for complete search history.

(56) References Cited

U.S. PATENT DOCUMENTS

| | | | |
|---|---|---|---|
| 2,203,703 | A | 6/1940 | Stahly et al. |
| 2,203,704 | A | 6/1940 | Stahly et al. |
| 2,344,179 | A | 3/1944 | Stahly et al. |
| 2,380,879 | A | 7/1945 | Stahly et al. |
| 2,961,439 | A | 11/1960 | Novak |
| 2,974,134 | A | 3/1961 | Pollitzer |
| 10,351,633 | B2 * | 7/2019 | Cheng ................. A23C 9/13 |
| 10,633,683 | B2 | 4/2020 | Paullin et al. |
| 10,822,574 | B2 * | 11/2020 | DiCosimo ........... C11D 11/0017 |
| 2014/0179913 | A1 | 6/2014 | Paullin et al. |
| 2015/0232785 | A1 | 8/2015 | Paullin et al. |
| 2015/0239995 | A1 | 8/2015 | Landschutze et al. |
| 2016/0304629 | A1 | 10/2016 | Kasat et al. |
| 2016/0311935 | A1 | 10/2016 | Dennes et al. |

* cited by examiner

Primary Examiner — Richard G Hutson

(57) ABSTRACT

Disclosed herein are proteins capable of forming glucans having alpha-1,2 linkages/branches, reactions and methods for producing such glucan, compositions comprising such glucan, and various applications thereof.

29 Claims, No Drawings
Specification includes a Sequence Listing.

```
SEQUENCE LISTING

<160> NUMBER OF SEQ ID NOS: 28

<210> SEQ ID NO 1
<211> LENGTH: 2771
<212> TYPE: PRT
<213> ORGANISM: Leuconostoc mesenteroides

<400> SEQUENCE: 1

Met Thr Ala Gly Ile Phe Ser Ala Val Ile Phe Gly Val Ser Thr Thr
1               5                   10                  15

Asn Val Ser Ala Asp Ser Thr Asn Asn Thr Gly Val Thr Val Ser Gln
            20                  25                  30

Ala Thr Asp Lys Val Ala Asp Thr Thr Ala Thr Thr Asp Lys Val Ala
        35                  40                  45

Asp Thr Thr Ala Thr Thr Asp Lys Val Ala Asp Thr Ala Ala Thr Thr
    50                  55                  60

Asp Lys Val Ala Asp Thr Thr Ala Thr Thr Asp Lys Val Ala Asp Thr
65                  70                  75                  80

Ala Ala Thr Thr Asp Lys Val Ala Asp Thr Thr Ala Thr Thr Asp Lys
                85                  90                  95

Val Ala Asp Thr Ala Ala Ala Thr Asp Lys Ala Ala Asp Thr Ala Ala
            100                 105                 110

Thr Thr Asp Lys Val Ala Asp Thr Ala Ala Thr Thr Asp Lys Val Ala
        115                 120                 125

Asp Thr Val Ala Ala Thr Asp Lys Val Ala Asp Thr Thr Ala Thr Thr
    130                 135                 140

Asp Lys Ala Ala Asp Thr Ala Thr Thr Asp Lys Val Ala Thr Asp Thr
145                 150                 155                 160

Thr Ala Ala Thr Asp Lys Ala Ala Asp Thr Thr Ala Thr Thr Asp Lys
                165                 170                 175
```

```
Val Ala Asp Thr Thr Ala Thr Ser Glu Lys Ser Lys Ser Ile Lys
                180                 185                 190

Gln Ile Asp Gly Lys Thr Tyr Phe Ile Gly Asn Asp Gly Gln Pro Lys
            195                 200                 205

Lys Asn Phe Thr Ala Ile Val Asp Gly Gln Val Leu Tyr Phe Asp Lys
210                 215                 220

Asp Thr Gly Ala Leu Thr Ser Asn Ser Ser Gln Tyr Thr Asp Gly Leu
225                 230                 235                 240

Ala Asn Ile Gly Asn Glu His Asn Ala Ala Tyr Ser Leu Ser Ser Asp
                245                 250                 255

Ser Phe Thr Gln Val Asp Gly Tyr Leu Thr Ala Asn Ser Trp Tyr Arg
            260                 265                 270

Pro Lys Asp Ile Leu Lys Asn Gly Thr Thr Trp Thr Ala Ala Thr Ala
        275                 280                 285

Asn Asp Phe Arg Pro Leu Leu Met Ser Trp Trp Pro Asp Lys Asp Thr
    290                 295                 300

Gln Val Ser Tyr Leu Lys Tyr Met Gln Ser Ala Gly Leu Leu Ser Asp
305                 310                 315                 320

Asp Val Ala Leu Ser Asn Asn Asp Ser Met Asn Ser Leu Thr Asp Thr
                325                 330                 335

Ala Met Thr Val Gln Lys Lys Ile Glu Glu Lys Ile Gly Leu Leu Gly
            340                 345                 350

Ser Thr Asp Trp Leu Lys Ala Asp Met Asn Gln Met Val Asp Ser Gln
        355                 360                 365

Ser Asn Trp Asn Ile Ser Ser Glu Ser Lys Gly Thr Asp His Leu Gln
    370                 375                 380

Gly Gly Ala Leu Leu Tyr Val Asn Ser Asp Leu Thr Pro Asn Ala Asn
385                 390                 395                 400

Ser Asp Tyr Arg Leu Leu Asn Arg Thr Pro Thr Asn Gln Lys Gly Gln
                405                 410                 415

Ile Thr Thr Asn Gly Asn Gln Gly Gly Tyr Glu Met Leu Leu Ala Asn
            420                 425                 430

Asp Val Asp Asn Ser Asn Pro Ile Val Gln Ala Glu Gln Leu Asn Trp
        435                 440                 445

Leu Tyr Tyr Met Met Asn Ile Gly Ser Ile Ala Gln Asn Asp Pro Thr
    450                 455                 460

Ala Asn Phe Asp Gly Tyr Arg Val Asp Ala Val Asp Asn Val Asn Ala
465                 470                 475                 480

Asp Leu Leu Gln Ile Ala Gly Asp Tyr Phe Lys Ala Ala Tyr Gly Thr
                485                 490                 495

Asn Gln Ser Asp Ala Asn Ala Asn Asn His Ile Ser Ile Leu Glu Asp
            500                 505                 510

Trp Asp Asn Asn Asp Pro Ala Tyr Val Lys Ala Gln Gly Asn Asn Gln
        515                 520                 525

Leu Thr Met Asp Phe Pro Met His Leu Ala Leu Lys Tyr Ser Leu Asn
    530                 535                 540

Met Pro Ser Ser Ala Arg Ser Gly Leu Glu Pro Ala Ile Ser Thr Ser
545                 550                 555                 560

Leu Val Asn Arg Ala Ala Asp Ala Thr Glu Asn Glu Ala Gln Pro Asn
                565                 570                 575

Tyr Ser Phe Ile Arg Ala His Asp Ser Glu Val Gln Thr Val Ile Ala
            580                 585                 590
```

```
Gln Ile Ile Lys Asp Lys Ile Asn Pro Ser Ser Asp Gly Leu Thr Val
            595                 600                 605

Ser Thr Asp Glu Ile Ala Lys Ala Phe Glu Ile Tyr Asn Ala Asp Glu
610                 615                 620

Leu Lys Ala Asp Lys Glu Tyr Thr Ala Tyr Asn Ile Pro Ser Ser Tyr
625                 630                 635                 640

Ala Leu Met Leu Thr Asn Lys Asp Thr Ile Pro Arg Val Tyr Tyr Gly
                645                 650                 655

Asp Leu Phe Thr Asp Asp Gly Gln Tyr Met Ser Ala Lys Ser Pro Tyr
            660                 665                 670

Tyr Asp Ala Leu Thr Ser Leu Leu Gln Ser Arg Val Lys Tyr Val Ser
            675                 680                 685

Gly Gly Gln Ser Met Asn Met Thr Tyr Leu His Asn Asn Gln Gly Leu
690                 695                 700

Leu Thr Ser Val Arg Tyr Gly Lys Asp Ala Met Thr Ala Asn Asp Thr
705                 710                 715                 720

Gly Thr Ser Glu Thr Arg Thr Gln Gly Ile Gly Leu Ile Val Gly Asn
                725                 730                 735

Lys Thr Asp Leu Asn Leu Asn Asn Asp Glu Gln Ile Val Leu Asn Met
            740                 745                 750

Gly Ala Ala His Lys Asn Gln Ala Tyr Arg Ala Leu Met Leu Ser Thr
            755                 760                 765

Lys Asp Gly Leu Lys Ile Tyr Asn Asn Asp Asp Glu Ala Pro Val Ser
770                 775                 780

Tyr Thr Asp Asp Gln Gly Arg Leu Ile Phe Lys Ser Asp Val Val Tyr
785                 790                 795                 800

Gly Val Ser Asp Ala Gln Val Ser Gly Tyr Leu Ala Ala Trp Val Pro
                805                 810                 815

Val Gly Ala Asn Asp Ser Gln Asp Ala Arg Thr Glu Ser Ser Thr Thr
            820                 825                 830

Ala Ser Thr Asp Gly Asn Thr Tyr His Ser Asn Ser Ala Leu Asp Ser
            835                 840                 845

Gln Leu Ile Tyr Glu Gly Phe Ser Asn Phe Gln Ala Met Pro Thr Gln
850                 855                 860

Ala Asp Glu Tyr Thr Asn Ile Lys Ile Ala Glu Asn Ala Gln Leu Phe
865                 870                 875                 880

Lys Ser Leu Gly Ile Thr Ser Phe Glu Leu Ala Pro Gln Tyr Arg Ser
                885                 890                 895

Ser Thr Asp Asn Ser Phe Leu Asp Ser Val Ile Gln Asn Gly Tyr Ala
            900                 905                 910

Phe Thr Asp Arg Tyr Asp Ile Gly Tyr Asn Thr Pro Thr Lys Tyr Gly
            915                 920                 925

Thr Val Asp Gln Leu Leu Asp Ala Leu Arg Ala Leu His Ala Gln Gly
930                 935                 940

Ile Gln Ala Ile Asn Asp Trp Val Pro Asp Gln Ile Tyr Asn Leu Pro
945                 950                 955                 960

Gly Glu Glu Ile Val Thr Ala Ser Arg Thr Asn Gly Ser Gly Lys Val
                965                 970                 975

Asn Glu Ser Ser Val Ile Asn Asn Thr Leu Tyr Asp Ser Arg Thr Val
            980                 985                 990

Gly Gly Gly Glu Tyr Gln Ala Ile  Tyr Gly Gly Ala Phe  Leu Asp Lys
            995                 1000                1005

Leu Lys  Gln Asp Tyr Pro Glu  Leu Phe Glu Thr Lys  Gln Ile Ser
```

```
                1010                1015                1020
Thr Gly Glu Ala Met Asn Pro Asp Val Lys Ile Thr Glu Trp Ser
    1025                1030                1035

Ala Lys Tyr Phe Asn Gly Ser Asn Ile Gln Gly Arg Gly Ala Trp
    1040                1045                1050

Tyr Val Leu Lys Asp Trp Ser Thr Asn Gln Tyr Phe Asn Val Ser
    1055                1060                1065

Ser Gly Ser Glu Phe Leu Pro Lys Gln Leu Leu Gly Glu Lys Thr
    1070                1075                1080

Ser Thr Gly Phe Thr Asn Val Asp Asn Gly Lys Thr Glu Phe Tyr
    1085                1090                1095

Ser Thr Ser Gly Tyr Gln Ala Lys Asn Thr Phe Ile Gln Asp Asn
    1100                1105                1110

Asp Asn Trp Tyr Tyr Phe Asp Asn Asp Gly Tyr Met Val Val Gly
    1115                1120                1125

Gly Gln Glu Ile Asn Gly Lys Lys Tyr Tyr Phe Leu Pro Asn Gly
    1130                1135                1140

Val Glu Leu Gln Asp Ala Tyr Leu Ser Asp Gly Thr Ser Glu Tyr
    1145                1150                1155

Tyr Tyr Ser Ser Asp Gly Arg Gln Ile Ser Asn Gln Tyr Tyr Gln
    1160                1165                1170

Gly Ser Asp Asn Asn Trp Arg Tyr Phe Phe Ala Asp Gly His Met
    1175                1180                1185

Ala Val Gly Leu Ala Thr Ile Thr Thr Glu Asn Gly Thr Thr Asn
    1190                1195                1200

Gln Gln Tyr Phe Asp Ala Asn Gly Val Gln Leu Lys Gly Val Ala
    1205                1210                1215

Ile Lys Asp Thr Asp Gly Asn Val His Tyr Phe Asp Gly Lys Thr
    1220                1225                1230

Gly Asn Met Val Ile Asn Ser Trp Gly Lys Ile Ser Asp Gly Ser
    1235                1240                1245

Trp Leu Tyr Leu Asn Asp Ser Gly Val Ala Val Thr Gly Pro Gln
    1250                1255                1260

Asn Ile Asn Gly Gln Asn Leu Tyr Phe Asn Glu Asp Gly Ile Gln
    1265                1270                1275

Val Lys Gly Glu Ala Ile Thr Asp Asn Ser Gly Asn Ile His Tyr
    1280                1285                1290

Tyr Asp Arg Ser Thr Gly Asn Met Val Val Asn Ser Trp Gly Glu
    1295                1300                1305

Thr Asn Asn Gly Ser Trp Leu Tyr Leu Asn Asp Lys Gly Asp Ala
    1310                1315                1320

Val Thr Gly Glu Gln Val Ile Asp Gly Gln Lys Leu Tyr Phe Ser
    1325                1330                1335

Ser Asn Gly Ile Gln Leu Lys Asn Thr Phe Lys Lys Leu Ser Asp
    1340                1345                1350

Gly Ser Trp Leu Tyr Leu Asn Asp Lys Gly Leu Pro Val Thr Gly
    1355                1360                1365

Ala Gln Val Ile Asp Gly Gln Asn Leu Tyr Phe Asp Gln Asp Gly
    1370                1375                1380

Lys Gln Val Lys Gly Asp Val Ala Thr Asp Gly Gln Gly Asn Thr
    1385                1390                1395

His Tyr Tyr Asp Gly Asn Thr Gly Asn Met Val Thr Asn Ser Trp
    1400                1405                1410
```

```
Ala Glu Leu Pro Asp Gly Ser Trp Met Tyr Leu Asp Asn Asp Gly
1415                1420                1425

Asn Pro Leu Thr Gly Gln Gln Lys Ile Asp Gly Gln Ser Leu Tyr
    1430                1435                1440

Phe Asn Asp Ala Gly Lys Gln Ile Lys Asn Ala Leu Val Lys Leu
    1445                1450                1455

Asp Asp Gly Ser Thr Ile Tyr Leu Asp Asp Lys Gly Val Ser Ser
    1460                1465                1470

Thr Gly Ile Gln Arg Ile Asp Asp Lys Ile Tyr Tyr Phe Asp Pro
1475                1480                1485

Asp Gly Lys Gln Val Val Cys Arg Phe Glu Glu Leu Pro Asp Gly
    1490                1495                1500

Ser Trp Met Tyr Leu Asp Asp Gly Val Ala Ala Thr Gly Ala
1505                1510                1515

Gln Lys Ile Asn Gly Gln Glu Leu Tyr Phe Asp Asn Ser Gly Lys
    1520                1525                1530

Gln Val Lys Asn Asp Lys Val Ile Asn Asp Asp Gly Thr Ile Asn
    1535                1540                1545

Tyr Tyr Thr Gly Met Ser Gly Glu Lys Leu Lys Asn Asp Phe Gly
1550                1555                1560

Glu Leu Pro Asp Gly Ser Trp Met Tyr Leu Asp Asn Gln Gly Asn
    1565                1570                1575

Ala Val Ile Gly Ala Gln Lys Ile Asn Gly Gln Asn Leu Tyr Phe
1580                1585                1590

Lys Thr Asp Gly Arg Gln Val Lys Gly Glu Ala Asn Val Asp Ser
    1595                1600                1605

Ser Gly Glu Met His Phe Tyr Asp Pro Asp Ser Gly Glu Leu Ile
    1610                1615                1620

Thr Asn Arg Phe Glu Gln Val Ala Ser Gly Val Trp Ala Tyr Phe
    1625                1630                1635

Asp Ala Lys Gly Val Ala Val Thr Gly Glu Gln Arg Ile Gly Lys
    1640                1645                1650

Gln Asn Leu Phe Phe Asp Pro Thr Gly Tyr Gln Val Lys Gly Asp
    1655                1660                1665

Lys Arg Thr Ile Asp Gly Val Leu Tyr Thr Phe Asp Lys Glu Ser
    1670                1675                1680

Gly Glu Arg Lys Gly Leu Asp Ser Ile Ser Val Leu Pro Thr Asn
    1685                1690                1695

Gly Gln Tyr Thr Thr Asp Lys Ala Gln Asn Trp Tyr Tyr Gln Val
    1700                1705                1710

Asp Gly Glu Asn Val Lys Gly Leu Tyr Thr Asn Asn Asp Gly Gln
    1715                1720                1725

Leu Arg Tyr Phe Asp Leu Thr Gly Val Gln Thr Lys Gly Asn
    1730                1735                1740

Phe Val Thr Ile Gly Asn Asp Thr Tyr Tyr Phe Thr Lys Glu Gln
    1745                1750                1755

Gly Asp Gly Gln Ile Val Ser Glu Val Val Ser Gly His Tyr Gly
    1760                1765                1770

Thr Val Gln Leu Ser Asp Asn Ser Ser Ala Trp Val Tyr Arg Gly
    1775                1780                1785

Ala Asn Asp Gln Ile Leu Lys Gly Leu Gln Asn Ile Asn Gly Arg
    1790                1795                1800
```

```
Leu Gln Tyr Phe Asp Leu Thr   Thr Gly Ala Gln Leu   Lys Gly Gly
    1805                  1810              1815

Ala Ala Asn Tyr Asp Gly Asn   Leu Tyr Tyr Phe Glu   Ser Ser Asp
    1820                  1825              1830

Gly Asn Leu Val Ser Lys Ile   Gln Gln Ser Tyr Ser   Thr Gly Asn
    1835                  1840              1845

Tyr Val Thr Asp Gly Asp Lys   Val Thr Tyr Ala Asp   Glu Gln Asn
    1850                  1855              1860

Asn Gln Val Thr Gly Leu Ala   Leu Ile Asp Asp Gln   Leu Gln Tyr
    1865                  1870              1875

Phe Asp Pro Ser Asp Gly Arg   Gln Val Lys Asn Glu   Gln Val Ile
    1880                  1885              1890

Val Asp Gly Val Thr Tyr Tyr   Phe Asp Lys Asn Gly   Asn Gly Gln
    1895                  1900              1905

Tyr Leu Phe Thr Asn Thr Ala   Thr Met Ser Thr Asn   Glu Phe Ala
    1910                  1915              1920

Lys His Ser Ala Ala Tyr Ser   Asn Asp Ser Ser Phe   Lys Asn
    1925                  1930              1935

Thr Ile Asp Gly Phe Leu Thr   Ala Asp Thr Trp Tyr   Arg Pro Lys
    1940                  1945              1950

Asp Ile Leu Glu Asn Gly Gln   Thr Trp Val Val Ser   Ser Thr Asn
    1955                  1960              1965

Asp Val Arg Pro Leu Ile Thr   Val Trp Trp Leu Asn   Lys Asp Val
    1970                  1975              1980

Gln Val Asn Tyr Ser Asn Phe   Met Lys Gln Asn Gly   Leu Leu Asp
    1985                  1990              1995

Thr Ser Ser Gln Phe Asn Leu   Gln Ser Asp Gln Tyr   Asp Leu Asn
    2000                  2005              2010

Val Ala Ala Gln Lys Val Gln   Val Ala Ile Glu Lys   Arg Ile Ser
    2015                  2020              2025

Lys Glu Lys Ser Thr Asp Trp   Leu Lys Asp Leu Leu   Phe Glu Ala
    2030                  2035              2040

His Glu Asp Thr Pro Ser Phe   Val Lys Gln Gln Phe   Ile Trp Asn
    2045                  2050              2055

Lys Asp Ser Glu Tyr Gln Gly   Gln Gly Asp Ala Trp   Phe Gln Gly
    2060                  2065              2070

Gly Tyr Leu Lys Tyr Gly Asn   Asn Glu Leu Thr Pro   Thr Thr Asn
    2075                  2080              2085

Ser Asp Tyr Arg Glu Ser Gly   Asn Thr Leu Asp Phe   Leu Leu Ala
    2090                  2095              2100

Asn Asp Val Asp Asn Ser Asn   Pro Ala Val Gln Ala   Glu Asn Leu
    2105                  2110              2115

Asn Trp Leu His Tyr Leu Met   Asn Phe Gly Thr Ile   Thr Ala Asn
    2120                  2125              2130

Asp Asp Asp Ala Asn Phe Asp   Ser Ile Arg Ile Asp   Ala Val Asp
    2135                  2140              2145

Phe Ile Asp Asn Asp Ala Ile   Gln Arg Thr Tyr Asp   Tyr Met Arg
    2150                  2155              2160

Asp Ala Tyr Lys Val Asp Ala   Ser Glu Asp Asn Ala   Asn Lys His
    2165                  2170              2175

Ile Ser Leu Val Glu Ala Gly   Leu Asp Ala Gly Thr   Ser Thr Ile
    2180                  2185              2190

Lys Ser Asp Ala Leu Val Glu   Ser Asn Phe Arg Glu   Ala Ala Thr
```

```
                    2195                2200                2205
Leu Ser  Leu Ala Asn Gln Ser  Gly Glu Asn Ser  Ser Leu Thr Asn
        2210                2215                2220

Met Leu Gln Asp Ile Asp Gly  Gly Gln Ile Ile  Ala Asp His Ala
        2225                2230                2235

Asn Asn Ala Thr Glu Asn Glu  Ser Thr Pro Asn  Tyr Ser Ile Ile
        2240                2245                2250

His Ala His Asp Lys Gly Ile  Gln Glu Lys Val  Gly Ala Ala Ile
        2255                2260                2265

Thr Asp Val Thr Gly Ala Asp  Trp Thr Asn Phe  Thr Asp Asp Gln
        2270                2275                2280

Leu Lys Glu Gly Leu Ala Ala  Tyr Tyr Gln Asp  Gln Arg Ser Thr
        2285                2290                2295

Asn Lys Lys Tyr Asn Ile Tyr  Asn Leu Pro Ser  Ile Tyr Ala Leu
        2300                2305                2310

Met Leu Thr Asn Lys Asp Thr  Val Pro Arg Val  Tyr Tyr Gly Asp
        2315                2320                2325

Met Tyr Gln Asp Asp Gly Gln  Tyr Met Glu Lys  Gln Ser Ile Tyr
        2330                2335                2340

Tyr Asp Ala Ile Val Ser Leu  Met Asn Thr Arg  Lys Ser Tyr Val
        2345                2350                2355

Ser Gly Gly Gln Thr Met Asp  Val Asp Glu His  Gly Leu Leu Lys
        2360                2365                2370

Ser Val Arg Phe Gly Lys Asp  Ala Met Thr Ala  Ser Asp Leu Gly
        2375                2380                2385

Thr Asn Glu Thr Arg Thr Glu  Gly Val Gly Val  Leu Val Gly Asn
        2390                2395                2400

Asp Ser Ser Leu Lys Leu Asn  Asp Ser Asp Thr  Val Thr Leu Glu
        2405                2410                2415

Met Gly Ala Ala His Lys Asn  Gln Lys Tyr Arg  Ala Ala Leu Leu
        2420                2425                2430

Thr Thr Ser Asp Gly Ile Val  Thr Tyr Asp Ala  Asp Asn Asp Ala
        2435                2440                2445

Pro Thr Ile Trp Thr Asp Asp  Arg Gly Thr Leu  Thr Phe Ser Asn
        2450                2455                2460

Lys Glu Ile Ala Gly Gln Asp  Tyr Thr Ser Val  Gln Gly Phe Ala
        2465                2470                2475

Asn Ser Gln Val Ser Gly Tyr  Leu Ala Val Trp  Val Pro Val Gly
        2480                2485                2490

Ala Ser Asp Asp Gln Asp Val  Arg Thr Ala Ala  Leu Thr Asp Ala
        2495                2500                2505

Asn Leu Asp Asp Lys Val Leu  His Ser Asn Ala  Ala Leu Asp Ser
        2510                2515                2520

Asn Leu Ile Tyr Glu Gly Phe  Ser Asn Phe Gln  Pro Lys Ala Thr
        2525                2530                2535

Thr Asn Asp Glu Leu Thr Asn  Val Val Ile Ala  Lys Asn Ala Asn
        2540                2545                2550

Leu Phe Glu Lys Trp Gly Ile  Thr Ser Phe Glu  Met Ala Pro Gln
        2555                2560                2565

Tyr Arg Ser Ser Gly Asp His  Thr Phe Leu Asp  Ser Thr Ile Asp
        2570                2575                2580

Asn Gly Tyr Ala Phe Thr Asp  Arg Tyr Asp Leu  Gly Phe Glu Thr
        2585                2590                2595
```

```
Pro Thr Lys Tyr Gly Thr Asp Lys Asp Leu Arg Thr Ala Ile Lys
    2600            2605            2610

Ala Leu His Gln Ser Asn Met Gln Val Met Ala Asp Val Val Asp
    2615            2620            2625

Asn Gln Val Tyr Asn Leu Ser Gly Gln Glu Val Val Ser Ala Ser
    2630            2635            2640

Arg Ala Gly Val Tyr Gly Asn Asp Val Ser Thr Gly Phe Gly Thr
    2645            2650            2655

Gln Leu Tyr Ala Val Asn Ser Val Gly Gly Lys Tyr Gln Ala
    2660            2665            2670

Gln Tyr Gly Gly Glu Tyr Leu Asn Glu Leu Lys Gln Gln Tyr Pro
    2675            2680            2685

Asp Leu Phe Glu Ala Lys Thr Tyr Asp Tyr Trp Val Lys Asn Tyr
    2690            2695            2700

Ser Asn Asp Gly Ser Asp Pro Tyr Tyr Thr Leu Ser Gln Asn Thr
    2705            2710            2715

Arg Lys Asp Met Pro Ser Ser Glu Val Ile Lys Gln Trp Ser Ala
    2720            2725            2730

Lys Tyr Met Asn Gly Thr Asn Val Leu Gly Asn Gly Met Gly Tyr
    2735            2740            2745

Val Leu Lys Asp Trp Asn Thr Gly Glu Tyr Phe Lys Ile Gly Glu
    2750            2755            2760

Lys Asn Ala Asp Phe Ile Thr Asn
    2765            2770

<210> SEQ ID NO 2
<211> LENGTH: 2821
<212> TYPE: PRT
<213> ORGANISM: Leuconostoc mesenteroides

<400> SEQUENCE: 2

Met Thr Ala Gly Ile Phe Ser Ala Val Ile Phe Gly Val Ser Thr Thr
1               5                   10                  15

Asn Val Ser Ala Asp Ser Thr Asn Asn Thr Gly Val Thr Val Ser Gln
                20                  25                  30

Ala Pro Asp Lys Val Ala Asp Thr Thr Ala Thr Thr Asp Lys Val Ala
            35                  40                  45

Asp Thr Thr Ala Thr Thr Asp Lys Ala Ala Asp Thr Thr Ala Thr Thr
        50                  55                  60

Asp Lys Val Ala Asp Thr Ala Ala Thr Asp Lys Val Ala Asp Thr
65                  70                  75                  80

Thr Ala Thr Thr Asp Lys Val Ala Asp Thr Ala Thr Thr Asp Lys
                85                  90                  95

Val Ala Asp Thr Ala Ala Ala Thr Asp Lys Val Ala Asp Thr Thr Ala
            100                 105                 110

Thr Thr Asp Lys Val Ala Asp Thr Thr Ala Thr Thr Asp Lys Val Ala
        115                 120                 125

Asp Thr Thr Ala Thr Thr Asp Lys Val Ala Asp Thr Ala Ala Ala Thr
    130                 135                 140

Asp Lys Ala Ala Asp Thr Thr Ala Thr Thr Asp Lys Ala Ala Asp Thr
145                 150                 155                 160

Thr Ala Thr Thr Asp Lys Val Ala Asp Thr Ala Ala Thr Thr Asp Lys
                165                 170                 175

Ala Ala Asp Thr Thr Ala Thr Thr Asp Lys Val Ala Asp Thr Ala Ala
```

```
            180                 185                 190
Thr Thr Asp Lys Ala Ala Asp Thr Ala Ala Thr Thr Asp Lys Val Thr
            195                 200                 205
Asp Thr Thr Val Ala Thr Asn Lys Ala Val Asp Thr Thr Ala Thr Thr
            210                 215                 220
Asp Lys Val Asp Asp Thr Thr Ala Thr Thr Ser Glu Lys Ser Lys Ser
225                 230                 235                 240
Ile Lys Gln Ile Asp Gly Lys Thr Tyr Phe Ile Gly Asp Asp Gly Gln
            245                 250                 255
Pro Lys Lys Asn Phe Thr Ala Ile Val Asp Gly Gln Val Leu Tyr Phe
            260                 265                 270
Asp Lys Asp Thr Gly Ala Leu Thr Ser Asn Ser Ser Gln Tyr Thr Asp
            275                 280                 285
Gly Leu Val Asn Ile Gly Asn Glu His Asn Ala Ala Tyr Ser Leu Ser
            290                 295                 300
Ser Asp Ser Phe Thr Gln Val Asp Gly Tyr Leu Thr Ala Asn Ser Trp
305                 310                 315                 320
Tyr Arg Pro Lys Asp Ile Leu Lys Asn Gly Thr Thr Thr Trp Thr Ala Ala
            325                 330                 335
Thr Ala Asn Asp Phe Arg Pro Leu Leu Met Ser Trp Trp Pro Asp Lys
            340                 345                 350
Asp Thr Gln Val Ser Tyr Leu Lys Tyr Met Gln Ser Ala Gly Leu Leu
            355                 360                 365
Ser Asp Asp Val Ala Leu Ser Asn Asn Asp Ser Met Asn Ser Leu Thr
370                 375                 380
Asp Thr Ala Met Thr Val Gln Lys Asn Ile Glu Glu Lys Ile Gly Leu
385                 390                 395                 400
Leu Gly Ser Thr Asp Trp Leu Lys Ala Asp Met Asn Gln Met Val Asp
            405                 410                 415
Ser Gln Ser Asn Trp Asn Ile Ser Ser Glu Ser Lys Gly Thr Asp His
            420                 425                 430
Leu Gln Gly Gly Ala Leu Leu Tyr Val Asn Ser Asp Leu Thr Pro Asn
            435                 440                 445
Ala Asn Ser Asp Tyr Arg Leu Leu Asn Arg Thr Pro Thr Asn Gln Lys
            450                 455                 460
Gly Gln Ile Thr Thr Asn Gly Asn Gln Gly Tyr Glu Met Leu Leu
465                 470                 475                 480
Ala Asn Asp Val Asp Asn Ser Asn Pro Ile Val Gln Ala Glu Gln Leu
            485                 490                 495
Asn Trp Leu Tyr Tyr Met Met Asn Ile Gly Ser Ile Ala Gln Asn Asp
            500                 505                 510
Pro Thr Ala Asn Phe Asp Gly Tyr Arg Val Asp Ala Val Asp Asn Val
            515                 520                 525
Asn Ala Asp Leu Leu Gln Ile Ala Gly Asp Tyr Phe Lys Ala Ala Tyr
            530                 535                 540
Gly Thr Asn Gln Ser Asp Ala Asn Ala Asn His His Ile Ser Ile Leu
545                 550                 555                 560
Glu Asp Trp Asp Asn Asn Asp Pro Ala Tyr Val Lys Ala Gln Gly Asn
            565                 570                 575
Asn Gln Leu Thr Met Asp Phe Pro Met His Leu Ala Leu Lys Tyr Ser
            580                 585                 590
Leu Asn Met Pro Ser Ser Ala Arg Ser Gly Leu Glu Pro Ala Ile Ser
            595                 600                 605
```

```
Thr Ser Leu Val Asn Arg Ala Asp Ala Thr Glu Asn Glu Ala Gln
    610                 615                 620

Pro Asn Tyr Ser Phe Ile Arg Ala His Asp Ser Glu Val Gln Thr Val
625                 630                 635                 640

Ile Ala Gln Ile Ile Lys Asp Lys Ile Asn Pro Ser Ser Asp Gly Leu
                645                 650                 655

Thr Val Ser Thr Asp Glu Ile Ala Lys Ala Phe Glu Ile Tyr Asn Ala
            660                 665                 670

Asp Glu Leu Lys Ala Asp Lys Glu Tyr Thr Ala Tyr Asn Ile Pro Ser
        675                 680                 685

Ser Tyr Ala Leu Met Leu Thr Asn Lys Asp Thr Ile Pro Arg Val Tyr
    690                 695                 700

Tyr Gly Asp Leu Phe Thr Asp Asp Gly Gln Tyr Met Ser Ala Lys Ser
705                 710                 715                 720

Pro Tyr Tyr Asp Ala Leu Thr Ser Leu Leu Gln Ser Arg Val Lys Tyr
                725                 730                 735

Val Ser Gly Gly Gln Ser Met Asn Met Thr Tyr Leu His Asn Asn Gln
                740                 745                 750

Gly Leu Leu Thr Ser Val Arg Tyr Gly Lys Asp Ala Met Thr Ala Asn
        755                 760                 765

Asp Thr Gly Thr Ser Glu Thr Arg Thr Gln Gly Ile Gly Leu Ile Val
    770                 775                 780

Gly Asn Lys Thr Asp Leu Asn Leu Asn Asn Asp Glu Gln Ile Val Leu
785                 790                 795                 800

Asn Met Gly Ala Ala His Lys Asn Gln Ala Tyr Arg Ala Leu Met Leu
                805                 810                 815

Ser Thr Lys Asp Gly Leu Lys Ile Tyr Asn Ser Asp Asp Glu Ala Pro
            820                 825                 830

Val Ser Tyr Thr Asp Asp Gln Gly Arg Leu Ile Phe Lys Ser Asp Val
        835                 840                 845

Val Tyr Gly Val Ser Asp Ala Gln Val Ser Gly Tyr Leu Ala Ala Trp
    850                 855                 860

Val Pro Val Gly Ala Asn Asp Ser Gln Asp Ala Arg Thr Glu Ser Ser
865                 870                 875                 880

Thr Thr Ala Ser Thr Asp Gly Asn Thr Tyr His Ser Asn Ser Ala Leu
                885                 890                 895

Asp Ser Gln Val Ile Tyr Glu Gly Phe Ser Asn Phe Gln Ala Met Pro
            900                 905                 910

Thr Gln Ala Asp Glu Tyr Thr Asn Ile Lys Ile Ala Glu Asn Ala Gln
        915                 920                 925

Leu Phe Lys Ser Leu Gly Ile Thr Ser Phe Gly Leu Ala Pro Gln Tyr
    930                 935                 940

Arg Ser Ser Thr Asp Asn Ser Phe Leu Asp Ser Val Ile Gln Asn Gly
945                 950                 955                 960

Tyr Ala Phe Thr Asp Arg Tyr Asp Ile Gly Tyr Asn Thr Pro Thr Lys
                965                 970                 975

Tyr Gly Thr Val Asp Gln Leu Leu Asp Ala Leu Arg Ala Leu His Ala
            980                 985                 990

Gln Gly Ile Gln Ala Ile Asn Asp Trp Val Pro Asp Gln Ile Tyr Asn
        995                 1000                1005

Leu Pro Gly Glu Glu Ile Val Thr Ala Ser Arg Thr Asn Gly Ser
    1010                1015                1020
```

```
Gly Lys Val Asn Glu Ser Ser Val Ile Asn Asn Thr Leu Tyr Asp
    1025                1030                1035

Ser Arg Thr Val Gly Gly Glu Tyr Gln Ala Ile Tyr Gly Gly
    1040                1045                1050

Ala Phe Leu Asp Lys Leu Lys Gln Asp Tyr Pro Glu Leu Phe Glu
    1055                1060                1065

Thr Lys Gln Ile Ser Thr Gly Glu Ala Met Asn Pro Asp Val Lys
    1070                1075                1080

Ile Thr Glu Trp Ser Ala Lys Tyr Phe Asn Gly Ser Asn Ile Gln
    1085                1090                1095

Gly Arg Gly Ala Trp Tyr Val Leu Lys Asp Trp Ser Thr Asn Gln
    1100                1105                1110

Tyr Phe Asn Val Ser Ser Gly Ser Glu Phe Leu Pro Lys Gln Leu
    1115                1120                1125

Leu Gly Glu Lys Thr Ser Thr Gly Phe Thr Asn Val Asp Asn Gly
    1130                1135                1140

Lys Thr Glu Phe Tyr Ser Thr Ser Gly Tyr Gln Ala Lys Asn Thr
    1145                1150                1155

Phe Ile Gln Asp Asn Asp Asn Trp Tyr Tyr Phe Asp Asn Asp Gly
    1160                1165                1170

Tyr Met Val Val Gly Gly Gln Glu Ile Asn Gly Lys Lys Tyr Tyr
    1175                1180                1185

Phe Leu Pro Asn Gly Val Glu Leu Gln Asp Ala Tyr Leu Ser Asp
    1190                1195                1200

Gly Thr Ser Glu Tyr Tyr Tyr Ser Ser Asp Gly Arg Gln Ile Ser
    1205                1210                1215

Asn Gln Tyr Tyr Gln Gly Ser Asp Asn Asn Trp Arg Tyr Phe Phe
    1220                1225                1230

Ala Asp Gly His Met Ala Val Gly Leu Ala Thr Ile Thr Thr Glu
    1235                1240                1245

Asn Gly Thr Thr Asn Gln Gln Tyr Phe Asp Ala Asn Gly Met Gln
    1250                1255                1260

Leu Lys Gly Val Ala Ile Lys Asp Thr Asp Gly Asn Val His Tyr
    1265                1270                1275

Phe Asp Gly Lys Thr Gly Asn Met Val Ile Asn Ser Trp Gly Lys
    1280                1285                1290

Ile Ser Asp Gly Ser Trp Leu Tyr Leu Asn Asp Ser Gly Val Ala
    1295                1300                1305

Val Thr Gly Pro Gln Asn Ile Asn Gly Gln Asn Leu Tyr Phe Asn
    1310                1315                1320

Glu Asp Gly Ile Gln Val Lys Gly Glu Ala Ile Thr Asp Asn Ser
    1325                1330                1335

Gly Asn Ile His Tyr Tyr Asp Arg Ser Thr Gly Asn Met Val Val
    1340                1345                1350

Asn Ser Trp Gly Glu Thr Asn Asn Gly Ser Trp Leu Tyr Leu Asn
    1355                1360                1365

Asp Lys Gly Asp Ala Val Thr Gly Glu Gln Val Ile Asp Gly Gln
    1370                1375                1380

Lys Leu Tyr Phe Ser Ser Asn Gly Ile Gln Leu Lys Asn Thr Phe
    1385                1390                1395

Lys Lys Leu Ser Asp Gly Ser Trp Leu Tyr Leu Asn Asp Lys Gly
    1400                1405                1410

Leu Pro Val Thr Gly Ala Gln Val Ile Asp Gly Gln Asn Leu Tyr
```

```
            1415                1420                1425

Phe Asp Gln Asp Gly Lys Gln Val Lys Gly Asp Val Ala Thr Asp
    1430                1435                1440

Gly Gln Gly Asn Thr His Tyr Tyr Asp Gly Asn Thr Gly Asn Met
    1445                1450                1455

Val Thr Asn Ser Trp Ala Glu Leu Ala Asp Gly Ser Trp Met Tyr
    1460                1465                1470

Leu Asp Asn Asp Gly Asn Pro Leu Thr Gly Pro Gln Lys Ile Asp
    1475                1480                1485

Gly Gln Ser Leu Tyr Phe Asn Asp Ala Gly Lys Gln Ile Lys Asn
    1490                1495                1500

Ala Leu Val Lys Leu Asp Asp Gly Ser Thr Ile Tyr Leu Asp Asp
    1505                1510                1515

Lys Gly Val Ser Ser Thr Gly Ile Gln Arg Ile Asp Asp Lys Ile
    1520                1525                1530

Tyr Tyr Phe Asp Pro Asp Gly Lys Gln Val Val Cys Arg Phe Glu
    1535                1540                1545

Glu Leu Pro Asp Gly Ser Trp Met Tyr Leu Asp Asp Asp Gly Val
    1550                1555                1560

Ala Ala Thr Gly Ala Gln Lys Ile Asn Gly Gln Glu Leu Tyr Phe
    1565                1570                1575

Asp Asn Asn Gly Lys Gln Val Lys Asn Asp Lys Val Ile Asn Asp
    1580                1585                1590

Asp Gly Thr Ile Asn Tyr Tyr Thr Gly Met Ser Gly Glu Lys Leu
    1595                1600                1605

Lys Asn Asp Phe Gly Glu Leu Pro Asp Gly Ser Trp Met Tyr Leu
    1610                1615                1620

Asp Asn Gln Gly Asn Ala Val Ile Gly Ala Gln Lys Ile Asn Gly
    1625                1630                1635

Gln Asn Leu Tyr Phe Lys Thr Asp Gly Arg Gln Val Lys Gly Glu
    1640                1645                1650

Ala Asn Val Asp Ser Ser Gly Glu Met His Phe Tyr Asp Pro Asp
    1655                1660                1665

Ser Gly Glu Leu Ile Thr Asn Arg Phe Glu Gln Val Ala Ser Gly
    1670                1675                1680

Val Trp Ala Tyr Phe Asp Ala Asn Gly Val Ala Val Thr Gly Glu
    1685                1690                1695

Gln Arg Ile Gly Lys Gln Asn Leu Phe Phe Asp Pro Thr Gly Tyr
    1700                1705                1710

Gln Val Lys Gly Asp Lys Arg Thr Ile Asp Gly Val Leu Tyr Thr
    1715                1720                1725

Phe Asp Lys Glu Ser Gly Glu Arg Lys Gly Leu Asp Ser Ile Ser
    1730                1735                1740

Val Leu Pro Thr Asn Gly Gln Tyr Thr Thr Asp Lys Ala Gln Asn
    1745                1750                1755

Trp Tyr Tyr Gln Val Asp Gly Glu Asn Val Lys Gly Leu Tyr Thr
    1760                1765                1770

Asn Asn Asp Gly Gln Leu Arg Tyr Phe Asp Leu Thr Thr Gly Val
    1775                1780                1785

Gln Thr Lys Gly Asn Phe Val Thr Ile Gly Asn Asp Thr Tyr Tyr
    1790                1795                1800

Phe Thr Lys Glu Gln Gly Asp Gly Gln Ile Val Ser Glu Val Val
    1805                1810                1815
```

Ser Gly His Tyr Gly Thr Val Gln Leu Ser Asp Asn Ser Ser Ala
    1820                1825            1830

Trp Val Tyr Arg Gly Ala Asn Asp Gln Ile Leu Lys Gly Leu Gln
    1835                1840            1845

Asn Ile Asn Gly Arg Leu Gln Tyr Phe Asp Leu Thr Thr Gly Ala
    1850                1855            1860

Gln Leu Lys Gly Gly Ala Ala Asn Tyr Asp Gly Asn Leu Tyr Tyr
    1865                1870            1875

Phe Glu Ser Ser Asp Gly Asn Leu Val Ser Lys Ile Gln Gln Ser
    1880                1885            1890

Tyr Ser Thr Gly Asn Tyr Val Thr Asp Gly Asp Lys Val Thr Tyr
    1895                1900            1905

Val Asp Glu Gln Asn Gln Val Thr Gly Leu Ala Leu Ile Asp
    1910                1915            1920

Asp Gln Leu Gln Tyr Phe Asn Pro Ser Asp Gly Ser Gln Val Lys
    1925                1930            1935

Asn Glu Gln Val Ile Val Asp Gly Val Thr Tyr Tyr Phe Asp Lys
    1940                1945            1950

Asn Gly Asn Gly Gln Tyr Leu Phe Thr Asn Thr Ala Thr Met Ser
    1955                1960            1965

Thr Asn Glu Phe Ala Lys His Ser Ala Ala Tyr Ser Asn Asp Ser
    1970                1975            1980

Ser Ser Phe Lys Asn Thr Ile Asp Gly Phe Leu Thr Ala Asp Thr
    1985                1990            1995

Trp Tyr Arg Pro Lys Asp Ile Leu Glu Asn Gly Gln Thr Trp Val
    2000                2005            2010

Val Ser Ser Thr Asn Asp Val Arg Pro Leu Ile Thr Val Trp Trp
    2015                2020            2025

Pro Asn Lys Asp Val Gln Val Asn Tyr Leu Asn Phe Met Lys Lys
    2030                2035            2040

Asn Gly Leu Leu Asp Thr Ser Ser Gln Phe Asn Leu Gln Phe Asp
    2045                2050            2055

Gln Tyr Asp Leu Asn Val Ala Ala Gln Lys Val Gln Val Ala Ile
    2060                2065            2070

Glu Lys Arg Ile Ser Lys Glu Lys Ser Thr Asp Trp Leu Lys Asp
    2075                2080            2085

Leu Leu Phe Glu Ala His Glu Asp Thr Pro Ser Phe Val Lys Gln
    2090                2095            2100

Gln Phe Ile Trp Asn Lys Asp Ser Glu Tyr Gln Gly Gln Gly Asp
    2105                2110            2115

Ala Trp Phe Gln Gly Gly Tyr Leu Lys Tyr Asp Asn Ser Glu Leu
    2120                2125            2130

Thr Pro Thr Thr Asn Ser Asp Tyr Arg Glu Ser Gly Asn Thr Leu
    2135                2140            2145

Asp Phe Leu Leu Ala Asn Asp Val Asp Asn Ser Asn Pro Ala Val
    2150                2155            2160

Gln Ala Glu Asn Leu Asn Trp Leu His Tyr Leu Met Asn Phe Gly
    2165                2170            2175

Thr Ile Thr Ala Asn Asp Asp Ala Asn Phe Asp Ser Ile Arg
    2180                2185            2190

Ile Asp Ala Val Asp Phe Ile Asp Asn Asp Ala Ile Gln Arg Thr
    2195                2200            2205

Tyr Asp Tyr Met Arg Asp Ala Tyr Lys Val Asp Ala Ser Glu Asp
2210                2215                2220

Asn Ala Asn Lys His Ile Ser Leu Val Glu Ala Gly Leu Asp Ala
2225                2230                2235

Gly Thr Ser Thr Ile Lys Asn Asn Ala Leu Val Glu Ser Asn Phe
2240                2245                2250

Arg Glu Ala Ala Thr Leu Ser Leu Ala Asn Gln Ser Gly Lys Asn
2255                2260                2265

Ser Ser Leu Thr Asn Met Leu Gln Asp Ile Asp Gly Gly Gln Ile
2270                2275                2280

Ile Ala Asp His Ala Asn Asn Ala Thr Glu Asn Glu Ala Thr Pro
2285                2290                2295

Asn Tyr Ser Ile Ile His Ala His Asp Lys Gly Ile Gln Glu Lys
2300                2305                2310

Val Gly Ala Ala Ile Thr Asp Val Thr Gly Ala Asp Trp Thr Asn
2315                2320                2325

Phe Thr Asp Asp Gln Leu Lys Glu Gly Leu Ala Ala Tyr Tyr Gln
2330                2335                2340

Asp Gln Arg Ser Thr Asn Lys Lys Tyr Asn Ile Tyr Asn Leu Pro
2345                2350                2355

Ser Ile Tyr Ala Leu Met Leu Thr Asn Lys Asp Thr Val Pro Arg
2360                2365                2370

Val Tyr Tyr Gly Asp Met Tyr Gln Asp Asp Gly Gln Tyr Met Glu
2375                2380                2385

Lys Gln Ser Ile Tyr Tyr Asp Ala Ile Val Ser Leu Met Asn Thr
2390                2395                2400

Arg Lys Ser Tyr Val Ser Gly Gly Gln Thr Met Asp Val Asp Glu
2405                2410                2415

His Gly Leu Leu Lys Ser Val Arg Phe Gly Lys Asp Ala Met Thr
2420                2425                2430

Ala Ser Glu Leu Gly Thr Asn Glu Thr Arg Thr Glu Gly Val Gly
2435                2440                2445

Val Leu Val Gly Asn Asp Ser Ser Leu Lys Leu Asn Asp Ser Asp
2450                2455                2460

Thr Val Thr Leu Glu Met Gly Ala Ala His Lys Asn Gln Glu Tyr
2465                2470                2475

Arg Ala Ala Leu Leu Thr Thr Ser Asp Gly Ile Val Thr Tyr Asp
2480                2485                2490

Ala Asp Asn Asp Ala Pro Thr Ile Trp Thr Asp Arg Gly Thr
2495                2500                2505

Leu Thr Phe Ser Asn Lys Glu Ile Ala Gly Gln Asp Tyr Thr Ser
2510                2515                2520

Val Gln Gly Phe Ala Asn Pro Gln Val Ser Gly Tyr Leu Ala Val
2525                2530                2535

Trp Val Pro Val Gly Ala Ser Asp Asp Gln Asp Ala Arg Thr Ala
2540                2545                2550

Ala Ser Thr Asp Lys Asn Thr Asp Asp Lys Val Leu His Ser Asn
2555                2560                2565

Ala Ala Leu Asp Ser Asn Leu Ile Tyr Glu Gly Phe Ser Asn Phe
2570                2575                2580

Gln Pro Lys Ala Thr Thr Asn Asp Glu Leu Thr Asn Val Val Ile
2585                2590                2595

Ala Lys Asn Ala Asn Leu Phe Glu Lys Trp Gly Ile Thr Ser Phe

```
                         2600                2605                2610
Glu Met Ala Pro Gln Tyr Arg Ser Ser Gly Asp His Thr Phe Leu
2615                2620                2625

Asp Ser Thr Ile Asp Asn Gly Tyr Val Phe Thr Asp Arg Tyr Asp
2630                2635                2640

Leu Gly Phe Glu Thr Pro Thr Lys Tyr Gly Thr Asp Lys Asp Leu
2645                2650                2655

Arg Thr Ala Ile Lys Ala Leu His Gln Ser Asn Met Gln Val Met
2660                2665                2670

Ala Asp Val Val Asp Asn Gln Val Tyr Asn Leu Ser Gly Gln Glu
2675                2680                2685

Val Val Ser Ala Ser Arg Ala Gly Val Tyr Gly Asn Asp Val Ser
2690                2695                2700

Thr Gly Phe Gly Thr Gln Leu Tyr Ala Val Asn Ser Val Gly Gly
2705                2710                2715

Gly Lys Tyr Gln Ala Gln Tyr Gly Gly Glu Tyr Leu Asn Glu Leu
2720                2725                2730

Lys Gln Gln Tyr Pro Asp Leu Phe Glu Ala Lys Thr Tyr Asp Tyr
2735                2740                2745

Trp Val Lys Asn Tyr Ser Asn Asp Gly Ser Asp Pro Tyr Tyr Thr
2750                2755                2760

Leu Ser Gln Asn Thr Arg Lys Asp Met Pro Ser Ser Glu Val Ile
2765                2770                2775

Lys Gln Trp Ser Ala Lys Tyr Met Asn Gly Thr Asn Val Leu Gly
2780                2785                2790

Asn Gly Met Gly Tyr Val Leu Lys Asp Trp Asn Thr Gly Glu Tyr
2795                2800                2805

Phe Lys Ile Gly Glu Lys Asn Ala Asp Phe Ile Thr Asn
2810                2815                2820

<210> SEQ ID NO 3
<211> LENGTH: 2844
<212> TYPE: PRT
<213> ORGANISM: Leuconostoc carnosum

<400> SEQUENCE: 3

Met Arg Asp Lys Asn Val Ile Cys Asp Arg Lys Lys Leu Tyr Lys Ser
1               5                   10                  15

Gly Lys Leu Leu Val Thr Ala Gly Ile Phe Ser Thr Val Val Phe Gly
                20                  25                  30

Met Ala Val Ser Asp Val Ser Ala Asn Asp Thr Asp Asn Thr Val Leu
            35                  40                  45

Thr Ser Asn Ser Gly Phe Leu Asp Lys Val Val Asp Thr Thr Ser Thr
        50                  55                  60

Asp Lys Ala Ala Thr Pro Asp Lys Val Val Asp Thr Thr Ser Thr Asp
65                  70                  75                  80

Lys Ala Val Thr Pro Asp Lys Val Ala Asp Thr Thr Ser Thr Asp Lys
                85                  90                  95

Ala Val Thr Pro Asp Lys Val Ala Asp Thr Thr Ser Thr Asp Lys Ala
            100                 105                 110

Ala Thr Pro Asp Lys Val Val Asp Thr Thr Ser Thr Asp Lys Ala Ala
        115                 120                 125

Thr Pro Asp Lys Val Val Asp Thr Thr Ser Thr Asp Lys Ala Ala Thr
        130                 135                 140
```

```
Pro Asp Lys Val Val Asp Thr Thr Ser Thr Asp Lys Ala Ala Thr Pro
145                 150                 155                 160

Asp Lys Val Val Asp Thr Thr Ser Thr Asp Lys Ala Ala Thr Pro Asp
            165                 170                 175

Lys Val Ala Asp Thr Thr Ser Thr Asp Lys Ala Ala Thr Pro Asp Lys
        180                 185                 190

Val Val Asp Thr Thr Ser Thr Asp Lys Ala Ala Thr Pro Asp Lys Val
    195                 200                 205

Val Asp Thr Thr Ser Thr Asp Lys Ala Ala Thr Pro Asp Lys Val Val
210                 215                 220

Asp Thr Thr Ser Thr Asp Lys Ala Ala Thr Pro Asp Lys Val Val Asp
225                 230                 235                 240

Thr Thr Ser Thr Asp Lys Ala Ala Asp Arg Thr Ile Ser Ile Ser Gly
            245                 250                 255

Lys Thr Val Lys Asn Ile Glu Glu Ile Gly Lys Thr Tyr Phe Val
        260                 265                 270

Gly Asp Asp Gly Lys Val Lys Lys Asn Phe Thr Val Ile Val Asp Gly
        275                 280                 285

Gln Val Met Tyr Phe Asp Lys Glu Ser Gly Ala Leu Thr Ser Asn His
    290                 295                 300

Lys Gln Tyr Lys Glu Gly Leu Ser Asp Ile Thr Asn Glu His Asn Ala
305                 310                 315                 320

Ala Tyr Ser Leu Glu Asn Asp Asn Phe Thr Gln Ile Asp Ser Tyr Leu
            325                 330                 335

Thr Ala Asn Ser Trp Tyr Arg Pro Lys Asp Ile Leu Lys Ser Gly Thr
            340                 345                 350

Thr Trp Thr Ala Ser Thr Asp Lys Asp Ser Arg Pro Leu Leu Met Ser
        355                 360                 365

Trp Trp Pro Asp Gln Gln Thr Glu Leu Ser Tyr Leu Lys Tyr Met Gln
        370                 375                 380

Ser Ala Gly Phe Leu Ala Glu Asp Val Asn Leu Ser Glu Asn Asn Ser
385                 390                 395                 400

Ile Asp Asp Leu Thr Ala Ala Met Asp Val Gln Lys Asn Val Glu
            405                 410                 415

Ala Lys Ile Ser Leu Ser Gly Asn Thr Asp Trp Leu Lys Glu Asp Met
            420                 425                 430

Asn Gln Phe Val Asp Ser Gln Ser Asn Trp Asn Ile Ser Ser Glu Ser
        435                 440                 445

Lys Gly Thr Asp His Leu Gln Gly Gly Ala Leu Leu Tyr Gly Asn Ser
    450                 455                 460

Asp Met Thr Pro Asp Ala Asn Ser Asp Tyr Arg Leu Leu Asn Arg Thr
465                 470                 475                 480

Pro Lys Asn Gln Thr Gly Gln Ile Ser Ala Thr Asn Asp Gln Gly Gly
            485                 490                 495

Tyr Glu Met Leu Leu Ala Asn Asp Val Asp Asn Ser Asn Pro Ile Val
            500                 505                 510

Gln Ala Glu Gln Leu Asn Trp Leu His Tyr Met Met Asn Ile Gly Ser
        515                 520                 525

Ile Thr Lys Asn Asp Ser Thr Ala Asn Phe Asp Gly Tyr Arg Val Asp
    530                 535                 540

Ala Val Asp Asn Val Asn Ala Asp Leu Leu Gln Ile Ala Gly Asp Tyr
545                 550                 555                 560

Phe Lys Ala Ala Tyr Gly Thr Asp Lys Ser Asp Ala Asn Ala Asn
```

-continued

```
                565                 570                 575
His Ile Ser Ile Leu Glu Asp Trp Asp Asn Ser Asp Pro Asp Tyr Val
            580                 585                 590

Lys Lys His Gly Asn Glu Gln Leu Thr Met Asp Phe Pro Met His Leu
            595                 600                 605

Ala Leu Lys Tyr Ala Leu Asn Met Pro Ile Asp Met Arg Ser Gly Leu
            610                 615                 620

Glu Pro Ala Ile Lys Thr Ser Leu Val Asn Arg Ser Gln Asp Ala Thr
625                 630                 635                 640

Glu Asn Glu Ala Gln Pro Asn Tyr Ser Phe Ile Arg Ala His Asp Ser
                645                 650                 655

Glu Val Gln Thr Val Ile Ala Gln Ile Ile Lys Asp Lys Ile Asn Pro
            660                 665                 670

Lys Ser Asp Gly Leu Thr Val Thr Pro Asp Glu Ile Ala Lys Ala Phe
            675                 680                 685

Glu Ile Tyr Asn Ala Asp Glu Leu Lys Ala Asp Lys Ala Tyr Thr Ala
            690                 695                 700

Phe Asn Ile Pro Ser Ser Tyr Ala Leu Leu Leu Thr Asn Lys Asp Thr
705                 710                 715                 720

Val Pro Arg Val Tyr Tyr Gly Asp Leu Phe Thr Asp Asp Gly Gln Tyr
                725                 730                 735

Met Ser Asp His Ser Pro Tyr Tyr Asp Ala Ile Thr Thr Leu Leu Ala
            740                 745                 750

Ser Arg Ile Lys Tyr Ala Ala Gly Gly Gln Ser Met Gly Met Thr Tyr
            755                 760                 765

Leu His Asp Asn Gln Glu Val Leu Thr Ser Val Arg Tyr Gly Lys Gly
            770                 775                 780

Ala Leu Thr Ala Asp Asp Leu Gly Asn Val Asp Thr Arg Thr Gln Gly
785                 790                 795                 800

Ile Gly Leu Val Ile Ser Asn Lys Thr Asp Leu Ser Leu Lys Ser Asp
                805                 810                 815

Glu Ser Val Val Leu Asn Met Gly Val Ala His Lys Asn Gln Ala Tyr
            820                 825                 830

Arg Pro Ala Met Leu Thr Thr Lys Ser Gly Leu Lys Ile Tyr Asp Thr
            835                 840                 845

Asp Asp Gly Ala Pro Ile Val Tyr Thr Asn Asn Leu Gly Gln Leu Ile
            850                 855                 860

Phe Asn Ala Asp Thr Val Tyr Gly Val Ser Asp Pro Gln Val Ser Gly
865                 870                 875                 880

Tyr Leu Ala Ala Trp Val Pro Val Gly Ala Thr Glu Asp Gln Asp Ala
                885                 890                 895

Arg Thr Lys Gly Ser His Asp Gly Thr Asp Gly Asn Val Tyr His
            900                 905                 910

Ser Asn Ala Ala Leu Asp Ser Gln Val Ile Tyr Glu Gly Phe Ser Asn
            915                 920                 925

Phe Gln Ala Met Pro Thr Thr Thr Asp Glu Tyr Thr Asn Val Lys Ile
            930                 935                 940

Ala Gln Asn Ala Gln Trp Phe Lys Lys Leu Gly Leu Thr Ser Phe Glu
945                 950                 955                 960

Leu Ala Pro Gln Tyr Arg Ser Ser Thr Asp Ser Ser Phe Leu Asp Ser
                965                 970                 975

Val Ile Gln Asn Gly Tyr Ala Phe Thr Asp Arg Tyr Asp Val Gly Tyr
            980                 985                 990
```

```
Asn Thr Pro Thr Lys Tyr Gly Thr  Val Asp Gln Leu Leu  Asp Ala Leu
    995             1000                  1005

Arg Ala  Leu His Ser Gln Asp  Ile Gln Ala Ile Asn  Asp Trp Val
    1010             1015                 1020

Pro Asp  Gln Ile Tyr Asn Leu  Pro Gly Glu Gln Ile  Val Thr Ala
    1025             1030                 1035

Ser Arg  Thr Asn Gly Ser Gly  Lys Tyr Asp Asp Asp  Ser Val Ile
    1040             1045                 1050

Ser Asn  Thr Leu Tyr Asp Ser  Arg Thr Ile Gly Gly  Gly Glu Tyr
    1055             1060                 1065

Gln Ala  Met Tyr Gly Gly Ala  Phe Leu Asp Gln Leu  Lys Gln Ala
    1070             1075                 1080

Tyr Pro  Gly Leu Phe Glu Thr  Lys Gln Leu Ser Thr  Gly Val Ala
    1085             1090                 1095

Met Asp  Pro Asp Val Lys Ile  Lys Glu Trp Ser Ala  Lys Tyr Phe
    1100             1105                 1110

Asn Gly  Ser Asn Ile Gln Gly  Arg Gly Ala Trp Tyr  Val Leu Lys
    1115             1120                 1125

Asp Trp  Ala Thr Asn Lys Tyr  Phe Ser Val Ser Ser  Asn Asn Thr
    1130             1135                 1140

Phe Leu  Pro Lys Gln Leu Leu  Gly Glu Lys Ala Ser  Thr Gly Phe
    1145             1150                 1155

Ile Thr  Asn Asp Gly Lys Thr  Glu Phe Tyr Ser Thr  Ser Gly Tyr
    1160             1165                 1170

Gln Ala  Lys Asn Thr Phe Ile  Glu Asp Asn Gly Asn  Trp Tyr Tyr
    1175             1180                 1185

Phe Asp  Asn Asp Gly Tyr Ser  Val Val Gly Lys Gln  Val Ile Asp
    1190             1195                 1200

Asn Lys  His Tyr Tyr Phe Leu  Pro Asn Gly Val Glu  Leu Gln Asp
    1205             1210                 1215

Ala Tyr  Leu Ser Asp Gly Asp  Lys Gln Tyr Tyr Tyr  Lys Lys Thr
    1220             1225                 1230

Gly Arg  Gln Ile Val Asn Gln  Tyr Tyr Arg Asp Glu  Gln Gly Asp
    1235             1240                 1245

Trp Arg  Tyr Phe Phe Ala Asp  Gly His Met Ala Leu  Gly Leu Thr
    1250             1255                 1260

Asp Ile  Val Ser Asn Asp Gly  Thr His Ala Thr Gln  Tyr Phe Asp
    1265             1270                 1275

Asn Asn  Gly Val Gln Val Lys  Gly Thr Ser Glu Arg  Asp Lys Asp
    1280             1285                 1290

Gly Asn  Ile His Tyr Phe Asp  Gly Thr Ser Gly Asn  Leu Val Val
    1295             1300                 1305

Ser Ser  Trp Gly Gln Leu Ser  Asp Gly Ser Trp Leu  Tyr Leu Asn
    1310             1315                 1320

Asp Lys  Gly Ile Ala Val Thr  Gly Ala Gln Gln Ile  Asp Gly Gln
    1325             1330                 1335

Ser Leu  Tyr Phe Asn Glu Asp  Gly Lys Glu Val Lys  Gly Asp Ala
    1340             1345                 1350

Val Thr  Asp Asn Gln Gly Asn  Ile Arg Tyr Phe Asp  Gly Glu Ser
    1355             1360                 1365

Gly His  Met Val Val Asn Ser  Trp Gly Lys Leu Pro  Asp Gly Ser
    1370             1375                 1380
```

-continued

```
Trp Met Tyr Leu Asn Asp Lys Gly Ile Ala Val Thr Gly Gln Gln
    1385                1390                1395

Lys Ile Asn Asn Glu Val Leu Tyr Phe Asn Ala Asp Gly Lys Gln
    1400                1405                1410

Ile Lys Ser Ala Phe Lys Glu Leu Val Asp Gly Ser Trp Leu Tyr
    1415                1420                1425

Leu Asn Asp Lys Gly Ile Ala Val Thr Gly Ala Gln Gln Ile Asp
    1430                1435                1440

Gly Gln Ser Leu Tyr Phe Asn Glu Asp Gly Lys Glu Val Lys Gly
    1445                1450                1455

Asp Ala Val Thr Asp Asn Gln Gly Asn Ile Arg Tyr Phe Asp Gly
    1460                1465                1470

Glu Ser Gly His Met Val Val Asn Ser Trp Gly Lys Leu Pro Asp
    1475                1480                1485

Gly Ser Trp Met Tyr Leu Asn Asp Lys Gly Ile Ala Val Thr Gly
    1490                1495                1500

Gln Gln Lys Ile Asn Asn Glu Ile Leu Tyr Phe Asp Ala Asp Gly
    1505                1510                1515

Lys Gln Leu Lys Asn Thr Leu Lys Thr Leu Ser Asp Gly Ser Arg
    1520                1525                1530

Ile Tyr Leu Asp Gly Lys Gly Val Ser Ala Thr Gly Val Gln Lys
    1535                1540                1545

Ile Asn Gly Lys Val Ser Tyr Phe Asp Val Asn Gly Lys Gln Val
    1550                1555                1560

Ser Asn His Ile Gln Glu Leu Pro Asp Gly Ser Trp Met Tyr Leu
    1565                1570                1575

Asp Asn Asp Gly Leu Ala Leu Ile Gly Asn Gln Asp Val Asp Gly
    1580                1585                1590

Lys Gln Leu Tyr Phe Asp Val Asp Gly Lys Gln Ile Lys Asn Asp
    1595                1600                1605

Lys Val Lys Asn Ser Asp Gly Thr Ile Asn Tyr Tyr Thr Gly Thr
    1610                1615                1620

Val Gly Glu Lys Leu Lys His Asp Phe Gly Gln Leu Ser Asp Gly
    1625                1630                1635

Ser Trp Met Tyr Leu Asp Glu Asn Gly Asn Ala Val Thr Gly Glu
    1640                1645                1650

Gln Asn Ile Asn Gly Gln His Leu Tyr Phe Lys Asp Asp Gly Gln
    1655                1660                1665

Gln Val Lys Gly Asp Val Phe Glu Asp Asp Leu Gly Arg Met Arg
    1670                1675                1680

Tyr Tyr Ser Ala Asn Ser Gly Glu Met Val Val Asn Gln Phe Glu
    1685                1690                1695

Gln Ile Ser Asp Gly Ala Trp Ala Tyr Phe Gly Asp Asp Gly Val
    1700                1705                1710

Ala Val Thr Gly Glu Gln His Ile Asn Gly Gln Asp Leu Phe Phe
    1715                1720                1725

Asp Ala Thr Gly Gln Gln Val Lys Gly Glu Ser Arg Thr Ile Asn
    1730                1735                1740

Gly Ile Pro Tyr Thr Phe Glu Lys Glu Ser Gly Glu Lys Arg Ser
    1745                1750                1755

Val Asn Ile Ala Pro Leu Leu Ala Met Gly Asn Tyr Val Thr Asn
    1760                1765                1770

Asn Gly Thr Asp Trp Gln Tyr Glu Val Gln Gly Asn Pro Val Lys
```

```
            1775                1780                1785

Gly Leu Tyr Ser Thr Ser Asp Asn Lys Leu Arg Tyr Phe Asp Leu
    1790                1795                1800

Thr Thr Gly Val Gln Ile Lys Gly Asn Phe Val Thr Ile Gly His
    1805                1810                1815

Asn Thr Tyr Tyr Phe Asn Pro Ala Asn Gly Asp Gly Glu Leu Leu
    1820                1825                1830

Pro Asp Val Ser Asp Gly His Tyr Gly Thr Ile Gln Val Lys Asp
    1835                1840                1845

Ala Asn Thr Asn Glu Lys Thr Val Trp Val Tyr Arg Asn Gln Ser
    1850                1855                1860

Asn Thr Ile Leu Lys Gly Ile Gln Asn Ile His Gly Asn Ile Gln
    1865                1870                1875

Tyr Phe Asp Leu Ser Thr Gly Glu Gln Ile Lys Gly Gly Ile Ala
    1880                1885                1890

Asn Tyr Asp Gly Asn Asp Tyr Tyr Phe Glu Ser Ala Lys Gly Asn
    1895                1900                1905

Leu Thr Ser Lys Ile Lys Gln Val Tyr Thr Asp Gly Gln Tyr Val
    1910                1915                1920

Thr Lys Asp Gly Lys Ser Ile Tyr Glu Asp Ala Gln Gln Gln Ser
    1925                1930                1935

Val Ser Gly Leu Val Ser Ile Asn Gly Gln Leu Gln Tyr Phe Asn
    1940                1945                1950

Pro Gln Asp Gly Val Gln Val Lys Asn Gln Gln Ile Ile Val Asp
    1955                1960                1965

Gly Val Thr Tyr Tyr Phe Asp Glu Asn Gly Asn Gly Gln Tyr Leu
    1970                1975                1980

Phe Thr Asn Thr Thr Val Met Pro Met Asp Asp Phe Thr Lys His
    1985                1990                1995

Asn Thr Val Tyr Ser Asp Asn Asp Asn Asn Phe Lys Asn Asn Val
    2000                2005                2010

Asp Gly Phe Leu Thr Ala Asp Thr Trp Tyr Arg Pro Lys Glu Ile
    2015                2020                2025

Leu Lys Ala Gly Thr Thr Trp Thr Thr Thr Ser Glu Ser Asp Met
    2030                2035                2040

Arg Pro Leu Ile Thr Thr Trp Trp Pro Asn Lys Asn Val Gln Val
    2045                2050                2055

Asn Tyr Leu Asn Phe Met Lys Gln Asn Asn Leu His Thr Asn
    2060                2065                2070

Val Glu Tyr Ser Leu Leu Ser Asp Gln Tyr Asp Leu Asn Ile Ala
    2075                2080                2085

Ala Gln Ala Val Gln Thr Ala Ile Glu Lys Arg Ile Ala Gln Glu
    2090                2095                2100

Asn Ser Thr Asp Trp Leu Gln Asn Leu Leu Phe Thr Ala Gln Asp
    2105                2110                2115

Asp Gln Pro Ser Phe Val Lys Gln Gln Phe Ile Trp Asn Lys Asp
    2120                2125                2130

Ser Glu Tyr Gln Gly Lys Gly Asp Ala Trp Phe Gln Gly Gly Tyr
    2135                2140                2145

Leu Lys Tyr Gly Asn Asn Lys Leu Thr Pro Asn Thr Asn Ser Asn
    2150                2155                2160

Tyr Arg Lys Thr Asp Asn Ala Phe Glu Phe Leu Leu Ala Asn Asp
    2165                2170                2175
```

-continued

```
Ile Asp Asn Ser Asn Pro Val Val Gln Ala Glu Asn Leu Asn Trp
    2180            2185             2190
Leu Glu Tyr Leu Met Asn Phe Gly Thr Ile Thr Gly Lys Asp Asp
    2195            2200             2205
Asp Ala Asn Phe Asp Ser Ile Arg Val Asp Ala Val Asp Phe Ile
    2210            2215             2220
Ser Asn Asp Thr Ile Gln Arg Thr Tyr Asp Tyr Leu Arg Asp Ala
    2225            2230             2235
Tyr Gln Val Asp Gln Ser Glu Ala Lys Ala Asn Gln His Ile Ser
    2240            2245             2250
Leu Val Glu Ala Gly Leu Asp Ala Gly Thr Ser Thr Val Lys Asn
    2255            2260             2265
Asp Ala Leu Ile Glu Ser Asn Leu Arg Glu Ala Ala Thr Leu Ser
    2270            2275             2280
Leu Ala Asn Ala Ser Gly Lys Asn Ser Ala Leu Thr Asn Met Leu
    2285            2290             2295
Gln Asp Val Asp Gly Gly Thr Leu Ile Ala Asp His Thr His Asn
    2300            2305             2310
Ser Thr Glu Asn Glu Ala Thr Pro Asn Tyr Ser Ile Ile His Ala
    2315            2320             2325
His Asp Lys Gly Ile Gln Glu Lys Val Gly Ala Ala Ile Ser Asp
    2330            2335             2340
Ala Thr Gly Ala Asp Trp Thr Asn Phe Thr Asp Thr Gln Leu Lys
    2345            2350             2355
Ser Gly Leu Asp Leu Tyr Tyr Lys Asp Gln Arg Ala Thr Asp Lys
    2360            2365             2370
Lys Tyr Asn Ile Tyr Asn Leu Pro Ser Ile Tyr Ala Leu Met Leu
    2375            2380             2385
Thr Asn Lys Asp Thr Val Pro Arg Val Tyr Tyr Gly Asp Met Tyr
    2390            2395             2400
Gln Asp Asn Gly Gln Tyr Met Ala Glu Lys Ser Ile Tyr Tyr Asn
    2405            2410             2415
Ala Leu Glu Ser Leu Met Ser Ala Arg Lys Ser Tyr Val Ser Gly
    2420            2425             2430
Gly Gln Thr Met Asp Val Asp Ser His Gly Leu Leu Lys Ser Val
    2435            2440             2445
Arg Phe Gly Lys Gly Ala Met Thr Ala Asp Thr Val Gly Asn Glu
    2450            2455             2460
Glu Thr Arg Thr Glu Gly Ile Gly Val Leu Val Gly Asn Asp Ala
    2465            2470             2475
Ser Leu Lys Leu Asn Asp Ser Asp Thr Val Thr Leu Asp Met Gly
    2480            2485             2490
Ala Ala His Lys Asn Gln Lys Tyr Arg Ala Ala Ile Leu Thr Thr
    2495            2500             2505
Asn Asn Gly Leu Ser Thr Phe Asp Ser Asp Lys Asp Ala Pro Ile
    2510            2515             2520
Ala Trp Thr Asn Asp Lys Gly Ile Leu Thr Phe Ser Asn Lys Asn
    2525            2530             2535
Val Ser Gly Gln Asp Asn Thr Asn Val His Gly Val Ala Asn Pro
    2540            2545             2550
Gln Val Ser Gly Tyr Leu Ala Val Trp Val Pro Val Gly Ala Lys
    2555            2560             2565
```

-continued

Asp Asp Gln Asn Ala Gly Thr Ser Ala Ser Thr Val Val Asn Thr
    2570                2575                2580

Asp Gly Lys Val Leu His Ser Asn Ala Ser Leu Asp Ser Asn Leu
    2585                2590                2595

Ile Phe Glu Gly Phe Ser Asn Phe Gln Pro Arg Ala Thr Thr Asn
    2600                2605                2610

Asp Glu Leu Thr Asn Val Val Ile Ala Lys Asn Ala Asp Leu Phe
    2615                2620                2625

Gln Lys Trp Gly Ile Thr Ser Phe Glu Met Ala Pro Gln Tyr Arg
    2630                2635                2640

Ser Ser Gln Asp His Thr Phe Leu Asp Ser Thr Ile Asp Asn Gly
    2645                2650                2655

Tyr Ala Phe Thr Asp Arg Tyr Asp Leu Gly Phe Asn Thr Pro Thr
    2660                2665                2670

Lys Tyr Gly Thr Asp Ser Asp Leu Arg Leu Ala Ile Lys Ser Leu
    2675                2680                2685

His Lys Ala Gly Met Gln Val Met Ala Asp Val Val Asp Asn Gln
    2690                2695                2700

Val Tyr Asn Leu Pro Asp Gln Glu Val Val Ser Ala Ser Arg Ala
    2705                2710                2715

Gly Val Tyr Gly Asn Asp Val Ala Thr Gly Phe Asp Thr Gln Leu
    2720                2725                2730

Tyr Ala Val Asn Ser Val Gly Gly Lys Tyr Gln Ala Gln Tyr
    2735                2740                2745

Gly Gly Gln Tyr Leu Ser Glu Leu Lys Asn Lys Tyr Pro Asp Leu
    2750                2755                2760

Phe Glu Ala Lys Ala Tyr Asp Tyr Trp Thr Lys Asn Tyr Ala Asn
    2765                2770                2775

Asp Gly Ser Asn Pro Tyr Tyr Thr Leu Ser Gln Gln Thr Arg Asp
    2780                2785                2790

Asp Ile Pro Ser Asp Glu Lys Ile Lys Gln Trp Ser Ala Lys Tyr
    2795                2800                2805

Met Asn Gly Thr Asn Val Leu Gly His Gly Met Gly Tyr Val Leu
    2810                2815                2820

Lys Asp Trp Asn Thr Gly Gln Tyr Phe Lys Ile Asn Lys Asp Gly
    2825                2830                2835

Asp Ser Asn Leu Pro Val
    2840

<210> SEQ ID NO 4
<211> LENGTH: 1672
<212> TYPE: PRT
<213> ORGANISM: Fructobacillus tropaeoli

<400> SEQUENCE: 4

Met Arg Lys Lys Leu Tyr Lys Ser Gly Lys Met Trp Val Ala Ala Ser
1               5                   10                  15

Val Ala Ile Ser Phe Ser Ala Leu Ser Ile Ser Val Gly Asn Asn Gly
                20                  25                  30

Ala Lys Ala Asp Asp Ser Gln Gln Ser Ser Thr Gln Ile Gln Ser Thr
            35                  40                  45

Gln Val Thr Thr Ala Leu Pro Ala Gly Gly Gln Tyr Ser Thr Thr Asn
        50                  55                  60

Gly Gly Gln Ser Trp Asn Tyr Leu Val Asn Gly Val Ala Ile Lys Gly
65                  70                  75                  80

```
Met Tyr Gln Asp Gly Gln Gly Gln Leu Arg Tyr Phe Asn Phe Ile Asp
                85                  90                  95

Gly Thr Gln Val Lys Gly Glu Phe Leu Ser Ile Asn Gly Thr Tyr Tyr
            100                 105                 110

Tyr Phe Asp Gln Asn Ser Gly Glu Gly His Leu Val Pro Thr Gln Ser
            115                 120                 125

Asn Gly His Tyr Thr Glu Ile Gly Asn Thr Gly Ala Trp Gly Tyr Gln
130                 135                 140

Asn Ser Asn Gly Glu Leu Val Lys Gly Ile Gln Asn Ile Asp Gly Gln
145                 150                 155                 160

Leu Arg Tyr Phe Asp Glu Asn Thr Gly Asn Gln Val Lys Gly Gly Ser
                165                 170                 175

Ala Thr Ile Gly Asn Lys Ser Tyr Tyr Phe Glu Pro Ser Gln Gly Thr
            180                 185                 190

Leu Thr Thr Thr Ile Asp Gln Val Ser Asp Ala Gln Asn Ala Asn Ile
            195                 200                 205

Arg Gly Leu Ala Thr Val Asn Gly Gln Leu Asn Tyr Phe Asp Pro Thr
210                 215                 220

Thr Gly Glu Gln Ala Lys His Lys Gln Val Ala Thr Asn Gly Ala Thr
225                 230                 235                 240

Tyr Tyr Phe Asn Asp Ser Gly Val Gly Thr Tyr Leu Phe Thr Asn Val
                245                 250                 255

Gln Asn Thr Pro Ala Asn Asp Val Ser Gln His Asn Ala Val Asn Ser
            260                 265                 270

Thr Asp Thr Lys Asp Tyr Thr Asn Thr Val Asp Gly Phe Leu Thr Ala
            275                 280                 285

Asp Thr Trp Tyr Arg Pro Lys Tyr Ile Leu Asp Asn Gly Glu Asn Trp
290                 295                 300

Arg Ala Ser Asn Glu Gly Glu Tyr Arg Pro Phe Ile Met Asn Trp Trp
305                 310                 315                 320

Pro Asn Lys Asn Val Glu Val Asn Tyr Leu Lys Leu Met Gln Asn Asn
                325                 330                 335

Asn Leu Leu Ser Ser Thr Val Gln Tyr Asp Leu Phe Thr Asp Gln Ala
            340                 345                 350

Ile Leu Asn Gln Ala Ala Tyr Gln Ala Gln Ile Ala Ile Glu Lys Arg
            355                 360                 365

Ile Lys Ser Glu Gly Ser Thr Asp Trp Leu Asn Thr Leu Leu Phe Gly
370                 375                 380

Gly Asp Asp Ser His Pro Ser Phe Val Lys Gln Gln Phe Ile Trp Asn
385                 390                 395                 400

Ser Asp Ser Glu Ser Pro Trp Gln Gly Asp Ala Trp Phe Gln Gly Gly
                405                 410                 415

Tyr Leu Lys Tyr Gly Asn Ser Val Met Thr Pro Thr Ser Asn Ser Asn
            420                 425                 430

Tyr Arg Gln Ala Gly Asn Ala Phe Asp Phe Leu Leu Ala Asn Asp Val
            435                 440                 445

Asp Asn Gln Asn Pro Ile Val Gln Ala Glu Asp Leu Asn Trp Leu Tyr
450                 455                 460

Tyr Leu Met Asn Phe Gly Ser Ile Thr Thr Asn Gly Leu Asp Asn Asp
465                 470                 475                 480

Ser Asn Phe Asp Ser Ile Arg Leu Asp Ala Val Asp Phe Ile His Asn
                485                 490                 495
```

```
Asp Ala Ile Gln Arg Thr Tyr Asp Tyr Leu Arg Gln Ala Phe Asn Leu
            500                 505                 510

Thr Lys Asn Glu Ala Thr Ala Asn Gln His Leu Ser Leu Val Glu Ala
        515                 520                 525

Gly Val Asp Ala Gly Thr Thr Thr Tyr Asn Ser Asp Gly Leu Ile Glu
    530                 535                 540

Ser Asn Ile Arg Pro Leu Ala Thr Asp Ser Leu Thr Asn Ala Pro Gly
545                 550                 555                 560

Lys Asn Ala Ser Leu Ser Asn Leu Ile Lys Asp Val Asp Ser Gly Glu
            565                 570                 575

Val Ile Ala Asp His Ala Asn Phe Ser Thr Asp Gly Ile Pro Asn
        580                 585                 590

Tyr Ser Ile Ile His Ala His Asp Lys Gly Ile Gln Glu Asn Val Gly
        595                 600                 605

Ala Ala Ile Thr Ala Ala Thr Gly Ala Asp Trp Thr Asn Phe Thr Thr
        610                 615                 620

Glu Gln Leu Glu Gln Gly Leu Asp Leu Tyr Tyr Gln Asp Gln Arg Ser
625                 630                 635                 640

Thr Asn Lys Lys Tyr Asn Ile Tyr Asn Leu Pro Ser Ile Tyr Ala Leu
            645                 650                 655

Met Leu Thr Asn Lys Gly Thr Val Pro Arg Val Tyr Tyr Gly Asp Met
            660                 665                 670

Tyr Gln Asp Asn Gly Gln Tyr Met Gln Gln Lys Ser Leu Tyr Tyr Asp
        675                 680                 685

Ala Ile Ser Ser Leu Met Thr Ala Arg Lys Gln Tyr Val Ala Gly Gly
        690                 695                 700

Gln Thr Met Ser Val Asp Glu Asn Gly Leu Leu Lys Ser Val Arg Phe
705                 710                 715                 720

Gly Lys Asn Ala Met Thr Ala Gln Asp Thr Gly Asp Ala Glu Thr Arg
            725                 730                 735

Thr Glu Gly Val Gly Val Ile Ile Gly Asn Asp Pro Ser Val Lys Val
            740                 745                 750

Ala Asp Gly Gln Thr Val Thr Leu Asp Met Gly Ala Ala His Lys Asn
        755                 760                 765

Gln Ala Tyr Arg Pro Leu Ile Leu Thr Thr Ser Asp Gly Ile Gln Thr
    770                 775                 780

Tyr Asp Ser Asp Glu Asn Ala Pro Val Val Tyr Thr Asp Asp Asn Gly
785                 790                 795                 800

Ile Leu Thr Phe Ser Asn Gln Asp Ile Asn Gly Gln Ala Asn Thr Lys
            805                 810                 815

Ile Val Gly Thr Leu Asn Pro Gln Val Ser Gly Tyr Leu Ala Val Trp
            820                 825                 830

Val Pro Val Gly Ala Ser Ala Asp Gln Asp Ala Arg Thr Ala Pro Ser
        835                 840                 845

Thr Gln Ser Thr Asn Asp Gly Lys Val Leu His Thr Gly Ala Ala Leu
    850                 855                 860

Asp Ser Asn Leu Ile Phe Glu Gly Phe Ser Asn Phe Gln Pro Met Pro
865                 870                 875                 880

Thr Thr His Asp Glu Met Thr Asn Val Val Ile Ser Gln Asn Ala Ser
            885                 890                 895

Gln Phe Ala Lys Trp Gly Ile Thr Ser Phe Glu Met Ala Pro Gln Tyr
        900                 905                 910

Arg Ser Ser Glu Asp His Ser Phe Leu Asp Ser Thr Ile Asp Asn Gly
```

-continued

```
                915                 920                 925
Tyr Ala Phe Ser Asp Arg Tyr Asp Leu Gly Phe Gly Thr Pro Thr Lys
    930                 935                 940

Tyr Gly Thr Asp Glu Asp Leu Arg Asn Ala Ile Lys Ala Leu His Gln
945                 950                 955                 960

Asn Gly Met Gln Val Met Ala Asp Val Val Met Asn Gln Leu Tyr Ser
                965                 970                 975

Leu Asn Gly Lys Glu Val Val Ser Ala Ser Arg Ala Gly Val Tyr Gly
            980                 985                 990

Asn Asp Val Asp Leu Pro Phe Gly Thr Gln Leu Tyr Val Val Asn Thr
                995                 1000                1005

Thr Gly Gly Gly Glu Tyr Gln Lys Lys Tyr Gly Gly Ala Phe Leu
    1010                1015                1020

Asn Ile Ile Lys Glu Lys Tyr Pro Thr Leu Phe Asp Ser Glu Ser
    1025                1030                1035

Tyr Asp Tyr Tyr Leu Lys Asn Tyr Ser Asp Asn Gly His Gly Pro
    1040                1045                1050

Ala Tyr Met Thr Thr Ala Thr Ala Thr Arg Glu Ala Ile Pro Ser
    1055                1060                1065

Asp Gln Pro Leu Lys Glu Trp Ser Ala Lys Tyr Met Asn Gly Thr
    1070                1075                1080

Asn Ile Leu Gly Leu Gly Met Gly Tyr Val Leu Lys Asp Trp Asn
    1085                1090                1095

Asn Gly Ala Tyr Phe Lys Leu Ser Gly Thr Asp Thr Thr Leu Pro
    1100                1105                1110

Gln Ser Leu Val Ala Leu Thr Gly Trp Asn Gln Asn Asp Asp Gly
    1115                1120                1125

Thr Trp Ser Tyr Tyr Ser Thr Asp Thr Asp Arg Val Thr Gly
    1130                1135                1140

Lys Gln Val Ile Asp Gly Arg Thr Leu Leu Phe Asp Asn Gln Gly
    1145                1150                1155

Asn Gln Ile Lys Gly Gly Trp Gly Glu Asn Pro Asp Gly Thr Trp
    1160                1165                1170

Ser Tyr Tyr Asn Ala Asp Thr Gly Asp Arg Val Ile Gly Glu Gln
    1175                1180                1185

Val Ile Asp Gly Arg Thr Leu Phe Phe Asp Asn Gln Gly Val Gln
    1190                1195                1200

Val Lys Gly Gly Trp Gly Glu Asn Tyr Asp Gly Thr Trp Ser Tyr
    1205                1210                1215

Tyr Asn Ala Asp Thr Gly Asp Arg Val Thr Gly Lys Gln Val Ile
    1220                1225                1230

Asp Gly Arg Thr Leu Leu Phe Asp Asn Arg Gly Val Gln Val Lys
    1235                1240                1245

Gly Gly Trp Gly Glu Asn Ser Asp Gly Thr Trp Ser Tyr Tyr Asn
    1250                1255                1260

Ala Asp Thr Gly Asp Arg Val Thr Gly Asn Gln Leu Ile Gly Gly
    1265                1270                1275

Arg Asn Leu Leu Phe Asp Asn Gln Gly Asn Gln Ile Lys Gly Gly
    1280                1285                1290

Trp Asp Glu Asn Pro Asp Gly Thr Trp Ser Tyr Tyr Asn Ala Asp
    1295                1300                1305

Thr Gly Asp Arg Val Thr Gly Val Gln Val Ile Asp Gly Lys Gln
    1310                1315                1320
```

Leu Leu Phe Asp Ser Asn Gly Ile Gln Val Lys Asn Ser Trp Gln
1325                1330                1335

Lys Asn Ala Asn Gly Thr Trp Ser Tyr Tyr Asp Ala Asn Asp Gly
1340                1345                1350

His Leu Val Pro Ala Asn Ser Ser Asn Asp Gly Thr Ser Ser Ser
1355                1360                1365

Thr Gln Asp Ser Gly Asn Lys Ser Asn Gln Asn Pro Ser Ser Ser
1370                1375                1380

Ser Asn Ala Val Asn Lys Thr Thr Gly Trp Ile Lys Asn Ser Asp
1385                1390                1395

Gly Thr Trp Ser Tyr Leu Ser Ala Lys Ser Gly Gln Lys Val Thr
1400                1405                1410

Gly Ser Gln Thr Ile Asp Gly Lys Gln Leu Leu Phe Asp Asp His
1415                1420                1425

Gly Val Gln Ile Lys Gly Gly Trp Gly Lys Asn Ala Asp Gly Thr
1430                1435                1440

Trp Ser Tyr Tyr Asp Ala Asn Ser Gly Glu Leu Thr Ser Thr Ser
1445                1450                1455

Asp Met Ser Asn Val Asn Pro Gln Gln Thr Thr Thr Thr Thr Asn
1460                1465                1470

Glu Gln Ser Thr Thr Asn Gln Pro Thr Asp Ile Thr Lys Asn Ser
1475                1480                1485

Asp Gly Val Tyr Val Tyr Lys Asn Asp Ser Asn Lys Lys Ala Gln
1490                1495                1500

Gly Tyr Leu Asn Asp Gly Ser Ser Trp Lys Trp Phe Asn Asp Gly
1505                1510                1515

Gln Leu Tyr Thr Gly Phe Gln Asn Tyr Met Gly Ala Tyr Tyr Tyr
1520                1525                1530

Phe Ile Asn Gly Ile Arg Gln Gln Asn Gln Trp Glu Asn Ile Trp
1535                1540                1545

Gly Leu Lys Tyr Tyr Val Gly Asp Asp Gly Arg Thr Val Glu Gly
1550                1555                1560

Ile His Ala Ile Asp Gly His Ala Tyr Asp Phe Gly Thr Asp Gly
1565                1570                1575

Thr Phe Asn Val Lys Gly Ser Ala Ser Gly Tyr Leu Asn Asp Gly
1580                1585                1590

Lys Ser Trp Met Trp Tyr Glu Gly Gly Asn Pro Tyr Thr Gly Phe
1595                1600                1605

Arg Tyr Tyr Met Asp Thr Tyr Tyr Trp Phe Glu Asn Gly Val Arg
1610                1615                1620

Gln Asp Asn Ala Trp His Gln Ala Trp Gly Leu Thr Tyr Tyr Thr
1625                1630                1635

Gly Ala Asp Gly Arg Ala Val Gln Gly Val Gln Asn Ile Asn Gly
1640                1645                1650

Lys Leu Tyr Tyr Phe Gly Asn Asp Gly Thr Phe Phe Met Arg Thr
1655                1660                1665

Asn Gln Glu Val
1670

<210> SEQ ID NO 5
<211> LENGTH: 1632
<212> TYPE: PRT
<213> ORGANISM: Lactobacillus kunkeei -continued

```
<400> SEQUENCE: 5

Met Asn Asn Asn Ser Glu Gln Lys Leu Arg Phe Lys Met Tyr Lys
1               5                   10                  15

Ser Gly Lys His Trp Val Val Ala Gly Leu Thr Thr Ala Val Val Ser
                20                  25                  30

Val Ala Ile Tyr Ser Gly Ser Ile Ile Asn Gly Val Thr Val
            35                  40                  45

Lys Ala Asp Val Gln Ser Thr Thr Gln Ala Thr Thr Ser Val Ser Asp
    50                  55                  60

Asn Ser Lys Asp Ser Ser Asn Ser Ile Ser Asn Asn Ser Asn Asp
65                  70                  75                  80

Asp Asn Gln Ile Ala Thr Leu Pro Gln Asp Gly Thr Tyr Ser Thr Gly
                85                  90                  95

Asp Asn Gly Gln Thr Trp Lys Tyr Val Glu Gln Asn Lys Asn Ile Gln
                100                 105                 110

Gly Leu Tyr Lys Asp Ser Asp Asn Gln Leu Arg Tyr Phe Asn Glu Tyr
                115                 120                 125

Asp Gly Thr Gln Ala Lys Gly Asp Ile Val Asn Val Asn Asn Asn Asn
    130                 135                 140

Tyr Tyr Phe Asp Ser Gly Ser Gly Gln Gly His Lys Ile Asp Asn Tyr
145                 150                 155                 160

Ser Gly Gly Asn Tyr Val Glu Ser Asn Val Asn Asn Glu Asn Gly Trp
                165                 170                 175

Ile Tyr Lys Ala Thr Asp Asn Thr Glu Val Lys Gly Ile Ala Thr Ile
                180                 185                 190

Asp Gly Asn Val Gln Tyr Phe Asp Gln Ser Thr Gly Leu Gln Leu Lys
    195                 200                 205

Gly Gly Ala Val Gln Val Gly Gly Ala Asp Tyr Tyr Phe Asp Pro Asn
210                 215                 220

Lys Gly Asn Leu Val Gly Lys Val Asp Gln Val Val Asn Ser Asn Asn
225                 230                 235                 240

Tyr Ser Asp Asn Lys Leu Leu Asp Ser Asn Lys Asn Val Val Lys Gly
                245                 250                 255

Leu Thr Val Asn Asn Gly Thr Leu Gln Tyr Tyr Asp Pro Ser Thr Gly
                260                 265                 270

Asp Gln Val Lys Asn Lys Gln Val Ile Ala Asn Gly Val Thr Tyr Tyr
                275                 280                 285

Phe Asp Ala Ser Gly Asn Gly Thr Tyr Leu Phe Thr Asn Thr Gly Asn
    290                 295                 300

Ser Ala Val Asn Asp Phe Ser Gln Arg Asn Ala Ala Asn Ser Val Asn
305                 310                 315                 320

Pro Ser Asp Tyr Lys Asn Val Val Asp Gly Phe Phe Thr Ala Asp Thr
                325                 330                 335

Trp Tyr Arg Pro Lys Gln Ile Ile Asp Asn Gly Thr Thr Trp Arg Asn
                340                 345                 350

Ser Asn Ser Asn Asp Leu Arg Pro Met Ile Thr Ala Trp Trp Pro Asn
    355                 360                 365

Lys Asp Val Gln Val Asn Tyr Leu Lys Leu Met Gln Asp Asn Gly Leu
    370                 375                 380

Leu Asp Lys Ser Asp Thr Tyr Thr Leu Gln Ser Asp Gln Val Leu
385                 390                 395                 400

Asn Gln Ala Ala Gln Ser Ala Gln Val Asn Ile Glu Lys Lys Ile Ser
                405                 410                 415
```

```
Gln Thr Gly Ser Thr Asp Trp Leu Asn Asp Leu Leu Phe Ala Ser His
            420                 425                 430

Gly Asn Asn Pro Ser Phe Val Lys Gln Gln Tyr Val Trp Asn Ser Asp
            435                 440                 445

Ser Glu Ser Pro Trp Gln Gly Asp Ala Trp Phe Gln Gly Gly Tyr Leu
450                 455                 460

Lys Tyr Gly Asn Ser Val Met Thr Pro Asn Thr Asn Ser Asn Tyr Arg
465                 470                 475                 480

Asp Ser Asn Asn Leu Phe Asp Phe Leu Leu Ala Asn Asp Val Asp Asn
            485                 490                 495

Ser Asn Pro Ala Val Gln Ala Glu Asp Leu Asn Trp Leu Tyr Tyr Leu
            500                 505                 510

Thr Asn Phe Gly Thr Ile Thr Ala Asn Asp Ser Asn Ala Asn Phe Asp
            515                 520                 525

Ser Ile Arg Ile Asp Ala Val Asp Phe Ile Ser Asn Asp Ile Ile Gln
            530                 535                 540

Arg Ser Tyr Asp Tyr Leu Arg Gln Lys Phe Asn Leu Thr Gln Ser Asp
545                 550                 555                 560

Ala Asn Ala Asp Ser His Ile Ser Leu Val Glu Gly Gly Val Asp Ala
            565                 570                 575

Gly Thr Thr Ser Tyr Ser Asn Asp Gly Leu Val Glu Ala Pro Phe Arg
            580                 585                 590

Leu Gly Ala Tyr Pro Leu Leu His Lys Gln Gly Gly Asp Val Phe Lys
            595                 600                 605

Asp Leu Ile Asn Glu Glu Asp Ser Gly Ile Asp Ile Ser Asn His Asn
            610                 615                 620

Gly Glu Thr Asn Thr Thr Asn Thr Ile Gly Gly Leu Thr Leu Ser Gly
625                 630                 635                 640

Gly Lys Pro Asn Tyr Ser Ile Val His Ala His Asp Lys Asp Val Gln
            645                 650                 655

Glu Lys Val Gly Gln Ala Ile Val Asp Thr Thr Gly Ile Lys Asp Trp
            660                 665                 670

Thr Asp Phe Thr Pro Ser Gln Leu Ala Gln Gly Leu Glu Thr Phe Tyr
            675                 680                 685

Asn Asp Gln Arg Gln Thr Asp Lys Lys Tyr Asn Asp Tyr Asn Val Pro
            690                 695                 700

Ser Ala Tyr Ala Ile Met Leu Thr Asn Lys Gly Thr Val Pro Arg Ile
705                 710                 715                 720

Tyr Tyr Gly Asp Met Tyr Gln Asp Asp Gly Gln Phe Met Gln Lys Lys
            725                 730                 735

Ser Leu Tyr Tyr Asp Asp Ile Ala Asn Leu Met Thr Ala Arg Lys Lys
            740                 745                 750

Tyr Val Ser Gly Gly Gln Tyr Met Val Asp Asn Asp Gly Ile Leu Thr
            755                 760                 765

Ser Val Arg Phe Gly Lys Gly Ala Asn Thr Val Asn Asp Ser Gly Thr
            770                 775                 780

Ser Asp Thr Arg Asn Gln Gly Ile Gly Leu Ile Val Gly Ser Asp Pro
785                 790                 795                 800

Lys Lys Val Leu Asn Asp Gly Asp Thr Ile Val Leu His Met Gly Ala
            805                 810                 815

Ala His Lys Asn Gln Lys Tyr Arg Ala Leu Met Leu Thr Thr Glu Asn
            820                 825                 830
```

Gly Val Gln Asn Tyr Ser Ser Asp Asn Ala Pro Val Ala Glu Thr
        835                 840                 845

Asp Asp Asn Gly Asp Leu Val Phe Ser Asn Lys Asp Ile Asn Gly Gln
850                 855                 860

Asp Asn Thr Ala Ile Lys Gln Val Ala Asn Pro Glu Val Asn Gly Tyr
865                 870                 875                 880

Leu Ala Ala Trp Val Pro Phe Gly Ala Ser Asp Gln Asp Ala Arg
                885                 890                 895

Thr Ser Pro Ser Thr Ser Gln Asn Asn Asp Gly Asn Val Leu His Glu
        900                 905                 910

Asn Asp Ala Leu Asp Ser Asn Leu Ile Phe Glu Gly Phe Ser Asn Phe
        915                 920                 925

Gln Pro Thr Pro Thr Asn His Asp Glu Tyr Ala Asn Val Val Ile Ala
        930                 935                 940

Lys Asn Ala Ser Leu Phe Lys Asp Trp Gly Val Thr Ser Phe Glu Met
945                 950                 955                 960

Ala Pro Gln Tyr Arg Ser Ser Gln Asp His Thr Phe Val Asp Ser Thr
                965                 970                 975

Ile Asp Asn Gly Tyr Ala Phe Ser Asp Arg Tyr Asp Leu Gly Phe Gly
        980                 985                 990

Thr Pro Thr Lys Tyr Gly Thr Asp Glu Asp Leu Arg Asn Ala Ile Lys
        995                 1000                1005

Ser Leu His Ala Asn Gly Met Gln Val Met Ala Asp Val Val Tyr
        1010                1015                1020

Asn Gln Leu Tyr Asn Leu Pro Gly Glu Glu Val Val Ser Ala Thr
        1025                1030                1035

Arg Ala Gly Val Thr Gly Asn Asp Asn Ala Leu Pro Phe Gly Thr
        1040                1045                1050

Gln Leu Tyr Val Val Asn Thr Val Gly Gly Gly Asp Tyr Gln Lys
        1055                1060                1065

Lys Tyr Gly Gly Ala Phe Leu Asn Gln Leu Gln Glu Gln Tyr Pro
        1070                1075                1080

Ser Leu Phe Gln Ser Gln Lys Tyr Lys Tyr Tyr Lys Asn Tyr
        1085                1090                1095

Ala Asn Asn Gly Ala Gly Pro Gly Tyr Leu Thr Val Thr Asp Gly
        1100                1105                1110

Glu Arg Ser Ala Ile Pro Ser Asp Gln Pro Ile Thr Ala Trp Ser
        1115                1120                1125

Ala Lys Tyr Met Asn Gly Thr Asn Ile Leu Gly Arg Gly Met Gly
        1130                1135                1140

Tyr Val Leu Lys Asp Trp Asn Thr Gly Ala Tyr Phe Lys Ile Ser
        1145                1150                1155

Gly Asp Asp Ser Thr Leu Pro Thr Ser Leu Thr Tyr Arg Ser Gly
        1160                1165                1170

Trp Val Glu Asn Pro Asp Ser Thr Trp Ser Tyr Tyr Ser Lys Asp
        1175                1180                1185

Ser Ile Ala Lys Leu Thr Gly Ala Gln Ile Val Asn Asp Gln Arg
        1190                1195                1200

Val Phe Phe Asp Asn Asn Gly Ile Gln Val Lys Gly Gly Trp Val
        1205                1210                1215

Glu Asn Pro Asp Gly Thr Tyr Ser Tyr Tyr Asp Lys Asn Ser Gly
        1220                1225                1230

Glu Leu Leu Val Gly Ser Gln Leu Val Asp Gly Arg His Val Phe

```
                1235                1240                1245

Phe Asp Asn Val Gly Val Gln Val Lys Gly Gly Trp Val Ala Asn
    1250                1255                1260

Thr Asp Gly Ser Tyr Ser Tyr Tyr Asn Ala Asn Asp Gly Thr Met
    1265                1270                1275

Leu Thr Gly Ala Gln Phe Ile Asp Gly Gln Asn Val Tyr Phe Asp
    1280                1285                1290

Ala Asp Gly Lys Gln Val Lys Gly Asn Trp Val Gln Asn Asn Asp
    1295                1300                1305

Gly Ser Trp Ala Tyr Tyr Asp Ala Asn Leu Gly His Leu Val Lys
    1310                1315                1320

Asp Ala Lys His Val Asp Ser Gln Pro Ser Thr Gln Gln Val Asn
    1325                1330                1335

Asn Lys Gln Ser Glu Glu Lys Ser Asn Ser Pro Leu Val Glu Ala
    1340                1345                1350

Gln Asn Asn Lys Asp Ser Ala Ser Val Glu Ser Gln Asn His Gln
    1355                1360                1365

Asn Ser Val Ser Val Glu Ser Lys Asn Glu Asn Lys Asn Gln Ser
    1370                1375                1380

Asn Asp Val Arg Asn Pro Ser Glu Lys Thr Asp Thr Lys Thr Ser
    1385                1390                1395

Asn Glu Lys Ser Lys Glu Val Ser Lys Glu Asp Ala Ala Tyr Asp
    1400                1405                1410

Asn Ala Lys Lys Ser Leu Val Glu Ala Lys Lys Leu Val Asp Lys
    1415                1420                1425

Lys Pro Asn Lys Thr Asn Ile Asn Lys Tyr Lys Lys Ala Leu Lys
    1430                1435                1440

Ser Tyr Glu Asn Ala Gln Lys Lys Met Asn Lys Ser Val Ile Ser
    1445                1450                1455

Ser Tyr Lys Lys Ala Ala Lys Glu Leu Asn Ala Ala Lys Lys Asn
    1460                1465                1470

Leu Ser Lys Lys Asn Asn Lys Val Asn Met Lys Lys Tyr Ser Ile
    1475                1480                1485

Ala Leu Asn Lys Tyr Arg Asn Ala Lys Lys Ser Tyr Val Val Ile
    1490                1495                1500

Lys Lys Lys Asp Leu Asp Lys Ser Lys Ser Ala Leu Asn Thr Ala
    1505                1510                1515

Lys Lys Ala Leu Ala Lys Lys Thr Lys Gln Ser Gln Lys Lys
    1520                1525                1530

Tyr Asn Asp Ala Leu Lys Tyr Tyr Asp Ala Glu Lys Thr Tyr
    1535                1540                1545

Leu Asn Leu Thr Gly Asn Tyr Thr Lys Lys Tyr Tyr Tyr Asp Phe
    1550                1555                1560

Asp Lys Val Gly Lys Lys Val Lys Val Ile Lys Ser Thr Ser Val
    1565                1570                1575

Tyr Asn Ser Leu Lys Pro Asn Ser Lys Lys Val Val Lys Lys Ile
    1580                1585                1590

Lys Lys Gly Ser Val Ile Lys Val Lys Lys Leu Ile Leu Ser Asn
    1595                1600                1605

Lys Lys Ser Tyr Phe Asp Leu Gly Tyr Asn Arg Phe Val Ile Ala
    1610                1615                1620

Ser Lys Ser Ser Ile Lys Lys Ala Lys
    1625                1630
```

<210> SEQ ID NO 6
<211> LENGTH: 1318
<212> TYPE: PRT
<213> ORGANISM: Lactobacillus kunkeei

<400> SEQUENCE: 6

```
Met Lys Ser Lys Asp Asn Ser Lys Ile His Phe Lys Met Tyr Lys
1               5                   10                  15

Ser Gly Lys Gln Trp Val Ile Ala Gly Leu Thr Thr Ala Val Ala Ala
                20                  25                  30

Val Ser Ile Tyr Gly Gly Thr Thr Ile Phe Asn Asp Ser Val Val Ala
            35                  40                  45

Lys Ala Asp Thr Ala Val Lys Ser Ser Gln Ser Ser Asn Ala Asp Thr
50                  55                  60

Thr Gln Ser Ser Ser Ala Val Val Asp Ser Ser Ala Asn Ser Ser
65                  70                  75                  80

Ser Pro Ser Ser Thr Glu Val Ser Val Asn Val Lys Asn Thr Ser Asn
                85                  90                  95

Ala Asp Thr Gln Gly Ile Gln Ala Leu Pro Asp Gly Gly Asn Tyr Thr
            100                 105                 110

Ser Glu Asp Asn Gly Gln Thr Trp Lys Tyr Ser Tyr Gln Asn Asn Asp
        115                 120                 125

Val Lys Gly Leu Tyr Gln Glu Asn Asn Ile Arg Tyr Phe Ser Glu
    130                 135                 140

Asn Asp Gly Ser Gln Val Lys Gly Asn Ile Leu Asn Val Asn Asn Lys
145                 150                 155                 160

Asn Tyr Tyr Phe Asp Ser Asn Asn Gly Asp Gly His Leu Ile Lys Asp
                165                 170                 175

Tyr Ser Gly Gly Asn Tyr Val Glu Gln Ser Gln Asp Lys Trp Thr Tyr
            180                 185                 190

Lys Thr Ser Asp Asn Asn Leu Val Lys Gly Ile Ala Thr Ile Asp Gly
        195                 200                 205

Gln Ile Lys Tyr Tyr Asp Pro Thr Thr Gly Ile Gln Leu Lys Gly Gly
    210                 215                 220

Ala Phe Glu Ile Gly Gly Ala Ala Tyr Tyr Val Asp Pro Ala Gln Gly
225                 230                 235                 240

Asn Val Val Gly Arg Val Asn Ser Ile Ile Asn Ser Gly Asn Tyr Val
                245                 250                 255

Asn Lys Asn Asn Asn Thr Thr Phe Val Asp Asp Asn Asn Thr Val
            260                 265                 270

Lys Gly Leu Asn Val Val Arg Gly Asn Leu Gln Tyr Phe Asn Ser Thr
        275                 280                 285

Thr Gly Tyr Gln Ala Lys Ser Glu Gln Val Val Ala Asn Gly Ala Thr
    290                 295                 300

Tyr Tyr Phe Asp Lys Asp Gly Asn Gly Thr Phe Leu Phe Asn Asn Thr
305                 310                 315                 320

Gly Ser Phe Ser Val Thr Asp Phe Ala Lys His Asn Val Ala Asn Ser
                325                 330                 335

Asn Gln Pro Ser Asp Phe Thr Asn Val Asp Gly Phe Leu Thr Ala
            340                 345                 350

Glu Thr Trp Tyr Arg Pro Lys Gln Ile Leu Asp Asn Gly Thr Lys Trp
        355                 360                 365

Arg Asn Ser Asn Lys Asp Asp Leu Arg Pro Leu Ile Thr Val Trp Trp
```

```
            370                 375                 380
Pro Asn Lys Asp Val Gln Val Asn Tyr Leu Lys Leu Met Gln Asp Asn
385                 390                 395                 400

Gly Leu Leu Asp Asn Ser Val Lys Tyr Thr Val Phe Ser Asp Gln Gln
                405                 410                 415

Thr Leu Asn Glu Ala Ala Gln Ser Ala Gln Val Asn Ile Glu Lys Arg
            420                 425                 430

Ile Thr Gln Gln Lys Ala Ser Ser Trp Leu Tyr Asp Leu Leu Phe Lys
        435                 440                 445

Gly Asp Ser Ser His Pro Ser Phe Met Asn Gln Gln Tyr Ile Trp Asn
        450                 455                 460

Met Gly Ser Glu Ser Gln Trp Gln Gly Asp Ala Trp Phe Gln Gly Gly
465                 470                 475                 480

Tyr Leu Lys Tyr Gly Asn Ser Pro Leu Thr Pro Thr Thr Asn Ser Lys
                485                 490                 495

Tyr Arg Lys Thr Asp Asn Gln Phe Asp Phe Leu Leu Ala Asn Asp Val
            500                 505                 510

Asp Asn Ser Asn Pro Ala Val Gln Ala Glu Asp Ile Asn Trp Leu Tyr
        515                 520                 525

Tyr Leu Thr His Phe Gly Thr Ile Thr Gly Lys Asn Asp Lys Ala Asn
        530                 535                 540

Phe Asp Ser Ile Arg Leu Asp Ala Val Asp Phe Val Ser Asn Glu Ile
545                 550                 555                 560

Ile Glu Arg Ser Asn Asp Tyr Leu Arg Asp Leu Tyr Lys Leu Thr Lys
                565                 570                 575

Ser Asp Ala Asn Ala Asp Lys His Ile Ser Leu Val Glu Ala Gly Val
            580                 585                 590

Asp Ala Gly Thr Ser Thr Asn Gly Asp Ser Leu Val Glu Ala Pro
        595                 600                 605

Phe Arg Leu Ser Ala Tyr Gly Leu Leu His Asn Ser Gly Lys Val Asp
        610                 615                 620

Ala Leu Gln Asp Leu Val Lys Glu Val Asp Ser Gly Val Leu Ile Ser
625                 630                 635                 640

Asp His Ser Lys Asn Ser Lys Asp Gly Val Pro Asn Tyr Ser Ile
                645                 650                 655

Val His Ala His Asp Lys Asp Val Gln Glu Arg Val Gly Gln Ala Ile
            660                 665                 670

Val Asp Ser Thr Gly Ile Lys Asp Trp Thr Asn Phe Thr Pro Ala Gln
        675                 680                 685

Leu Ala Lys Gly Leu Ser Val Tyr Tyr Ala Asp Gln Arg Lys Thr Val
        690                 695                 700

Lys Lys Tyr Asn Asp Tyr Asn Met Pro Ser Ala Tyr Ala Ile Met Leu
705                 710                 715                 720

Thr Asn Lys Gly Thr Val Pro Arg Ile Tyr Tyr Gly Asp Met Tyr Gln
                725                 730                 735

Asp Asp Gly Gln Phe Met Gln Lys Lys Ser Phe Tyr Tyr Asp Asp Ile
            740                 745                 750

Val Lys Leu Met Thr Ala Arg Leu Lys Tyr Val Ala Gly Gly Gln Thr
        755                 760                 765

Met Ser Val Asp Ser Asn Gly Phe Leu Lys Ser Val Arg Phe Gly Lys
        770                 775                 780

Gly Ala Lys Thr Val Asn Ser Lys Gly Thr Lys Glu Thr Arg His Glu
785                 790                 795                 800
```

```
Gly Ile Gly Leu Ile Val Gly Asn Asp Ala Lys Lys Val Leu Ser Asn
                805                 810                 815
Gly Gln Lys Val Thr Leu Asn Met Gly Ala Ala His Lys Asn Gln Lys
            820                 825                 830
Tyr Arg Ala Leu Met Leu Thr Thr Asn Lys Gly Val Gln Thr Phe Ala
        835                 840                 845
Ser Asp Lys Asn Ala Pro Val Val Lys Thr Asp Gly Asn Gly Val Leu
    850                 855                 860
Thr Phe Thr Asn Lys Asp Ile Lys Gly Gln Ala Asn Thr Ser Val Arg
865                 870                 875                 880
Gly Val Leu Asn Pro Lys Val Ser Gly Tyr Leu Ala Val Trp Val Pro
                885                 890                 895
Val Gly Ala Lys Asp Asn Gln Asp Ala Arg Thr Gln Pro Ser Lys Lys
            900                 905                 910
Asn Arg Asn Asp Gly Lys Val Leu His Ser Asn Asp Ala Leu Asp Ser
        915                 920                 925
Asn Leu Ile Tyr Glu Gly Phe Ser Asn Phe Gln Pro Gln Pro Lys Lys
    930                 935                 940
Arg Ser Gln Tyr Ala Asn Val Val Ile Ala Lys Asn Ala Lys Leu Phe
945                 950                 955                 960
Lys Lys Trp Gly Ile Thr Ser Phe Glu Met Ala Pro Gln Tyr Arg Ser
                965                 970                 975
Ser Asn Asp Lys Thr Phe Val Asp Ser Thr Ile Asn Asn Gly Tyr Ala
            980                 985                 990
Phe Ser Asp Arg Tyr Asp Leu Gly Phe Gly Lys Pro Thr Lys Tyr Gly
        995                 1000                1005
Thr Asp Lys Asp Leu Arg Lys Ala Ile Glu Ser Leu His Asp Gln
    1010                1015                1020
Gly Met Gln Val Met Ala Asp Ala Val Leu Asn Gln Leu Tyr Asn
    1025                1030                1035
Leu Pro Gly Lys Gln Val Val Ser Ala Gln Arg Ala Gly Val Thr
    1040                1045                1050
Gly Asn Ile Ala Asp Leu Pro Phe Gly Lys Gln Leu Tyr Val Val
    1055                1060                1065
Asn Thr Ile Gly Gly Gly Lys Tyr Gln Lys Lys Tyr Gly Gly Lys
    1070                1075                1080
Phe Leu Lys Ala Leu Lys Ala Lys Tyr Pro Asn Ile Phe Lys Gly
    1085                1090                1095
Lys Thr Tyr Lys Tyr Asn Tyr Lys Asn Tyr Ser Pro Thr Gly Glu
    1100                1105                1110
Gly Tyr Leu Thr Leu Asn Thr Gly Lys Thr Val Ser Ile Pro Ser
    1115                1120                1125
Asn Gln Pro Ile Thr Glu Trp Ser Ala Lys Tyr Met Asn Gly Thr
    1130                1135                1140
Asn Ile Leu Gly Arg Gly Met Gly Tyr Val Leu Lys Asp Trp Asn
    1145                1150                1155
Thr Gly Thr Tyr Phe Lys Leu Asn Gly Leu Lys Thr Val Leu Pro
    1160                1165                1170
Ser Glu Leu Thr Asp Lys Ser Asn Trp Val Asn Glu Val Ser Thr
    1175                1180                1185
Ser Ser Lys Asp Val Tyr Asn Lys Ser Val Ser Asn Leu Lys Asp
    1190                1195                1200
```

```
Ala Lys Lys Lys Leu Ala Ala Lys Lys Ser Lys Glu Asn Thr Gln
    1205                1210                1215

Leu Tyr Asn Asn Ala Leu Asn Ser Tyr Tyr Lys Ala Glu Lys Glu
    1220                1225                1230

Tyr Leu Ser Ser Ala Lys Leu Tyr Asn Lys Lys Tyr Tyr Tyr Asp
    1235                1240                1245

Phe Asp Lys Leu Pro Ser Lys Val Lys Val Ala Lys Val Thr Tyr
    1250                1255                1260

Ser Tyr Lys Ser Thr Asp Phe Ser Lys Asp Asn Arg Ile Lys Lys
    1265                1270                1275

Leu Lys Lys Gly Thr Val Leu Asn Val Lys Gly Leu Val Leu Asn
    1280                1285                1290

Gly Lys Val Thr Arg Ile Asn Ile Gly Asn Gly Lys Phe Val Thr
    1295                1300                1305

Ala Ser Lys Asp Phe Ile Lys Ala Ile Arg
    1310                1315

<210> SEQ ID NO 7
<211> LENGTH: 1139
<212> TYPE: PRT
<213> ORGANISM: Lactobacillus kunkeei

<400> SEQUENCE: 7

Met Lys Ala Glu His Asn Asn Leu Lys Leu His Phe Lys Met Tyr Lys
1               5                   10                  15

Ser Gly Lys Gln Trp Val Ile Ala Gly Leu Thr Thr Val Val Ala Ser
                20                  25                  30

Ile Ala Ile Phe Ser Gly Asn Gln Leu Phe Ser Gly Asn Val Val Ala
            35                  40                  45

Lys Ala Asp Gly Val Thr Thr Thr Gln Val Ser Gln Asn Ser Asn Ser
        50                  55                  60

Ser Asn Gly Ile Ser Thr Leu Pro Lys Asp Gly Lys Tyr Val Ser Ser
65                  70                  75                  80

Asp Asn Gly Lys Thr Trp Lys Tyr Val Ser Gln Asn Asn Ala Ala Lys
                85                  90                  95

Gly Leu Tyr Ser Asp Gly Ser Asn Ile Phe Tyr Phe Asn Glu Ser Asp
            100                 105                 110

Gly Thr Gln Val Lys Gly Asn Ile Ile Ser Val Gly Lys Asn Thr Tyr
        115                 120                 125

Tyr Phe Asp Ser Lys Thr Gly Gln Gly Thr Lys Ile Ser Asp Tyr Thr
    130                 135                 140

Gly Gly Lys Tyr Thr Asn Pro Ser Thr Asp Asn Lys Ala Ala Trp Thr
145                 150                 155                 160

Tyr Gln Asp Lys Ser Asn Asn Thr Val Lys Gly Val Ala Thr Ile Gly
                165                 170                 175

Asp Ser Val Gln Tyr Tyr Asp Glu Lys Asp Gly Phe Gln Leu Lys Gly
            180                 185                 190

Gly Ser Ile Asn Leu Gly Asn Thr Asn Tyr Tyr Val Asp Ser Asn Gln
        195                 200                 205

Gly Asn Val Thr Ser Lys Val Asn Arg Val Val Ser Ser Asn Asp Gly
    210                 215                 220

Thr Leu Lys Gly Leu Asn Val Asn Gly Asn Leu Gln Tyr Leu Asp
225                 230                 235                 240

Tyr Lys Thr Gly Lys Gln Val Lys Asn Lys Gln Val Ala Val Asn Gly
                245                 250                 255
```

```
Val Thr Tyr Tyr Phe Asp Asp Asn Gly Asn Gly Ser Tyr Leu Phe Thr
            260                 265                 270

Asn Leu Gly Lys Ser Val Arg Thr Asn Phe Asp Lys Tyr Asn Ala Val
            275                 280                 285

Asn Gly Val Asn Lys Ser Asn Phe Thr Asn Thr Val Asp Gly Phe Leu
    290                 295                 300

Thr Ala Asp Ser Trp Tyr Arg Pro Lys Gln Val Leu Ala Asn Gly Lys
305                 310                 315                 320

Lys Trp Arg Lys Ser Thr Ser Lys Asp Phe Arg Pro Leu Val Thr Val
                325                 330                 335

Ala Trp Pro Asn Lys Asp Val Gln Val Asn Tyr Leu Ala Leu Met Gln
            340                 345                 350

Met Asn Gly Leu Leu Ser Asn Lys Glu Lys Tyr Thr Val Phe Ser Asp
        355                 360                 365

Gln Gln Thr Leu Asn Ala Ala Ala Gln Lys Ala Gln Val Asn Ile Glu
    370                 375                 380

Lys Arg Ile Ser Lys Lys Lys Ser Thr Lys Trp Leu Asp Lys Leu Leu
385                 390                 395                 400

Phe Gln Gly Thr Thr Thr Glu Pro Ser Phe Ile Lys Arg Gln Tyr Val
                405                 410                 415

Trp Ser Ser Ala Ser Glu Tyr Pro Gly Gln Gly Asp Ala Gln Trp Phe
            420                 425                 430

Gln Gly Gly Tyr Leu Lys Tyr Gly Asn Asn Arg Leu Thr Pro Lys Thr
        435                 440                 445

Asn Ser Lys Tyr Arg Gln Ile Gly Asn Ala Phe Asp Phe Leu Leu Ala
    450                 455                 460

Asn Asp Val Asp Asn Ser Asn Pro Ser Val Gln Ala Glu Asp Ile Asn
465                 470                 475                 480

Trp Leu His Tyr Leu Thr His Phe Gly Ser Ile Thr Ala Lys Asp Pro
                485                 490                 495

Lys Ala Asn Phe Asp Ser Ile Arg Ile Asp Ala Val Asp Phe Ile Ser
            500                 505                 510

Asn Asp Ile Val Gln Arg Ser Asn Asp Tyr Leu Arg Asp Leu Tyr Lys
        515                 520                 525

Leu Thr Lys Asn Asp Ser Asn Ala Asp Lys His Ile Ser Leu Val Glu
    530                 535                 540

Gly Ser Leu Glu Ala Ala Thr Ser Tyr Ser His Ser Asp Ser Leu Ile
545                 550                 555                 560

Glu Ser Pro Tyr Arg Asn Asp Ile Asp Gly Leu Leu Gly Asn Ser Gly
                565                 570                 575

Asn Ser Ala Asp Leu Ser Lys Leu Ile Lys Glu Tyr Asp Ser Gly Ile
            580                 585                 590

Ile Ile Ser Asp His Ser Gly Thr Thr Asn Ser Ser Ile Pro Thr
        595                 600                 605

Tyr Ser Ile Val His Ala His Asp Lys Gly Val Gln Glu Arg Val Gly
    610                 615                 620

Gln Ala Ile Met Asp Asn Ser Gly Ile Thr Asp Trp Ala Asn Phe Thr
625                 630                 635                 640

Pro Lys Gln Leu Arg Asp Gly Leu Lys Leu Tyr Tyr Asp Asp Gln Arg
                645                 650                 655

Lys Thr Val Lys Lys Tyr Asn Asp Tyr Asn Val Pro Ser Ala Tyr Ala
            660                 665                 670
```

-continued

Ile Met Leu Thr Asn Asn Thr Val Pro Arg Ile Tyr Tyr Gly Asp
            675                 680                 685

Met Tyr Gln Asp Asp Gly Gln Phe Met Gln Lys Lys Ser Leu Tyr Tyr
    690                 695                 700

Asp Asp Ile Val Ser Leu Met Leu Ala Arg Thr Lys Tyr Val Ala Gly
705                 710                 715                 720

Gly Gln Ser Met Ser Met Asp Ser Asn Gly Phe Leu Thr Ser Val Arg
                725                 730                 735

Tyr Gly Lys Gly Ala Asn Asn Val Asn Ser Gln Gly Thr Ser Glu Thr
            740                 745                 750

Arg Asn Glu Gly Ile Gly Val Ile Val Gly Asn Asp Thr Asn Lys Val
        755                 760                 765

Leu Asn Asp Gly Gln Thr Val Thr Leu Asn Met Gly Ala Ala His Lys
    770                 775                 780

Asn Gln Gln Tyr Arg Pro Val Leu Leu Thr Thr Lys Asp Gly Ile Lys
785                 790                 795                 800

Thr Tyr Ser Ser Asp Lys Asn Ala Pro Val Val Glu Thr Asp Ser Asn
                805                 810                 815

Gly Val Leu Thr Phe Ser Asn Lys Asp Val Asn Gly Gln Ser Asp Thr
            820                 825                 830

Ser Val Arg Gly Thr Leu Asn Pro Gln Val Ser Gly Tyr Leu Ala Val
        835                 840                 845

Trp Val Pro Val Gly Ala Lys Asn Gly Gln Asp Ala Arg Thr Lys Pro
    850                 855                 860

Ser Lys Lys Ala Arg Asn Asp Gly Lys Val Leu His Leu Asn Asp Ala
865                 870                 875                 880

Leu Ala Ser Asn Leu Ile Phe Glu Gly Phe Ser Asn Phe Gln Pro Met
                885                 890                 895

Pro Lys Asn Lys Ser Gln Tyr Thr Asn Val Ile Ala Lys Asn Ala
            900                 905                 910

Lys Thr Phe Lys Lys Trp Gly Ile Thr Ser Phe Glu Met Ala Pro Gln
        915                 920                 925

Tyr Arg Ser Thr Asn Asp Lys Ser Phe Val Asp Ser Thr Ile Lys Asn
    930                 935                 940

Gly Tyr Ala Phe Ser Asp Arg Tyr Asp Leu Gly Phe Gly Lys Pro Thr
945                 950                 955                 960

Lys Tyr Gly Thr Asp Lys Asp Leu Arg Lys Ala Ile Lys Ser Leu His
                965                 970                 975

Ala Gln Gly Met Gln Val Met Ala Asp Val Val Tyr Asn Gln Leu Tyr
            980                 985                 990

Asn Leu Pro Gly Lys Glu Val Val Ser Thr Ser Arg Ala Ser Ala Tyr
        995                 1000                1005

Gly Asn Asn Val Asp Val Pro Phe Gly Asn Gln Leu Tyr Val Val
    1010                1015                1020

Asn Thr Ile Gly Gly Lys Tyr Gln Thr Lys Phe Gly Gly Lys
    1025                1030                1035

Tyr Leu Lys Glu Leu Lys Lys Lys Tyr Pro Ser Leu Phe Lys Ala
    1040                1045                1050

Lys Thr Tyr Lys Tyr Tyr Lys Asp Asn Gln Lys Asp Gly Ser
    1055                1060                1065

Val Lys Leu Ala Leu Thr Ser Ser Lys Arg Ser Ser Ile Pro Ala
    1070                1075                1080

Asn Lys Pro Ile Lys Glu Trp Ser Ala Lys Tyr Met Asn Gly Thr

-continued

```
               1085                1090                1095
Asn  Val  Leu  Gly  Leu  Gly  Met  Gly  Tyr  Val  Leu  Lys  Asp  Trp  Asn
               1100                1105                1110

Asn  Gly  Lys  Tyr  Phe  Lys  Ile  Asn  Gly  Thr  Lys  Thr  Ser  Leu  Pro
               1115                1120                1125

Ser  Ser  Ile  Tyr  Tyr  Lys  Ser  Thr  Lys  Asn  Lys
               1130                1135

<210> SEQ ID NO 8
<211> LENGTH: 1463
<212> TYPE: PRT
<213> ORGANISM: Lactobacillus kunkeei

<400> SEQUENCE: 8

Met  Asn  Ile  Asn  Ser  Asn  Glu  Arg  Lys  Val  Arg  Phe  Lys  Met  Tyr  Lys
1                 5                  10                 15

Ser  Gly  Lys  Gln  Trp  Ile  Val  Ala  Gly  Leu  Thr  Thr  Ala  Val  Ile  Ser
                 20                  25                 30

Ile  Ala  Val  Tyr  Gly  Gly  Ser  Ile  Ala  Asn  Gly  Gly  Ile  Glu  Ala
             35                  40                 45

Lys  Ala  Asp  Ala  Gln  Asn  Ala  Ala  Thr  Ser  Ser  Ile  Val  Asn  Thr  Asn
         50                  55                      60

Asn  Ser  Thr  Asn  Ser  Ser  Asn  Ala  Asn  Ser  Ile  Ala  Ser  Leu  Pro  Gln
65                  70                  75                      80

Asn  Gly  Thr  Tyr  Ser  Thr  Asn  Asp  Asn  Gly  Gln  Thr  Trp  Lys  Tyr  Val
             85                       90                  95

Ser  Gln  Asn  Lys  Asp  Ile  Gln  Gly  Leu  Tyr  Lys  Asp  Asn  Asn  Asp  Gln
             100                      105                 110

Leu  Arg  Tyr  Phe  Asn  Glu  Tyr  Asp  Gly  Thr  Gln  Ala  Lys  Gly  Asp  Ile
             115                      120                 125

Val  Asn  Val  Asn  Asp  Asn  Tyr  Tyr  Phe  Asp  Lys  Asp  Ser  Gly  Gln
         130                      135                 140

Gly  His  Lys  Ile  Asp  Ser  Tyr  Thr  Gly  Gly  Ser  Tyr  Ser  Glu  Ser  Lys
145                 150                      155                 160

Val  Asn  Asn  Gln  Asp  Gly  Trp  Ile  Tyr  Lys  Ser  Ser  Asp  Asn  Asn  Asp
                 165                      170                 175

Val  Lys  Gly  Val  Ala  Thr  Val  Asp  Gly  Asn  Ile  Gln  Tyr  Phe  Asp  Gln
             180                      185                 190

Asn  Thr  Gly  Leu  Gln  Leu  Lys  Gly  Gly  Ser  Ala  Gln  Ile  Gly  Gly  Val
             195                      200                 205

Asp  Tyr  Tyr  Phe  Asp  Pro  Asn  Lys  Gly  Asn  Leu  Val  Gly  Lys  Val  Asp
         210                      215                 220

Gln  Val  Val  Asn  Ser  Asn  Asp  Tyr  Ser  Asp  Asn  Lys  Leu  Leu  Asp  Ser
225                 230                      235                 240

Asn  Lys  Asn  Val  Val  Lys  Gly  Leu  Val  Val  Asn  Asn  Gly  Gln  Leu  Gln
                 245                      250                 255

Phe  Phe  Asp  Thr  Ser  Asn  Gly  Asn  Gln  Ala  Lys  Asn  Lys  Gln  Val  Ile
             260                      265                 270

Ala  Asn  Gly  Ile  Thr  Tyr  Tyr  Phe  Asp  Thr  Asn  Gly  Asn  Gly  Gln  Tyr
             275                      280                 285

Leu  Phe  Thr  Asn  Thr  Gly  Lys  Ser  Ala  Val  Asp  Asp  Phe  Thr  Gln  Arg
         290                      295                 300

Asn  Ala  Ala  Asn  Ser  Val  Asn  Pro  Ser  Asp  Tyr  Lys  Asn  Val  Val  Asp
305                 310                      315                 320
```

```
Gly Phe Phe Thr Ala Asp Thr Trp Tyr Arg Pro Lys Gln Ile Leu Asp
                325                 330                 335

Asn Gly Thr Thr Trp Arg Asn Ser Asn Ser Asn Glu Leu Arg Pro Met
            340                 345                 350

Ile Thr Ala Trp Trp Pro Asn Lys Asp Val Gln Val Asn Tyr Leu Lys
        355                 360                 365

Leu Met Gln Asn Asn Gly Leu Leu Asp Lys Ser Asn Ser Tyr Ser Ile
    370                 375                 380

Gln Ser Asp Gln Gln Thr Leu Asn Gln Ala Ala Gln Lys Ala Gln Val
385                 390                 395                 400

Asn Ile Glu Lys Lys Ile Ser Gln Thr Gly Asn Thr Asp Trp Leu Asn
                405                 410                 415

Asp Leu Leu Phe Lys Gly Asn Gly Asp Asn Pro Ser Phe Val Lys Gln
            420                 425                 430

Gln Tyr Ile Trp Ser Ser Asp Ser Glu Ser Pro Trp Gln Gly Asp Ala
        435                 440                 445

Trp Phe Gln Gly Gly Tyr Leu Lys Tyr Gly Asn Ser Val Met Thr Pro
    450                 455                 460

Asn Thr Asn Ser Asn Tyr Arg Asp Ser Asn Asn Leu Phe Asp Phe Leu
465                 470                 475                 480

Leu Ala Asn Asp Val Asp Asn Ser Asn Pro Ala Val Gln Ala Glu Asp
                485                 490                 495

Leu Asn Trp Leu Tyr Tyr Leu Thr Asn Phe Gly Thr Ile Thr Ala Asn
            500                 505                 510

Asp Ser Asn Ala Asn Phe Asp Ser Ile Arg Ile Asp Ala Val Asp Phe
        515                 520                 525

Ile Ser Asn Asp Ile Ile Gln Arg Ser Tyr Asp Tyr Leu Arg Gln Lys
    530                 535                 540

Phe Asn Leu Met Gln Ser Asp Ala Asn Ala Asp Ser His Ile Ser Leu
545                 550                 555                 560

Val Glu Gly Gly Val Asp Ala Gly Thr Thr Ser Tyr Ser Asn Asp Gly
                565                 570                 575

Leu Val Glu Ala Pro Phe Arg Leu Asp Ala Tyr Pro Leu Leu His Lys
            580                 585                 590

Gln Asp Gly Asp Val Phe Lys Asn Leu Ile Asp Glu Asp Ser Gly
        595                 600                 605

Ile Asp Ile Ser Asn His Asn Gly Glu Thr Asn Thr Asn Asn Thr Ile
    610                 615                 620

Gly Gly Ile Thr Leu Ser Gly Lys Pro Asn Tyr Ser Ile Val His
625                 630                 635                 640

Ala His Asp Lys Asp Val Gln Glu Lys Val Gly Gln Ala Ile Ile Asp
                645                 650                 655

Thr Thr Gly Ile Lys Asp Trp Thr Asp Phe Thr Pro Ser Gln Leu Ala
            660                 665                 670

Gln Gly Leu Glu Thr Phe Tyr Asn Asp Gln Arg Gln Thr Val Lys Lys
        675                 680                 685

Tyr Asn Asp Tyr Asn Val Pro Ser Ala Tyr Ala Ile Met Leu Thr Asn
    690                 695                 700

Lys Gly Thr Val Pro Arg Ile Tyr Tyr Gly Asp Met Tyr Gln Asp Asp
705                 710                 715                 720

Gly Gln Phe Met Gln Lys Lys Ser Leu Tyr Tyr Asp Asp Ile Ala Asn
                725                 730                 735

Leu Met Thr Ala Arg Lys Lys Tyr Val Ser Gly Gly Gln Ser Met Val
```

```
                740                 745                 750
Asp Asn Asn Gly Ile Leu Thr Ser Val Arg Phe Gly Lys Gly Ala Asn
            755                 760                 765

Thr Val Ser Asp Ser Gly Thr Glu Asp Thr Arg Asn Gln Gly Ile Gly
770                 775                 780

Leu Ile Val Gly Ser Asp Pro Lys Lys Val Leu Asn Asp Gly Asp Thr
785                 790                 795                 800

Val Val Leu His Met Gly Ala Ala His Lys Asn Gln Lys Tyr Arg Ala
            805                 810                 815

Leu Met Leu Thr Thr Glu Asn Gly Ile Gln Asn Tyr Asn Ser Asp Asp
                820                 825                 830

Asn Ala Pro Val Ala Glu Thr Asp Asp Asn Gly Asp Leu Val Phe Ser
            835                 840                 845

Asn Lys Asp Ile Asn Gly Gln Ala Asn Thr Ala Ile Lys Gln Val Ala
        850                 855                 860

Asn Pro Glu Val Asn Gly Tyr Leu Ala Ala Trp Val Pro Val Gly Ala
865                 870                 875                 880

Ser Asp Asp Gln Asp Ser Arg Thr Ala Pro Ser Thr Ser Gln Asn Asn
                885                 890                 895

Asp Gly Asn Val Leu His Glu Asn Asp Ala Leu Asp Ser Asn Leu Ile
            900                 905                 910

Phe Glu Gly Phe Ser Asn Phe Gln Pro Thr Pro Thr Asn His Asp Glu
        915                 920                 925

Tyr Ala Asn Val Val Ile Ala Lys Asn Ala Ser Leu Phe Lys Asp Trp
    930                 935                 940

Gly Val Thr Ser Phe Glu Met Ala Pro Gln Tyr Arg Ser Ser Gln Asp
945                 950                 955                 960

His Thr Phe Val Asp Ser Thr Ile Asp Asn Gly Tyr Ala Phe Ser Asp
                965                 970                 975

Arg Tyr Asp Leu Gly Phe Gly Thr Pro Thr Lys Tyr Gly Thr Asp Glu
            980                 985                 990

Asp Leu Arg Asn Ala Ile Lys Ser Leu His Asp Asn Gly Met Gln Val
        995                 1000                1005

Met Ala Asp Val Val Tyr Asn Gln Leu Tyr Asn Leu Pro Gly Gln
    1010                1015                1020

Glu Val Val Ser Ala Thr Arg Ala Gly Val Thr Gly Asn Thr Asn
    1025                1030                1035

Ala Leu Pro Phe Gly Thr Gln Leu Tyr Val Val Asn Thr Ile Gly
    1040                1045                1050

Gly Gly Asp Tyr Gln Lys Lys Tyr Gly Gly Ala Phe Leu Asn Glu
    1055                1060                1065

Leu Gln Glu Gln Tyr Pro Ser Leu Phe Lys Ser Gln Lys Tyr Lys
    1070                1075                1080

Tyr Tyr Tyr Lys Asn Tyr Ala Asn Asn Gly Ala Gly Pro Gly Tyr
    1085                1090                1095

Leu Thr Val Asn Asp Ala Glu Arg Ser Asp Ile Pro Tyr Asn Gln
    1100                1105                1110

Pro Ile Thr Glu Trp Ser Ala Lys Tyr Met Asn Gly Thr Asn Ile
    1115                1120                1125

Leu Gly Arg Gly Met Gly Tyr Val Leu Lys Asp Trp Asn Thr Gly
    1130                1135                1140

Asp Tyr Phe Lys Leu Ser Gly Ser Asp Ser Thr Leu Pro Ser Ser
    1145                1150                1155
```

Leu Thr Tyr Lys Ser Gly Trp Val Glu Asn Pro Asp Ser Thr Trp
1160            1165                1170

Ser Tyr Tyr Glu Lys Asn Asn Ile Asp Lys Leu Thr Gly Ser Gln
1175            1180                1185

Val Ile Asn Glu Glu Arg Val Phe Phe Asp Asn Asn Gly Ile Gln
1190            1195                1200

Val Lys Gly Gly Trp Val Lys Asn Ser Asn Gly Thr Tyr Ser Tyr
1205            1210                1215

Tyr Asp Lys Asn Ser Gly Asn Ile Leu Thr Gly Asp Gln Leu Ile
1220            1225                1230

Asp Gly Glu His Phe Phe Asp Asn Asn Gly Val Gln Val Lys
1235            1240                1245

Gly Lys Trp Ile Lys Asn Ser Asp Gly Ser Lys Ser Tyr Tyr Asp
1250            1255                1260

Ser His Leu Gly Lys Leu Ile Lys Thr Asp Lys Lys Val Ser Ser
1265            1270                1275

Asn Ala Arg Lys Lys Ser Lys Glu Glu Leu Leu Tyr Glu Asn
1280            1285                1290

Ala Leu Lys Val Leu Arg Lys Asp Lys Lys Arg Leu Asp Lys Asn
1295            1300                1305

Lys Thr Lys Ala Asn Ile Arg Lys Tyr Asn Lys Ser Leu Lys Lys
1310            1315                1320

Tyr Arg Lys Ala Lys Lys Lys Leu Leu Ala Ile Thr Lys Asn Arg
1325            1330                1335

Val Ala Asn Ala Arg Lys Ala Ile Lys Ile Ala Lys Lys Val Leu
1340            1345                1350

Ser Lys Arg Lys Asn Ile Asn Asn Glu Lys Arg Tyr Tyr Lys Ala
1355            1360                1365

Leu Lys Glu Tyr Tyr Val Ala Glu Lys Ser Tyr Leu Lys Ile Thr
1370            1375                1380

Gly Asn Tyr Asn Lys Lys Tyr Tyr Glu Phe Asp Lys Leu Thr
1385            1390                1395

Pro Lys Val Lys Val Lys Asn Ile Tyr Ser Tyr Lys Ser Arg
1400            1405                1410

His Phe Thr Lys Lys Asn Arg Val Lys Lys Ile Lys Lys Gly Thr
1415            1420                1425

Leu Val Arg Val Lys Ser Ile Val Arg Ser Gly Lys Val Ala Arg
1430            1435                1440

Ile Asn Ile Gly Asn Gly His Phe Ile Thr Ser Ser Lys Asp Phe
1445            1450                1455

Ile Lys Met Phe Lys
1460

<210> SEQ ID NO 9
<211> LENGTH: 2841
<212> TYPE: PRT
<213> ORGANISM: Leuconostoc mesenteroides

<400> SEQUENCE: 9

Met Arg Asp Lys Arg Ile Ile Cys Asp Arg Lys Lys Leu Tyr Lys Ser
1               5                   10                  15

Gly Lys Leu Leu Val Thr Ala Gly Ile Phe Ser Ala Val Ile Phe Gly
                20                  25                  30

Val Ser Thr Thr Asn Val Ser Ala Asp Ser Thr Asn Asn Thr Gly Val

-continued

```
                35                  40                  45
Thr Val Ser Gln Ala Pro Asp Lys Val Ala Asp Thr Thr Ala Thr Thr
 50                  55                  60
Asp Lys Val Ala Asp Thr Thr Ala Thr Thr Asp Lys Ala Ala Asp Thr
 65                  70                  75                  80
Thr Ala Thr Thr Asp Lys Val Ala Asp Thr Ala Ala Thr Asp Lys
                 85                  90                  95
Val Ala Asp Thr Thr Ala Thr Thr Asp Lys Val Ala Asp Thr Thr Ala
                100                 105                 110
Thr Thr Asp Lys Val Ala Asp Thr Ala Ala Thr Asp Lys Val Ala
                115                 120                 125
Asp Thr Thr Ala Thr Thr Asp Lys Val Ala Asp Thr Thr Ala Thr Thr
                130                 135                 140
Asp Lys Val Ala Asp Thr Thr Ala Thr Thr Asp Lys Val Ala Asp Thr
145                 150                 155                 160
Ala Ala Ala Thr Asp Lys Ala Ala Asp Thr Thr Ala Thr Thr Asp Lys
                165                 170                 175
Ala Ala Asp Thr Thr Ala Thr Thr Asp Lys Val Ala Asp Thr Ala Ala
                180                 185                 190
Thr Thr Asp Lys Ala Ala Asp Thr Thr Ala Thr Thr Asp Lys Val Ala
                195                 200                 205
Asp Thr Ala Ala Thr Thr Asp Lys Ala Ala Asp Thr Ala Ala Thr Thr
                210                 215                 220
Asp Lys Val Thr Asp Thr Val Ala Thr Asn Lys Ala Val Asp Thr
225                 230                 235                 240
Thr Ala Thr Thr Asp Lys Val Asp Thr Thr Ala Thr Thr Ser Glu
                245                 250                 255
Lys Ser Lys Ser Ile Lys Gln Ile Asp Gly Lys Thr Tyr Phe Ile Gly
                260                 265                 270
Asp Asp Gly Gln Pro Lys Lys Asn Phe Thr Ala Ile Val Asp Gly Gln
                275                 280                 285
Val Leu Tyr Phe Asp Lys Asp Thr Gly Ala Leu Thr Ser Asn Ser Ser
                290                 295                 300
Gln Tyr Thr Asp Gly Leu Val Asn Ile Gly Asn Glu His Asn Ala Ala
305                 310                 315                 320
Tyr Ser Leu Ser Ser Asp Ser Phe Thr Gln Val Asp Gly Tyr Leu Thr
                325                 330                 335
Ala Asn Ser Trp Tyr Arg Pro Lys Asp Ile Leu Lys Asn Gly Thr Thr
                340                 345                 350
Trp Thr Ala Ala Thr Ala Asn Asp Phe Arg Pro Leu Leu Met Ser Trp
                355                 360                 365
Trp Pro Asp Lys Asp Thr Gln Val Ser Tyr Leu Lys Tyr Met Gln Ser
                370                 375                 380
Ala Gly Leu Leu Ser Asp Asp Val Ala Leu Ser Asn Asn Asp Ser Met
385                 390                 395                 400
Asn Ser Leu Thr Asp Thr Ala Met Thr Val Gln Lys Asn Ile Glu Glu
                405                 410                 415
Lys Ile Gly Leu Leu Gly Ser Thr Asp Trp Leu Lys Ala Asp Met Asn
                420                 425                 430
Gln Met Val Asp Ser Gln Ser Asn Trp Asn Ile Ser Ser Glu Ser Lys
                435                 440                 445
Gly Thr Asp His Leu Gln Gly Gly Ala Leu Leu Tyr Val Asn Ser Asp
                450                 455                 460
```

```
Leu Thr Pro Asn Ala Asn Ser Asp Tyr Arg Leu Leu Asn Arg Thr Pro
465                 470                 475                 480

Thr Asn Gln Lys Gly Gln Ile Thr Thr Asn Gly Asn Gln Gly Gly Tyr
            485                 490                 495

Glu Met Leu Leu Ala Asn Asp Val Asp Asn Ser Asn Pro Ile Val Gln
                500                 505                 510

Ala Glu Gln Leu Asn Trp Leu Tyr Tyr Met Met Asn Ile Gly Ser Ile
        515                 520                 525

Ala Gln Asn Asp Pro Thr Ala Asn Phe Asp Gly Tyr Arg Val Asp Ala
        530                 535                 540

Val Asp Asn Val Asn Ala Asp Leu Leu Gln Ile Ala Gly Asp Tyr Phe
545                 550                 555                 560

Lys Ala Ala Tyr Gly Thr Asn Gln Ser Asp Ala Asn Ala Asn Asn His
                565                 570                 575

Ile Ser Ile Leu Glu Asp Trp Asp Asn Asn Asp Pro Ala Tyr Val Lys
                580                 585                 590

Ala Gln Gly Asn Asn Gln Leu Thr Met Asp Phe Pro Met His Leu Ala
        595                 600                 605

Leu Lys Tyr Ser Leu Asn Met Pro Ser Ser Ala Arg Ser Gly Leu Glu
610                 615                 620

Pro Ala Ile Ser Thr Ser Leu Val Asn Arg Ala Ala Asp Ala Thr Glu
625                 630                 635                 640

Asn Glu Ala Gln Pro Asn Tyr Ser Phe Ile Arg Ala His Asp Ser Glu
                645                 650                 655

Val Gln Thr Val Ile Ala Gln Ile Ile Lys Asp Lys Ile Asn Pro Ser
                660                 665                 670

Ser Asp Gly Leu Thr Val Ser Thr Asp Glu Ile Ala Lys Ala Phe Glu
        675                 680                 685

Ile Tyr Asn Ala Asp Glu Leu Lys Ala Asp Lys Glu Tyr Thr Ala Tyr
690                 695                 700

Asn Ile Pro Ser Ser Tyr Ala Leu Met Leu Thr Asn Lys Asp Thr Ile
705                 710                 715                 720

Pro Arg Val Tyr Tyr Gly Asp Leu Phe Thr Asp Gly Gln Tyr Met
                725                 730                 735

Ser Ala Lys Ser Pro Tyr Tyr Asp Ala Leu Thr Ser Leu Leu Gln Ser
                740                 745                 750

Arg Val Lys Tyr Val Ser Gly Gly Gln Ser Met Asn Met Thr Tyr Leu
                755                 760                 765

His Asn Asn Gln Gly Leu Leu Thr Ser Val Arg Tyr Gly Lys Asp Ala
        770                 775                 780

Met Thr Ala Asn Asp Thr Gly Thr Ser Glu Thr Arg Thr Gln Gly Ile
785                 790                 795                 800

Gly Leu Ile Val Gly Asn Lys Thr Asp Leu Asn Leu Asn Asn Asp Glu
                805                 810                 815

Gln Ile Val Leu Asn Met Gly Ala Ala His Lys Asn Gln Ala Tyr Arg
            820                 825                 830

Ala Leu Met Leu Ser Thr Lys Asp Gly Leu Lys Ile Tyr Asn Ser Asp
            835                 840                 845

Asp Glu Ala Pro Val Ser Tyr Thr Asp Asp Gln Gly Arg Leu Ile Phe
        850                 855                 860

Lys Ser Asp Val Val Tyr Gly Val Ser Asp Ala Gln Val Ser Gly Tyr
865                 870                 875                 880
```

```
Leu Ala Ala Trp Val Pro Val Gly Ala Asn Asp Ser Gln Asp Ala Arg
            885                 890                 895

Thr Glu Ser Ser Thr Thr Ala Ser Thr Asp Gly Asn Thr Tyr His Ser
            900                 905                 910

Asn Ser Ala Leu Asp Ser Gln Val Ile Tyr Glu Gly Phe Ser Asn Phe
            915                 920                 925

Gln Ala Met Pro Thr Gln Ala Asp Glu Tyr Thr Asn Ile Lys Ile Ala
930                 935                 940

Glu Asn Ala Gln Leu Phe Lys Ser Leu Gly Ile Thr Ser Phe Glu Leu
945                 950                 955                 960

Ala Pro Gln Tyr Arg Ser Ser Thr Asp Asn Ser Phe Leu Asp Ser Val
            965                 970                 975

Ile Gln Asn Gly Tyr Ala Phe Thr Asp Arg Tyr Asp Ile Gly Tyr Asn
            980                 985                 990

Thr Pro Thr Lys Tyr Gly Thr Val Asp Gln Leu Leu Asp Ala Leu Arg
            995                 1000                1005

Ala Leu His Ala Gln Gly Ile Gln Ala Ile Asn Asp Trp Val Pro
        1010                1015                1020

Asp Gln Ile Tyr Asn Leu Pro Gly Glu Glu Ile Val Thr Ala Ser
        1025                1030                1035

Arg Thr Asn Gly Ser Gly Lys Val Asn Glu Ser Ser Val Ile Asn
        1040                1045                1050

Asn Thr Leu Tyr Asp Ser Arg Thr Val Gly Gly Glu Tyr Gln
        1055                1060                1065

Ala Ile Tyr Gly Gly Ala Phe Leu Asp Lys Leu Lys Gln Asp Tyr
        1070                1075                1080

Pro Glu Leu Phe Glu Thr Lys Gln Ile Ser Thr Gly Glu Ala Met
        1085                1090                1095

Asn Pro Asp Val Lys Ile Thr Glu Trp Ser Ala Lys Tyr Phe Asn
        1100                1105                1110

Gly Ser Asn Ile Gln Gly Arg Gly Ala Trp Tyr Val Leu Lys Asp
        1115                1120                1125

Trp Ser Thr Asn Gln Tyr Phe Asn Val Ser Ser Gly Ser Glu Phe
        1130                1135                1140

Leu Pro Lys Gln Leu Leu Gly Glu Lys Thr Ser Thr Gly Phe Thr
        1145                1150                1155

Asn Val Asp Asn Gly Lys Thr Glu Phe Tyr Ser Thr Ser Gly Tyr
        1160                1165                1170

Gln Ala Lys Asn Thr Phe Ile Gln Asp Asn Asp Asn Trp Tyr Tyr
        1175                1180                1185

Phe Asp Asn Asp Gly Tyr Met Val Val Gly Gly Gln Glu Ile Asn
        1190                1195                1200

Gly Lys Lys Tyr Tyr Phe Leu Pro Asn Gly Val Glu Leu Gln Asp
        1205                1210                1215

Ala Tyr Leu Ser Asp Gly Thr Ser Glu Tyr Tyr Ser Ser Asp
        1220                1225                1230

Gly Arg Gln Ile Ser Asn Gln Tyr Tyr Gln Gly Ser Asp Asn Asn
        1235                1240                1245

Trp Arg Tyr Phe Phe Ala Asp Gly His Met Ala Val Gly Leu Ala
        1250                1255                1260

Thr Ile Thr Thr Glu Asn Gly Thr Thr Asn Gln Gln Tyr Phe Asp
        1265                1270                1275

Ala Asn Gly Met Gln Leu Lys Gly Val Ala Ile Lys Asp Thr Asp
```

```
                1280                1285                1290
Gly Asn Val His Tyr Phe Asp Gly Lys Thr Gly Asn Met Val Ile
    1295                1300                1305
Asn Ser Trp Gly Lys Ile Ser Asp Gly Ser Trp Leu Tyr Leu Asn
    1310                1315                1320
Asp Ser Gly Val Ala Val Thr Gly Pro Gln Asn Ile Asn Gly Gln
    1325                1330                1335
Asn Leu Tyr Phe Asn Glu Asp Gly Ile Gln Val Lys Gly Glu Ala
    1340                1345                1350
Ile Thr Asp Asn Ser Gly Asn Ile His Tyr Tyr Asp Arg Ser Thr
    1355                1360                1365
Gly Asn Met Val Val Asn Ser Trp Gly Glu Thr Asn Asn Gly Ser
    1370                1375                1380
Trp Leu Tyr Leu Asn Asp Lys Gly Asp Ala Val Thr Gly Glu Gln
    1385                1390                1395
Val Ile Asp Gly Gln Lys Leu Tyr Phe Ser Ser Asn Gly Ile Gln
    1400                1405                1410
Leu Lys Asn Thr Phe Lys Lys Leu Ser Asp Gly Ser Trp Leu Tyr
    1415                1420                1425
Leu Asn Asp Lys Gly Leu Pro Val Thr Gly Ala Gln Val Ile Asp
    1430                1435                1440
Gly Gln Asn Leu Tyr Phe Asp Gln Asp Gly Lys Gln Val Lys Gly
    1445                1450                1455
Asp Val Ala Thr Asp Gly Gln Gly Asn Thr His Tyr Tyr Asp Gly
    1460                1465                1470
Asn Thr Gly Asn Met Val Thr Asn Ser Trp Ala Glu Leu Ala Asp
    1475                1480                1485
Gly Ser Trp Met Tyr Leu Asp Asn Asp Gly Asn Pro Leu Thr Gly
    1490                1495                1500
Pro Gln Lys Ile Asp Gly Gln Ser Leu Tyr Phe Asn Asp Ala Gly
    1505                1510                1515
Lys Gln Ile Lys Asn Ala Leu Val Lys Leu Asp Asp Gly Ser Thr
    1520                1525                1530
Ile Tyr Leu Asp Asp Lys Gly Val Ser Ser Thr Gly Ile Gln Arg
    1535                1540                1545
Ile Asp Asp Lys Ile Tyr Tyr Phe Asp Pro Asp Gly Lys Gln Val
    1550                1555                1560
Val Cys Arg Phe Glu Glu Leu Pro Asp Gly Ser Trp Met Tyr Leu
    1565                1570                1575
Asp Asp Asp Gly Val Ala Ala Thr Gly Ala Gln Lys Ile Asn Gly
    1580                1585                1590
Gln Glu Leu Tyr Phe Asp Asn Asn Gly Lys Gln Val Lys Asn Asp
    1595                1600                1605
Lys Val Ile Asn Asp Asp Gly Thr Ile Asn Tyr Tyr Thr Gly Met
    1610                1615                1620
Ser Gly Glu Lys Leu Lys Asn Asp Phe Gly Glu Leu Pro Asp Gly
    1625                1630                1635
Ser Trp Met Tyr Leu Asp Asn Gln Gly Asn Ala Val Ile Gly Ala
    1640                1645                1650
Gln Lys Ile Asn Gly Gln Asn Leu Tyr Phe Lys Thr Asp Gly Arg
    1655                1660                1665
Gln Val Lys Gly Glu Ala Asn Val Asp Ser Ser Gly Glu Met His
    1670                1675                1680
```

```
Phe Tyr Asp Pro Asp Ser Gly Glu Leu Ile Thr Asn Arg Phe Glu
    1685            1690                1695

Gln Val Ala Ser Gly Val Trp Ala Tyr Phe Asp Ala Asn Gly Val
    1700            1705                1710

Ala Val Thr Gly Glu Gln Arg Ile Gly Lys Gln Asn Leu Phe Phe
    1715            1720                1725

Asp Pro Thr Gly Tyr Gln Val Lys Gly Asp Lys Arg Thr Ile Asp
    1730            1735                1740

Gly Val Leu Tyr Thr Phe Asp Lys Glu Ser Gly Glu Arg Lys Gly
    1745            1750                1755

Leu Asp Ser Ile Ser Val Leu Pro Thr Asn Gly Gln Tyr Thr Thr
    1760            1765                1770

Asp Lys Ala Gln Asn Trp Tyr Tyr Gln Val Asp Gly Glu Asn Val
    1775            1780                1785

Lys Gly Leu Tyr Thr Asn Asn Asp Gly Gln Leu Arg Tyr Phe Asp
    1790            1795                1800

Leu Thr Thr Gly Val Gln Thr Lys Gly Asn Phe Val Thr Ile Gly
    1805            1810                1815

Asn Asp Thr Tyr Tyr Phe Thr Lys Glu Gln Gly Asp Gly Gln Ile
    1820            1825                1830

Val Ser Glu Val Val Ser Gly His Tyr Gly Thr Val Gln Leu Ser
    1835            1840                1845

Asp Asn Ser Ser Ala Trp Val Tyr Arg Gly Ala Asn Asp Gln Ile
    1850            1855                1860

Leu Lys Gly Leu Gln Asn Ile Asn Gly Arg Leu Gln Tyr Phe Asp
    1865            1870                1875

Leu Thr Thr Gly Ala Gln Leu Lys Gly Gly Ala Ala Asn Tyr Asp
    1880            1885                1890

Gly Asn Leu Tyr Tyr Phe Glu Ser Ser Asp Gly Asn Leu Val Ser
    1895            1900                1905

Lys Ile Gln Gln Ser Tyr Ser Thr Gly Asn Tyr Val Thr Asp Gly
    1910            1915                1920

Asp Lys Val Thr Tyr Val Asp Glu Gln Asn Asn Gln Val Thr Gly
    1925            1930                1935

Leu Ala Leu Ile Asp Asp Gln Leu Gln Tyr Phe Asn Pro Ser Asp
    1940            1945                1950

Gly Ser Gln Val Lys Asn Glu Gln Val Ile Val Asp Gly Val Thr
    1955            1960                1965

Tyr Tyr Phe Asp Lys Asn Gly Asn Gly Gln Tyr Leu Phe Thr Asn
    1970            1975                1980

Thr Ala Thr Met Ser Thr Asn Glu Phe Ala Lys His Ser Ala Ala
    1985            1990                1995

Tyr Ser Asn Asp Ser Ser Ser Phe Lys Asn Thr Ile Asp Gly Phe
    2000            2005                2010

Leu Thr Ala Asp Thr Trp Tyr Arg Pro Lys Asp Ile Leu Glu Asn
    2015            2020                2025

Gly Gln Thr Trp Val Ser Ser Thr Asn Asp Val Arg Pro Leu
    2030            2035                2040

Ile Thr Val Trp Trp Pro Asn Lys Asp Val Gln Val Asn Tyr Leu
    2045            2050                2055

Asn Phe Met Lys Lys Asn Gly Leu Leu Asp Thr Ser Ser Gln Phe
    2060            2065                2070
```

```
Asn Leu Gln Phe Asp Gln Tyr Asp Leu Asn Val Ala Ala Gln Lys
2075                2080                2085

Val Gln Val Ala Ile Glu Lys Arg Ile Ser Lys Glu Lys Ser Thr
2090                2095                2100

Asp Trp Leu Lys Asp Leu Leu Phe Glu Ala His Glu Asp Thr Pro
2105                2110                2115

Ser Phe Val Lys Gln Gln Phe Ile Trp Asn Lys Asp Ser Glu Tyr
2120                2125                2130

Gln Gly Gln Gly Asp Ala Trp Phe Gln Gly Gly Tyr Leu Lys Tyr
2135                2140                2145

Asp Asn Ser Glu Leu Thr Pro Thr Thr Asn Ser Asp Tyr Arg Glu
2150                2155                2160

Ser Gly Asn Thr Leu Asp Phe Leu Leu Ala Asn Asp Val Asp Asn
2165                2170                2175

Ser Asn Pro Ala Val Gln Ala Glu Asn Leu Asn Trp Leu His Tyr
2180                2185                2190

Leu Met Asn Phe Gly Thr Ile Thr Ala Asn Asp Asp Ala Asn
2195                2200                2205

Phe Asp Ser Ile Arg Ile Asp Ala Val Asp Phe Ile Asp Asn Asp
2210                2215                2220

Ala Ile Gln Arg Thr Tyr Asp Tyr Met Arg Asp Ala Tyr Lys Val
2225                2230                2235

Asp Ala Ser Glu Asp Asn Ala Asn Lys His Ile Ser Leu Val Glu
2240                2245                2250

Ala Gly Leu Asp Ala Gly Thr Ser Thr Ile Lys Asn Asn Ala Leu
2255                2260                2265

Val Glu Ser Asn Phe Arg Glu Ala Ala Thr Leu Ser Leu Ala Asn
2270                2275                2280

Gln Ser Gly Lys Asn Ser Ser Leu Thr Asn Met Leu Gln Asp Ile
2285                2290                2295

Asp Gly Gly Gln Ile Ile Ala Asp His Ala Asn Asn Ala Thr Glu
2300                2305                2310

Asn Glu Ala Thr Pro Asn Tyr Ser Ile Ile His Ala His Asp Lys
2315                2320                2325

Gly Ile Gln Glu Lys Val Gly Ala Ala Ile Thr Asp Val Thr Gly
2330                2335                2340

Ala Asp Trp Thr Asn Phe Thr Asp Asp Gln Leu Lys Glu Gly Leu
2345                2350                2355

Ala Ala Tyr Tyr Gln Asp Gln Arg Ser Thr Asn Lys Lys Tyr Asn
2360                2365                2370

Ile Tyr Asn Leu Pro Ser Ile Tyr Ala Leu Met Leu Thr Asn Lys
2375                2380                2385

Asp Thr Val Pro Arg Val Tyr Tyr Gly Asp Met Tyr Gln Asp Asp
2390                2395                2400

Gly Gln Tyr Met Glu Lys Gln Ser Ile Tyr Tyr Asp Ala Ile Val
2405                2410                2415

Ser Leu Met Asn Thr Arg Lys Ser Tyr Val Ser Gly Gly Gln Thr
2420                2425                2430

Met Asp Val Asp Glu His Gly Leu Leu Lys Ser Val Arg Phe Gly
2435                2440                2445

Lys Asp Ala Met Thr Ala Ser Glu Leu Gly Thr Asn Glu Thr Arg
2450                2455                2460

Thr Glu Gly Val Gly Val Leu Val Gly Asn Asp Ser Ser Leu Lys
```

```
                    2465                2470                2475

Leu Asn Asp Ser Asp Thr Val Thr Leu Glu Met Gly Ala Ala His
             2480                2485                2490

Lys Asn Gln Glu Tyr Arg Ala Ala Leu Leu Thr Thr Ser Asp Gly
             2495                2500                2505

Ile Val Thr Tyr Asp Ala Asp Asn Asp Ala Pro Thr Ile Trp Thr
             2510                2515                2520

Asp Asp Arg Gly Thr Leu Thr Phe Ser Asn Lys Glu Ile Ala Gly
             2525                2530                2535

Gln Asp Tyr Thr Ser Val Gln Gly Phe Ala Asn Pro Gln Val Ser
             2540                2545                2550

Gly Tyr Leu Ala Val Trp Val Pro Val Gly Ala Ser Asp Asp Gln
             2555                2560                2565

Asp Ala Arg Thr Ala Ala Ser Thr Asp Lys Asn Thr Asp Asp Lys
             2570                2575                2580

Val Leu His Ser Asn Ala Ala Leu Asp Ser Asn Leu Ile Tyr Glu
             2585                2590                2595

Gly Phe Ser Asn Phe Gln Pro Lys Ala Thr Thr Asn Asp Glu Leu
             2600                2605                2610

Thr Asn Val Val Ile Ala Lys Asn Ala Asn Leu Phe Glu Lys Trp
             2615                2620                2625

Gly Ile Thr Ser Phe Glu Met Ala Pro Gln Tyr Arg Ser Ser Gly
             2630                2635                2640

Asp His Thr Phe Leu Asp Ser Thr Ile Asp Asn Gly Tyr Val Phe
             2645                2650                2655

Thr Asp Arg Tyr Asp Leu Gly Phe Glu Thr Pro Thr Lys Tyr Gly
             2660                2665                2670

Thr Asp Lys Asp Leu Arg Thr Ala Ile Lys Ala Leu His Gln Ser
             2675                2680                2685

Asn Met Gln Val Met Ala Asp Val Val Asp Asn Gln Val Tyr Asn
             2690                2695                2700

Leu Ser Gly Gln Glu Val Val Ser Ala Ser Arg Ala Gly Val Tyr
             2705                2710                2715

Gly Asn Asp Val Ser Thr Gly Phe Gly Thr Gln Leu Tyr Ala Val
             2720                2725                2730

Asn Ser Val Gly Gly Gly Lys Tyr Gln Ala Gln Tyr Gly Gly Glu
             2735                2740                2745

Tyr Leu Asn Glu Leu Lys Gln Gln Tyr Pro Asp Leu Phe Glu Ala
             2750                2755                2760

Lys Thr Tyr Asp Tyr Trp Val Lys Asn Tyr Ser Asn Asp Gly Ser
             2765                2770                2775

Asp Pro Tyr Tyr Thr Leu Ser Gln Asn Thr Arg Lys Asp Met Pro
             2780                2785                2790

Ser Ser Glu Val Ile Lys Gln Trp Ser Ala Lys Tyr Met Asn Gly
             2795                2800                2805

Thr Asn Val Leu Gly Asn Gly Met Gly Tyr Val Leu Lys Asp Trp
             2810                2815                2820

Asn Thr Gly Glu Tyr Phe Lys Ile Gly Glu Lys Asn Ala Asp Phe
             2825                2830                2835

Ile Thr Asn
             2840

<210> SEQ ID NO 10
```

```
<211> LENGTH: 2580
<212> TYPE: PRT
<213> ORGANISM: Lactobacillus kunkeei

<400> SEQUENCE: 10

Met Asn Asn Tyr Gln Asp Arg Lys Leu His Tyr Lys Met Tyr Lys Ser
1               5                   10                  15

Gly Lys Asn Trp Val Val Ala Gly Ile Val Ser Ala Thr Met Ser Ile
            20                  25                  30

Val Leu Phe Gln Asn Ile Asn Asp Val Thr Ala Lys Ala Ser Gln Asn
        35                  40                  45

Gln Ile Thr Tyr Ser Gly Ser Tyr Ala Ser Thr Asp Ser Gly Ser Ala
    50                  55                  60

Lys Ser Ala Tyr Ser Ala Ser Tyr Ile Asn Gly Ser Ser Ser Leu
65                  70                  75                  80

Ser Val Pro Ser Thr Asp Asn Ser Asn Lys Ser Ser Leu Ala Ser Ser
                85                  90                  95

Thr Asn Ser Ser Val Val Thr Ser Ser Leu Ser Ser Asn Val Met Asn
            100                 105                 110

Gln Ser Ser Asn Ser His Ala Ser Ser Ile Ser Ser Asp Val Ser Asn
        115                 120                 125

Gln Ser Gln Ser Ser Lys Ser Ala Ser Thr Ser Ser Asn Ser Ser Glu
    130                 135                 140

Lys Ser Asp Ser Ala Ser Gln Ser Asn Asn Ser Val Gln Ser Tyr Glu
145                 150                 155                 160

Ser Val Ser Leu Ser Val Ser Leu Ala Ser Asn Ala Ser Gln Asn Leu
                165                 170                 175

Lys Ser His Thr Lys Asn Ile Asp Gly Lys Thr Tyr Phe Tyr Asp Leu
            180                 185                 190

Asn Asn Asn Glu Val Lys Ser Ala Leu Ile Asp Asp Asn Asn Thr Tyr
        195                 200                 205

Tyr Tyr Phe Gly Pro Asn Gly Tyr Leu Thr Thr Phe Asp Asp Ser Lys
    210                 215                 220

Phe Ser Asp Gly Ser Ile Asn Ser Ser Asp Gln Leu Ser Ile Tyr Thr
225                 230                 235                 240

Pro Asp Gly Lys Ser Ile Thr Asn Val Asp Gly Phe Leu Thr Ala Asp
                245                 250                 255

Ser Trp Tyr Arg Pro Lys Gln Ile Gln Val Ser Asp Thr Gln Trp Arg
            260                 265                 270

Asn Ser Thr Asn Ala Asp Phe Arg Pro Leu Leu Ser Val Trp Trp Pro
        275                 280                 285

Asn Lys Thr Val Glu Ile Asn Tyr Leu Asn Tyr Met Ser Lys Asn Gly
    290                 295                 300

Leu Val Asn Gly His Phe Asp Asn Asn Ser Ala Asn Asp Ile Asn
305                 310                 315                 320

Gln Ala Ala Ala Thr Val Arg Leu Ser Ile Glu Asn Lys Ile Lys Ala
                325                 330                 335

Asp Asn Gly Asp Leu Ser Ala Ile Arg Ser Leu Phe Thr Thr Phe Ile
            340                 345                 350

Asn Ser Gln Asp Glu Trp Asn Ile Asp Ser Glu Asp Tyr Asn Ser Gly
        355                 360                 365

Asp Gly Leu Gln Gly Gly Ser Leu Leu Phe Gly Asn Asn Ser Glu Thr
    370                 375                 380

Lys Asp Ala Asn Ser Asn Tyr Arg Leu Leu Asn Arg Asn Pro Thr Gln
```

```
              385                 390                 395                 400
         Gln Asp Gly Lys Ile Asp Tyr Thr His Thr Gln Asp Pro Gly Phe Glu
                         405                 410                 415

Phe Leu Leu Ala Asn Asp Val Asp Asn Ser Asn Pro Val Val Gln Ala
                     420                 425                 430

Glu Thr Leu Asn Trp Leu His Tyr Leu Met Asn Phe Gly Ser Ile Val
                     435                 440                 445

Asn Lys Asp Ser Ser Ala Asn Phe Asp Gly Val Arg Val Asp Ala Val
                     450                 455                 460

Asp Asn Met Asp Ala Asp Val Leu Asn Ile Ile Ser Gln Tyr Phe Arg
         465                 470                 475                 480

Asp Ala Tyr Lys Ile Asn Ala Asn Asp Val Asn Ser Asn Asn His Leu
                         485                 490                 495

Ser Ile Leu Glu Asp Trp Ser Gly Asn Asp Pro Tyr Tyr Gln Lys Asp
                     500                 505                 510

His Gly Thr Asn Gln Met Thr Leu Asp Ser Asp Tyr Leu Ser Ser Leu
                     515                 520                 525

Arg Ser Ile Leu Met Tyr Asn Pro Ser Val Arg Ser Asp Met Ser Thr
                     530                 535                 540

Ile Ile Asn Ala Gly Ile Val Asp Arg Ala Asp Asn Thr Thr Asn
         545                 550                 555                 560

Lys Ala Ile Pro Asn Tyr Glu Ile Val Arg Ala His Asp Ala Gly Val
                         565                 570                 575

Gln Asp Ile Ile Ser Gln Ile Ile Asp Asn Ile Asp Pro His Ala
                     580                 585                 590

Ser Ala Ser Asn Pro Thr Trp Glu Gln Met Arg Glu Ala Phe Lys Ile
                     595                 600                 605

Tyr Asp Ala Asp Glu Asn Ser Thr Val Lys Lys Tyr Thr Gln Tyr Asn
                     610                 615                 620

Ile Pro Ala Ser Tyr Ala Leu Thr Leu Thr Asn Lys Asp Thr Thr Pro
         625                 630                 635                 640

Arg Val Tyr Tyr Gly Asp Leu Tyr Thr Asp Asp Gly Gln Phe Met Glu
                         645                 650                 655

Gln Lys Thr Pro Tyr Tyr Asp Ala Ile Ala Glu Met Leu Lys Ser Arg
                     660                 665                 670

Val Lys Tyr Val Ala Gly Gly Gln His Met Glu Ala Val Lys Val Asn
                     675                 680                 685

Asn Gly Glu Asp Thr Ile Leu Thr Ser Val Arg Tyr Gly Lys Asp Ala
                     690                 695                 700

Leu Asn Ala Asp Asp Leu Gly Asp Ser Leu Thr Arg Thr Ser Gly Ile
         705                 710                 715                 720

Ala Val Val Glu Ser Asn Asn Pro Thr Leu Ser Leu Ser Asp Lys Asp
                         725                 730                 735

Lys Val Val Ile His Met Gly Ala Ala His Lys Asn Gln Glu Tyr Arg
                     740                 745                 750

Gln Leu Leu Thr Ala Ser Asn Ser Gly Ile Asp Ser Phe Asp Ser Asp
                     755                 760                 765

Ser Ser Lys Gly Tyr Val Val Arg Thr Asp Asn Gly Asp Leu
                     770                 775                 780

Thr Leu Asp Gly Asn Ile Ile Lys Gly Tyr Ala Asn Pro Gln Val Ser
         785                 790                 795                 800

Gly Tyr Leu Ser Met Trp Val Pro Leu Gly Ala Ser Asp Asn Gln Asp
                         805                 810                 815
```

-continued

```
Ile Arg Thr Ala Pro Ser Ser Glu Ser Ser Thr Asp Gly Gln Ser Ile
                820                 825                 830

His Ser Asn Glu Ala Ser Asp Ser Asn Val Ile Leu Glu Ala Phe Ser
                835                 840                 845

Asn Phe Gln Asn Phe Pro Gln Thr Thr Asp Gln Tyr Glu Asn Val Val
                850                 855                 860

Ile Gln Lys Asn Ala Glu Asp Phe Lys Asn Leu Gly Phe Thr Tyr Leu
865                 870                 875                 880

Glu Leu Pro Pro Gln Tyr Lys Ser Thr Lys Asp Gly Ser Phe Ile Asp
                885                 890                 895

Ser Val Val Gln Asn Gly Tyr Ser Phe Asn Asp Arg Tyr Asp Leu Gly
                900                 905                 910

Phe Asp Thr Pro Thr Lys Tyr Gly Thr Ala Glu Gln Leu Ile Asp Ala
                915                 920                 925

Ile Lys Ser Leu His Ala Gln Gly Ile Lys Val Leu Ala Asp Ile Val
930                 935                 940

Pro Asp Gln Ile Tyr Ser Leu Pro Asn Gln Gln Ile Val Asn Ala Thr
945                 950                 955                 960

Arg Thr Asn Pro Tyr Gly Asp Ala Asn Phe Asn Ser Asn Leu Ile Asn
                965                 970                 975

Val Leu Tyr Asp Ala Phe Ser Lys Gly Ser Gly Thr Asp Tyr Gln Tyr
                980                 985                 990

Lys Tyr Gly Gly Glu Phe Leu Glu  Gln Leu Lys Lys Leu  Tyr Pro Asp
                995                 1000                1005

Leu Phe Thr Thr Lys Gln Ile  Ser Thr Gly Gln Pro  Ile Asp Ala
1010                1015                1020

Ser Lys Lys Leu Lys Ile Trp  Thr Ala Glu Tyr Leu  Asn Gly Ser
1025                1030                1035

Asn Ile Gln Gly Arg Gly Ser  Gly Tyr Val Leu Ser  Ser Thr Pro
1040                1045                1050

Asn Ser Asn Tyr Tyr Thr Val  Val Asp Asp Gly Asn  Thr Asn Ile
1055                1060                1065

Lys Ser Ser Asn Leu Pro Lys  Gly Leu Leu Gly Asp  Asn Val Glu
1070                1075                1080

Tyr Gly Leu Lys Leu Ile Asp  Gly Lys Met Lys Tyr  Val Ser Thr
1085                1090                1095

Gly Gly Phe Ile Ala Lys Asn  Thr Phe Ile Gln Asp  Asp Asn His
1100                1105                1110

Asn Trp Tyr Tyr Val Asp Asn  Asn Gly Asp Phe Val  Thr Ser Pro
1115                1120                1125

Gln Val Ile Asn Gly Asn Lys  Tyr Phe Phe Leu Ser  Asn Gly Val
1130                1135                1140

Asn Leu Arg Asp Phe Ile Ser  Val Asn Ser Asp Gly  Thr Met Asn
1145                1150                1155

Tyr Tyr Gln Ser Asn Gly Ile  Leu Ala Asn Asn Pro  Gly Tyr Tyr
1160                1165                1170

Tyr Ser Asn Asn Ile Asn Gln  Met Val His Val Asn  Asn Asn Gly
1175                1180                1185

Val Leu Asp Thr Gly Ile Val  Asn Val Asn Gly Tyr  Val Gln Tyr
1190                1195                1200

Phe Asp Asp Asn Gly Tyr Gln  Val Lys Gly Asp Ile  Val Asn Phe
1205                1210                1215
```

```
Asn Gly Arg Lys Met Tyr Phe Asp Asp Gly Ser Gly Asn Leu Val
    1220                1225                1230

Tyr Asn Arg Phe Val Ser Tyr Asn Gly Asn Trp Tyr Tyr Ala Gly
    1235                1240                1245

Ser Asn Gly Leu Leu Val Asn Gly Leu Gln Asn Ile Asn Asn Gln
    1250                1255                1260

Ser Leu Tyr Phe Asp Asp Asn Gly Lys Gln Val Lys Gly Gly Met
    1265                1270                1275

Ile Ser Leu Asp Asn His Lys Met Tyr Phe Asp Ala Asn Ser Gly
    1280                1285                1290

Asn Leu Tyr Lys Asn Ser Phe Val Leu Leu Asp Gly Asp Val Tyr
    1295                1300                1305

Tyr Ala Asn Asn Asp Gly Tyr Ile Val Asn Gly Tyr Gln Asn Ile
    1310                1315                1320

Gly Gly Arg Asn Leu Tyr Phe Asp Ser Asp Gly Lys Gln Val Lys
    1325                1330                1335

Asp Gln Phe Val Asn Ile Asn Gly Asn Lys Val Tyr Phe Asn Gly
    1340                1345                1350

Thr Asp Gly Ser Glu Val Lys Asp Asp Phe Ile Ile His Asp Asp
    1355                1360                1365

Lys Glu Tyr Tyr Ala Asp Asn Gln Gly His Leu Leu Thr Gly Tyr
    1370                1375                1380

Asn Phe Val Asn Gly Gln Asn Met Tyr Phe Asn Glu Asp Gly Ser
    1385                1390                1395

Gln Val Lys Asn Ser Ile Val Ser Leu Asp Gly Lys Leu Met Tyr
    1400                1405                1410

Phe Asp Glu Asn Ser Gly Asn Gln Val Lys Asn Gly Phe Ile Leu
    1415                1420                1425

His Asn Gly Asn Val Tyr Tyr Ser Asn Lys Asp Gly Ile Leu Val
    1430                1435                1440

Thr Gly Tyr Gln Asn Ile Asp Gly Gln Asp Leu Phe Phe Asn Ala
    1445                1450                1455

Asp Gly Thr Gln Ile Lys Gly Gly Thr Ala Glu Ile Asp Gly Val
    1460                1465                1470

Asn Tyr Tyr Phe Glu Asn Gly Glu Gly His Leu Val Gly Lys Val
    1475                1480                1485

Asp Gln Val Ile Asn Ser Asn Arg Phe Ser Asp Asn Lys Leu Leu
    1490                1495                1500

Asp Ala Asn Asn Asn Val Val Lys Gly Leu Ile Phe Asn Asn Gly
    1505                1510                1515

Gln Leu Gln Tyr Phe Asp Ser Leu Thr Gly Asp Gln Ala Lys Asn
    1520                1525                1530

Lys Gln Ile Ile Ala Asp Gly Asn Thr Tyr Tyr Phe Asp Asn Ser
    1535                1540                1545

Gly Asn Gly Thr Tyr Leu Phe Thr Asn Ile Gly Glu Ser Glu Thr
    1550                1555                1560

Asn Asp Phe Ser Gln Arg Asn Ala Ala Asn Ser Val Asn Leu Ser
    1565                1570                1575

Asp Tyr Lys Asn Val Val Asp Gly Phe Phe Thr Ala Asp Thr Trp
    1580                1585                1590

Tyr Arg Pro Lys Gln Ile Leu Asp Asn Gly Thr Thr Trp Arg Asn
    1595                1600                1605

Ser Asn Ser Asn Asp Phe Arg Pro Met Ile Thr Val Trp Trp Pro
```

```
               1610                1615                1620

Asn Lys Asn Val Gln Val Asn Tyr Leu Lys Leu Met Gln Asn Asn
        1625                1630                1635

Asn Leu Leu Asp Lys Ser Thr Asn Tyr Thr Leu Gln Ser Asn Gln
        1640                1645                1650

Gln Met Leu Asn Gln Ala Ala Gln Asn Ala Gln Val Asn Ile Glu
        1655                1660                1665

Lys Lys Ile Ala Gln Thr Gly Asn Thr Asp Trp Leu Asn Asp Leu
        1670                1675                1680

Leu Phe Lys Gly Asn Gly Asp Thr Pro Ser Phe Val Lys Gln Gln
        1685                1690                1695

Tyr Ile Trp Asn Ile Leu Ser Glu Ser Pro Gly Gln Asp Asp Ala
        1700                1705                1710

Leu Leu Gln Asn Gly Tyr Phe Lys Tyr Val Asn Ser Glu Leu Thr
        1715                1720                1725

Pro Asn Thr Asn Ser Ser Tyr Arg Ile Ser Asn Asn Leu Cys Asp
        1730                1735                1740

Phe Leu Leu Ala Asn Asp Val Asp Asn Ser Asn Pro Ala Val Gln
        1745                1750                1755

Ala Glu Asp Leu Asn Trp Leu Tyr Tyr Leu Thr Asn Phe Gly Thr
        1760                1765                1770

Ile Thr Ala Asn Asp Pro Asn Ala Asn Phe Asp Ser Ile Arg Ile
        1775                1780                1785

Asp Ala Tyr Ala Phe Ile Asn Asn Asp Ile Val Gln Arg Ser Asn
        1790                1795                1800

Asp Tyr Met Lys Gln Lys Tyr Lys Leu Thr Glu Ser Ser Asn Asn
        1805                1810                1815

Ala Asn Ser His Leu Ser Ile Val Glu Ala Gly Val Asp Ala Gly
        1820                1825                1830

Thr Thr Ser Thr Asn Asn Asp Glu Leu Val Glu Ser Pro Phe Arg
        1835                1840                1845

Thr Ile Ser Tyr Gly Leu Ile His Lys Asp Arg Asn Pro Gln Asp
        1850                1855                1860

Met Asn Asn Phe Ile Lys Glu Val Asp Thr Gly Val Val Ile Ala
        1865                1870                1875

Asp His Glu Asn Asn Ser Gln Glu Ile Gly Gln Pro Asn Tyr Ser
        1880                1885                1890

Ile Val His Ala His Asp Lys Asp Ile Gln Asp Lys Val Gly Glu
        1895                1900                1905

Ala Ile Val Asp Ala Thr Gly Ile Lys Asp Trp Thr Asn Phe Thr
        1910                1915                1920

Pro Ser Glu Leu Ser Ala Gly Leu Lys Leu Tyr Tyr Asp Asp Gln
        1925                1930                1935

Arg Ser Ser Glu Lys Lys Tyr Asn Asp Tyr Asn Ile Pro Ser Ala
        1940                1945                1950

Tyr Ala Ile Met Leu Thr Asn Lys Gly Thr Val Pro Arg Ile Tyr
        1955                1960                1965

Tyr Gly Asp Met Tyr Gln Asp Asp Gly Gln Phe Met Gln Lys Gln
        1970                1975                1980

Ser Val Tyr Tyr Asp Asp Ile Val Ser Leu Leu Thr Ala Arg Lys
        1985                1990                1995

Lys Tyr Val Ser Gly Gly Gln Ser Met Ser Val Asp His Asn Asn
        2000                2005                2010
```

```
Phe Leu Glu Ser Val Arg Phe Gly Lys Gly Ala Gly Ser Glu Ser
    2015                2020                2025

Asp Ser Gly Asn Ala Glu Thr Arg Asn Glu Gly Ile Gly Leu Ile
    2030                2035                2040

Val Gly Asn Asp Gln Asn Lys Lys Leu Asn Asp Gly Asp Thr Val
    2045                2050                2055

Val Leu His Met Gly Ala Ala His Arg Asn Gln Lys Tyr Arg Ala
    2060                2065                2070

Leu Met Leu Thr Thr Asn Asp Gly Ile Lys Asn Tyr Asp Ser Asp
    2075                2080                2085

Glu Asn Ala Pro Ile Ala Glu Thr Asp Ser Asn Gly Asp Leu Val
    2090                2095                2100

Phe Ser Asn Lys Asp Ile Asn Gly Gln Ala Asn Thr Ser Val Arg
    2105                2110                2115

Gly Val Leu Asn Pro Glu Val Ala Gly Tyr Val Ala Ala Trp Val
    2120                2125                2130

Pro Leu Gly Ala Ser Asp Asp Gln Asp Ser Arg Thr Leu Ser Ser
    2135                2140                2145

Asn Lys Ser Tyr Asn Asp Gly Lys Val Leu His Ser Gly Asp Asp
    2150                2155                2160

Leu Asp Ser Asn Val Ile Phe Glu Ala Phe Ser Asn Phe Gln Pro
    2165                2170                2175

Glu Pro Thr Asn Glu Asn Glu Tyr Glu Asn Val Val Ile Pro Gln
    2180                2185                2190

Lys Ala Ser Leu Phe Lys Asp Trp Gly Ile Thr Ser Phe Glu Leu
    2195                2200                2205

Pro Pro Gln Tyr Arg Ser Ser Asn Asp His Thr Phe Val Asp Ala
    2210                2215                2220

Thr Ile Asn Asn Gly Tyr Ala Phe Ser Asp Arg Tyr Asp Leu Gly
    2225                2230                2235

Phe Gly Gln Pro Thr Lys Tyr Gly Thr Asp Val Asp Leu Arg Asn
    2240                2245                2250

Thr Ile Lys Ser Leu His Asp Asn Gly Met Gln Val Met Ala Asp
    2255                2260                2265

Val Val Tyr Asn Gln Leu Tyr Asn Leu Pro Gly Gln Glu Val Val
    2270                2275                2280

Ser Ala Val Arg Ala Gly Phe Thr Gly Asn Thr Val Ser Leu Pro
    2285                2290                2295

Phe Gly Asn Gln Leu Tyr Val Val Asn Thr Val Gly Gly Gly Asp
    2300                2305                2310

Tyr Gln Lys Lys Tyr Gly Gly Ala Phe Leu Gln Lys Leu Tyr Gln
    2315                2320                2325

Glu Tyr Pro Ser Leu Phe Asp Ser Glu Lys Tyr Gln Tyr Asn Ser
    2330                2335                2340

Lys Asn Tyr Val Thr Asp Leu Leu Val Met Thr Asp Gly Glu Arg
    2345                2350                2355

Ser Ala Ile Pro Ser Asp Gln Pro Ile Thr Glu Trp Ser Ala Lys
    2360                2365                2370

Tyr Met Asn Gly Thr Asn Ile Leu Gly Arg Gly Met Gly Tyr Val
    2375                2380                2385

Leu Lys Asp Trp Asn Thr Gly Thr Tyr Phe Lys Leu Asn Gly Asn
    2390                2395                2400
```

-continued

```
Asn Ser Val Leu Pro Asp Val Leu Thr Tyr Arg Asn Ser Phe Asp
    2405                2410                2415

Asp Asn Thr Gly Thr Gln Ser Ser Ser Ser Ala Gln Ser Ser Ala
    2420                2425                2430

Ser Asn His Glu Thr Gln Ile Ser Ser Ser Ala Gln Ser Ser Ala
    2435                2440                2445

Ser Asn His Glu Ala Gln Ser Ser Ser Ser Ala Gln Ser Ser Val
    2450                2455                2460

Ser Ser His Glu Val Gln Ser Ser Ser Ala Gln Ser Ser Ala
    2465                2470                2475

Ser Ser His Glu Val Gln Ser Ser Ser Ala Gln Ser Ser Ala
    2480                2485                2490

Ser Ser His Glu Val Gln Ser Ser Ser Ala Gln Ser Ser Ala
    2495                2500                2505

Ser Ser Tyr Glu Ala Gln Ser Ser Ser Ala Gln Ser Ser Ala
    2510                2515                2520

Ser Ser His Glu Val Gln Ser Ser Ser Ala Gln Ser Ser Val
    2525                2530                2535

Ser Ser His Glu Thr Gln Ser Ser Ser Ala Gln Ser Ser Ala
    2540                2545                2550

Ser Ser His Glu Val Gln Ser Ser Ser Ala Gln Ser Ser Ala
    2555                2560                2565

Ser Ser Asn Glu Ala Gln Ser Ser Ser Ser Ala Gln
    2570                2575                2580

<210> SEQ ID NO 11
<211> LENGTH: 1463
<212> TYPE: PRT
<213> ORGANISM: Lactobacillus kunkeei

<400> SEQUENCE: 11

Met Asn Ile Asn Ser Asn Glu Arg Lys Val Arg Phe Lys Met Tyr Lys
1               5                   10                  15

Ser Gly Lys Gln Trp Ile Val Ala Gly Leu Thr Thr Ala Val Ile Ser
            20                  25                  30

Ile Ala Val Tyr Gly Gly Ser Ser Ile Ala Asn Gly Gly Ile Glu Ala
        35                  40                  45

Lys Ala Asp Ala Gln Asn Ala Ala Thr Ser Ser Ile Val Asn Thr Asn
    50                  55                  60

Asn Ser Thr Asn Ser Ser Asn Ala Asn Ser Ile Ala Ser Leu Pro Gln
65                  70                  75                  80

Asn Gly Thr Tyr Ser Thr Asn Asp Asn Gly Gln Thr Trp Lys Tyr Val
                85                  90                  95

Ser Gln Asn Lys Asp Ile Gln Gly Leu Tyr Lys Asp Asn Asn Asp Gln
            100                 105                 110

Leu Arg Tyr Phe Asn Glu Tyr Asp Gly Thr Gln Ala Lys Gly Asp Ile
        115                 120                 125

Val Asn Val Asn Asn Asp Asn Tyr Tyr Phe Lys Asp Ser Gly Gln
    130                 135                 140

Gly His Lys Ile Asp Ser Tyr Thr Gly Gly Ser Tyr Ser Glu Ser Lys
145                 150                 155                 160

Val Asn Asn Gln Asp Gly Trp Ile Tyr Lys Ser Ser Asp Asn Asp
                165                 170                 175

Val Lys Gly Val Ala Thr Val Asp Gly Asn Ile Gln Tyr Phe Asp Gln
            180                 185                 190
```

```
Asn Thr Gly Leu Gln Leu Lys Gly Gly Ser Ala Gln Ile Gly Gly Val
        195                 200                 205

Asp Tyr Tyr Phe Asp Pro Asn Lys Gly Asn Leu Val Gly Lys Val Asp
        210                 215                 220

Gln Val Val Asn Ser Asn Asp Tyr Ser Asp Asn Lys Leu Leu Asp Ser
225                 230                 235                 240

Asn Lys Asn Val Val Lys Gly Leu Val Val Asn Asn Gly Gln Leu Gln
                245                 250                 255

Phe Phe Asp Thr Ser Asn Gly Asn Gln Ala Lys Asn Lys Gln Val Ile
                260                 265                 270

Ala Asn Gly Ile Thr Tyr Tyr Phe Asp Thr Asn Gly Asn Gly Gln Tyr
            275                 280                 285

Leu Phe Thr Asn Thr Gly Lys Ser Ala Val Asp Asp Phe Thr Gln Arg
        290                 295                 300

Asn Ala Ala Asn Ser Val Asn Pro Ser Asp Tyr Lys Asn Val Val Asp
305                 310                 315                 320

Gly Phe Phe Thr Ala Asp Thr Trp Tyr Arg Pro Lys Gln Ile Leu Asp
                325                 330                 335

Asn Gly Thr Thr Trp Arg Asn Ser Asn Ser Asn Glu Leu Arg Pro Met
            340                 345                 350

Ile Thr Ala Trp Trp Pro Asn Lys Asp Val Gln Val Asn Tyr Leu Lys
        355                 360                 365

Leu Met Gln Asn Asn Gly Leu Leu Asp Lys Ser Asn Ser Tyr Ser Ile
        370                 375                 380

Gln Ser Asp Gln Gln Thr Leu Asn Gln Ala Ala Gln Lys Ala Gln Val
385                 390                 395                 400

Asn Ile Glu Lys Lys Ile Ser Gln Thr Gly Asn Thr Asp Trp Leu Asn
                405                 410                 415

Asp Leu Leu Phe Lys Gly Asn Gly Asp Asn Pro Ser Phe Val Lys Gln
                420                 425                 430

Gln Tyr Ile Trp Ser Ser Asp Ser Glu Ser Pro Trp Gln Gly Asp Ala
            435                 440                 445

Trp Phe Gln Gly Gly Tyr Leu Lys Tyr Gly Asn Ser Val Met Thr Pro
        450                 455                 460

Asn Thr Asn Ser Asn Tyr Arg Asp Ser Asn Asn Leu Phe Asp Phe Leu
465                 470                 475                 480

Leu Ala Asn Asp Val Asp Asn Ser Asn Pro Ala Val Gln Ala Glu Asp
                485                 490                 495

Leu Asn Trp Leu Tyr Tyr Leu Thr Asn Phe Gly Thr Ile Thr Ala Asn
            500                 505                 510

Asp Ser Asn Ala Asn Phe Asp Ser Ile Arg Ile Asp Ala Val Asp Phe
        515                 520                 525

Ile Ser Asn Asp Ile Ile Gln Arg Ser Tyr Asp Tyr Leu Arg Gln Lys
        530                 535                 540

Phe Asn Leu Met Gln Ser Asp Ala Asn Ala Asp Ser His Ile Ser Leu
545                 550                 555                 560

Val Glu Gly Gly Val Asp Ala Gly Thr Thr Ser Tyr Ser Asn Asp Gly
                565                 570                 575

Leu Val Glu Ala Pro Phe Arg Leu Asp Ala Tyr Pro Leu Leu His Lys
            580                 585                 590

Gln Asp Gly Asp Val Phe Lys Asn Leu Ile Asp Glu Glu Asp Ser Gly
        595                 600                 605
```

```
Ile Asp Ile Ser Asn His Asn Gly Glu Thr Asn Thr Asn Asn Thr Ile
610                 615                 620

Gly Gly Ile Thr Leu Ser Gly Gly Lys Pro Asn Tyr Ser Ile Val His
625                 630                 635                 640

Ala His Asp Lys Asp Val Gln Glu Lys Val Gly Gln Ala Ile Ile Asp
                645                 650                 655

Thr Thr Gly Ile Lys Asp Trp Thr Asp Phe Thr Pro Ser Gln Leu Ala
                660                 665                 670

Gln Gly Leu Glu Thr Phe Tyr Asn Asp Gln Arg Gln Thr Val Lys Lys
                675                 680                 685

Tyr Asn Asp Tyr Asn Val Pro Ser Ala Tyr Ala Ile Met Leu Thr Asn
690                 695                 700

Lys Gly Thr Val Pro Arg Ile Tyr Tyr Gly Asp Met Tyr Gln Asp Asp
705                 710                 715                 720

Gly Gln Phe Met Gln Lys Lys Ser Leu Tyr Tyr Asp Asp Ile Ala Asn
                725                 730                 735

Leu Met Thr Ala Arg Lys Lys Tyr Val Ser Gly Gly Gln Ser Met Val
                740                 745                 750

Asp Asn Asn Gly Ile Leu Thr Ser Val Arg Phe Gly Lys Gly Ala Asn
                755                 760                 765

Thr Val Ser Asp Ser Gly Thr Glu Asp Thr Arg Asn Gln Gly Ile Gly
                770                 775                 780

Leu Ile Val Gly Ser Ala Pro Lys Lys Val Leu Asn Asp Gly Asp Thr
785                 790                 795                 800

Val Val Leu His Met Gly Ala His Lys Asn Gln Lys Tyr Arg Ala
                805                 810                 815

Leu Met Leu Thr Thr Glu Asn Gly Ile Gln Asn Tyr Asn Ser Asp Asp
                820                 825                 830

Asn Ala Pro Val Ala Glu Thr Asp Asp Asn Gly Asp Leu Val Phe Ser
                835                 840                 845

Asn Lys Asp Ile Asn Gly Gln Ala Asn Thr Ala Ile Lys Gln Val Ala
850                 855                 860

Asn Pro Glu Val Asn Gly Tyr Leu Ala Ala Trp Val Pro Val Gly Ala
865                 870                 875                 880

Ser Asp Asp Gln Asp Ser Arg Thr Ala Pro Ser Thr Ser Gln Asn Asn
                885                 890                 895

Asp Gly Asn Val Leu His Glu Asn Asp Ala Leu Asp Ser Asn Leu Ile
                900                 905                 910

Phe Glu Gly Phe Ser Asn Phe Gln Pro Thr Pro Thr Asn His Asp Glu
                915                 920                 925

Tyr Ala Asn Val Val Ile Ala Lys Asn Ala Ser Leu Phe Lys Asp Trp
930                 935                 940

Gly Val Thr Ser Phe Glu Met Ala Pro Gln Tyr Arg Ser Ser Gln Asp
945                 950                 955                 960

His Thr Phe Val Asp Ser Thr Ile Asp Asn Gly Tyr Ala Phe Ser Asp
                965                 970                 975

Arg Tyr Asp Leu Gly Phe Gly Thr Pro Thr Lys Tyr Gly Thr Asp Glu
                980                 985                 990

Asp Leu Arg Asn Ala Ile Lys Ser Leu His Asp Asn Gly Met Gln Val
                995                 1000                1005

Met Ala Asp Val Val Tyr Asn Gln Leu Tyr Asn Leu Pro Gly Gln
            1010                1015                1020

Glu Val Val Ser Ala Thr Arg Ala Gly Val Thr Gly Asn Thr Asn
```

-continued

```
               1025                1030                1035

Ala Leu Pro Phe Gly Thr Gln Leu Tyr Val Val Asn Thr Ile Gly
            1040                1045                1050

Gly Gly Asp Tyr Gln Lys Lys Tyr Gly Gly Ala Phe Leu Asn Glu
            1055                1060                1065

Leu Gln Glu Gln Tyr Pro Ser Leu Phe Lys Ser Gln Lys Tyr Lys
            1070                1075                1080

Tyr Tyr Tyr Lys Asn Tyr Ala Asn Asn Gly Ala Gly Pro Gly Tyr
            1085                1090                1095

Leu Thr Val Asn Asp Ala Glu Arg Ser Asp Ile Pro Tyr Asn Gln
            1100                1105                1110

Pro Ile Thr Glu Trp Ser Ala Lys Tyr Met Asn Gly Thr Asn Ile
            1115                1120                1125

Leu Gly Arg Gly Met Gly Tyr Val Leu Lys Asp Trp Asn Thr Gly
            1130                1135                1140

Asp Tyr Phe Lys Leu Ser Gly Ser Asp Ser Thr Leu Pro Ser Ser
            1145                1150                1155

Leu Thr Tyr Lys Ser Gly Trp Val Glu Asn Pro Asp Ser Thr Trp
            1160                1165                1170

Ser Tyr Tyr Glu Lys Asn Asn Ile Asp Lys Leu Thr Gly Ser Gln
            1175                1180                1185

Val Ile Asn Glu Glu Arg Val Phe Phe Asp Asn Asn Gly Ile Gln
            1190                1195                1200

Val Lys Gly Gly Trp Val Lys Asn Ser Asn Gly Thr Tyr Ser Tyr
            1205                1210                1215

Tyr Asp Lys Asn Ser Gly Asn Ile Leu Thr Gly Asp Gln Leu Ile
            1220                1225                1230

Asp Gly Glu His Phe Phe Asp Asn Asn Gly Val Gln Val Lys
            1235                1240                1245

Gly Lys Trp Ile Lys Asn Ser Asp Gly Ser Lys Ser Tyr Tyr Asp
            1250                1255                1260

Ser His Leu Gly Lys Leu Ile Lys Thr Asp Lys Lys Val Ser Ser
            1265                1270                1275

Asn Ala Arg Lys Lys Lys Ser Lys Glu Glu Leu Leu Tyr Glu Asn
            1280                1285                1290

Ala Leu Lys Val Leu Arg Lys Asp Lys Lys Arg Leu Asp Lys Asn
            1295                1300                1305

Lys Thr Lys Ala Asn Ile Arg Lys Tyr Asn Lys Ser Leu Lys Lys
            1310                1315                1320

Tyr Arg Lys Ala Lys Lys Lys Leu Leu Ala Ile Thr Lys Asn Arg
            1325                1330                1335

Val Ala Asn Ala Arg Lys Ala Ile Lys Ile Ala Lys Lys Val Leu
            1340                1345                1350

Ser Lys Arg Lys Asn Ile Asn Asn Glu Lys Arg Tyr Tyr Lys Ala
            1355                1360                1365

Leu Lys Glu Tyr Tyr Val Ala Glu Lys Ser Tyr Leu Lys Ile Thr
            1370                1375                1380

Gly Asn Tyr Asn Lys Lys Tyr Tyr Tyr Glu Phe Asp Lys Leu Thr
            1385                1390                1395

Pro Lys Val Lys Val Val Lys Asn Ile Tyr Ser Tyr Lys Ser Arg
            1400                1405                1410

His Phe Thr Lys Lys Asn Arg Val Lys Lys Ile Lys Lys Gly Thr
            1415                1420                1425
```

```
Leu Val Arg Val Lys Ser Ile Val Arg Ser Gly Lys Val Ala Arg
    1430                1435                1440

Ile Asn Ile Gly Asn Gly His Phe Ile Thr Ser Ser Lys Asp Phe
    1445                1450                1455

Ile Lys Met Phe Lys
    1460

<210> SEQ ID NO 12
<211> LENGTH: 2824
<212> TYPE: PRT
<213> ORGANISM: Leuconostoc carnosum JB16

<400> SEQUENCE: 12

Met Thr Ala Gly Ile Phe Ser Thr Val Val Phe Gly Met Ala Val Ser
1               5                   10                  15

Asp Val Ser Ala Asn Asp Thr Asp Asn Thr Val Leu Thr Ser Asn Ser
                20                  25                  30

Gly Phe Leu Asp Lys Val Val Asp Thr Thr Ser Thr Asp Lys Ala Ala
            35                  40                  45

Thr Pro Asp Lys Val Val Asp Thr Thr Ser Thr Asp Lys Ala Val Thr
    50                  55                  60

Pro Asp Lys Val Ala Asp Thr Thr Ser Thr Asp Lys Ala Val Thr Pro
65                  70                  75                  80

Asp Lys Val Ala Asp Thr Thr Ser Thr Asp Lys Ala Ala Thr Pro Asp
                85                  90                  95

Lys Val Val Asp Thr Thr Ser Thr Asp Lys Ala Ala Thr Pro Asp Lys
            100                 105                 110

Val Val Asp Thr Thr Ser Thr Asp Lys Ala Ala Thr Pro Asp Lys Val
        115                 120                 125

Val Asp Thr Thr Ser Thr Asp Lys Ala Ala Thr Pro Asp Lys Val Val
    130                 135                 140

Asp Thr Thr Ser Thr Asp Lys Ala Ala Thr Pro Asp Lys Val Ala Asp
145                 150                 155                 160

Thr Thr Ser Thr Asp Lys Ala Ala Thr Pro Asp Lys Val Val Asp Thr
                165                 170                 175

Thr Ser Thr Asp Lys Ala Ala Thr Pro Asp Lys Val Val Asp Thr Thr
            180                 185                 190

Ser Thr Asp Lys Ala Ala Thr Pro Asp Lys Val Val Asp Thr Thr Ser
        195                 200                 205

Thr Asp Lys Ala Ala Thr Pro Asp Lys Val Val Asp Thr Thr Ser Thr
    210                 215                 220

Asp Lys Ala Ala Asp Arg Thr Ile Ser Ile Ser Gly Lys Thr Val Lys
225                 230                 235                 240

Asn Ile Glu Glu Ile Gly Gly Lys Thr Tyr Phe Val Gly Asp Asp Gly
                245                 250                 255

Lys Val Lys Lys Asn Phe Thr Val Ile Val Asp Gly Gln Val Met Tyr
            260                 265                 270

Phe Asp Lys Glu Ser Gly Ala Leu Thr Ser Asn His Lys Gln Tyr Lys
        275                 280                 285

Glu Gly Leu Ser Asp Ile Thr Asn Glu His Asn Ala Tyr Ser Leu
    290                 295                 300

Glu Asn Asp Asn Phe Thr Gln Ile Asp Ser Tyr Leu Thr Ala Asn Ser
305                 310                 315                 320

Trp Tyr Arg Pro Lys Asp Ile Leu Lys Ser Gly Thr Thr Trp Thr Ala
```

```
                    325                 330                 335
Ser Thr Asp Lys Asp Ser Arg Pro Leu Leu Met Ser Trp Trp Pro Asp
                340                 345                 350
Gln Gln Thr Glu Leu Ser Tyr Leu Lys Tyr Met Gln Ser Ala Gly Phe
                355                 360                 365
Leu Ala Glu Asp Val Asn Leu Ser Glu Asn Asn Ser Ile Asp Asp Leu
                370                 375                 380
Thr Ala Ala Met Asp Val Gln Lys Asn Val Glu Ala Lys Ile Ser
385                 390                 395                 400
Leu Ser Gly Asn Thr Asp Trp Leu Lys Glu Asp Met Asn Gln Phe Val
                405                 410                 415
Asp Ser Gln Ser Asn Trp Asn Ile Ser Ser Glu Ser Lys Gly Thr Asp
                420                 425                 430
His Leu Gln Gly Gly Ala Leu Leu Tyr Gly Asn Ser Asp Met Thr Pro
                435                 440                 445
Asp Ala Asn Ser Asp Tyr Arg Leu Leu Asn Arg Thr Pro Lys Asn Gln
                450                 455                 460
Thr Gly Gln Ile Ser Ala Thr Asn Asp Gln Gly Gly Tyr Glu Met Leu
465                 470                 475                 480
Leu Ala Asn Asp Val Asp Asn Ser Asn Pro Ile Val Gln Ala Glu Gln
                485                 490                 495
Leu Asn Trp Leu His Tyr Met Met Asn Ile Gly Ser Ile Thr Lys Asn
                500                 505                 510
Asp Ser Thr Ala Asn Phe Asp Gly Tyr Arg Val Asp Ala Val Asp Asn
                515                 520                 525
Val Asn Ala Asp Leu Leu Gln Ile Ala Gly Asp Tyr Phe Lys Ala Ala
                530                 535                 540
Tyr Gly Thr Asp Lys Ser Asp Ala Asn Ala Asn His Ile Ser Ile
545                 550                 555                 560
Leu Glu Asp Trp Asp Asn Ser Asp Pro Asp Tyr Val Lys Lys His Gly
                565                 570                 575
Asn Glu Gln Leu Thr Met Asp Phe Pro Met His Leu Ala Leu Lys Tyr
                580                 585                 590
Ala Leu Asn Met Pro Ile Asp Met Arg Ser Gly Leu Glu Pro Ala Ile
                595                 600                 605
Lys Thr Ser Leu Val Asn Arg Ser Gln Asp Ala Thr Glu Asn Glu Ala
                610                 615                 620
Gln Pro Asn Tyr Ser Phe Ile Arg Ala His Asp Ser Glu Val Gln Thr
625                 630                 635                 640
Val Ile Ala Gln Ile Ile Lys Asp Lys Ile Asn Pro Lys Ser Asp Gly
                645                 650                 655
Leu Thr Val Thr Pro Asp Glu Ile Ala Lys Ala Phe Glu Ile Tyr Asn
                660                 665                 670
Ala Asp Glu Leu Lys Ala Asp Lys Ala Tyr Thr Ala Phe Asn Ile Pro
                675                 680                 685
Ser Ser Tyr Ala Leu Leu Leu Thr Asn Lys Asp Thr Val Pro Arg Val
                690                 695                 700
Tyr Tyr Gly Asp Leu Phe Thr Asp Gly Gln Tyr Met Ser Asp His
705                 710                 715                 720
Ser Pro Tyr Tyr Asp Ala Ile Thr Thr Leu Leu Ala Ser Arg Ile Lys
                725                 730                 735
Tyr Ala Ala Gly Gly Gln Ser Met Gly Met Thr Tyr Leu His Asp Asn
                740                 745                 750
```

```
Gln Glu Val Leu Thr Ser Val Arg Tyr Gly Lys Gly Ala Leu Thr Ala
        755                 760                 765

Asp Asp Leu Gly Asn Val Asp Thr Arg Thr Gln Gly Ile Gly Leu Val
        770                 775                 780

Ile Ser Asn Lys Thr Asp Leu Ser Leu Lys Ser Asp Glu Ser Val Val
785                 790                 795                 800

Leu Asn Met Gly Val Ala His Lys Asn Gln Ala Tyr Arg Pro Ala Met
                805                 810                 815

Leu Thr Thr Lys Ser Gly Leu Lys Ile Tyr Asp Thr Asp Gly Ala
        820                 825                 830

Pro Ile Val Tyr Thr Asn Asn Leu Gly Gln Leu Ile Phe Asn Ala Asp
        835                 840                 845

Thr Val Tyr Gly Val Ser Asp Pro Gln Val Ser Gly Tyr Leu Ala Ala
        850                 855                 860

Trp Val Pro Val Gly Ala Thr Glu Asp Gln Asp Ala Arg Thr Lys Gly
865                 870                 875                 880

Ser His Asp Gly Thr Thr Asp Gly Asn Val Tyr His Ser Asn Ala Ala
                885                 890                 895

Leu Asp Ser Gln Val Ile Tyr Glu Gly Phe Ser Asn Phe Gln Ala Met
        900                 905                 910

Pro Thr Thr Thr Asp Glu Tyr Thr Asn Val Lys Ile Ala Gln Asn Ala
        915                 920                 925

Gln Trp Phe Lys Lys Leu Gly Leu Thr Ser Phe Glu Leu Ala Pro Gln
        930                 935                 940

Tyr Arg Ser Ser Thr Asp Ser Ser Phe Leu Asp Ser Val Ile Gln Asn
945                 950                 955                 960

Gly Tyr Ala Phe Thr Asp Arg Tyr Asp Val Gly Tyr Asn Thr Pro Thr
                965                 970                 975

Lys Tyr Gly Thr Val Asp Gln Leu Leu Asp Ala Leu Arg Ala Leu His
                980                 985                 990

Ser Gln Asp Ile Gln Ala Ile Asn  Asp Trp Val Pro Asp  Gln Ile Tyr
        995                 1000                1005

Asn Leu  Pro Gly Glu Gln Ile  Val Thr Ala Ser Arg  Thr Asn Gly
        1010                1015                1020

Ser Gly  Lys Tyr Asp Asp Asp  Ser Val Ile Ser Asn  Thr Leu Tyr
        1025                1030                1035

Asp Ser  Arg Thr Ile Gly Gly  Gly Glu Tyr Gln Ala  Met Tyr Gly
        1040                1045                1050

Gly Ala  Phe Leu Asp Gln Leu  Lys Gln Ala Tyr Pro  Gly Leu Phe
        1055                1060                1065

Glu Thr  Lys Gln Leu Ser Thr  Gly Val Ala Met Asp  Pro Asp Val
        1070                1075                1080

Lys Ile  Lys Glu Trp Ser Ala  Lys Tyr Phe Asn Gly  Ser Asn Ile
        1085                1090                1095

Gln Gly  Arg Gly Ala Trp Tyr  Val Leu Lys Asp Trp  Ala Thr Asn
        1100                1105                1110

Lys Tyr  Phe Ser Val Ser Ser  Asn Asn Thr Phe Leu  Pro Lys Gln
        1115                1120                1125

Leu Leu  Gly Glu Lys Ala Ser  Thr Gly Phe Ile Thr  Asn Asp Gly
        1130                1135                1140

Lys Thr  Glu Phe Tyr Ser Thr  Ser Gly Tyr Gln Ala  Lys Asn Thr
        1145                1150                1155
```

```
Phe Ile Glu Asp Asn Gly Asn Trp Tyr Tyr Phe Asp Asn Asp Gly
    1160                1165                1170

Tyr Ser Val Val Gly Lys Gln Val Ile Asp Asn Lys His Tyr Tyr
    1175                1180                1185

Phe Leu Pro Asn Gly Val Glu Leu Gln Asp Ala Tyr Leu Ser Asp
    1190                1195                1200

Gly Asp Lys Gln Tyr Tyr Lys Lys Thr Gly Arg Gln Ile Val
    1205                1210                1215

Asn Gln Tyr Tyr Arg Asp Glu Gln Gly Asp Trp Arg Tyr Phe Phe
    1220                1225                1230

Ala Asp Gly His Met Ala Leu Gly Leu Thr Asp Ile Val Ser Asn
    1235                1240                1245

Asp Gly Thr His Ala Thr Gln Tyr Phe Asp Asn Asn Gly Val Gln
    1250                1255                1260

Val Lys Gly Thr Ser Glu Arg Asp Lys Asp Gly Asn Ile His Tyr
    1265                1270                1275

Phe Asp Gly Thr Ser Gly Asn Leu Val Val Ser Ser Trp Gly Gln
    1280                1285                1290

Leu Ser Asp Gly Ser Trp Leu Tyr Leu Asn Asp Lys Gly Ile Ala
    1295                1300                1305

Val Thr Gly Ala Gln Gln Ile Asp Gly Gln Ser Leu Tyr Phe Asn
    1310                1315                1320

Glu Asp Gly Lys Glu Val Lys Gly Asp Ala Val Thr Asp Asn Gln
    1325                1330                1335

Gly Asn Ile Arg Tyr Phe Asp Gly Glu Ser Gly His Met Val Val
    1340                1345                1350

Asn Ser Trp Gly Lys Leu Pro Asp Gly Ser Trp Met Tyr Leu Asn
    1355                1360                1365

Asp Lys Gly Ile Ala Val Thr Gly Gln Gln Lys Ile Asn Asn Glu
    1370                1375                1380

Val Leu Tyr Phe Asn Ala Asp Gly Lys Gln Ile Lys Ser Ala Phe
    1385                1390                1395

Lys Glu Leu Val Asp Gly Ser Trp Leu Tyr Leu Asn Asp Lys Gly
    1400                1405                1410

Ile Ala Val Thr Gly Ala Gln Gln Ile Asp Gly Gln Ser Leu Tyr
    1415                1420                1425

Phe Asn Glu Asp Gly Lys Glu Val Lys Gly Asp Ala Val Thr Asp
    1430                1435                1440

Asn Gln Gly Asn Ile Arg Tyr Phe Asp Gly Glu Ser Gly His Met
    1445                1450                1455

Val Val Asn Ser Trp Gly Lys Leu Pro Asp Gly Ser Trp Met Tyr
    1460                1465                1470

Leu Asn Asp Lys Gly Ile Ala Val Thr Gly Gln Gln Lys Ile Asn
    1475                1480                1485

Asn Glu Ile Leu Tyr Phe Asp Ala Asp Gly Lys Gln Leu Lys Asn
    1490                1495                1500

Thr Leu Lys Thr Leu Ser Asp Gly Ser Arg Ile Tyr Leu Asp Gly
    1505                1510                1515

Lys Gly Val Ser Ala Thr Gly Val Gln Lys Ile Asn Gly Lys Val
    1520                1525                1530

Ser Tyr Phe Asp Val Asn Gly Lys Gln Val Ser Asn His Ile Gln
    1535                1540                1545

Glu Leu Pro Asp Gly Ser Trp Met Tyr Leu Asp Asn Asp Gly Leu
```

```
                1550                1555                1560

Ala Leu Ile Gly Asn Gln Asp Val Asp Gly Lys Gln Leu Tyr Phe
    1565                1570                1575

Asp Val Asp Gly Lys Gln Ile Lys Asn Asp Lys Val Lys Asn Ser
    1580                1585                1590

Asp Gly Thr Ile Asn Tyr Tyr Thr Gly Thr Val Gly Glu Lys Leu
    1595                1600                1605

Lys His Asp Phe Gly Gln Leu Ser Asp Gly Ser Trp Met Tyr Leu
    1610                1615                1620

Asp Glu Asn Gly Asn Ala Val Thr Gly Glu Gln Asn Ile Asn Gly
    1625                1630                1635

Gln His Leu Tyr Phe Lys Asp Asp Gly Gln Gln Val Lys Gly Asp
    1640                1645                1650

Val Phe Glu Asp Asp Leu Gly Arg Met Arg Tyr Tyr Ser Ala Asn
    1655                1660                1665

Ser Gly Glu Met Val Val Asn Gln Phe Glu Gln Ile Ser Asp Gly
    1670                1675                1680

Ala Trp Ala Tyr Phe Gly Asp Asp Gly Val Ala Val Thr Gly Glu
    1685                1690                1695

Gln His Ile Asn Gly Gln Asp Leu Phe Phe Asp Ala Thr Gly Gln
    1700                1705                1710

Gln Val Lys Gly Glu Ser Arg Thr Ile Asn Gly Ile Pro Tyr Thr
    1715                1720                1725

Phe Glu Lys Glu Ser Gly Glu Lys Arg Ser Val Asn Ile Ala Pro
    1730                1735                1740

Leu Leu Ala Met Gly Asn Tyr Val Thr Asn Asn Gly Thr Asp Trp
    1745                1750                1755

Gln Tyr Glu Val Gln Gly Asn Pro Val Lys Gly Leu Tyr Ser Thr
    1760                1765                1770

Ser Asp Asn Lys Leu Arg Tyr Phe Asp Leu Thr Thr Gly Val Gln
    1775                1780                1785

Ile Lys Gly Asn Phe Val Thr Ile Gly His Asn Thr Tyr Tyr Phe
    1790                1795                1800

Asn Pro Ala Asn Gly Asp Gly Glu Leu Leu Pro Asp Val Ser Asp
    1805                1810                1815

Gly His Tyr Gly Thr Ile Gln Val Lys Asp Ala Asn Thr Asn Glu
    1820                1825                1830

Lys Thr Val Trp Val Tyr Arg Asn Gln Ser Asn Thr Ile Leu Lys
    1835                1840                1845

Gly Ile Gln Asn Ile His Gly Asn Ile Gln Tyr Phe Asp Leu Ser
    1850                1855                1860

Thr Gly Glu Gln Ile Lys Gly Gly Ile Ala Asn Tyr Asp Gly Asn
    1865                1870                1875

Asp Tyr Tyr Phe Glu Ser Ala Lys Gly Asn Leu Thr Ser Lys Ile
    1880                1885                1890

Lys Gln Val Tyr Thr Asp Gly Gln Tyr Val Thr Lys Asp Gly Lys
    1895                1900                1905

Ser Ile Tyr Glu Asp Ala Gln Gln Gln Ser Val Ser Gly Leu Val
    1910                1915                1920

Ser Ile Asn Gly Gln Leu Gln Tyr Phe Asn Pro Gln Asp Gly Val
    1925                1930                1935

Gln Val Lys Asn Gln Gln Ile Ile Val Asp Gly Val Thr Tyr Tyr
    1940                1945                1950
```

```
Phe Asp Glu Asn Gly Asn Gly Gln Tyr Leu Phe Thr Asn Thr Thr
    1955            1960                1965

Val Met Pro Met Asp Asp Phe Thr Lys His Asn Thr Val Tyr Ser
    1970            1975                1980

Asp Asn Asp Asn Asn Phe Lys Asn Asn Val Asp Gly Phe Leu Thr
    1985            1990                1995

Ala Asp Thr Trp Tyr Arg Pro Lys Glu Ile Leu Lys Ala Gly Thr
    2000            2005                2010

Thr Trp Thr Thr Thr Ser Glu Ser Asp Met Arg Pro Leu Ile Thr
    2015            2020                2025

Thr Trp Trp Pro Asn Lys Asn Val Gln Val Asn Tyr Leu Asn Phe
    2030            2035                2040

Met Lys Gln Asn Asn Leu Leu His Thr Asn Val Glu Tyr Ser Leu
    2045            2050                2055

Leu Ser Asp Gln Tyr Asp Leu Asn Ile Ala Ala Gln Ala Val Gln
    2060            2065                2070

Thr Ala Ile Glu Lys Arg Ile Ala Gln Glu Asn Ser Thr Asp Trp
    2075            2080                2085

Leu Gln Asn Leu Leu Phe Thr Ala Gln Asp Asp Gln Pro Ser Phe
    2090            2095                2100

Val Lys Gln Gln Phe Ile Trp Asn Lys Asp Ser Glu Tyr Gln Gly
    2105            2110                2115

Lys Gly Asp Ala Trp Phe Gln Gly Gly Tyr Leu Lys Tyr Gly Asn
    2120            2125                2130

Asn Lys Leu Thr Pro Asn Thr Asn Ser Asn Tyr Arg Lys Thr Asp
    2135            2140                2145

Asn Ala Phe Glu Phe Leu Leu Ala Asn Asp Ile Asp Asn Ser Asn
    2150            2155                2160

Pro Val Val Gln Ala Glu Asn Leu Asn Trp Leu Glu Tyr Leu Met
    2165            2170                2175

Asn Phe Gly Thr Ile Thr Gly Lys Asp Asp Ala Asn Phe Asp
    2180            2185                2190

Ser Ile Arg Val Asp Ala Val Asp Phe Ile Ser Asn Asp Thr Ile
    2195            2200                2205

Gln Arg Thr Tyr Asp Tyr Leu Arg Asp Ala Tyr Gln Val Asp Gln
    2210            2215                2220

Ser Glu Ala Lys Ala Asn Gln His Ile Ser Leu Val Glu Ala Gly
    2225            2230                2235

Leu Asp Ala Gly Thr Ser Thr Val Lys Asn Asp Ala Leu Ile Glu
    2240            2245                2250

Ser Asn Leu Arg Glu Ala Ala Thr Leu Ser Leu Ala Asn Ala Ser
    2255            2260                2265

Gly Lys Asn Ser Ala Leu Thr Asn Met Leu Gln Asp Val Asp Gly
    2270            2275                2280

Gly Thr Leu Ile Ala Asp His Thr His Asn Ser Thr Glu Asn Glu
    2285            2290                2295

Ala Thr Pro Asn Tyr Ser Ile Ile His Ala His Asp Lys Gly Ile
    2300            2305                2310

Gln Glu Lys Val Gly Ala Ala Ile Ser Asp Ala Thr Gly Ala Asp
    2315            2320                2325

Trp Thr Asn Phe Thr Asp Thr Gln Leu Lys Ser Gly Leu Asp Leu
    2330            2335                2340
```

```
Tyr Tyr Lys Asp Gln Arg Ala Thr Asp Lys Lys Tyr Asn Ile Tyr
2345                2350                2355

Asn Leu Pro Ser Ile Tyr Ala Leu Met Leu Thr Asn Lys Asp Thr
2360                2365                2370

Val Pro Arg Val Tyr Tyr Gly Asp Met Tyr Gln Asp Asn Gly Gln
2375                2380                2385

Tyr Met Ala Glu Lys Ser Ile Tyr Tyr Asn Ala Leu Glu Ser Leu
2390                2395                2400

Met Ser Ala Arg Lys Ser Tyr Val Ser Gly Gly Gln Thr Met Asp
2405                2410                2415

Val Asp Ser His Gly Leu Leu Lys Ser Val Arg Phe Gly Lys Gly
2420                2425                2430

Ala Met Thr Ala Asp Thr Val Gly Asn Glu Glu Thr Arg Thr Glu
2435                2440                2445

Gly Ile Gly Val Leu Val Gly Asn Asp Ala Ser Leu Lys Leu Asn
2450                2455                2460

Asp Ser Asp Thr Val Thr Leu Asp Met Gly Ala Ala His Lys Asn
2465                2470                2475

Gln Lys Tyr Arg Ala Ala Ile Leu Thr Thr Asn Asn Gly Leu Ser
2480                2485                2490

Thr Phe Asp Ser Asp Lys Asp Ala Pro Ile Ala Trp Thr Asn Asp
2495                2500                2505

Lys Gly Ile Leu Thr Phe Ser Asn Lys Asn Val Ser Gly Gln Asp
2510                2515                2520

Asn Thr Asn Val His Gly Val Ala Asn Pro Gln Val Ser Gly Tyr
2525                2530                2535

Leu Ala Val Trp Val Pro Val Gly Ala Lys Asp Asp Gln Asn Ala
2540                2545                2550

Gly Thr Ser Ala Ser Thr Val Val Asn Thr Asp Gly Lys Val Leu
2555                2560                2565

His Ser Asn Ala Ser Leu Asp Ser Asn Leu Ile Phe Glu Gly Phe
2570                2575                2580

Ser Asn Phe Gln Pro Arg Ala Thr Thr Asn Asp Glu Leu Thr Asn
2585                2590                2595

Val Val Ile Ala Lys Asn Ala Asp Leu Phe Gln Lys Trp Gly Ile
2600                2605                2610

Thr Ser Phe Glu Met Ala Pro Gln Tyr Arg Ser Ser Gln Asp His
2615                2620                2625

Thr Phe Leu Asp Ser Thr Ile Asp Asn Gly Tyr Ala Phe Thr Asp
2630                2635                2640

Arg Tyr Asp Leu Gly Phe Asn Thr Pro Thr Lys Tyr Gly Thr Asp
2645                2650                2655

Ser Asp Leu Arg Leu Ala Ile Lys Ser Leu His Lys Ala Gly Met
2660                2665                2670

Gln Val Met Ala Asp Val Val Asp Asn Gln Val Tyr Asn Leu Pro
2675                2680                2685

Asp Gln Glu Val Val Ser Ala Ser Arg Ala Gly Val Tyr Gly Asn
2690                2695                2700

Asp Val Ala Thr Gly Phe Asp Thr Gln Leu Tyr Ala Val Asn Ser
2705                2710                2715

Val Gly Gly Gly Lys Tyr Gln Ala Gln Tyr Gly Gly Gln Tyr Leu
2720                2725                2730

Ser Glu Leu Lys Asn Lys Tyr Pro Asp Leu Phe Glu Ala Lys Ala
```

```
                     2735                2740                2745
Tyr Asp Tyr Trp Thr Lys Asn Tyr Ala Asn Asp Gly Ser Asn Pro
    2750                2755                2760

Tyr Tyr Thr Leu Ser Gln Gln Thr Arg Asp Asp Ile Pro Ser Asp
    2765                2770                2775

Glu Lys Ile Lys Gln Trp Ser Ala Lys Tyr Met Asn Gly Thr Asn
    2780                2785                2790

Val Leu Gly His Gly Met Gly Tyr Val Leu Lys Asp Trp Asn Thr
    2795                2800                2805

Gly Gln Tyr Phe Lys Ile Asn Lys Asp Gly Asp Ser Asn Leu Pro
    2810                2815                2820

Val

<210> SEQ ID NO 13
<211> LENGTH: 2771
<212> TYPE: PRT
<213> ORGANISM: Leuconostoc mesenteroides

<400> SEQUENCE: 13

Met Thr Ala Gly Ile Phe Ser Ala Val Ile Phe Gly Val Ser Thr Thr
1               5                   10                  15

Asn Val Ser Ala Asp Ser Thr Asn Asn Thr Gly Val Thr Val Ser Gln
            20                  25                  30

Ala Thr Asp Lys Val Ala Asp Thr Ala Thr Thr Asp Lys Val Ala
        35                  40                  45

Asp Thr Thr Ala Thr Thr Asp Lys Val Ala Asp Thr Ala Ala Thr
    50                  55                  60

Asp Lys Val Ala Asp Thr Thr Ala Thr Asp Lys Val Ala Asp Thr
65                  70                  75                  80

Ala Ala Thr Thr Asp Lys Val Ala Asp Thr Ala Thr Thr Asp Lys
                85                  90                  95

Val Ala Asp Thr Ala Ala Ala Thr Asp Lys Ala Ala Asp Thr Ala Ala
            100                 105                 110

Thr Thr Asp Lys Val Ala Asp Thr Ala Ala Thr Asp Lys Val Ala
        115                 120                 125

Asp Thr Val Ala Ala Thr Asp Lys Val Ala Asp Thr Thr Ala Thr Thr
    130                 135                 140

Asp Lys Ala Ala Asp Thr Ala Ala Thr Thr Asp Lys Val Thr Asp Thr
145                 150                 155                 160

Thr Ala Thr Asp Lys Ala Ala Asp Thr Thr Ala Thr Thr Asp Lys
                165                 170                 175

Val Ala Asp Thr Thr Ala Thr Thr Ser Glu Lys Ser Lys Ser Ile Lys
            180                 185                 190

Gln Ile Asp Gly Lys Thr Tyr Phe Ile Gly Asn Asp Gly Gln Pro Lys
        195                 200                 205

Lys Asn Phe Thr Ala Ile Val Asp Gly Gln Val Leu Tyr Phe Asp Lys
    210                 215                 220

Asp Thr Gly Ala Leu Thr Ser Asn Ser Ser Gln Tyr Thr Asp Gly Leu
225                 230                 235                 240

Ala Asn Ile Gly Asn Glu His Asn Ala Ala Tyr Ser Leu Ser Ser Asp
                245                 250                 255

Ser Phe Thr Gln Val Asp Gly Tyr Leu Thr Ala Asn Ser Trp Tyr Arg
            260                 265                 270

Pro Lys Asp Ile Leu Lys Asn Gly Thr Thr Trp Thr Ala Ala Thr Ala
```

-continued

```
            275                 280                 285
Asn Asp Phe Arg Pro Leu Leu Met Ser Trp Trp Pro Asp Lys Asp Thr
290                 295                 300
Gln Val Ser Tyr Leu Lys Tyr Met Gln Ser Ala Gly Leu Leu Ser Asp
305                 310                 315                 320
Asp Val Ala Leu Ser Asn Asp Ser Met Asn Ser Leu Thr Asp Thr
                325                 330                 335
Ala Met Thr Val Gln Lys Lys Ile Glu Glu Lys Ile Gly Leu Leu Gly
                340                 345                 350
Ser Thr Asp Trp Leu Lys Ala Asp Met Asn Gln Met Val Asp Ser Gln
                355                 360                 365
Ser Asn Trp Asn Ile Ser Ser Glu Ser Lys Gly Thr Asp His Leu Gln
370                 375                 380
Gly Gly Ala Leu Leu Tyr Val Asn Ser Asp Leu Thr Pro Asn Ala Asn
385                 390                 395                 400
Ser Asp Tyr Arg Leu Leu Asn Arg Thr Pro Thr Asn Gln Lys Gly Gln
                405                 410                 415
Ile Thr Thr Asn Gly Asn Gln Gly Gly Tyr Glu Met Leu Leu Ala Asn
                420                 425                 430
Asp Val Asp Asn Ser Asn Pro Ile Val Gln Ala Glu Gln Leu Asn Trp
                435                 440                 445
Leu Tyr Tyr Met Met Asn Ile Gly Ser Ile Ala Gln Asn Asp Pro Thr
450                 455                 460
Ala Asn Phe Asp Gly Tyr Arg Val Asp Ala Val Asp Asn Val Asn Ala
465                 470                 475                 480
Asp Leu Leu Gln Ile Ala Gly Asp Tyr Phe Lys Ala Ala Tyr Gly Thr
                485                 490                 495
Asn Gln Ser Asp Ala Asn Ala Asn His Ile Ser Ile Leu Glu Asp
                500                 505                 510
Trp Asp Asn Asn Asp Pro Ala Tyr Val Lys Ala Gln Gly Asn Asn Gln
                515                 520                 525
Leu Thr Met Asp Phe Pro Met His Leu Ala Leu Lys Tyr Ser Leu Asn
530                 535                 540
Met Pro Ser Ser Ala Arg Ser Gly Leu Glu Pro Ala Ile Ser Thr Ser
545                 550                 555                 560
Leu Val Asn Arg Ala Ala Asp Ala Thr Glu Asn Glu Ala Gln Pro Asn
                565                 570                 575
Tyr Ser Phe Ile Arg Ala His Asp Ser Glu Val Gln Thr Val Ile Ala
                580                 585                 590
Gln Ile Ile Lys Asp Lys Ile Asn Pro Ser Ser Asp Gly Leu Thr Val
                595                 600                 605
Ser Thr Asp Glu Ile Ala Lys Ala Phe Glu Ile Tyr Asn Ala Asp Glu
610                 615                 620
Leu Lys Ala Asp Lys Glu Tyr Thr Ala Tyr Asn Ile Pro Ser Ser Tyr
625                 630                 635                 640
Ala Leu Met Leu Thr Asn Lys Asp Thr Ile Pro Arg Val Tyr Tyr Gly
                645                 650                 655
Asp Leu Phe Thr Asp Asp Gly Gln Tyr Met Ser Ala Lys Ser Pro Tyr
                660                 665                 670
Tyr Asp Ala Leu Thr Ser Leu Leu Gln Ser Arg Val Lys Tyr Val Ser
                675                 680                 685
Gly Gly Gln Ser Met Asn Met Thr Tyr Leu His Asn Asn Gln Gly Leu
                690                 695                 700
```

-continued

Leu Thr Ser Val Arg Tyr Gly Lys Asp Ala Met Thr Ala Asn Asp Thr
705                 710                 715                 720

Gly Thr Ser Glu Thr Arg Thr Gln Gly Ile Gly Leu Ile Val Gly Asn
            725                 730                 735

Lys Thr Asp Leu Asn Leu Asn Asn Asp Glu Gln Ile Val Leu Asn Met
        740                 745                 750

Gly Ala Ala His Lys Asn Gln Ala Tyr Arg Ala Leu Met Leu Ser Thr
            755                 760                 765

Lys Asp Gly Leu Lys Ile Tyr Asn Asn Asp Asp Glu Ala Pro Val Ser
        770                 775                 780

Tyr Thr Asp Asp Gln Gly Arg Leu Ile Phe Lys Ser Asp Val Val Tyr
785                 790                 795                 800

Gly Val Ser Asp Ala Gln Val Ser Gly Tyr Leu Ala Ala Trp Val Pro
                805                 810                 815

Val Gly Ala Asn Asp Ser Gln Asp Ala Arg Thr Glu Ser Ser Thr Thr
            820                 825                 830

Ala Ser Thr Asp Gly Asn Thr Tyr His Ser Asn Ser Ala Leu Asp Ser
            835                 840                 845

Gln Leu Ile Tyr Glu Gly Phe Ser Asn Phe Gln Ala Met Pro Thr Gln
850                 855                 860

Ala Asp Glu Tyr Thr Asn Ile Lys Ile Ala Glu Asn Ala Gln Leu Phe
865                 870                 875                 880

Lys Ser Leu Gly Ile Thr Ser Phe Glu Leu Ala Pro Gln Tyr Arg Ser
                885                 890                 895

Ser Thr Asp Asn Ser Phe Leu Asp Ser Val Ile Gln Asn Gly Tyr Ala
            900                 905                 910

Phe Thr Asp Arg Tyr Asp Ile Gly Tyr Asn Thr Pro Thr Lys Tyr Gly
            915                 920                 925

Thr Val Asp Gln Leu Leu Asp Ala Leu Arg Ala Leu His Ala Gln Gly
    930                 935                 940

Ile Gln Ala Ile Asn Asp Trp Val Pro Asp Gln Ile Tyr Asn Leu Pro
945                 950                 955                 960

Gly Glu Glu Ile Val Thr Ala Ser Arg Thr Asn Gly Ser Gly Lys Val
                965                 970                 975

Asn Glu Ser Ser Val Ile Asn Asn Thr Leu Tyr Asp Ser Arg Thr Val
            980                 985                 990

Gly Gly Gly Glu Tyr Gln Ala Ile Tyr Gly Gly Ala Phe Leu Asp Lys
        995                 1000                1005

Leu Lys Gln Asp Tyr Pro Glu Leu Phe Glu Thr Lys Gln Ile Ser
    1010                1015                1020

Thr Gly Glu Ala Met Asn Pro Asp Val Lys Ile Thr Glu Trp Ser
    1025                1030                1035

Ala Lys Tyr Phe Asn Gly Ser Asn Ile Gln Gly Arg Gly Ala Trp
    1040                1045                1050

Tyr Val Leu Lys Asp Trp Ser Thr Asn Gln Tyr Phe Asn Val Ser
    1055                1060                1065

Ser Gly Ser Glu Phe Leu Pro Lys Gln Leu Leu Gly Glu Lys Thr
    1070                1075                1080

Ser Thr Gly Phe Thr Asn Val Asp Asn Gly Lys Thr Glu Phe Tyr
    1085                1090                1095

Ser Thr Ser Gly Tyr Gln Ala Lys Asn Thr Phe Ile Gln Asp Asn
    1100                1105                1110

```
Asp Asn Trp Tyr Tyr Phe Asp Asn Asp Gly Tyr Met Val Val Gly
    1115                1120                1125

Gly Gln Glu Ile Asn Gly Lys Lys Tyr Tyr Phe Leu Pro Asn Gly
    1130                1135                1140

Val Glu Leu Gln Asp Ala Tyr Leu Ser Asp Gly Thr Ser Glu Tyr
    1145                1150                1155

Tyr Tyr Ser Ser Asp Gly Arg Gln Ile Ser Asn Gln Tyr Tyr Gln
    1160                1165                1170

Gly Ser Asp Asn Asn Trp Arg Tyr Phe Phe Ala Asp Gly His Met
    1175                1180                1185

Ala Val Gly Leu Ala Thr Ile Thr Thr Glu Asn Gly Thr Thr Asn
    1190                1195                1200

Gln Gln Tyr Phe Asp Ala Asn Gly Val Gln Leu Lys Gly Val Ala
    1205                1210                1215

Ile Lys Asp Thr Asp Gly Asn Val His Tyr Phe Asp Gly Lys Thr
    1220                1225                1230

Gly Asn Met Val Ile Asn Ser Trp Gly Lys Ile Ser Asp Gly Ser
    1235                1240                1245

Trp Leu Tyr Leu Asn Asp Ser Gly Val Ala Val Thr Gly Pro Gln
    1250                1255                1260

Asn Ile Asn Gly Gln Asn Leu Tyr Phe Asn Glu Asp Gly Ile Gln
    1265                1270                1275

Val Lys Gly Glu Ala Ile Thr Asp Asn Ser Gly Asn Ile His Tyr
    1280                1285                1290

Tyr Asp Arg Ser Thr Gly Asn Met Val Val Asn Ser Trp Gly Glu
    1295                1300                1305

Thr Asn Asn Gly Ser Trp Leu Tyr Leu Asn Asp Lys Gly Asp Ala
    1310                1315                1320

Val Thr Gly Glu Gln Val Ile Asp Gly Gln Lys Leu Tyr Phe Ser
    1325                1330                1335

Ser Asn Gly Ile Gln Leu Lys Asn Thr Phe Lys Lys Leu Ser Asp
    1340                1345                1350

Gly Ser Trp Leu Tyr Leu Asn Asp Lys Gly Leu Pro Val Thr Gly
    1355                1360                1365

Ala Gln Val Ile Asp Gly Gln Asn Leu Tyr Phe Asp Gln Asp Gly
    1370                1375                1380

Lys Gln Val Lys Gly Asp Val Ala Thr Asp Gly Gln Gly Asn Thr
    1385                1390                1395

His Tyr Tyr Asp Gly Asn Thr Gly Asn Met Val Thr Asn Ser Trp
    1400                1405                1410

Ala Glu Leu Pro Asp Gly Ser Trp Met Tyr Leu Asp Asn Asp Gly
    1415                1420                1425

Asn Pro Leu Thr Gly Gln Gln Lys Ile Asp Gly Gln Ser Leu Tyr
    1430                1435                1440

Phe Asn Asp Ala Gly Lys Gln Ile Lys Asn Ala Leu Val Lys Leu
    1445                1450                1455

Asp Asp Gly Ser Thr Ile Tyr Leu Asp Asp Lys Gly Val Ser Ser
    1460                1465                1470

Thr Gly Ile Gln Arg Ile Asp Asp Lys Ile Tyr Tyr Phe Asp Pro
    1475                1480                1485

Asp Gly Lys Gln Val Val Cys Arg Phe Glu Glu Leu Pro Asp Gly
    1490                1495                1500

Ser Trp Met Tyr Leu Asp Asp Asp Gly Val Ala Ala Thr Gly Ala
```

```
              1505                1510                1515

Gln Lys Ile Asn Gly Gln Glu Leu Tyr Phe Asp Asn Ser Gly Lys
              1520                1525                1530

Gln Val Lys Asn Asp Lys Val Ile Asn Asp Asp Gly Thr Ile Asn
              1535                1540                1545

Tyr Tyr Thr Gly Met Ser Gly Glu Lys Leu Lys Asn Asp Phe Gly
              1550                1555                1560

Glu Leu Pro Asp Gly Ser Trp Met Tyr Leu Asp Asn Gln Gly Asn
              1565                1570                1575

Ala Val Ile Gly Ala Gln Lys Ile Asn Gly Gln Asn Leu Tyr Phe
              1580                1585                1590

Lys Thr Asp Gly Arg Gln Val Lys Gly Glu Ala Asn Val Asp Ser
              1595                1600                1605

Ser Gly Glu Met His Phe Tyr Asp Pro Asp Ser Gly Glu Leu Ile
              1610                1615                1620

Thr Asn Arg Phe Glu Gln Val Ala Ser Gly Val Trp Ala Tyr Phe
              1625                1630                1635

Asp Ala Lys Gly Val Ala Val Thr Gly Glu Gln Arg Ile Gly Lys
              1640                1645                1650

Gln Asn Leu Phe Phe Asp Pro Thr Gly Tyr Gln Val Lys Gly Asp
              1655                1660                1665

Lys Arg Thr Ile Asp Gly Val Leu Tyr Thr Phe Asp Lys Glu Ser
              1670                1675                1680

Gly Glu Arg Lys Gly Leu Asp Ser Ile Ser Val Leu Pro Thr Asn
              1685                1690                1695

Gly Gln Tyr Thr Thr Asp Lys Ala Gln Asn Trp Tyr Tyr Gln Val
              1700                1705                1710

Asp Gly Glu Asn Val Lys Gly Leu Tyr Thr Asn Asn Asp Gly Gln
              1715                1720                1725

Leu Arg Tyr Phe Asp Leu Thr Thr Gly Val Gln Thr Lys Gly Asn
              1730                1735                1740

Phe Val Thr Ile Gly Asn Asp Thr Tyr Tyr Phe Thr Lys Glu Gln
              1745                1750                1755

Gly Asp Gly Gln Ile Val Ser Glu Val Val Ser Gly His Tyr Gly
              1760                1765                1770

Thr Val Gln Leu Ser Asp Asn Ser Ser Ala Trp Val Tyr Arg Gly
              1775                1780                1785

Ala Asn Asp Gln Ile Leu Lys Gly Leu Gln Asn Ile Asn Gly Arg
              1790                1795                1800

Leu Gln Tyr Phe Asp Leu Thr Thr Gly Ala Gln Leu Lys Gly Gly
              1805                1810                1815

Ala Ala Asn Tyr Asp Gly Asn Leu Tyr Tyr Phe Glu Ser Ser Asp
              1820                1825                1830

Gly Asn Leu Val Ser Lys Ile Gln Gln Ser Tyr Ser Thr Gly Asn
              1835                1840                1845

Tyr Val Thr Asp Gly Asp Lys Val Thr Tyr Ala Asp Glu Gln Asn
              1850                1855                1860

Asn Gln Val Thr Gly Leu Ala Leu Ile Asp Asp Gln Leu Gln Tyr
              1865                1870                1875

Phe Asp Pro Ser Asp Gly Arg Gln Val Lys Asn Glu Gln Val Ile
              1880                1885                1890

Val Asp Gly Val Thr Tyr Tyr Phe Asp Lys Asn Gly Asn Gly Gln
              1895                1900                1905
```

```
Tyr Leu Phe Thr Asn Thr Ala Thr Met Ser Thr Asn Glu Phe Ala
    1910            1915            1920

Lys His Ser Ala Ala Tyr Ser Asn Asp Ser Ser Ser Phe Lys Asn
    1925            1930            1935

Thr Ile Asp Gly Phe Leu Thr Ala Asp Thr Trp Tyr Arg Pro Lys
    1940            1945            1950

Asp Ile Leu Glu Asn Gly Gln Thr Trp Val Val Ser Ser Thr Asn
    1955            1960            1965

Asp Val Arg Pro Leu Ile Thr Val Trp Trp Leu Asn Lys Asp Val
    1970            1975            1980

Gln Val Asn Tyr Ser Asn Phe Met Lys Gln Asn Gly Leu Leu Asp
    1985            1990            1995

Thr Ser Ser Gln Phe Asn Leu Gln Ser Asp Gln Tyr Asp Leu Asn
    2000            2005            2010

Val Ala Ala Gln Lys Val Gln Val Ala Ile Glu Lys Arg Ile Ser
    2015            2020            2025

Lys Glu Lys Ser Thr Asp Trp Leu Lys Asp Leu Leu Phe Glu Ala
    2030            2035            2040

His Glu Asp Thr Pro Ser Phe Val Lys Gln Gln Phe Ile Trp Asn
    2045            2050            2055

Lys Asp Ser Glu Tyr Gln Gly Gln Gly Asp Ala Trp Phe Gln Gly
    2060            2065            2070

Gly Tyr Leu Lys Tyr Gly Asn Asn Glu Leu Thr Pro Thr Thr Asn
    2075            2080            2085

Ser Asp Tyr Arg Glu Ser Gly Asn Thr Leu Asp Phe Leu Leu Ala
    2090            2095            2100

Asn Asp Val Asp Asn Ser Asn Pro Ala Val Gln Ala Glu Asn Leu
    2105            2110            2115

Asn Trp Leu His Tyr Leu Met Asn Phe Gly Thr Ile Thr Ala Asn
    2120            2125            2130

Asp Asp Asp Ala Asn Phe Asp Ser Ile Arg Ile Asp Ala Val Asp
    2135            2140            2145

Phe Ile Asp Asn Asp Ala Ile Gln Arg Thr Tyr Asp Tyr Met Arg
    2150            2155            2160

Asp Ala Tyr Lys Val Asp Ala Ser Glu Asp Asn Ala Asn Lys His
    2165            2170            2175

Ile Ser Leu Val Glu Ala Gly Leu Asp Ala Gly Thr Ser Thr Ile
    2180            2185            2190

Lys Ser Asp Ala Leu Val Glu Ser Asn Phe Arg Glu Ala Ala Thr
    2195            2200            2205

Leu Ser Leu Ala Asn Gln Ser Gly Glu Asn Ser Ser Leu Thr Asn
    2210            2215            2220

Met Leu Gln Asp Ile Asp Gly Gly Gln Ile Ile Ala Asp His Ala
    2225            2230            2235

Asn Asn Ala Thr Glu Asn Glu Ser Thr Pro Asn Tyr Ser Ile Ile
    2240            2245            2250

His Ala His Asp Lys Gly Ile Gln Glu Lys Val Gly Ala Ala Ile
    2255            2260            2265

Thr Asp Val Thr Gly Ala Asp Trp Thr Asn Phe Thr Asp Asp Gln
    2270            2275            2280

Leu Lys Glu Gly Leu Ala Ala Tyr Tyr Gln Asp Gln Arg Ser Thr
    2285            2290            2295
```

-continued

| | | | | | | | | | | | |
|---|---|---|---|---|---|---|---|---|---|---|---|
| Asn | Lys | Lys | Tyr | Asn | Ile | Tyr | Asn | Leu | Pro | Ser | Ile | Tyr | Ala | Leu |
| | 2300 | | | | 2305 | | | | 2310 | | |

Asn Lys Lys Tyr Asn Ile Tyr Asn Leu Pro Ser Ile Tyr Ala Leu
    2300                2305              2310

Met Leu Thr Asn Lys Asp Thr Val Pro Arg Val Tyr Tyr Gly Asp
    2315                2320              2325

Met Tyr Gln Asp Asp Gly Gln Tyr Met Glu Lys Gln Ser Ile Tyr
    2330                2335              2340

Tyr Asp Ala Ile Val Ser Leu Met Asn Thr Arg Lys Ser Tyr Val
    2345                2350              2355

Ser Gly Gly Gln Thr Met Asp Val Asp Glu His Gly Leu Leu Lys
    2360                2365              2370

Ser Val Arg Phe Gly Lys Asp Ala Met Thr Ala Ser Asp Leu Gly
    2375                2380              2385

Thr Asn Glu Thr Arg Thr Glu Gly Val Gly Val Leu Val Gly Asn
    2390                2395              2400

Asp Ser Ser Leu Lys Leu Asn Asp Ser Asp Thr Val Thr Leu Glu
    2405                2410              2415

Met Gly Ala Ala His Lys Asn Gln Lys Tyr Arg Ala Ala Leu Leu
    2420                2425              2430

Thr Thr Ser Asp Gly Ile Val Thr Tyr Asp Ala Asp Asn Asp Ala
    2435                2440              2445

Pro Thr Ile Trp Thr Asp Asp Arg Gly Thr Leu Thr Phe Ser Asn
    2450                2455              2460

Lys Glu Ile Ala Gly Gln Asp Tyr Thr Ser Val Gln Gly Phe Ala
    2465                2470              2475

Asn Ser Gln Val Ser Gly Tyr Leu Ala Val Trp Val Pro Val Gly
    2480                2485              2490

Ala Ser Asp Asp Gln Asp Val Arg Thr Ala Ala Leu Thr Asp Ala
    2495                2500              2505

Asn Leu Asp Asp Lys Val Leu His Ser Asn Ala Ala Leu Asp Ser
    2510                2515              2520

Asn Leu Ile Tyr Glu Gly Phe Ser Asn Phe Gln Pro Lys Ala Thr
    2525                2530              2535

Thr Asn Asp Glu Leu Thr Asn Val Val Ile Ala Lys Asn Ala Asn
    2540                2545              2550

Leu Phe Glu Lys Trp Gly Ile Thr Ser Phe Glu Met Ala Pro Gln
    2555                2560              2565

Tyr Arg Ser Ser Gly Asp His Thr Phe Leu Asp Ser Thr Ile Asp
    2570                2575              2580

Asn Gly Tyr Ala Phe Thr Asp Arg Tyr Asp Leu Gly Phe Glu Thr
    2585                2590              2595

Pro Thr Lys Tyr Gly Thr Asp Lys Asp Leu Arg Thr Ala Ile Lys
    2600                2605              2610

Ala Leu His Gln Ser Asn Met Gln Val Met Ala Asp Val Val Asp
    2615                2620              2625

Asn Gln Val Tyr Asn Leu Ser Gly Gln Glu Val Val Ser Ala Ser
    2630                2635              2640

Arg Ala Gly Val Tyr Gly Asn Asp Val Ser Thr Gly Phe Gly Thr
    2645                2650              2655

Gln Leu Tyr Ala Val Asn Ser Val Gly Gly Gly Lys Tyr Gln Ala
    2660                2665              2670

Gln Tyr Gly Gly Glu Tyr Leu Asn Glu Leu Lys Gln Gln Tyr Pro
    2675                2680              2685

Asp Leu Phe Glu Ala Lys Thr Tyr Asp Tyr Trp Val Lys Asn Tyr

```
                2690                2695                2700
Ser Asn Asp Gly Ser Asp Pro Tyr Tyr Thr Leu Ser Gln Asn Thr
    2705                2710                2715

Arg Lys Asp Met Pro Ser Ser Glu Val Ile Lys Gln Trp Ser Ala
    2720                2725                2730

Lys Tyr Met Asn Gly Thr Asn Val Leu Gly Asn Gly Met Gly Tyr
    2735                2740                2745

Val Leu Lys Asp Trp Asn Thr Gly Glu Tyr Phe Lys Ile Gly Glu
    2750                2755                2760

Lys Asn Ala Asp Phe Ile Thr Asn
    2765                2770

<210> SEQ ID NO 14
<211> LENGTH: 8316
<212> TYPE: DNA
<213> ORGANISM: Leuconostoc mesenteroides

<400> SEQUENCE: 14
gtgacagccg gtattttttc tgctgtgata tttggcgttt ccacaactaa cgtaagcgct      60
gatagcacta acaacactgg tgttacggtg tcacaagcaa cagataaagt agcagacacg     120
acggctacaa cggacaaagt agcggacaca acagctacaa cagataaagt ggccgacaca     180
gcagctacaa cggacaaagt agcggacaca acagctacaa cagataaagt ggccgacaca     240
gcagctacaa cggacaaagt agcggacaca acagctacaa cagataaagt ggccgacaca     300
gcagctgcaa cagataaagc agccgataca gcggctacaa cggataaagt ggccgacaca     360
gcagctgcaa cggataaagt agcggacaca gtagctgcaa cggacaaagt agcggacaca     420
acagctacaa cagataaagc agccgataca gcggctacaa cggataaagt aaccgacaca     480
acagctgcaa cggataaagc agcggacacg acggctacaa cagataaagt ggccgacaca     540
acagccacaa catcagaaaa atcaaaaagt attaaacaaa ttgatggtaa aacttatttc     600
attggtaatg atggtcagcc taagaaaaat tttacagcca ttgttgacgg tcaagtatta     660
tatttcgaca aagatactgg tgcttttgaca tcaaatagta gtcaatatac cgatggttta     720
gccaatatag gaaatgagca taatgcggct tattcattgt cttcggatag ttttacacaa     780
gttgatggct atctaacggc taacagttgg taccgaccta agatatatt aaaaaatggt     840 acaacttgga cggctgcaac agcaaacgat tttcgaccat tgttaatgtc ttggtggcca     900
gataaagata cccaagtttc atacttaaaa tatatgcaat ctgcgggatt attatcagat    960
gacgttgcat tatcaaacaa tgatagtatg aacagtttga cggatacggc tatgactgtt   1020
caaaaaaaaa ttgaagaaaa aattggctta ttgggcagta ctgactggct taaggccgat   1080
atgaaccaaa tggttgattc acaatcgaat tggaacatta gtagtgagtc taaaggaaca   1140
gatcatttgc aaggtggtgc gctcctatac gttaatagtg atttaacacc aaatgccaat   1200
tctgattatc gtttattaaa tcgaacgcca actaaccaaa aagtcaaat acaacaaat    1260 ggtaatcaag gtggctatga tgctgttg gccaacgatg ttgataattc aacccaatt    1320 gttcaagctg aacaattaaa ttggttatac tacatgatga atatcggtag catcgcccaa   1380
aatgatccaa cagcaaattt tgacggttac agagttgatg ctgttgataa cgtgaatgct   1440
gacttgttgc aaattgctgg agattatttt aaagcagcat atggaacaaa tcaaagtgac   1500
gctaatgcaa acaatcacat ttccatctta gaagactggg acaataatga tccagcgtat   1560
gtaaaagcac agggggaacaa ccaattaacc atggattttc caatgcattt ggcattgaag   1620
```

```
tattcattga atatgccaag tagtgctcgt agcggtttgg aaccagcaat ttcaacaagc    1680
ctagtaaatc gtgcagcaga cgccacagaa aatgaagccc aaccgaacta ttcattattt    1740
cgtgcacatg atagtgaagt acaaacggtt attgctcaaa ttattaaaga taaaattaat    1800
cctagttccg atggattgac tgtctcaaca gatgaaattg ccaaagcatt cgaaatatat    1860
aatgctgacg aattaaaggc tgataaagag tataccgcat ataatatacc ctcatcatat    1920
gcattgatgt taactaacaa agatacaatt cctcgtgtgt attatggtga tttgtttacg    1980
gatgatggac aatatatgtc tgcaaaatca ccatattatg atgcacttac ttcattgctt    2040
caatcgcgag taaatatatgt ttcaggtggt caatctatga atatgactta ccttcataat    2100
aatcaaggcc ttttgacgtc agtccgctat ggaaaagacg ccatgacagc taacgacact    2160
ggtacaagtg aaacgcgcac acaaggtatt ggattaattg tcggcaacaa aactgattta    2220
aacctgaata atgatgagca aattgtactt aacatggggg ccgcacacaa aaatcaagct    2280
taccgtgcat taatgttaag tactaaagat ggcttgaaaa tttataataa tgatgacgag    2340
gcaccggtat cgtatacaga tgaccaaggc cgtttgattt taaatctga tgtggtttat    2400
ggtgtgagtg atgctcaggt ttctggttat ttagcagctt gggtgccagt cggtgcaaac    2460
gatagccaag atgctagaac agaaagtagt acaacagcgt caacagatgg taataccgat    2520
cattcaaata gtgccttaga ttctcaactt atatatgaag cttttcaaa cttccaagcc    2580
atgccaacac aggccgatga gtataccaat atcaagattc cgaaaatgc acaattattc    2640
aagagccttg ggataacaag ctttgaattg gcacctcaat accgttcaag tacggataac    2700
agtttcttag attcagttat tcaaaatggc tatgccttca cggatcgcta cgacattggt    2760
tataatacgc ctacaaagta cggtacagtt gaccaactat tagatgcttt aagagcattg    2820
catgctcaag gcattcaggc tatcaatgat tgggtcccag accaaattta taatttgcct    2880
ggggaagaaa tagtgacagc cagtcgaaca aacggttcgg gaaaggtgaa tgaaagttca    2940
gttattaata atacgctata tgattctcgt actgttggtg gcggagagta tcaagcaata    3000
tatggaggtg ctttcttaga taagttaaaa caagattatc ctgagttatt tgaaacaaaa    3060
caaatttcaa caggtgaagc aatgaaccct gatgtcaaaa tcacagaatg gtcagctaag    3120
tattttaatg gctcaaacat tcaaggacgt ggtgcatggt atgttctcaa ggattggtca    3180
acaaatcaat actttaatgt ttcaagtggt agtgaatttt tacctaagca actgttaggc    3240
gaaaaacaa gtacagggtt taccaacgtg acaatggca agactgagtt ttattctacg    3300
agtggctacc aagcaaagaa tacatttatt caagataatg acaattggta ttatttttgat    3360
aatgatggct atatggttgt tggcggtcaa gaaattaatg gtaaaaaata ttatttccta    3420
ccaaatggtg tagagttaca agatgcttat ttgtctgatg ggactagtga gtattactac    3480
agtagtgatg gtcgtcaaat ttctaatcaa tattatcaag gatcagacaa caactggcgt    3540
tatttctttg cagatggtca tatggctgta gggttagcaa caattactac agaaaatggt    3600
acaacaaatc aacaatattt cgatgcaaat ggtgtgcaac ttaagggcgt agctataaag    3660
gatactgatg gcaatgtgca ctattttgat ggcaagacag gaaacatggt tataaattcc    3720
tgggtaaaa taagcgatgg ttcatggtta tacttaaatg atagcggtgt agcggtcaca    3780
ggaccgcaaa atattaacgg ccaaaatctt tacttcaacg aagacggtat tcaagtaaag    3840
ggtgaagcca ttactgataa tagtggaaac atacattatt atgatcgcag cacaggaaat    3900
atggttgtga actcatgggg tgaaacgaat aatggttcat ggctatactt gaacgacaag    3960
ggtgatgccg ttacaggaga acaagttatt gacggtcaaa aactatattt cagtagtaat    4020
```

```
ggaatccaac ttaaaaatac attcaagaag ctatccgatg gttcatggct atatttgaac   4080
gataaaggtc ttccagtgac aggagcacag gtcattgatg acaaaacttt gtatttcgac   4140
caagatggga agcaagtcaa gggtgacgtt gctacagatg gacaaggtaa cactcattat   4200
tatgatggca acacaggaaa tatggttact aattcatggg cagagttacc ggacggttca   4260
tggatgtatc tagacaatga tggcaatcct ttaacaggac agcaaaagat tgatggccag   4320
tcactctact ttaatgatgc tggtaagcaa atcaaaaacg cattggttaa actagatgat   4380
gggtcaacaa tttacctcga tgataaaggt gtttcatcaa ctggtattca agaattgat    4440 gataagatat attattttga tcctgatggt aaacaagtag tatgtcgttt tgaagaatta   4500
ccagatggtt catggatgta tctagatgat gacggtgttg ctgctacggg cgctcaaaaa   4560
attaatggcc aggaattata tttcgacaat agcgggaaac aagtcaagaa cgacaaagta   4620
attaatgacg atggaacaat aaactattac acaggtatga gcggtgaaaa actaaaaaat   4680
gattttggtg aattaccaga cggttcatgg atgtacttgg ataatcaagg taatgctgta   4740
ataggtgccc aaaaaattaa tggccagaat ctttacttca agacagacgg acgacaggtt   4800
aagggtgaag caaatgttga ttcatcaggt gaaatgcact tctatgatcc tgattctggc   4860
gagctaatta caaatagatt tgaacaagtt gctagtggtg tatgggctta ctttgatgcc   4920
aaaggtgttg ctgtaactgg tgagcaacgc attggtaagc aaaatttatt ttttgatcca   4980
actggttatc aagttaaagg cgacaaacga acaattgacg gcgttctcta tacctttgat   5040
aaagaaagtg gtgagagaaa gggttttagat tctatatcgg tattacccac caatggacaa   5100
tacacaaccg ataaggccca aaattggtat taccaagtcg atggtgaaaa tgtaaaaggg   5160
ctatatacaa ataatgatgg tcaattacgt tacttcgatt tgacaactgg cgtgcagact   5220
aaaggtaatt ttgtgacaat tggcaatgat acctactatt tcaccaagga acaaggggat   5280
ggacagatag tttctgaggt tgtgtcagga cactatggta ctgtccagtt gagtgacaat   5340
tcgtctgcat gggtttatcg cggtgcaaat gatcaaattt tgaaaggcct acagaatata   5400
aacggtcgtc tgcaatattt tgatctaacc accggtgcgc aattaaaagg cggtgctgca   5460
aactatgatg gcaaccttta ttattttgaa tcatcagatg gtaacctagt cagtaaaatt   5520
cagcaatctt attctactgg gaattatgtg accgatggtg ataaagtaac atatgctgat   5580
gagcaaaaca ccaagtcac gggattagcg ttgattgatg atcaactaca atacttcgat   5640
ccaagtgacg gtcgtcaagt caagaatgag caggttatcg ttgatggcgt cacatactac   5700
tttgataaaa atggtaatgg acaatacttg tttacaaata ctgcaacgat gtcaactaat   5760
gaatttgcca acatagtgc tgcttatagc aatgatagtt ctagcttcaa gaatacgata   5820
gatggtttct tgacggccga tacctggtat cgccctaaag atatcttgga aaacggacaa   5880
acgtgggtag tttcttcaac aaatgacgtg cgaccactga taacagtttg gtggctaaat   5940
aaagatgttc aagttaatta ttcaaatttt atgaagcaaa atggtttgct agatacaagt   6000
agtcaattta atctacaatc tgatcaatat gacttgaatg tcgccgcgca aaaagttcaa   6060
gtggctattg aaaacgcat ttcgaaagaa aagagtacag attggttgaa agatcttttg   6120
tttgaagctc atgaagatac gccttcattt gtgaacaac aatttatttg gaataaagat   6180
tctgaatatc aaggtcaagg ggatgcgtgg ttccaaggtg gttatctgaa atatggtaac   6240
aatgaattaa ccccaacaac gaactcagat tatcgtgaat ccggtaatac attagacttc   6300
ttgcttgcta atgatgtcga caattctaac ccagcggttc aagctgaaaa tttgaattgg   6360
```

| | |
|---|---|
| ttacattatt taatgaactt tggcacgatt acagctaatg atgatgatgc taattttgac | 6420 |
| agtattcgta ttgatgccgt tgactttatt gataatgatg ccattcagag aacctacgat | 6480 |
| tacatgcgtg atgcttataa agttgatgca agtgaagaca acgctaataa gcatatttca | 6540 |
| ctagtggaag ctggattaga tgctggtacc tctacaatta agagtgatgc tttagttgaa | 6600 |
| tctaacttta gagaggcagc tacactatcg ctagcaaatc aatcagggga aaatagttcc | 6660 |
| ttgactaata tgttgcaaga cattgatggt ggccagatta tagctgatca cgccaacaat | 6720 |
| gcaacagaaa atgaatcaac gccaaattat tcaattattc atgctcatga taaggggatt | 6780 |
| caagaaaagg ttggtgcagc aattaccgac gttactggtg cagactggac gaatttcacc | 6840 |
| gatgaccaat taaagaagg attagcagct tattatcaag atcaacgttc aacgaataaa | 6900 |
| aagtataaca tctataactt acctagtatc tatgctttaa tgttgaccaa taaggacaca | 6960 |
| gttcctcgtg tttattacgg tgatatgtat caagatgatg ccagtatat ggaaaagcaa | 7020 |
| agtatttatt atgatgccat tgtttccttg atgaacacta gaaagagtta tgtgagtggt | 7080 |
| gggcaaacta tggatgtaga tgaacatggt ttgttgaaga gtgttcgttt tggtaaagac | 7140 |
| gcaatgacag ctagtgaccct tggtacgaat gaaacacgca ctgaaggtgt tggtgtgctg | 7200 |
| gtcggcaatg attcttcact aaaactaaat gattcagata cagttacttt agagatgggg | 7260 |
| gcggctcata aaaccaaaa gtaccgagct gcattgttga caactagtga tggtattgtt | 7320 |
| acgtatgatg ctgataatga tgcaccaaca atctggacag atgaccgtgg tacattgacg | 7380 |
| ttctcaaata aggagattgc tggtcaagat tatactagtg tgcaaggatt cgctaattca | 7440 |
| caagtatcag gttacttagc agtttgggtg cccgtaggag ctagtgacga tcaagatgtc | 7500 |
| cgaacagcag cattaacaga tgcaaatctt gatgacaaag tactgcattc taatgctgca | 7560 |
| ttagattcga acttgattta cgaaggcttt tctaactttc aacctaaagc aaccaccaat | 7620 |
| gatgaattga ctaacgtagt aattgctaaa aatgctaatt tatttgaaaa gtggggaatc | 7680 |
| acaagttttg agatggcacc acaatatcgt tcaagtgggg accacacgtt cttagattca | 7740 |
| acgattgata atggttatgc atttactgac cgatacgatt tgggatttga aacaccaact | 7800 |
| aagtacggta ctgataagga tttgcgtact gcaattaaag cattgcacca atcaaatatg | 7860 |
| caggttatgg ctgatgtagt tgataaccaa gtttataatt tatctggaca ggaggtcgta | 7920 |
| tcagcttcac gtgccggtgt ttacggcaat gatgtgtcaa ctggatttgg gacacaactc | 7980 |
| tatgcggtta atagtgttgg tggtggtaaa tatcaagccc aatacggtgg tgaatatttg | 8040 |
| aatgaattga agcaacaata cccagatttg ttcgaagcta agacgtatga ctattgggtt | 8100 |
| aaaaattatt caaatgacgg atcggatccg tattacacac tgtcgcaaaa cacacgaaaa | 8160 |
| gatatgccaa gtagtgaggt cattaaacaa tggtcagcta aatatatgaa tggtactaat | 8220 |
| gtattaggaa acggtatggg atatgttttg aaagattgga atacaggtga gtatttcaaa | 8280 |
| attggagaaa agaatgctga ttttataaca aattaa | 8316 |

<210> SEQ ID NO 15
<211> LENGTH: 8466
<212> TYPE: DNA
<213> ORGANISM: Leuconostoc mesenteroides

<400> SEQUENCE: 15

| | |
|---|---|
| gtgacagccg gtatttttc tgctgtgata tttggcgttt ccacaactaa cgtaagcgct | 60 |
| gatagcacta acaacactgg tgttacggtg tcacaagcac cagataaagt agcggacaca | 120 |
| acagctacaa cagataaagt agcagacacg acggctacaa cggataaagc agcggacaca | 180 |

```
acagctacaa cagataaagt ggccgacaca gcagctgcaa cggacaaagt agcggacaca    240
acagctacaa cggacaaagt agcggacaca acagctacaa cagataaagt ggccgacaca    300
gcagctgcaa cggacaaagt agcggacaca acagctacaa cagataaagt agcggacaca    360
acagctacaa cggacaaagt agcggacaca acagctacaa cagataaagt agcggacaca    420
gcagctgcaa cggataaagc agcggacacg acggctacaa cagataaagc agcggacacg    480
acggctacaa cagataaagt ggccgacaca gcagctacaa cagataaagc agcggacacg    540
acggctacaa cagataaagt ggccgacaca gcagctacaa cagataaagc agccgataca    600
gcggctacaa cggataaagt aaccgacaca acagttgcaa cgaataaagc agtggacaca    660
acagctacaa cagataaagt ggacgacaca acagccacaa cgtcagaaaa atcaaaaagt    720
attaaacaaa ttgatggtaa aacttatttc attggtgatg atggtcagcc taagaaaaat    780
tttacagcca ttgttgacgg tcaagtatta tatttcgaca aagatactgg tgctttgaca    840
tcaaatagta gtcaatatac cgatggttta gtcaatatag gaaatgagca taatgcggct    900
tattcattgt cttcggatag ttttacacaa gttgatggct atctaacggc taacagttgg    960
taccgaccta aagatatatt aaaaaatggt acaacttgga cggctgcaac agcaaacgat   1020
tttcgaccat tgttaatgtc ttggtggcca gataaagata cccaagtttc atacttaaaa   1080
tatatgcaat ctgcgggatt attatcagat gacgttgcat tatcaaacaa tgatagtatg   1140
aacagtttga cggatacggc tatgactgtt caaaaaaaca ttgaagaaaa aattggccta   1200
ttgggcagta ctgactggct taaggccgat atgaaccaaa tggttgattc acaatcgaat   1260
tggaacatta gtagtgagtc taaaggaaca gatcatttgc aaggtggtgc gctcctatac   1320
gttaatagtg atttaacacc aaatgccaat tctgattatc gtttattaaa tcgaacgcca   1380
actaaccaaa aaggtcaaat tacaacaaat ggtaatcaag gtggctatga gatgctgttg   1440
gccaacgatg ttgataattc taacccaatt gttcaagctg aacaattgaa ttggttatac   1500
tacatgatga atatcggtag catcgcccaa aatgatccaa cagcaaattt tgacggttac   1560
agagttgatg ctgttgataa cgtgaatgct gacttgttgc aaaattgctgg agattatttt   1620 aaagcagcat atggaacaaa tcaaagtgac gctaatgcaa acaatcacat ttccatctta   1680
gaagactggg acaataatga tccagcgtat gtaaaagcac aggggaacaa ccaattaacc   1740
atggattttc caatgcattt ggcattgaag tattcattga atatgccaag tagtgctcgt   1800
agcggtttgg aaccagcaat ttcaacaagc ctagtaaatc gtgcagcaga cgccacagaa   1860
aatgaagccc aaccgaacta ttcatttatt cgtgcacatg atagtgaagt acaaacggtt   1920
attgctcaaa ttattaaaga taaaattaat cctagttccg atggattgac tgtctcaaca   1980
gatgaaattg ccaaagcatt cgaaatatat aatgctgacg aattaaaggc tgataaagag   2040
tataccgcat ataatatacc ctcatcatat gcattgatgt aactaacaa agatacaatt   2100 cctcgtgtgt attatggtga tttgtttacg gatgatggac aatatatgtc tgcaaaatca   2160
ccatattatg atgcacttac ttcattgctt caatcgcgag taaaatatgt ttcaggtggt   2220
caatctatga atatgactta ccttcataat aatcaaggcc ttttgacgtc agtccgctat   2280
ggaaaagacg ccatgacagc taacgacact ggtacaagtg aaacgcgcac acaaggtatt   2340
ggattaattg tcggcaacaa aactgattta aacctgaata atgatgagca aattgtgctt   2400
aacatgggcg ccgcacacaa aaatcaagct taccgtgcat taatgttaag tactaaagat   2460
ggcttgaaaa tttataatag tgatgacgag gcaccggtat cgtatacaga tgatcaaggc   2520
```

```
cgtttgattt ttaaatctga tgtggtttat ggtgtgagtg atgctcaggt ttctggttat    2580
ttagcagctt gggtgccagt cggtgcaaac gatagccaag atgctagaac agaaagtagt    2640
acaacagcgt caacagatgg taataccat cattcaaata gtgccttaga ttctcaagtt    2700
atatatgaag gtttttcaaa cttccaagcc atgccaacac aggccgatga gtataccaat    2760
atcaagattg ccgaaaatgc acaattattc aagagccttg ggataacaag ctttgaattg    2820
gcacctcaat accgttcaag tacgataac agtttcttag attcagttat tcaaaatggc    2880
tatgccttca cggatcgcta cgacattggt tataatacgc ctacaaagta cggtacagtt    2940
gaccaactat tagatgcttt aagagcattg catgcccaag gcattcaggc tatcaatgat    3000
tgggtcccag accaaattta taatttgcct ggcgaagaaa tagtgacagc cagtcgaaca    3060
aacggttcgg gaaaggtgaa tgaaagttca gttattaata atacgctata tgattctcgt    3120
actgttggtg gcggagagta tcaagcaata tatgagggtg ctttcttaga taagttaaaa    3180
caagattatc ctgagttatt tgaaacaaaa caaatttcaa caggtgaagc aatgaaccct    3240
gatgtcaaaa tcacagaatg gtcagctaag tatttaatg gctcaaacat tcaaggacgt    3300
ggtgcatggt atgttctcaa ggattggtca acaaatcaat actttaatgt ttcaagtggt    3360
agtgaatttt tacctaagca actgttaggc gaaaaaacaa gtacagggtt taccaacgtg    3420
gacaatggca agactgagtt ttattctacg agtggctacc aagcaaagaa tacatttatt    3480
caagataatg acaattggta ttattttgat aatgatggct atatggttgt tggcggtcaa    3540
gaaattaatg gtaaaaaata ttatttccta ccaaatggtg tagagttaca agatgcttat    3600
ttgtctgatg ggactagtga gtattactac agtagtgatg tcgtcaaat ttctaatcaa    3660 tattatcaag gatcagacaa caactggcgt tatttctttg cagatggtca tatggctgta    3720
gggttagcaa caattactac agaaaatggt acaacaaatc aacatatttt cgatgcaaat    3780
ggtatgcaac ttaagggcgt agctataaag gatactgatg gcaatgtgca ctattttgat    3840
ggtaagacag gaaacatggt tataaattcc tggggcaaaa taagcgatgg ttcatggtta    3900
tacttaaatg atagcggtgt agcggtcaca ggaccgcaaa atattaacgg tcaaaatctt    3960
tacttcaacg aagacggtat tcaagtaaag ggtgaagcca ttactgataa tagtggaaac    4020
atacattatt atgatcgcag cacaggaaat atggttgtga actcatgggg tgaaacgaat    4080
aatggttcat ggctatactt gaacgacaag ggtgatgccg ttacaggaga acaagttatt    4140
gacggtcaaa aactatattt cagtagtaat ggaatccaac ttaaaaatac attcaagaag    4200
ctatccgatg gttcatggct atatttgaac gataaaggtc ttccagtgac aggagcacag    4260
gtcattgatg gacaaaactt gtatttcgac caagatggga agcaagtcaa aggtgacgtt    4320
gctacagatg gacaaggtaa cactcattat tatgacggca acacaggaaa tatggttact    4380
aattcatggg cagagttagc ggacggttca tggatgtatc tagataatga tggcaatcct    4440
ttaacaggac cgcaaaagat tgatggccag tcactctact ttaatgatgc tggtaagcaa    4500
atcaaaaacg cattggttaa actagatgat gggtcaacaa tttacctcga tgataaaggt    4560
gtttcatcaa ccggtattca agaattgat gataagatat attattttga tcctgatggt    4620
aaacaagtag tatgtcgttt tgaagaatta ccagatggtt catggatgta tctagatgat    4680
gacggtgttg ctgctacggg cgctcaaaaa attaatggcc aggaattata tttcgacaat    4740
aacgggaaac aagtcaaaaa tgacaaagta attaatgacg atggaacaat aaactattac    4800
acaggtatga gcggtgaaaa actaaaaaat gatttggtg aattaccaga cggttcatgg    4860
atgtacttgg ataatcaagg taatgctgta ataggtgccc aaaaaattaa tggccagaat    4920
```

```
ctttacttca agacagacgg acgacaggtt aagggtgaag caaatgttga ttcatcgggt   4980
gaaatgcact tctatgatcc tgattctggc gagctaatta caaatagatt tgaacaagtt   5040
gctagtggtg tatgggctta ctttgatgcc aacggtgttg ctgtaactgg tgagcaacgc   5100
attggtaagc aaaatttatt ttttgatcca actggttatc aagttaaagg cgacaaacga   5160
acaattgacg gcgttctcta tacctttgat aaagaaagtg gtgagagaaa gggtttagat   5220
tctatatcgg tattacccac caatggacaa tacacaaccg ataaggccca aaattggtat   5280
taccaagtcg atggtgaaaa tgtaaaaggg ctatatacaa ataatgatgg tcaattacgt   5340
tacttcgatt tgacaactgg cgtgcagact aaaggtaatt tgtgacaat tggcaatgat   5400
acctactatt tcaccaagga acaagggat ggacagatag tttctgaggt tgtgtcagga   5460
cactatggta ctgtccagtt gagtgacaat tcgtctgcat gggtttatcg cggtgcaaat   5520
gatcaaattt tgaaaggcct acagaatata aacggtcgtc tgcaatattt tgatctaacc   5580
accggtgcgc aattaaaagg cggtgctgca aactatgatg caaccttta ttattttgaa   5640
tcatcagatg gtaacctagt cagtaaaatt cagcaatctt attctactgg gaattatgtg   5700
accgatggta taaagtaac atatgttgat gagcaaaaca accaagtcac gggattagcg   5760
ttgattgatg atcaactaca atacttcaat ccaagtgacg gtagtcaagt caagaatgag   5820
caggttatcg ttgatggcgt cacatactac tttgataaaa atggtaatgg acaatacttg   5880
tttacaaata ctgcaacgat gtctactaat gaatttgcca acatagtgc tgcttatagc   5940
aatgatagtt ctagcttcaa gaatacgata gatggtttct tgacggccga tacctggtat   6000
cgccctaaag atatcttgga aaacggacaa acgtgggtag tttcttcaac aaatgacgtg   6060
cgaccactga taacagtttg gtggccaaat aaagatgttc aagttaatta tttaaatttt   6120
atgaagaaaa atggtttgct agatacaagt agtcaattta atctacaatt tgatcaatat   6180
gacttgaatg tcgccgcgca aaaagttcaa gtggctattg aaaaacgcat ttcgaaagaa   6240
aagagtacag attggttgaa agatcttttg tttgaagctc atgaagatac gccttcattt   6300
gtgaaacaac aatttatttg gaataaagat tctgaatatc aaggtcaagg ggatgcgtgg   6360
ttccaaggtg gttatctgaa atatgataat agtgaattaa ccccaacaac gaactcagat   6420
tatcgtgaat ccggtaatac attagacttc ttgcttgcta atgatgtcga caattctaac   6480
ccagcggttc aagctgaaaa tttgaattgg ttacattatt taatgaactt tggcacgatt   6540
acagctaatg atgatgatgc caactttgac agtattcgta ttgatgccgt tgactttatt   6600
gataatgatg ccattcagag aacctacgat tacatgcgtg atgcttataa agttgatgca   6660
agtgaagaca acgctaataa gcatatttca ctagttgaag ctggattaga tgctggtacc   6720
tctacaatta agaataatgc tttagttgaa tctaacttta gagaggcagc tacactatcg   6780
ctagcaaatc aatcagggaa aaatagttcc ttgactaata tgttgcaaga cattgatggt   6840
ggccagatta tagctgatca cgccaacaat gcaacagaaa atgaagcaac gccaaattat   6900
tcaattattc atgctcatga taagggggatt caagaaaagg ttggtgcagc aattaccgac   6960
gttactggtg cagactggac gaatttcacc gatgaccaat aaaagaaggg attagcagct   7020
tattatcaag atcaacgttc aacgaataaa agtataaca tctataactt acctagtatc   7080
tatgctttga tgttgaccaa taaggacaca gttcctcgtg tttattacgg tgatatgtat   7140
caagatgatg gccagtatat ggaaaagcaa agtatttatt atgatgccat tgtttccttg   7200
atgaacacta gaaagagtta tgtgagcggt ggacaaacca tggatgtaga tgaacatggt   7260
```

-continued

```
ttgttgaaga gcgttcgttt tggtaaagac gcaatgacag ctagtgaact tggtacgaat     7320
gaaacacgca ctgaaggtgt tggtgtgctg gtcggtaatg attcttcact aaaactaaat     7380
gattcagata cagttacttt agagatgggg gcggctcata aaaaccaaga gtaccgagct     7440
gcattgttga caactagtga tggtattgtt acgtatgatg ctgataatga tgcaccaacg     7500
atctggacag atgaccgggg tacattaacg ttctcaaata aggagattgc tggtcaagat     7560
tatactagtg tgcaaggatt cgctaatcca caagtatcag gttacttagc agtttgggtg     7620
cccgtaggag ctagtgacga tcaagatgcc cgaacagcag catcaacaga taaaaatact     7680
gatgacaaag tactgcattc taatgctgca ttagattcga acttgattta cgaaggtttt     7740
tcgaactttc aacctaaagc aaccaccaat gatgaactga ctaacgtagt aattgctaaa     7800
aatgctaatt tatttgaaaa gtggggaatc acaagttttg agatggcacc acaatatcgt     7860
tcaagtgggg accacacgtt cttagattca acgattgata atggttatgt atttactgac     7920
cgatacgatt tgggatttga acaccaact aagtacggta ctgataagga tttgcgtact      7980
gcaattaaag cattgcacca atcaaatatg caggttatgg ctgatgtagt tgataaccaa     8040
gtttataatt tatctggaca agaggtcgta tcagcttcac gtgctggtgt ttacggcaat     8100
gatgtgtcaa ctgatttggg gacacaactc tatgcggtta atagtgttgg tggtggtaaa     8160
tatcaagccc aatacggtgg tgaatatttg aatgaattga agcaacaata cccagatttg     8220
ttcgaagcta agacgtatga ctattgggtt aaaaattatt caaatgacgg atcggatccg     8280
tattacacac tgtcgcaaaa cacacgaaaa gatatgccaa gtagtgaggt cattaaacaa     8340
tggtcagcta aatatatgaa tggtactaat gtattaggaa acggtatggg atatgttttg     8400
aaagattgga atacaggtga gtacttcaaa attggagaaa agaatgctga ttttataaca     8460
aattaa                                                                8466
```

<210> SEQ ID NO 16
<211> LENGTH: 8535
<212> TYPE: DNA
<213> ORGANISM: Leuconostoc carnosum

<400> SEQUENCE: 16

```
atgagagaca agaatgtaat atgcgatcga aaaaaattgt ataaatccgg aaaattgtta      60
gtgcacagcag gaattttctc tacggttgtg tttggtatgg ccgtatctga cgttagtgct     120
aatgacactg acaacactgt gttaacttcg aacagtggat ttttagataa agtagtagat     180
acgacaagta cggataaggc agccacacca gataaagtag tagatacgac aagtacggat     240
aaggcagtca caccagataa agtagcagat acgacaagta cggataaggc agtcacacca     300
gataaagtag cagatacgac aagtacggat aaggcagcca caccggataa agtagtagat     360
acgacaagta cggataaggc agccacaccg gataaagtag tagatacgac aagtacggat     420
aaggcagcca caccggataa agtagtagat acgacaagta cggataaggc agccacacca     480
gataaagtag tagatacgac gagtacggat aaggcagcca caccggataa agtagcagat     540
acaacgagta cggataaggc agccacacca gataaagtag tagatacgac gagtacagat     600
aaggcagcca caccagataa agtagtagat acgacgagta cagataaggc agccacacca     660
gataaagtag tagatacgac aagtacagat aaggcagcca caccggataa agtggtagat     720
acgacaagta cggataaggc agcagataga accattagta tttctggtaa aacagttaaa     780
aatattgagg aaattggtgg gaaaacttat tttgtagggg atgatggcaa agtcaaaaaa     840
aacttcacgg ttattgttga tgggcaagta atgtatttg acaaagagtc tggagcattg     900
```

```
acttcgaacc ataagcaata taaagaaggt ctttcagata taacaaatga acataatgct      960
gcctattcat tagaaaacga caactttaca caaattgata gttacttaac tgccaatagt     1020
tggtaccgtc caaaagatat attaaaaagt ggcacaacat ggacagcctc aaccgataaa     1080
gactctcgcc cattacttat gtcatggtgg ccagatcaac aaacagaact atcttattta     1140
aagtatatgc aatcagcagg tttcttagca gaggatgtta atttatcaga aaataatagc     1200
attgatgatc taacagctgc agcaatggat gttcagaaaa atgttgaagc aaagattagc     1260
ctatcaggta atacagattg gttgaaagaa gatatgaatc agtttgttga ttcacagtca     1320
aattggaata tcagcagtga gtcaaaaggc actgatcatc ttcagggcgg cgctttattg     1380
tatggtaaca gtgatatgac accagatgct aattctgatt atcggttact gaatcgcaca     1440
ccaaaaaacc aaaccggaca aatcagtgct acgaatgatc agggtggtta tgagatgtta     1500
ttggctaatg atgtcgataa ttctaatcca attgttcaag ccgaacaatt aaattggtta     1560
cactacatga tgaacattgg tagtattaca aaaaatgatt caacggctaa ttttgatggt     1620
tatagagttg atgcggtaga taacgtgaac gctgatttgt tacaaattgc tggtgactac     1680
ttcaaggccg cttatgggac ggacaaaagt gatgcaaatg ctaataatca tatttctatt     1740
cttgaagatt gggataatag tgatcctgac tacgtcaaaa agcacgggaa tgaacaatta     1800
actatggatt ttccgatgca tttggcatta aaatatgctt taaatatgcc tattgatatg     1860
cgtagtgggc ttgaaccggc aattaagaca agtctggtga accgatcaca agatgcaaca     1920
gaaaatgagg cacagccaaa ctactcgttt atacgtgccc atgatagtga agtacagact     1980
gttattgctc aaattattaa agataaaatt aatccaaagt cagatggttt gacagttaca     2040
cctgatgaaa ttgcgaaagc ttttgaaatc tataatgcag atgaactaaa agctgataag     2100
gcatacacag cttttaatat cccgtcatct tatgcacttt tgttgactaa taagatacg      2160
gtgcctcgtg tttactatgg cgatttattt acagatgatg acaaatatat gtctgatcat     2220
tcaccatatt atgatgctat tacgacttta ttagcgtcac gtattaaata tgcggctggt     2280
ggtcaaagca tgggtatgac gtatttacac gataatcaag aagttttgac atctgtacgt     2340
tatggtaaag gggctctgac agcagatgat ttgggtaatg ttgacacacg tacacaaggt     2400
attggacttg ttatcagtaa taaaacggat ttgagtttaa agagtgatga gagcgttgtg     2460
ctgaatatgg gtgtcgcaca taaaaatcaa gcatatcgcc cggcaatgtt gactactaag     2520
tcaggattaa aaatttacga tactgatgat ggtgcaccaa ttgttatac  aaataattta     2580
ggacagctaa tttttaacgc agatacagtc tatggtgtga gtgatccaca agtttcaggg     2640
taccttgctg cgtgggttcc tgttggcgca actgaagatc aagatgctag aactaaaggc     2700
agtcatgatg aacaactgat tgggaatgtc tatcattcca acgctgcatt agattctcag     2760
gtcatatatg aaggtttctc taatttccag gcaatgccaa cgaccactga tgaatatact     2820
aacgtaaaga ttgcacaaaa tgcacagtgg tttaaaaaat taggactgac aagttttgaa     2880
ctggcaccgc aatatcgttc tagcacagat agtagctttt tagactctgt tattcaaaat     2940
ggatacgctt ttactgatcg atatgatgtg ggttataata caccaacaaa atatggtaca     3000
gtcgatcaat tattagatgc attgagagca ttacattcac aagatatcca agcaattaat     3060
gattgggtac ctgatcaaat ttataactta cccggggagc aaattgtaac agcgagtcgt     3120
accaatggat ccgaaaaata cgatgatgat tcagtgatta gtaatacttt atatgattca     3180
cgtactatcg gtggtggaga atatcaagcg atgtatggcg gggctttctt agatcaattg     3240
```

```
aagcaagcat atcctggttt gtttgaaaca aaacagcttt ctactggtgt tgcaatggat    3300
cctgatgtaa aaataaaaga atggtctgct aagtatttta atggttctaa cattcaaggg    3360
cgtggtgctt ggtatgtact aaaagactgg gcaactaata agtacttcag tgtctcgagt    3420
aataatacat ttttacctaa gcaattattg ggtgaaaaag ctagtacagg atttattacg    3480
aacgatggaa aaacagaatt ttattcaaca agtggctacc aggcaaagaa tacatttatt    3540
gaagacaacg gtaactggta ttacttcgat aatgatggtt atagcgtagt tggaaagcaa    3600
gtgattgata ataaacacta ctatttcttg cctaatggtg tcgaattgca agatgcctat    3660
ttatcagatg gggataagca atattattat aaaaaaactg gtcgacaaat agtaaatcag    3720
tattatagag atgagcaagg tgattggagg tatttctttg cagatgggca tatggctctt    3780
gggttaactg acattgtttc aaatgatgga actcatgcga cacagtattt tgataacaat    3840
ggtgttcaag tgaaaggaac atcagaacga gataaagatg gtaatattca ctattttgat    3900
ggtacatctg gtaatttagt tgttagttca tgggacaat tgtcggacgg atcatggctt    3960
tacctgaatg ataaaggcat tgctgttacg ggtgctcaac aaattgatgg tcaatcacta    4020
tactttaatg aagatggtaa agaagtaaag ggtgatgcgg taacagataa tcaagggaat    4080
atacgttatt ttgatggtga atctggtcac atggtggtta attcatgggg taaattacct    4140
gatggttcat ggatgtattt gaatgataag ggtattgctg ttaccgggca acaaaaaatc    4200
aacaatgaag tcttatattt caatgctgat ggtaagcaaa tcaaaagtgc atttaaagaa    4260
ctagtggacg gatcatggct ttacctgaat gataaaggca ttgctgttac gggtgctcaa    4320
caaattgatg gtcaatcact atactttaat gaagatggta agaagtaaa gggtgatgcg    4380 gtaacagata atcaagggaa tatacgttat tttgatggtg aatctggtca catggtggtt    4440
aattcatggg gtaaattacc cgatggttca tggatgtatt tgaatgataa gggtattgct    4500
gttaccgggc aacaaaaaat caacaatgaa atcttatatt ttgatgctga tggtaagcag    4560
ttaaagaata cactgaaaac attatccgat ggttcacgta tttatttgga tggtaaaggt    4620
gtttctgcaa caggtgttca aaaattaat ggtaaagtgt catactttga tgttaatggc    4680
aaacaagtta gcaatcatat tcaagaactc cctgatggtt catggatgta cctagataat    4740
gatggattag ctctaattgg taatcaagac gttgatggca acaactttta ctttgatgtt    4800
gatggtaagc aaataaaaaa tgacaaagtc aaaaatagtg atggaacaat taattattac    4860
acgggtactg ttggtgaaaa actaaagcat gattttggtc agttatccga tggttcgtgg    4920
atgtatttag atgaaaatgg taatgctgtt actggtgaac aaaatattaa tgggcaacat    4980
ttatacttta agatgatgg acagcaagtt aaaggagatg ttttgagga tgacttaggc    5040 cgtatgcgtt attatagtgc taactcaggt gagatggttg tcaatcaatt tgaacaaatt    5100
tctgatggtg cctgggctta ctttggtgat gatggtgtgg cggtaactgg tgaacaacat    5160
atcaatggac aagatctttt ctttgatgcg acaggtcaac aggttaaagg tgaaagtcga    5220
accattaatg gtattcctta taccttgaa aaggagagtg tgagaaacg gtctgttaat    5280 atagcaccat tactagccat gggaaattat gttacaaata tggtacaga ttggcaatat    5340 gaagtgcaag gcaatcctgt taaagggtta tatagcactt ctgataataa gttgcgttat    5400
tttgatctga caacaggtgt acagattaaa ggcaactttg ttactattgg acataacaca    5460
tactatttca atccagctaa tggagacggt gaattattgc cagatgtttc tgatggccat    5520
tatggtacga tccaagttaa agatgcgaat acaaatgaaa agacagtttg ggtttaccgt    5580
aatcaaagta atactatttt gaaggtatt caaaatattc atggtaatat acaatacttt    5640
```

```
gacttatcaa ctggggagca aataaagggt ggtattgcaa actatgatgg caatgattat    5700
tactttgaat cagcaaaggg taacctcaca agtaaaatta agcaagtcta tacagatggt    5760
caatatgtaa ctaaagatgg aaaaagcatt tatgaagacg cacaacaaca aagtgtcagt    5820
gggttagtgt ctattaatgg tcagttacaa tacttcaatc cacaagatgg cgtacaagtt    5880
aaaaatcaac aaattattgt tgatggcgtt acttactact ttgatgaaaa tggcaatggt    5940
cagtatttgt ttacgaatac aacggtcatg ccaatggatg attttacaaa gcacaataca    6000
gtttatagtg ataacgacaa caactttaaa aataatgttg atgggttctt aactgctgat    6060
acatggtatc gtccaaagga aatcttaaaa gcaggaacaa cttggacaac aacatcggaa    6120
agtgacatga gaccactgat cacgacatgg tggccaaata aaaatgtgca agttaactat    6180
ctaaacttta tgaaacaaaa taatctattg cacacaaatg tggagtatag cttgctatct    6240
gaccaatatg atttgaatat tgcagctcaa gcagtacaaa cagctattga aaagcgaatt    6300
gctcaagaaa atagcactga ttggttgcaa aatcttctat tcacagctca agacgatcaa    6360
ccatcttttg ttaagcaaca gtttatttgg aataaagatt ctgaatacca aggaaaaggt    6420
gatgcttggt tccagggtgg ttacctgaaa tacgggaaca ataaattgac acctaatacc    6480
aactcaaatt atcgtaaaac tgacaacgcg tttgaatttt tgttagcaaa tgatatcgat    6540
aattcgaatc cggtcgttca agctgaaaat cttaattggt tagaatatct gatgaatttt    6600
ggtactataa ctggtaagga tgacgatgca aactttgata gtattcgtgt tgatgctgtt    6660
gattttatta gtaatgatac aattcaacga acatatgatt attacgtgta tgcctatcaa    6720
gtagatcaga gtgaagccaa ggctaatcaa catatttcat tagtagaggc tggattagat    6780
gcaggaacat caacagttaa aaatgatgcg cttattgaat ctaatttgcg tgaagcggct    6840
acgttatctt tggccaatgc atctggtaaa aatagtgcgt taaccaatat gttgcaagat    6900
gttgatggtg aacattgat tgcagatcat acccataatt caaccgaaaa tgaagccaca    6960
ccaaattatt caattattca tgctcatgac aaaggtattc aagagaaagt ggggggctgca    7020 atttccgatg ctactggggc cgactggact aatttttacag atacacaatt aaaatctggt    7080
ttggatcttt attataagga tcaacgtgct acggataaga aatataatat ttataacttg    7140
ccaagtattt atgcattaat gctcaccaat aaagacaccg taccacgtgt ttattatggt    7200
gatatgtatc aagataatgg tcagtatatg gcagagaaaa gtatctatta taatgcttta    7260
gaatcattaa tgtcagcacg taaaagctat gtaagtggtg acaaactat ggatgttgat    7320 agccacggtt tgctaaaaag tgttcgtttt ggtaaagggg ctatgactgc tgacacggta    7380
ggtaatgaag aaacaagaac tgaaggtatc ggtgtgttag ttggtaacga tgcttcattg    7440
aaactcaatg attcagatac agtgaccttta gatatgggcg cagcacacaa aaatcaaaag    7500
tatcgtgcag caattttgac tactaataat ggtctatcaa cgttcgattc tgataaagat    7560
gcaccgattg cttggactaa tgataagggg atactaacat tttcaaataa aaatgttagt    7620
ggacaagata atactaatgt ccatggtgtt gctaatccac aggtatctgg ttatttggca    7680
gtatgggttc cagttggtgc taaagatgat caaaatgctg gacaagcgc atctacagta    7740 gtcaacacag atggtaaagt attacactct aatgcatcat tagattccaa cttaatttt    7800 gaaggattct ctaacttcca acctagagcg acaacaaatg acgaattaac caatgtcgtt    7860
atagctaaaa atgccgattt attccagaaa tggggtatta ctagctttga aatggcaccg    7920
caatatcgct caagtcagga ccacacattt ttagattcaa ccattgataa cggttatgcc    7980
```

| | |
|---|---|
| ttcacagatc gttatgactt aggatttaac acaccaacga aatatggaac agatagtgat | 8040 |
| ttgcgattgg caatcaaatc attacataaa gctggcatgc aagtaatggc tgatgttgtt | 8100 |
| gataatcaag tctataactt accagaccaa gaagttgttt ctgcttcacg cgcaggtgta | 8160 |
| tatggtaatg atgtcgcgac cggatttgat acacaattgt atgctgttaa ttctgttggc | 8220 |
| ggcggtaaat atcaagcaca gtatggtgga cagtatttga gtgagttaaa gaataagtat | 8280 |
| ccagatttgt ttgaagctaa agcttatgat tattggacaa aaaattatgc taatgatgga | 8340 |
| tcaaacccgt actacacatt atcacaacag actcgagatg atataccatc agacgagaaa | 8400 |
| attaagcaat ggtcagcgaa atatatgaac gggaccaatg ttttgggaca tggtatgggt | 8460 |
| tacgtactta aggattggaa tacgggtcaa tattttaaga ttaataaaga tggcgattcc | 8520 |
| aacttaccag tttaa | 8535 |

<210> SEQ ID NO 17
<211> LENGTH: 5016
<212> TYPE: DNA
<213> ORGANISM: Fructobacillus tropaeoli

<400> SEQUENCE: 17

| | |
|---|---|
| atgagaaaga aattgtataa gtcagggaaa atgtgggttg ccgcttcagt tgccatctcc | 60 |
| ttttccgcgt tatctattag cgtggggaat aatggtgcta aagcagatga ttcacaacaa | 120 |
| tcatcaactc agattcagtc aacgcaagta acaactgcgt tgccagctgg tggacaatat | 180 |
| tcaactacaa atggtgggca aagctggaat tatttagtca atggtgttgc aattaaaggg | 240 |
| atgtaccaag atgccaaggt tcagctgcgc tattttaatt tcattgatgg tactcaagtt | 300 |
| aaaggtgaat ttttaagtat taatggtact tattattatt ttgatcaaaa tagtggcgag | 360 |
| ggacatttgg ttccaactca agtaacggc cattatacgg aaattggcaa tactggtgct | 420 |
| tggggctatc agaatagtaa tggggaactt gttaagggaa ttcaaaatat cgatggtcaa | 480 |
| cttaggtatt ttgatgagaa tactggtaac caagttaaag gtggctcggc tactattggt | 540 |
| aataagagtt attattttga accaagtcaa ggaacactta caacaacaat tgatcaagta | 600 |
| tccgatgctc aaaatgctaa tattcgagga ttggcaaccg ttaatggtca gttaaattac | 660 |
| tttgatccta caactggtga acaagctaag cataagcaag tggctacaaa tggtgcaacg | 720 |
| tattatttca atgatagtgg tgttggaaca tatttgttca ccaatgtaca aaatacaccg | 780 |
| gctaatgatg tttcacaaca caatgctgta atagtactg atactaagga ttatacgaat | 840 |
| actgttgatg gcttcttaac ggctgatact tggtatcgac caagtatatt tttggataat | 900 |
| ggtgaaaatt ggcgcgcttc aaacgaaggg gagtatcgcc ctttcattat gaattggtgg | 960 |
| cctaataaaa acgttgaagt taattatctg aaattaatgc aaaataataa tttgctatca | 1020 |
| agtacggttc aatatgatct tttcacagat caggctattt tgaatcaagc cgcttatcag | 1080 |
| gctcaaattg caattgaaaa gcgaattaag tcagagggta gcacagattg gttaaatacg | 1140 |
| ctgttatttg gtggtgatga tagccatcct tcatttgtta agcaacaatt tatttggaat | 1200 |
| tctgattctg aatctccatg gcagggtgac gcttggttcc agggtgggta tttgaaatac | 1260 |
| gggaatagtg ttatgacgcc tacaagtaat tcaaattacc gccaggcagg aaatgctttt | 1320 |
| gatttcttgt tagctaatga tgttgataat caaaatccaa ttgtgcaggc tgaggatttg | 1380 |
| aattggctat attatttgat gaattttggt tctattacga ctaatggttt agataatgat | 1440 |
| tccaattttg atagtattcg attagatgct gttgatttta ttcataatga cgctattcaa | 1500 |
| agaacatacg attatttgag acaggcattc aatttaacga aaaatgaagc tactgcaaat | 1560 |

```
caacatttat cattagtgga agcaggggtt gatgctggaa caaccactta taatagcgat    1620
ggcttaattg aatcaaatat tcgtccgtta gcaactgatt ctttaactaa cgctccagtt    1680
aaaaatgcat cactgtcaaa cttaataaag gatgtcgata gtggtgaagt gattgcggat    1740
catgctaatt tttctactga tgatggtatt ccaaattatt ctattattca tgcacatgat    1800
aaaggaattc aggaaaacgt tggtgcagcg attactgctg caacaggggc tgattggact    1860
aattttacta ccgaacaatt agaacaaggc cttgatttat attatcaaga tcaacggtca    1920
accaacaaaa agtataatat ttataattta ccaagtatat atgctttaat gctgacaaat    1980
aagggtactg ttccaagagt atattatgga gatatgtatc aagataatgg tcagtatatg    2040
caacaaaaaa gcctatatta tgatgccatt agttcactaa tgactgctag aaagcaatac    2100
gtcgctggtg tcaaacaat gagcgttgat gaaaatgggt tattaaagag tgtacgtttt    2160
ggaaaaaacg caatgactgc tcaagataca ggtgatgctg aaacaagaac agaaggtgtt    2220
ggtgtcatta ttggtaatga tccatcagtg aaggttgcgg atggtcaaac agttaccttg    2280
gatatgggtg ctgctcataa aaaccaagct tatcgtccat taatcttgac gacaagcgat    2340
ggcattcaaa cttacgatag tgatgaaaat gcaccagttg tatatacaga tgacaatgga    2400
atcttgactt tttcaaatca agatattaat ggtcaagcta acacaaaaat tgttggaact    2460
ttgaatccac aggtttcggg ttaccttgct gtttgggttc cggttggtgc cagtgctgat    2520
caagatgcta gaacagcacc atctactcaa agtactaatg atgggaaagt attgcatacg    2580
ggagctgcgt tggattcaaa ccttattttt gagggatttt ctaatttcca accaatgcca    2640
actacacatg atgagatgac aaatgttgtg attagtcaaa atgctagtca attcgctaaa    2700
tggggtatta ctagttttga aatggcaccg cagtatcgct catcagagga tcatagtttc    2760
ttagattcaa caattgataa tggatatgct ttttcagatc gctatgattt gggatttgga    2820
acgcctacta aatatggtac tgatgaagat ttaaggaacg caatcaaggc tcttcatcaa    2880
aatggcatgc aggtgatggc tgatgtcgta atgaatcagt tatattcctt aaacggaaag    2940
gaagttgttt cagctagtcg tgcgggtgtt tacggaaatg atgtagattt gccttttgga    3000
acacagctat acgtggtcaa tactaccggt ggtggtgagt atcagaagaa atatggtggt    3060
gctttcttaa acattattaa agaaaaatat ccaactttat ttgattcaga gtcttacgat    3120
tattatttga aaaattattc tgataatggc cacggaccag catatatgac aacagctaca    3180
gcaactcgag aggcgattcc atctgatcag ccgcttaaag aatggtcggc taaatatatg    3240
aatggtacga acatttagg acttggtatg ggatatgttc ttaaagattg gaataatggt    3300
gcctatttca aattatcagg aactgataca acgcttccac aatcattggt tgccttgact    3360
gggtggaatc aaaacgatga tggcacttgg tcatattaca gcactgacac tgatgatcga    3420
gtaacaggga acaagtgat tgatggaaga accctacttt tcgataatca aggaaaccag    3480
attaagggtg gttggggtga aaaccctgat ggtacatggt cgtattacaa tgctgacact    3540
ggtgatcgag taataggtga gcaagtaatt gatggaagaa ctctatttt tgataatcag    3600 ggagttcaag ttaaaggcgg ttggggtgaa actatgatg gtacatggtc atattacaac    3660
gctgataccg gtgatcgagt aacgggaaag caagtaattg atggaagaac attattgttt    3720
gataatcggg gagttcaagt gaaaggcggt tgggtgaaa actctgatgg tacatggtca    3780
tattacaacg ctgacaccgg tgaccgagta acaggcaatc aattgattgg gggaagaaat    3840 ttactttcg ataatcaagg aaatcaaatc aagggcggtt gggatgaaaa ccctgatgga    3900
```

```
acttggtcat attacaatgc cgatactggt gatcgagtaa ccggggtgca agtgattgat      3960
ggaaagcagt tgctattcga tagtaatggt attcaggtta aaaattcatg cagaaaaat      4020 gccaatggaa cttggtcata ttatgatgct aatgacggac atttagtccc tgcaaatagc      4080
tcaaatgatg aacttcatc atctactcaa gatagtggga ataagagcaa tcaaaatcct      4140
tcaagtagta gcaatgctgt aaataagact actggttgga ttaagaatag tgatggaacc      4200
tggtcttatc tatctgcaaa aagtggtcaa aaggtcactg gaagtcaaac tatcgatggc      4260
aagcaattgt tgtttgatga ccatggcgtc caaattaaag gtggctgggg taaaaatgct      4320
gatggtacat ggtcatatta tgatgcgaac tcaggggaac tgacttcaac tagtgatatg      4380
agtaatgtaa atccacagca aacaacaact actacgaatg aacagagtac aaccaatcag      4440
ccaacagata tcacaaaaaa tagtgatggt gtttatgtat ataagaatga ttccaataag      4500
aaggcgcaag gctacttgaa tgatggatca tcatggaagt ggtttaatga tggtcaactt      4560
tacaccggtt tccaaaatta catgggtgct tactattact ttattaatgg tattcgtcaa      4620
caaaaccagt gggaaaatat ctggggattg aagtattatg ttggtgatga tggtcgaaca      4680
gttgaaggaa ttcatgctat cgacggtcat gcttatgact ttggtaccga tgggactttc      4740
aatgtgaagg gatcggctag tggctacttg aatgatggca agagctggat gtggtacgaa      4800
ggtggtaacc catatactgg tttccgctac tacatggata cttactattg gttcgaaaat      4860
ggtgtgcgtc aagataatgc cttggcatca agcttggggtc tgacatacta cacaggtgca      4920
gacggtcgag cagttcaggg tgttcaaaac atcaatggta agctttacta cttcggtaat      4980
gacggcacct tctttatgcg gacaaaccaa gaagta                                5016
```

```
<210> SEQ ID NO 18
<211> LENGTH: 4899
<212> TYPE: DNA
<213> ORGANISM: Lactobacillus kunkeei

<400> SEQUENCE: 18
```

```
atgaataata ataatagtga acaaaaactt cgttttaaaa tgtataaatc gggaaagcat        60
tgggttgttg caggtttaac aacagctgtt gtatcagttg caatatacag tggctcttca      120
atcattaatg gtggagtaac tgtaaaggca gatgtgcaaa gcactacaca agcaactaca      180
tcagtttctg ataattcaaa agattcatca aatagtatta gtaataataa ttcaaatgat      240
gacaatcaaa ttgcaacact tcctcaagat ggtacatatt caactggaga taacggtcaa      300
acttggaagt atgttgaaca aaataaaaac atacagggac tttataaaga tagtgacaac      360
caactaagat actttaatga atatgatgga actcaagcaa agggtgatat cgtaaatgtt      420
aataataata actattattt tgatagtggt agtggtcaag gacataagat agataactac      480
tcaggtggaa attatgttga atctaacgtc aataatgaaa atggttggat ttataaagct      540
actgacaata ctgaagtaaa agggattgcc actatcgatg gtaatgttca atattttgat      600
caatcaactg gacttcaact aaagggtgga gcggttcaag taggaggagc cgactactat      660
tttgatccaa acaagggaaa cttagttggt aaagttgatc aagttgtaaa ttcaaacaat      720
tatagtgata taaaattact agatagtaat aaaaatgtag taaaaggatt aacagttaat      780
aatggaacat acaatactca tgatccttct actggtgatc aagttaaaaa taaacaagtg      840
attgctaatg gcgtcacata ttattttgat gcaagtggta acggaacata cttgttcaca      900
aatacaggca atagtgccgt taatgatttc tcacaacgta acgctgcaaa tagtgtaaat      960
ccaagtgatt acaaaaatgt agtagatgga ttttcaccg cagatacttg gtatcgacca     1020
```

-continued

```
aaacaaatta tcgataacgg tacaacatgg agaaattcca atagtaatga cttacgtcca    1080
atgattaccg cttggtggcc aaataaggat gttcaagtta attatttgaa attgatgcaa    1140
gacaatggac ttttagataa aagtgatact tatacattgc aatcagatca acaagtttta    1200
aatcaagccg cccagagcgc tcaagtaaat attgaaaaga aaatatcaca gacaggaagt    1260
acagattggt taaacgattt attgtttgca agtcatggca ataatccttc atttgtaaaa    1320
caacaatatg tatggaattc tgactctgaa tctccatggc aaggtgatgc ttggttccaa    1380
ggaggatact taaaatatgg gaatagtgtt atgacaccaa acactaattc taattacaga    1440
gattcaaata atttatttga tttcttgcta gcaaacgatg tagataattc aaatccagca    1500
gttcaagctg aggacttaaa ttggctatat tacttaacta attttgggac aattactgct    1560
aatgattcaa atgctaattt tgatagtatt agaatcgatg ctgttgattt tattagtaac    1620
gatatcatac aaagaagtta tgattacctt cgccaaaagt ttaatttaac acaaagtgat    1680
gctaatgctg attcacatat ttcattagtt gaaggtggag tagatgcagg aaccacttct    1740
tacagtaatg atggattagt tgaagcgcca tttagactag gtgcctatcc attgctacat    1800
aagcaaggtg gagacgtatt taaagattta ataaacgaag aagattctgg aatcgatatt    1860
tcaaatcata acggtgaaac taatacaact aacactattg gtggattaac tttatctggt    1920
ggaaaaccta actactcaat tgttcatgca catgataaag atgttcagga aaaagttggg    1980
caagccattg ttgataccac aggtattaag gattggactg attttactcc aagtcagtta    2040
gcacaaggtc tagaaacatt ctataacgat caaagacaaa cagacaagaa atacaatgat    2100
tataacgttc ctagtgcata cgcaattatg ttaactaata agggaacggt tcctcgtatt    2160
tactatggtg atatgtacca agatgatggt caattcatgc aaaagaagag tctttactat    2220
gatgatatag caaacttgat gactgcaaga aagaaatatg tatctggtgg tcaatatatg    2280
gttgataacg atggaattct aactagtgta cgttttggta agggcgcaaa tacagtcaat    2340
gattctggta catcagatac tagaaaccaa gggattggat taatagttgg atcagatcct    2400
aaaaaggtat taaacgatgg ggataccatt gtttttacaca tgggtgctgc acataaaaat    2460
caaaagtatc gtgcattaat gctaacaact gaaaacggag ttcaaaatta tagttcagat    2520
gataacgctc cagttgctga aactgatgat aacggtgatt tagttttcag taacaaagat    2580
attaatggac aagataatac tgcaattaaa caagtcgcta atccagaagt aaatggttat    2640
ttagctgcct gggttccatt tggcgcttct gatgatcaag atgctagaac atcaccatca    2700
actagccaaa ataacgatgg taatgtttta catgaaaatg atgcattgga ctcaaatctt    2760 attttttgaag gattttcaaa cttccaacct actccaacaa atcatgatga atatgcaaat    2820
gtagtaattg caaaaaatgc atcattattt aaagattggg gtgtaacaag ttttgaaatg    2880
gcacctcaat atagatcaag ccaagatcat actttcgttg actcaactat agataatggt    2940
tacgcttttt ctgatagata cgatttagga ttcgggacac caactaaaata tggaacagat    3000 gaagatctaa gaaatgccat taaatcactt catgcaaatg gaatgcaagt aatggccgat    3060
gttgtttata atcaactata aacttacca ggagaagaag ttgtttcggc aacaagagct    3120
ggagtaactg gaaatgataa tgcacttcct tttggaacac aactatatgt tgttaataca    3180
gttggtggtg gagactatca aaagaaatac ggaggggcat tcttaaacca attacaagaa    3240 caatacccctt cattattcca atctcaaaaa tacaagtatt actacaagaa ttatgctaat    3300
aatggtgctg gaccaggtta tttaactgta actgatggag aacgttctgc aattccttct    3360
```

```
gatcaaccaa ttactgcatg gtcagctaag tatatgaatg gtaccaatat tcttggtcgt    3420
ggtatgggat atgttctaaa agactggaac actggcgctt acttcaagat aagtggtgat    3480
gactctactc ttcctacgag cttaacttat agaagcggat gggtagaaaa tccagacagc    3540
acttggtcat actattcaaa ggatagcatt gccaaattaa ctggagcaca aattgttaat    3600
gatcaaagag tattctttga taacaacggt attcaggtta aaggtggatg ggtagaaaat    3660
ccagatggaa cttattcata ctatgacaaa aatagcggtg aacttttggt aggttctcaa    3720
ctagtagacg gaagacatgt attctttgat aatgttggag tgcaagttaa aggtggatgg    3780
gtagctaaca ctgatggtag ttattcatac tacaatgcta atgatggtac catgttaacg    3840
ggtgctcaat ttatcgatgg acaaaatgta tactttgatg ctgatggtaa acaggttaag    3900
ggtaactggg tgcaaaataa cgatggttct tgggcatatt atgatgctaa tttaggtcat    3960
cttgtaaaag atgctaagca tgttgattca caaccaagca ctcaacaagt taataataaa    4020
caatccgagg aaaaatcaaa ttcaccatta gttgaagctc aaaacaataa agattcagct    4080
tcagtagaat ctcaaaatca tcaaaattca gtgtcagtag aatctaagaa tgaaaacaaa    4140
aatcaatcaa acgatgtaag aaatccttcc gaaaaaacag acaccaaaac atctaatgaa    4200
aaatcaaaag aagtatccaa agaagatgct gcatatgaca atgccaaaaa atcattagta    4260
gaagctaaaa agttggtaga taagaagcca aataaaacta atattaataa atataaaaag    4320
gcattgaagt cttatgaaaa tgcacaaaag aagatgaata agtctgtgat ttcatcatat    4380
aaaaaggctg caaagaact aaacgctgct aagaaaaacc tttctaagaa aaataataag    4440
gttaatatga agaaatatag tattgcttta acaaatatc gtaatgctaa gaaatcttac    4500
gtggtaatta agaaaaaga tttagataaa tctaaatctg cgttaaatac tgctaaaaaa    4560
gcacttgcta aaaagaagac aaagcaaagt caaaagaagt ataacgatgc attgaaaaaa    4620
tattacgatg cagaaaaaac ttatctaaac ttgactggta attacactaa aaaatattat    4680
tatgatttcg ataaagtagg gaaaaaggtt aaagttatca aatcaacttc cgtatataat    4740
tcattgaaac caaatagtaa aaaagtagta aagaagatta aaaaaggatc agtaattaaa    4800
gtgaagaaac ttattttgtc aaataagaag tcatactttg atttaggata taccgttttt    4860
gtaatcgcaa gtaaatcttc tataaaaaaa gctaagtaa                            4899
```

<210> SEQ ID NO 19
<211> LENGTH: 3957
<212> TYPE: DNA
<213> ORGANISM: Lactobacillus kunkeei

<400> SEQUENCE: 19

```
atgaaatcaa agataacaa ttcaaaaata catttcaaaa tgtataaatc tggaaaacaa     60
tgggttattg ctggattaac tacagcggtt gctgctgttt ctatttatgg tggaacaact    120
atatttaatg acagcgtggt agctaaggct gatacagcag ttaaatcttc acaaagttcc    180
aacgctgata ctactcaatc ttcatctgct gttgttgatt ctagctctgc aaattcaagc    240
agtccatcat cgactgaagt atcagtaaac gtaaaaaata catcaaatgc agatacacaa    300
ggtattcaag cattaccaga tggtggtaac tacacatcag aagataatgg tcaaacttgg    360
aaatactcat atcaaaacaa tgatgttaaa ggtctatatc aagaaaacaa taacattcgt    420
tattttagtg aaaatgatgg atcacaagta aaaggaaaca tcttaaatgt aaataacaaa    480
aactattatt ttgatagtaa taatggtgat ggccatttaa ttaaagacta ttctggtgga    540
aactatgttg aacaaagtca agataaatgg acttataaga catctgataa taaccttgtt    600
```

```
aaaggtatcg caactattga tggacaaatt aaatattacg atcctactac aggtatccaa    660 ttaaaggtg  gagcttttga gattggtggg gctgcttatt acgttgaccc cgctcaagga    720
aacgttgtcg gaagagtaaa ttcaattatt aactctggaa attatgtcaa taagaacaac    780
aatactactt ttgttgatga taataacaat acagttaagg gattgaatgt agtaaggggt    840
aacttacaat actttaactc aacaacagga tatcaagcta agagtgaaca agttgttgct    900 aacgagcca  catattactt tgataaagat ggtaacggaa ctttcttatt taataacaca    960
ggttcatttt cagtaactga ttttgcaaaa cacaacgttg ctaacagtaa tcaaccatct   1020
gattttacca atactgtaga tggtttcttg acagctgaaa catggtatcg tccaaaacaa   1080
attttagata atggtactaa gtggcgcaac tcaaataaag atgatcttag acctcttatt   1140
acagtttggt ggcctaacaa agacgtacag gttaattact tgaaactaat gcaagataat   1200
ggactattgg ataatagtgt taaatatact gtattttctg accaacaaac tttaaatgaa   1260
gcagctcaat cagctcaagt taatatcgaa aagagaatca ctcaacaaaa agcatcatca   1320
tggttatatg atttattatt caagggagat tcatctcatc catcatttat gaaccaacaa   1380
tatatttgga atatgggttc agaatcacaa tggcaagggg atgcttggtt ccaaggagga   1440
tacctaaaat atggtaatag tccttttaacc ccaacaacca actcaaaata tagaaaaaca   1500
gataatcaat ttgatttcct tttggccaat gatgttgata attctaatcc agcagttcaa   1560
gctgaagata ttaattggtt atattactta actcatttcg gaacaattac cggtaaaaat   1620
gataaagcca attttgatag cattagattg gatgcagtcg attttgtaag taacgagatt   1680
attgaacgaa gcaatgatta tctaagagat ttatataagt taaccaagag tgatgcaaat   1740
gctgataagc atatatcact tgttgaagcc ggtgttgacg ctggaactag ttcaacaaat   1800
ggtgattctt tggttgaagc acctttttaga ttatcagcct atggattact tcataattct   1860
ggtaaagttg atgcattgca agacttagtt aaagaagttg attcaggtgt tcttatttcc   1920
gatcacagta aaaactctaa ggatggtggg gttcctaatt attccatcgt gcatgctcat   1980
gataaagatg ttcaagaaag agtaggacaa gcaattgttg attccactgg cattaaagat   2040
tggacaaact ttacacctgc tcagttagct aaaggattaa gcgtttacta tgctgatcaa   2100
agaaagacag ttaaaaaata taatgattac aatatgccaa gtgcttatgc aattatgttg   2160
acaaacaagg gtacagttcc acgtatttat tacggtgata tgtatcaaga tgatggtcaa   2220
tttatgcaaa agaagagctt ctactatgat gatattgtca aattgatgac tgctagattg   2280
aaatacgttg caggtggtca aacaatgagc gttgattcta acggatttttt gaagagtgtt   2340 cgttttggta aaggcgcaaa gacagttaat tctaagggaa caaaagaaac aagacacgaa   2400
ggtattggtt taattgttgg aaatgatgct aagaaagttc tatcaaatgg acaaaagta    2460 acattgaaca tgggtgctgc tcataagaac caaaaatatc gtgcattaat gttaacaact   2520
aacaagggag ttcaaacatt tgcttcgat  aaaaatgctc ctgtagttaa gacagatgga   2580
aatggtgttt taacatttac taacaaggat attaaaggtc aagctaatac cagtgttaga   2640
ggagttttaa atcctaaggt ttctggatac cttgctgtat gggtaccagt aggcgctaaa   2700
gataaccaag atgcccgtac tcaaccatct aagaaaaata gaaatgatgg taaagtgctt   2760
cattcaaatg atgctttaga ttctaattta atttacgaag gattctccaa tttccaacca   2820
caaccaaaga aacgcagcca atatgcaaat gttgtaattg ccaaaaatgc aaagctattc   2880
aaaaaatggg gaatcactag ttttgaaatg gctccacaat atcgttcaag taatgataaa   2940
```

-continued

| | |
|---|---|
| acttttgttg attcaacaat caacaacgga tatgcattct cagatagata tgacttaggt | 3000 |
| ttcggtaagc caaccaagta tggtactgat aaggacttaa gaaaggctat tgaatcactg | 3060 |
| catgatcaag gcatgcaagt tatggctgat gctgtattaa atcaactata caacttacct | 3120 |
| ggaaaacaag ttgtttcagc acaaagagct ggagtaacag gtaacatagc tgatttgcca | 3180 |
| tttggaaagc aattatacgt tgttaataca attggtggcg gtaagtatca aaagaaatat | 3240 |
| ggtggaaaat tcttaaaggc tttaaaagct aaatatccaa acatatttaa gggtaagact | 3300 |
| tataaatata actacaagaa ttattctcca actggtgaag atatttaac acttaataca | 3360 |
| ggtaagacgg tttcaattcc atccaaccag cctattactg aatggtcagc taaatacatg | 3420 |
| aatggtacta atatccttgg tagaggtatg ggttatgtat tgaaggattg aatacagga | 3480 |
| acatacttta agttgaacgg actaaagaca gttcttcctt ctgaactaac agataagagt | 3540 |
| aactgggtta atgaagtttc tacatcttca aaagatgtat ataataagtc tgtttcaaat | 3600 |
| ttaaagacg ctaaaagaa attagctgca aagaaatcaa aagaaacac acaactatat | 3660 |
| aacaatgctc taaattctta ttacaaagca gaaaaagaat acttgagcag tgctaaactt | 3720 |
| tacaataaaa agtactacta tgattttgat aaattacctt caaaagttaa agtagctaag | 3780 |
| gtcacttact catataaatc aactgatttc agcaaagata ataggattaa aaagcttaaa | 3840 |
| aaaggaactg ttttaaatgt taagggatta gttcttaacg aaaagttac aagaattaat | 3900 |
| attggtaacg gtaagtttgt aactgcatct aaagatttca taaagcaat tagatag | 3957 |

<210> SEQ ID NO 20
<211> LENGTH: 3420
<212> TYPE: DNA
<213> ORGANISM: Lactobacillus kunkeei

<400> SEQUENCE: 20

| | |
|---|---|
| atgaaagcag aacataataa tttaaaatta catttcaaaa tgtataaatc tggaaaacaa | 60 |
| tgggttattg cggactaac aactgtggta gcttcaattg ctatcttcag tggaaaccaa | 120 |
| ctatttagtg ggaatgttgt agcaaaggca gacggggtaa caacaaccca agtttctcaa | 180 |
| aatagcaata gtagtaatgg aatttctaca cttccaaaag atggaaagta tgtatctagt | 240 |
| gataatggaa aaacatggaa gtatgtttct caaaacaatg ctgcaaaagg attatatagt | 300 |
| gatggttcaa acattttcta ctttaatgaa agtgatggaa ctcaagtaaa aggtaacatt | 360 |
| attagtgttg gaaaaacac ttattatttc gatagcaaaa ctggtcaagg aacaaaaata | 420 |
| tcagattata ctggtggaaa gtacactaac ccaagtactg ataataaagc tgcttggacc | 480 |
| taccaagata agagcaataa cactgtaaag ggtgttgcaa caattggaga ttcagttcaa | 540 |
| tattacgatg aaaaagatgg atttcagcta aaaggtggat ctattaactt aggaaacaca | 600 |
| aattattatg tagattcaaa ccaaggaaat gtaactagta agtaaatag agttgtttct | 660 |
| tctaatgacg ggactttaaa aggattaaac gtcgtaaatg gtaatttaca gtaccttgat | 720 |
| tataaaactg gaaacaagt aaagaataaa caagtagcag ttaatggtgt tacatactac | 780 |
| tttgatgata atggaaatgg ttcatatta ttaccaatt taggtaaatc tgttcgtact | 840 |
| aattttgata aatataatgc tgttaatggt gtaaataaat ctaatttcac aaacacagtt | 900 |
| gatggattct taacagcaga ttcatggtat cgtcctaaac aagtttggc taacggtaag | 960 |
| aaatggcgta agtctacttc taagattttt agaccattag taacagtagc atggccaaac | 1020 |
| aaagatgttc aggttaatta tttagcttta atgcaaatga acggtttgtt atctaataag | 1080 |
| gaaaagtaca ctgttttctc tgatcaacaa acattaaatg ctgctgctca aaaagcccaa | 1140 |

```
gttaatattg agaaacgcat tagtaaaaag aaaagtacta aatggttaga caagttgtta   1200
ttccaaggta caactactga accatcattt ataaagagac aatatgtttg gagttctgca   1260
tctgaatatc ctggacaagg ggatgctcaa tggttccaag gaggatactt gaagtatggt   1320
aataatcgtt taactccaaa aactaattca agtatcgtc aaattggtaa tgcttttgac    1380
tttttattag caaatgatgt tgataactct aacccatcag ttcaagctga agatattaat   1440
tggctacatt atttaactca ctttggttca ataactgcta aagatcctaa agctaatttc   1500
gatagtatca gaattgatgc tgtggacttt atcagtaatg atatagttca agaagtaat    1560 gattacctaa gggatttata caaacttaca agaatgata gcaatgctga taagcatatt    1620
tcattggttg aaggtagtct agaagcggca acaagttatt cacattcaga ttctctaatt   1680
gaatctcctt atagaaatga tattgatgga ctattaggaa actcaggaaa ttctgcagac   1740
ttaagtaaat taattaaaga gtatgattct ggaatcatta tttcagatca ttcaggaact   1800
actaacaata gttctattcc aacttattct attgttcatg cccatgataa gggagttcaa   1860
gaaagagttg acaagcaat tatggataat tctggtataa ctgattgggc aaactttact   1920
cctaagcaat taagagatgg attgaagtta tactatgatg atcaaagaaa aactgttaag   1980
aaatacaatg actataacgt tccaagtgcc tatgcaataa tgctaactaa caacaacact   2040
gttcctcgta tctactatgg tgatatgtat caagatgatg gacaattcat gcaaaaaaag   2100
agtctatatt atgatgacat cgttagtttg atgctggcta gaaccaaata tgttgccggt   2160
ggtcaaagta tgagcatgga ttcaaatgga ttcctaacaa gtgttcgtta tggaaaaggt   2220
gctaataatg ttaattcaca aggtacatct gaaactagaa atgaaggaat tggagtaatt   2280
gttggtaacg cactaataa agttcttaat gatggacaaa cagttacttt aaatatgggt   2340
gcagctcata agaaccaaca atatcgtcct gttttattaa caaccaaaga tggaatcaag   2400
acatattctt ctgataaaaa tgcgcctgtt gtagaaactg attcaaatgg ggttcttaca   2460
tttagcaata aagatgttaa tggacaaagt gacacaagtg taaggggaac attaaatcca   2520
caagtttccg atatttagc tgtatgggta cctgttggtg ctaagaatgg acaagatgct   2580
agaacaaaac catcaaagaa agccagaaat gatggtaaag tacttcattt aaatgatgct   2640
ttagcttcta acttgatttt tgaaggattc tcaaactttc aacctatgcc aaaaaataag   2700
agtcaataca ctaacgttgt aattgccaaa atgctaaaa catttaaaaa atgggggtatt   2760 acaagttttg aaatggcacc tcaatatcgt tctaccaacg ataagagttt tgtcgattca   2820
actataaaaa acgggtatgc attctcagac agatatgatt taggtttcgg taagccaacc   2880
aaatacggta cagataaaga tttaagaaag gccattaagt ccctacatgc tcaaggcatg   2940
caagttatgg ctgatgttgt atataatcaa ctatataacc ttcctggtaa agaagtagta   3000
tctacttctc gagctagtgc ttatggtaat aatgttgatg ttccatttgg aaaccaatta   3060
tatgttgtaa atactattgg tggtggaaag tatcaaacta gtttggtgg aaaataccttt   3120 aaagaactaa agaagaaata tcctagttta tttaaggcaa aaacatataa atactattac   3180
aaagacaatc aaaagatgg ctcagttaaa ttagctctta cttcaagcaa gagatcaagc   3240
attccagcaa acaaacctat taaggaatgg tctgctaaat atatgaacgg tacaaatgta   3300
ttgggattag aatgggata tgtcttaaaa gattggaata atggtaaata ctttaagatt   3360
aatgggacaa agacttcgtt accaagttct atttattaca aaagtacaaa aaataagtaa   3420
```

<210> SEQ ID NO 21

<211> LENGTH: 4392
<212> TYPE: DNA
<213> ORGANISM: Lactobacillus kunkeei

<400> SEQUENCE: 21

```
atgaatatca atagtaatga acgtaaggtt cgatttaaaa tgtataaatc tggtaaacaa      60
tggattgtag ctggattaac tacagcagta atatctattg ctgtgtatgg tggttcttca     120
attgccaatg gtgaattga agctaaagct gatgcacaaa acgcagctac ttcttcaatt     180
gtgaatacta ataattctac aaatagtagt aatgctaatt caattgcatc tcttcctcaa     240
aatggtacat attcaacaaa tgataacgga caaacttgga agtatgtatc acaaaataag     300
gacattcaag gtttatataa ggataataat gatcagttaa gatattttaa cgaatatgat     360
ggcactcaag ccaagggtga tattgtaaat gttaataatg acaattacta ttttgataaa     420
gacagtggtc agggacataa gattgatagc tacactgggg aagctactc tgaaagtaag     480
gtcaataacc aggatggttg gatttataaa tcaagtgata acaatgatgt taaaggagtc     540
gctactgtcg acggtaatat tcaatatttt gatcaaaata caggtctgca attaaaaggt     600
ggatctgcgc aaattggtgg agttgattac tattttgacc caaacaaggg taatttagtt     660
ggaaaagttg atcaagtagt aaactcaaat gattatagcg ataataagtt actggatagc     720
aacaaaaatg tagttaaagg tttagtagta aataatggtc agttacaatt ttttgataca     780
tctaacggta atcaggctaa gataagcaa gtaaagctaa atggaattac ctactatttt     840
gatactaatg gaaatggtca atacttgttt actaatacag gtaagagtgc tgttgatgac     900
tttacacaaa gaaatgctgc taacagtgtt aacccaagtg attacaaaaa tgttgtagat     960
ggatttttta cagcagatac ttggtaccgt ccaaaacaaa tattagataa tggtactact    1020
tggcgtaatt caaatagtaa tgaactccgt cctatgatta ctgcttggtg gccaaacaag    1080
gatgttcaag ttaattattt gaaattaatg caaaataacg gactattaga taaaagcaat    1140
tcgtattcaa tacaatctga tcaacagaca ttaaatcaag cagcacagaa agctcaagta    1200
aatattgaaa agaaaatttc acaaacgggg aatactgatt ggttaaatga tttgttattt    1260
aaaggaaacg gcgataaccc atcatttgtg aagcaacagt atatttggag ttcagattca    1320
gaatcgccat ggcaaggaga tgcatggttc aaggtggat atttaaaata tggcaatagt    1380
gtcatgacac aaatactaa ttctaattat agagattcta ataacttgtt tgatttcttg    1440
ttagctaatg atgtagataa ttcaaaccct gcagttcaag cggaggactt aaattggcta    1500
tactacttaa ctaacttcgg aactattacc gctaatgatt ctaatgctaa ttttgatagt    1560
attagaattg atgccgttga ttttattagt aacgatatta caaagaag ttatgattac    1620
ttacgtcaaa agtttaattt aatgcaaagt gatgcaaatg ctgattcgca tatttcgtta    1680
gttgaaggtg gagtggatgc aggaactaca tcttatagca atgacggatt agttgaggca    1740
ccattcagac tggatgctta tccttttgcta cataagcaag atggagacgt attaaaaac    1800
ttaatagatg aagaagattc tggaatcgac atttcaaatc ataatggaga accaatacaa    1860
aataatacta ttggtggaat aactctatct ggtggaaaac ctaactattc aattgttcat    1920
gcccatgata aggatgttca agaaaaagta ggtcaagcta aatcgatac aactggaatt    1980
aaggattgga ctgactttac accaagtcaa ttagcacaag gattagaaac tttctataac    2040
gatcaaagac aaacagtaaa aaatacaat gattataatg tgcctagtgc atatgcaatc    2100
atgctaacta caagggaac agttcctcgt atttattatg gtgatatgta ccaagatgac    2160
ggtcaattta tgcaaaagaa gagtctttat tatgatgata tagcaaactt gatgactgcg    2220
```

```
agaaagaaat atgtatctgg tggtcaatct atggttgata ataatggaat tctaacaagc    2280
gtacgttttg gtaaaggtgc caatacagtt agtgattcag gaacagaaga tacaaggaat    2340
caaggtattg gattaatagt tggatctgac cccaaaaagg ttttaaatga tggggatacc    2400
gttgttttac acatgggtgc agcccataag aaccaaaaat atcgtgcctt gatgctaact    2460
actgaaaatg gaattcaaaa ttataattca gatgataatg caccagttgc tgaaacagat    2520
gataatggtg atttagtttt cagtaacaaa gatattaatg gtcaagctaa cactgcaatt    2580
aaacaagttg ccaatccaga ggtgaatggt tatctagcag catgggttcc ggttggggct    2640
tccgatgacc aagattcaag aacagcacca tccactagtc aaaataatga tggtaatgtt    2700
ttgcacgaaa acgacgcact agattcaaat cttattttg aaggatttc taacttccaa    2760 ccaactccaa caaatcatga tgaatatgca acgttgtaa ttgctaagaa tgcgtcacta    2820
tttaaggatt ggggtgtaac aagtttcgaa atggcaccac aatacagatc tagtcaagat    2880
catacattcg ttgattctac aatcgataac ggttacgcct tttcagatag atatgacttg    2940
ggatttggta caccaactaa atatggaaca gatgaagact aagaaatgc aataaaatct    3000 cttcatgata atggtatgca agtaatggct gatgtagtat acaaccaatt atataatttg    3060
ccaggacaag aagttgtatc tgcaaccaga gcaggtgtta ctggtaatac aaatgcatta    3120
ccttttggta ctcaattgta tgtagttaat acaatcggtg gtggagatta tcaaaagaaa    3180
tatggtggag cattcttaaa tgaactgcaa gaacaatatc catcattatt caaatctcaa    3240
aagtacaagt attactacaa aaattatgct aataatggtg ctggaccagg ttatttaaca    3300
gttaatgatg cagaacgttc ggatattcca tataatcaac caatcactga atggtcagct    3360
aagtatatga atggaactaa tattcttgga cgtggtatgg ttatgtatt aaaggactgg    3420 aatacaggtg attattcaa gttaagcggg agcgattcaa cactaccaag tagtttaact    3480
tacaagagcg gttgggttga aaatcctgat agtacttggt catactatga aaagaataat    3540
attgacaaat taactggatc tcaagttatt aatgaggaaa gagttttctt tgataacaac    3600
ggtattcaag ttaaaggagg atgggtaaaa aattcaaatg gtacctattc ttactatgac    3660
aagaatagtg gaaacatcct aactggtgat caattaatcg acggtgaaca tttcttcttt    3720
gataacaatg gtgttcaagt aaaaggaaaa tggataaaga atagtgatgg gtctaagtca    3780
tattacgatt ctcacttagg aaaacttata aagacggata aaaagtatc ttctaatgct    3840 cgaaaaaga atctaagga agaattattg tatgagaatg ccttaaaagt tttaagaaaa    3900
gataagaaac gtctcgataa aataagaca aaggcaaata tcagaaaata taataaaatct    3960 ctaaaaaaat atcgtaaagc aaagaagaaa cttttagcga ttactaagaa tagagttgct    4020
aatgctagaa aagcgattaa aattgctaaa aaagttcttt ctaagagaaa aaatattaat    4080
aatgaaaaaa gatattataa agctctaaaa gaatatattatg tagcggaaaa atcatatttg    4140
aaaattactg gaaattacaa taagaagtat tattacgaat ttgataaact tactccaaaa    4200
gtcaaagtgg ttaagaacat ttattcctat aagagtagac atttactaa aaagaataga    4260 gttaaaaaga ttaaaaaagg tactcttgtt agagttaaaa gtatagttcg aagtggtaaa    4320
gtcgctcgaa ttaatatcgg aaatggtcat tttataactt catctaaaga ttttattaag    4380
atgtttaaat aa                                                        4392
```

<210> SEQ ID NO 22
<211> LENGTH: 8526
<212> TYPE: DNA

<213> ORGANISM: Leuconostoc mesenteroides

<400> SEQUENCE: 22

```
atgagagaca aaagaataat atgcgatcgt aaaaaattgt ataaatctgg gaaactgtta      60
gtgacagccg gtattttttc tgctgtgata tttggcgttt ccacaactaa cgtaagcgct     120
gatagcacta acaacactgg tgttacggtg tcacaagcac cagataaagt agcggacaca     180
acagctacaa cagataaagt agcagacacg acggctacaa cggataaagc agcggacaca     240
acagctacaa cagataaagt ggccgacaca gcagctgcaa cggacaaagt agcggacaca     300
acagctacaa cggacaaagt agcggacaca acagctacaa cagataaagt ggccgacaca     360
gcagctgcaa cggacaaagt agcggacaca acagctacaa cagataaagt agcggacaca     420
acagctacaa cggacaaagt agcggacaca acagctacaa cagataaagt agcggacaca     480
gcagctgcaa cggataaagc agcggacacg acggctacaa cagataaagc agcggacacg     540
acggctacaa cagataaagt ggccgacaca gcagctacaa cagataaagc agcggacacg     600
acggctacaa cagataaagt ggccgacaca gcagctacaa cagataaagc agccgataca     660
gcggctacaa cggataaagt aaccgacaca acagttgcaa cgaataaagc agtggacaca     720
acagctacaa cagataaagt ggacgacaca acagccacaa cgtcagaaaa atcaaaaagt     780
attaaacaaa ttgatggtaa aacttatttc attggtgatg atggtcagcc taagaaaaat     840
tttacagcca ttgttgacgg tcaagtatta tatttcgaca agatactggg tgctttgaca     900
tcaaatagta gtcaatatac cgatggttta gtcaatatag gaatgagcaa taatgcggct     960
tattcattgt cttcggatag ttttacacaa gttgatggct atctaacggc taacagttgg    1020
taccgaccta agatatatt aaaaaatggt acaacttgga cggctgcaac agcaaacgat    1080
tttcgaccat tgttaatgtc ttggtggcca gataaagata cccaagtttc atacttaaaa    1140
tatatgcaat ctgcgggatt attatcagat gacgttgcat atcaaacaa tgatagtatg    1200
aacagtttga cggatacggc tatgactgtt caaaaaaaca ttgaagaaaa aattggccta    1260
ttgggcagta ctgactggct taaggccgat atgaaccaaa tggttgattc acaatcgaat    1320
tggaacatta gtagtgagtc taaaggaaca gatcatttgc aaggtggtgc gctcctatac    1380
gttaatagtg atttaacacc aaatgccaat tctgattatc gtttattaaa tcgaacgcca    1440
actaaccaaa aagtcaaat tacaacaaat ggtaatcaag gtggctatga gatgctgttg    1500
gccaacgatg ttgataattc taacccaatt gttcaagctg aacaattgaa ttggttatac    1560
tacatgatga atatcggtag catcgcccaa aatgatccaa cagcaaattt tgacggttac    1620
agagttgatg ctgttgataa cgtgaatgct gacttgttgc aaattgctgg agattatttt    1680
aaagcagcat atggaacaaa tcaaagtgac gctaatgcaa acaatcacat ttccatctta    1740
gaagactggg acaataatga tccagcgtat gtaaaagcac aggggaacaa ccaattaacc    1800
atggattttc caatgcattt ggcattgaag tattcattga atatgccaag tagtgctcgt    1860
agcggtttgg aaccagcaat ttcaacaagc ctagtaaatc gtgcagcaga cgccacagaa    1920
aatgaagccc aaccgaacta ttcatttatt cgtgcacatg atagtgaagt acaaacggtt    1980
attgctcaaa ttattaaaga taaaattaat cctagttccg atggattgac tgtctcaaca    2040
gatgaaattg ccaaagcatt cgaaatatat aatgctgacg aattaaaggc tgataaagag    2100
tataccgcat ataatatacc ctcatcatat gcattgatgt taactaacaa agatacaatt    2160
cctcgtgtgt attatggtga tttgtttacg gatgatggac aatatatgtc tgcaaaatca    2220
ccatattatg atgcacttac ttcattgctt caatcgcgag taaaatatgt ttcaggtggt    2280
```

```
caatctatga atatgactta ccttcataat aatcaaggcc ttttgacgtc agtccgctat   2340
ggaaaagacg ccatgacagc taacgacact ggtacaagtg aaacgcgcac acaaggtatt   2400
ggattaattg tcggcaacaa aactgattta aacctgaata atgatgagca aattgtgctt   2460
aacatgggcg ccgcacacaa aaatcaagct taccgtgcat taatgttaag tactaaagat   2520
ggcttgaaaa tttataatag tgatgacgag gcaccggtat cgtatacaga tgatcaaggc   2580
cgtttgattt ttaaatctga tgtggtttat ggtgtgagtg atgctcaggt ttctggttat   2640
ttagcagctt gggtgccagt cggtgcaaac gatagccaag atgctagaac agaaagtagt   2700
acaacagcgt caacagatgg taatacctat cattcaaata gtgccttaga ttctcaagtt   2760
atatatgaag gttttttcaaa cttccaagcc atgccaacac aggccgatga gtataccaat   2820
atcaagattg ccgaaaatgc acaattattc aagagccttg gataacaag ctttgaattg   2880 gcacctcaat accgttcaag tacggataac agtttcttag attcagttat tcaaaatggc   2940
tatgccttca cggatcgcta cgacattggt tataatacgc ctacaaagta cggtacagtt   3000
gaccaactat tagatgcttt aagagcattg catgcccaag gcattcaggc tatcaatgat   3060
tgggtcccag accaaattta taatttgcct ggcgaagaaa tagtgacagc cagtcgaaca   3120
aacggttcgg gaaaggtgaa tgaaagttca gttattaata atacgctata tgattctcgt   3180
actgttggtg gcggagagta tcaagcaata tatggaggtg ctttcttaga taagttaaaa   3240
caagattatc ctgagttatt tgaaacaaaa caaatttcaa caggtgaagc aatgaaccct   3300
gatgtcaaaa tcacagaatg gtcagctaag tattttaatg gctcaaacat tcaaggacgt   3360
ggtgcatggt atgttctcaa ggattggtca acaaatcaat actttaatgt ttcaagtggt   3420
agtgaatttt tacctaagca actgttaggc gaaaaaacaa gtacagggtt taccaacgtg   3480
gacaatggca agactgagtt ttattctacg agtggctacc aagcaaagaa tacatttatt   3540
caagataatg acaattggta ttattttgat aatgatggct atatggttgt tggcggtcaa   3600
gaaattaatg gtaaaaaata ttatttccta ccaaatggtg tagagttaca agatgcttat   3660
ttgtctgatg ggactagtga gtattactac agtagtgatg gtcgtcaaat ttctaatcaa   3720
tattatcaag gatcagacaa caactggcgt tatttctttg cagatggtca tatggctgta   3780
gggttagcaa caattactac agaaaatggt acaacaaatc aacatatttt cgatgcaaat   3840
ggtatgcaac ttaagggcgt agctataaag gatactgatg gcaatgtgca ctattttgat   3900
ggtaagacag gaaacatggt tataaattcc tggggcaaaa taagcgatgg ttcatggtta   3960
tacttaaatg atagccggtgt agcggtcaca ggaccgcaaa atattaacgg tcaaaatctt   4020
tacttcaacg aagacggtat tcaagtaaag ggtgaagcca ttactgataa tagtggaaac   4080
atacattatt atgatcgcag cacaggaaat atggttgtga actcatgggg tgaaacgaat   4140
aatggttcat ggctatactt gaacgacaag ggtgatgccg ttacaggaga acaagttatt   4200
gacggtcaaa aactatattt cagtagtaat ggaatccaac ttaaaaatac attcaagaag   4260
ctatccgatg gttcatggct atatttgaac gataaaggtc ttccagtgac aggagcacag   4320
gtcattgatg acaaaaactt gtatttcgac caagatggga agcaagtcaa aggtgacgtt   4380
gctacagatg gacaaggtaa cactcattat tatgacggca acacaggaaa tatggttact   4440
aattcatggg cagagttagc ggacggttca tggatgtatc tagataatga tggcaatcct   4500
ttaacaggac cgcaaaagat tgatggccag tcactctact ttaatgatgc tggtaagcaa   4560
atcaaaaacg cattggttaa actagatgat gggtcaacaa tttacctcga tgataaaggt   4620
```

```
gtttcatcaa ccggtattca agaattgat gataagatat attattttga tcctgatggt    4680
aaacaagtag tatgtcgttt tgaagaatta ccagatggtt catggatgta tctagatgat    4740
gacggtgttg ctgctacggg cgctcaaaaa attaatggcc aggaattata tttcgacaat    4800
aacgggaaac aagtcaaaaa tgacaaagta attaatgacg atggaacaat aaactattac    4860
acaggtatga gcggtgaaaa actaaaaaat gattttggtg aattaccaga cggttcatgg    4920
atgtacttgg ataatcaagg taatgctgta ataggtgccc aaaaaattaa tggccagaat    4980
ctttacttca agacagacgg acgacaggtt aagggtgaag caaatgttga ttcatcgggt    5040
gaaatgcact tctatgatcc tgattctggc gagctaatta caaatagatt tgaacaagtt    5100
gctagtggtg tatgggctta ctttgatgcc aacggtgttg ctgtaactgg tgagcaacgc    5160
attggtaagc aaaatttatt ttttgatcca actggttatc aagttaaagg cgacaaacga    5220
acaattgacg gcgttctcta tacctttgat aaagaaagtg gtgagagaaa gggtttagat    5280
tctatatcgg tattacccac caatggacaa tacacaaccg ataaggccca aaattggtat    5340
taccaagtcg atggtgaaaa tgtaaaaggg ctatatacaa ataatgatgg tcaattacgt    5400
tacttcgatt tgacaactgg cgtgcagact aaaggtaatt ttgtgacaat tggcaatgat    5460
acctactatt tcaccaagga acaaggggat ggacagatag tttctgaggt tgtgtcagga    5520
cactatggta ctgtccagtt gagtgacaat tcgtctgcat gggtttatcg cggtgcaaat    5580
gatcaaattt tgaaaggcct acagaatata acggtcgtc tgcaatattt tgatctaacc    5640
accggtgcgc aattaaaagg cggtgctgca aactatgatg gcaaccttta ttattttgaa    5700
tcatcagatg gtaacctagt cagtaaaatt cagcaatctt attctactgg gaattatgtg    5760
accgatggtg ataaagtaac atatgttgat gagcaaaaca ccaagtcac gggattagcg    5820 ttgattgatg atcaactaca atacttcaat ccaagtgacg gtagtcaagt caagaatgag    5880
caggttatcg ttgatggcgt cacatactac tttgataaaa atggtaatgg acaatacttg    5940
tttacaaata ctgcaacgat gtctactaat gaatttgcca acatagtgc tgcttatagc    6000 aatgatagtt ctagcttcaa gaatacgata gatggtttct tgacggccga tacctggtat    6060
cgccctaaag atatcttgga aaacggacaa acgtgggtag tttcttcaac aaatgacgtg    6120
cgaccactga taacagtttg gtggccaaat aaagatgttc aagttaatta tttaaatttt    6180
atgaagaaaa atggtttgct agatacaagt agtcaattta atctacaatt tgatcaatat    6240
gacttgaatg tcgccgcgca aaaagttcaa gtggctattg aaaacgcat ttcgaaagaa    6300 aagagtacag attggttgaa agatctttg tttgaagctc atgaagatac gccttcattt    6360
gtgaaacaac aatttatttg gaataaagat tctgaatatc aaggtcaagg ggatgcgtgg    6420
ttccaaggtg gttatctgaa atatgataat agtgaattaa ccccaacaac gaactcagat    6480
tatcgtgaat ccggtaatac attagacttc ttgcttgcta atgatgtcga caattctaac    6540
ccagcggttc aagctgaaaa tttgaattgg ttacattatt taatgaactt tggcacgatt    6600
acagctaatg atgatgatgc caactttgac agtattcgta ttgatgccgt tgactttatt    6660
gataatgatg ccattcagag aacctacgat tacatgcgtg atgcttataa agttgatgca    6720
agtgaagaca cgctaataa gcatatttca ctagttgaag ctggattaga tgctggtacc    6780
tctacaatta agaataatgc tttagttgaa tctaacttta gagaggcagc tacactatcg    6840
ctagcaaatc aatcagggaa aaatagttcc ttgactaata tgttgcaaga cattgatggt    6900
ggccagatta tagctgatca cgccaacaat gcaacgaaaa atgaagcaac gccaaattat    6960
tcaattattc atgctcatga taaggggatt caagaaaagg ttggtgcagc aattaccgac    7020
```

| | |
|---|---|
| gttactggtg cagactggac gaatttcacc gatgaccaat taaaagaagg attagcagct | 7080 |
| tattatcaag atcaacgttc aacgaataaa aagtataaca tctataactt acctagtatc | 7140 |
| tatgctttga tgttgaccaa taaggacaca gttcctcgtg tttattacgg tgatatgtat | 7200 |
| caagatgatg gccagtatat ggaaaagcaa agtatttatt atgatgccat tgtttccttg | 7260 |
| atgaacacta gaaagagtta tgtgagcggt ggacaaacca tggatgtaga tgaacatggt | 7320 |
| ttgttgaaga gcgttcgttt tggtaaagac gcaatgacag ctagtgaact tggtacgaat | 7380 |
| gaaacacgca ctgaaggtgt tggtgtgctg gtcggtaatg attcttcact aaaactaaat | 7440 |
| gattcagata cagttacttt agagatgggg gcggctcata aaaccaaga gtaccgagct | 7500 |
| gcattgttga caactagtga tggtattgtt acgtatgatg ctgataatga tgcaccaacg | 7560 |
| atctggacag atgaccgggg tacattaacg ttctcaaata aggagattgc tggtcaagat | 7620 |
| tatactagtg tgcaaggatt cgctaatcca caagtatcag gttacttagc agtttgggtg | 7680 |
| cccgtaggag ctagtgacga tcaagatgcc cgaacagcag catcaacaga taaaaatact | 7740 |
| gatgacaaag tactgcattc taatgctgca ttagattcga acttgattta cgaaggtttt | 7800 |
| tcgaactttc aacctaaagc aaccaccaat gatgaactga ctaacgtagt aattgctaaa | 7860 |
| aatgctaatt tatttgaaaa gtggggaatc acaagttttg agatggcacc acaatatcgt | 7920 |
| tcaagtgggg accacacgtt cttagattca acgattgata atggttatgt atttactgac | 7980 |
| cgatacgatt tgggatttga acaccaact aagtacggta ctgataagga tttgcgtact | 8040 |
| gcaattaaag cattgcacca atcaaatatg caggttatgg ctgatgtagt tgataaccaa | 8100 |
| gtttataatt tatctggaca agaggtcgta tcagcttcac gtgctggtgt ttacggcaat | 8160 |
| gatgtgtcaa ctggatttgg gacacaactc tatgcggtta atagtgttgg tggtggtaaa | 8220 |
| tatcaagccc aatacggtgg tgaatatttg aatgaattga agcaacaata cccagatttg | 8280 |
| ttcgaagcta agacgtatga ctattgggtt aaaaattatt caaatgacgg atcggatccg | 8340 |
| tattacacac tgtcgcaaaa cacacgaaaa gatatgccaa gtagtgaggt cattaaacaa | 8400 |
| tggtcagcta aatatatgaa tggtactaat gtattaggaa acggtatggg atatgttttg | 8460 |
| aaagattgga atacaggtga gtacttcaaa attggagaaa agaatgctga ttttataaca | 8520 |
| aattaa | 8526 |

<210> SEQ ID NO 23
<211> LENGTH: 7740
<212> TYPE: DNA
<213> ORGANISM: Lactobacillus kunkeei

<400> SEQUENCE: 23

| | |
|---|---|
| atgaataatt atcaagatag aaaattgcat tataaaatgt ataaaagtgg aaaaaactgg | 60 |
| gttgttgcag gtattgtttc agcaacaatg tctattgtat tattccaaaa tattaatgat | 120 |
| gttacagcaa aagctagtca aaatcagatt acatattcag gtagctatgc ttcgacagat | 180 |
| tccggtagtg ctaaaagtgc atattcagcg tcatcttaca taaacggatc aagttctttg | 240 |
| tctgtaccta gcactgataa ttcaaacaaa tcaagcttag cgtcttcaac aaactctagt | 300 |
| gttgtgactt cttcattaag ttcaaatgtt atgaatcaat catctaattc acatgcgtca | 360 |
| tcaataagtt cagacgtttc aaatcaatca caaagttcaa atcagcatc aacgagttca | 420 |
| aattcgtcag aaaaatctga ttcagcatca cagtctaata atttctgtgca atcatatgaa | 480 |
| tcggtttctt taagtgtatc tttagcatcc aatgcttcac aaaaacttaaa atcgcataca | 540 |

-continued

```
aagaacattg atggaaagac atatttttat gatttaaata ataatgaagt taagtctgct    600
ttaattgacg ataacaacac atactattat tttggaccca atggatatct gactacattt    660
gatgattcaa agttttcgga tggctcaatc aactcatcag atcagttatc tatttatacc    720
ccagatggta aatcaattac aaatgttgat ggcttttaa cagctgactc atggtatcgt     780
cctaagcaaa ttcaagtaag cgatactcaa tggagaaatt ctactaatgc agattttcga    840
ccactattga gtgtgtggtg gcctaacaag acagttgaaa ttaattactt aaattatatg    900
agcaaaaatg gtctagttaa tggtcatttt gataataata gtagtgcaaa cgatatcaac    960
caagcagctg caactgtaag attaagcatt gaaaacaaaa ttaaagcaga taatggtgat   1020
ttaagtgcga ttagatcttt atttactact ttcataaatt ctcaggatga atggaatatc   1080
gacagtgaag actataattc tggagatggt ttacaaggtg ggtcacttct ttttggaaac   1140
aatagtgaaa ctaaagatgc caactcaaac tacagattac ttaatagaaa tccgactcaa   1200
caagatggaa aaattgatta tacacataca caagatccag gctttgaatt tttgttggct   1260
aacgacgttg ataattctaa tcctgtcgta caagctgaaa cactcaattg gttgcattac   1320
ctaatgaatt ttgggtcaat tgttaacaaa gatagttcag caaattttga tggcgtgcgt   1380
gttgatgctg ttgataatat ggacgccgat gtgctaaata tcattagcca atattttaga   1440
gatgcataca aaattaacgc caatgacgtt aattctaata atcatctttc tattctagaa   1500
gactggagtg gaaatgaccc atattaccaa aaagatcatg gaacaaatca aatgactctt   1560
gatagtgact atttaagctc attacgatcg attttaatgt acaatccttc tgttagatct   1620
gatatgtcaa ctattattaa tgctggtatt gtggatagag ctgatgacaa tacaactaac   1680
aaagctattc caaattatga aattgtaagg gctcatgatg caggtgttca agacatcatt   1740
tcacaaatta ttattgacaa cattgatccc catgcttcag cttctaatcc aacgtgggaa   1800
caaatgagag aagctttcaa gatatacgat gctgatgaaa atagcactgt aaaaaaatac   1860
acacaatata acattcccgc atcatatgca ttgacccctta caaataaaga tacaaccca    1920 agagtttact atggtgacct atacactgac gacggtcaat ttatggaaca aaagactcca   1980
tattatgatg ctattgctga aatgcttaaa tcaagagtta agtatgtagc tggtggacaa   2040
catatggaag cggttaaggt taataatggt gaagatacga ttcttacttc tgttagatat   2100
gggaaggatg cattaaatgc agatgactta ggtgatagtc taactagaac atctggaata   2160
gctgttgttg aaagtaataa tcctactttg tcactttcgg ataaagacaa agttgttatt   2220
catatggggg cagcccataa gaatcaagaa tatcgtcaat tattaacggc ttcaaattca   2280
ggaattgatt cttttgacag tgatagttca aaaggttatg ttgtcgttcg tacagatgat   2340
aatggtgact taacattaga tggaaatatc attaagggat atgctaaccc gcaagtatct   2400
ggatacttat caatgtgggt accactaggg gcttctgata atcaagacat tagaactgct   2460
ccttcttcag aatcaagtac tgatggtcaa tccattcatt ctaatgaagc atctgactcg   2520
aacgttatat tagaagcatt ttctaacttt caaaattttc cacaaacaac tgatcaatat   2580
gaaaatgttg ttattcaaaa aaatgcagaa gattttaaaa atttaggttt tacttattta   2640
gaattaccac cacaatataa gtcaacaaaa gatggttcgt ttattgattc ggttgtacaa   2700
aatggttatt catttaatga tagatatgac ctaggatttg atacgccaac taagtatggt   2760
acggctgaac aattgattga tgcaattaaa tctctacatg cacaaggaat aaaagtactt   2820
gctgatatcg ttccagatca gatatattca ttgccaaacc aacaaattgt aaacgcaact   2880
agaacaaatc cttatggaga tgcaaacttt aattcaaatc ttattaatgt tttgtatgat   2940
```

```
gcgtttagta agggttctgg aactgattat caatataagt atggtggtga gttcttagaa    3000
caactaaaaa aattatatcc tgacttattt accacaaaac aaatttcaac aggacaacca    3060
atcgatgctt ctaaaaagtt aaagatttgg actgctgaat atttaaatgg ttcaaatatc    3120
caaggtcgag gttcggggta tgtattaagt agtacaccaa attctaatta ctacactgtt    3180
gtagatgatg gaaacacaaa cataaagagt tctaatctac ccaaaggatt attaggtgat    3240
aatgttgaat atggtttaaa acttattgat ggcaagatga agtacgtttc caccggtgga    3300
tttattgcta aaaatacttt tattcaagat gataatcaca attggtacta tgttgataat    3360
aacggtgatt ttgttacttc tccacaagtt atcaatggaa ataagtattt cttcctatca    3420
aacggtgtta atttaagaga cttcatttca gttaatagtg atggaacgat gaattattat    3480
caaagtaatg gaattttagc aaataacccc gggtattatt acagtaataa tataaatcaa    3540
atggtacatg ttaataataa cggtgtttta gatactggga ttgttaatgt taatggttat    3600
gttcaatatt ttgatgataa tggttaccaa gttaagggag acatagttaa ttttaatggt    3660
cgaaaaatgt attttgacga tggatctggt aatttagttt acaatcgatt tgtttcttac    3720
aatggaaatt ggtactatgc aggttccaac gggctattgg taaacggatt acaaaatata    3780
aataaccaaa gtctttactt cgatgataat ggaaaacaag ttaaaggtgg aatgatttca    3840
ttagataatc ataaaatgta ttttgatgct aatagtggaa acctttataa aaatagtttt    3900
gtattgttag atggagatgt ctattatgca aataatgatg gatatattgt aaatggatat    3960
caaaacatag gcggaagaaa tctatatttt gattcagacg gaaaacaagt aaaagaccaa    4020
tttgttaata ttaacgggaa taaagtatat tttaatggta ctgatggttc tgaagtaaaa    4080
gacgatttta ttattcatga tgacaaagaa tattatgcgg acaatcaagg acatcttttg    4140
acgggatata attttgttaa tgggcaaaat atgtatttca atgaggatgg atcgcaagta    4200
aaaaattcga ttgttagttt agatggtaaa ttaatgtatt ttgacgaaaa ttcaggtaac    4260
caggttaaga atggctttat tttacacaat gggaatgttt actattctaa caaagacggc    4320
attttggtta ctggatatca gaatatagac gggcaagatt tgtttttaa tgcagatggt    4380 actcaaatta aggtggtac tgctgaaata gatggtgtta attattattt tgaaaatgga    4440
gaaggacatt tagttggcaa agttgaccaa gtaattaact caaatagatt tagtgacaat    4500
aagcttttgg atgctaataa taatgttgtt aaaggattaa tttttaataa tggtcaattg    4560
caatacttcg attcattaac tggagatcaa gctaaaaata aacaaattat tgctgatggc    4620
aatacttatt attttgataa ttctggtaat ggaacttatt tatttaccaa tattggtgaa    4680
agtgaaacaa atgatttttc acaaaggaat gcagctaata gtgttaacct aagtgattac    4740
aaaaatgttg tagatggatt ctttacagca gatacttggt accgtccaaa acaaatatta    4800
gataatggta ctacttggcg taattcaaat agtaatgatt tccgaccaat gattacagta    4860
tggtggccaa ataaaaacgt tcaagttaat tatttaaagt taatgcaaaa taataatctc    4920
ttagataaga gcaccaatta tacattacag tccaatcaac aaatgttaaa tcaagctgct    4980
caaaatgcgc aggttaacat tgaaaagaaa attgcacaaa cgggaaatac tgattggtta    5040
aatgatctgt tatttaaagg aaatggagat acaccatcat ttgtaaagca acaatatatt    5100
tggaatattt tatctgaatc accaggacaa gatgatgctt tgttacaaaa tggatatttt    5160
aaatatgtta acagcgagct aacaccaaat accaattctt catatagaat atcaaataat    5220
ttatgtgatt tcttacttgc taatgatgtg gataattcca atccagctgt tcaggctgaa    5280
```

```
gacttaaact ggttatatta tttaactaat tttggaacta ttaccgccaa tgatccaaat    5340
gcaaactttg acagtattag aattgatgcg tatgccttta taaataatga tattgtccaa    5400
agaagtaatg actacatgaa acaaaaatat aaattaactg aaagttctaa taacgcaaat    5460
agccatttgt caattgtgga ggcaggtgtc gatgctggaa cgacatcaac taataatgat    5520
gagttagtgg aatcaccttt tagaacaata tcgtatggat taatacacaa agatagaaat    5580
cctcaagata tgaataactt tataaaagaa gtggatacag gtgtcgttat tgccgatcat    5640
gaaaataatt cacaagaaat tggacagcct aactattcta tcgttcatgc gcatgataag    5700
gatatacaag acaaagttgg cgaagcgatt gttgatgcaa ccggaatcaa ggactggacg    5760
aattttactc cttctgaatt atctgcaggt ttgaaattat attatgatga tcaacgaagt    5820
tctgaaaaaa aatataatga ttataatata cctagcgctt acgcaattat gttgacaaat    5880
aaaggtacag tcccacgaat atattatggt gatatgtatc aggatgatgg acaatttatg    5940
caaaaacaaa gcgtttatta tgacgatatt gtttcactat tgacagctag aaaaaaatac    6000
gtttctggtg gtcaatcaat gtctgtagat cataacaatt tcttagaaag tgtacgtttt    6060
ggtaagggag ctggtagtga aagcgattct ggtaatgcag aaacgcgtaa tgaaggaatc    6120
ggcttgattg ttggaaatga ccagaataag aaattaaatg atggagacac tgttgttttg    6180
catatgggtg ctgctcatag aaatcaaaag tatcgtgcat taatgttaac gacaaatgat    6240
ggtataaaaa attacgattc tgatgaaaat gctcctattg ccgaaacaga tagtaatgga    6300
gatcttgttt ttagtaataa ggatattaac ggacaagcca acacaagtgt tagaggtgtt    6360
ttaaacccag aagttgccgg atatgttgca gcatgggttc ctttaggagc atctgatgat    6420
caggattcga gaacattatc tagtaataaa tcttataatg atggaaaagt acttcattca    6480
ggagatgatt tagattctaa tgttattttt gaagcctttt caaattttca accagaacca    6540
acaaatgaaa atgaatatga gaatgtagta atcccccaaa aagcttcatt atttaaagac    6600
tggggtatta ctagttttga acttcctcca caatacaggt ctagtaatga ccatactttt    6660
gttgatgcaa ccattaataa tggttatgcg ttctctgata gatatgacct gggatttggt    6720
caacccacta aatatggaac tgatgtagat ttaagaaaca caattaaatc attgcatgat    6780
aacggaatgc aggtcatggc agatgtagtt tataatcaac tatataattt gccggggcaa    6840
gaagttgttt ctgctgtaag agcaggattt actggtaaca cagtttcatt gccatttgga    6900
aatcaattat atgttgtgaa tactgttggt ggtggtgact atcaaaagaa atatggtgga    6960
gcatttttgc agaagctata ccaagaatat ccaagcttgt ttgattcaga aaaatatcaa    7020
tataatagta agaattatgt tactgattta cttgttatga cagatggaga acgttcggcg    7080
attccttctg atcaaccaat cacagaatgg tctgccaagt acatgaatgg aactaacatt    7140
cttggacgtg gtatgggata tgtattaaaa gattggaaca caggaactta ctttaaactg    7200
aatggaaaca attctgtgct tccggatgtt ttaacttata gaaatagttt tgatgataat    7260
acaggaactc aatcaagctc aagtgcgcaa agcagtgcat caaaccatga acacaaatt    7320 agctcaagtg cccaaagcag tgcatcaaac catgaagcac aaagtagctc aagtgcgcaa    7380
agcagtgtat caagtcatga agtacaaagt agctcaagtg cgcaaagcag tgcttcaagt    7440
catgaagtac aaagtagctc aagtgcgcaa agcagtgctt caagccatga agtacaaagt    7500
agctcaagtg cgcaaagcag tgcatcaagt tatgaagcac aaagtagctc aagtgcgcaa    7560
agcagtgctt caagccatga agtacaaagt agctcaagtg cgcaaagcag tgtatcaagt    7620
catgaaacac aaagtagctc aagtgcgcaa agcagtgctt caagccatga agtacaaagt    7680
```
agctcaagtg cgcaaagcag tgcatcaagt aatgaagcac aaagtagctc aagtgcccaa    7740

<210> SEQ ID NO 24
<211> LENGTH: 4392
<212> TYPE: DNA
<213> ORGANISM: Lactobacillus kunkeei

<400> SEQUENCE: 24
atgaatatca atagtaatga acgtaaggtt cgatttaaaa tgtataaatc tggtaaacaa      60
tggattgtag ctggattaac tacagcagta atatctattg ctgtgtatgg tggttcttca     120
attgccaatg gtgaattga agctaaagct gatgcacaaa acgcagctac ttcttcaatt     180
gtgaatacta ataattctac aaatagtagt aatgctaatt caattgcatc tcttcctcaa     240
aatggtacat attcaacaaa tgataacgga caaacttgga agtatgtatc acaaaataag     300
gacattcaag gtttatataa ggataataat gatcagttaa gatattttaa cgaatatgat     360
ggcactcaag ccaagggtga tattgtaaat gttaataatg acaattacta ttttgataaa     420
gacagtggtc agggacataa gattgatagc tacactgggg gaagctactc tgaaagtaag     480
gtcaataacc aggatggttg gatttataaa tcaagtgata acaatgatgt taaaggagtc     540
gctactgtcg acgtaatat tcaatatttt gatcaaaata caggtctgca attaaaaggt     600
ggatctgcgc aaattggtgg agttgattac tattttgacc caaacaaggg taatttagtt     660
ggaaaagttg atcaagtagt aaactcaaat gattatagcg ataataagtt actggatagc     720
aacaaaaatg tagttaaagg tttagtagta aataatggtc agttacaatt ttttgataca     780
tctaacggta atcaggctaa gaataagcaa gtaatagcta atggaattac ctactatttt     840
gatactaatg gaaatggtca atacttgttt actaatacag gtaagagtgc tgttgatgac     900
tttacacaaa gaaatgctgc taacagtgtt aacccaagtg attacaaaaa tgttgtagat     960
ggatttttta cagcagatac ttggtaccgt ccaaaacaaa tattagataa tggtactact    1020
tggcgtaatt caaatagtaa tgaactccgt cctatgatta ctgcttggtg gccaaacaag    1080
gatgttcaag ttaattattt gaattaatg caaaataacg gactattaga taaaagcaat    1140
tcgtattcaa tacaatctga tcaacagaca ttaaatcaag cagcacagaa agctcaagta    1200
aatattgaaa agaaaatttc acaaacgggg aatactgatt ggttaaatga tttgttattt    1260
aaaggaaacg gcgataaccc atcatttgtg aagcaacagt atatttggag ttcagattca    1320
gaatcgccat ggcaaggaga tgcatggttc caggtggat attttaaaata tggcaatagt    1380
gtcatgacac aaatactaa ttctaattat agagattcta ataacttgtt tgatttcttg    1440
ttagctaatg atgtagataa ttcaaaccct gcagttcaag cggaggactt aaattggcta    1500
tactacttaa ctaacttcgg aactattacc gctaatgatt ctaatgctaa ttttgatagt    1560
attagaattg atgccgttga ttttattagt aacgatatta tacaaagaag ttatgattac    1620
ttacgtcaaa agtttaattt aatgcaaagt gatgcaaatg ctgattcgca tatttcgtta    1680
gttgaaggtg gagtggatgc aggaactaca tcttatagca atgacggatt agttgaggca    1740
ccattcagac tggatgctta tccttttgcta cataagcaag atggagacgt atttaaaaac    1800
ttaatagatg aagaagattc tggaatcgac atttcaaatc ataatggaga accaatacaa    1860
aataatacta ttggtggaat aactctatct ggtggaaaac ctaactattc aattgttcat    1920
gcccatgata aggatgttca agaaaaagta ggtcaagcta aatcgatac aactggaatt    1980
aaggattgga ctgactttac accaagtcaa ttagcacaag gattagaaac tttctataac    2040

```
gatcaaagac aaacagtaaa aaaatacaat gattataatg tgcctagtgc atatgcaatc    2100
atgctaacta acaagggaac agttcctcgt atttattatg gtgatatgta ccaagatgac    2160
ggtcaattta tgcaaaagaa gagtctttat tatgatgata tagcaaactt gatgactgcg    2220
agaaagaaat atgtatctgg tggtcaatct atggttgata ataatggaat tctaacaagc    2280
gtacgttttg gtaaaggtgc caatacagtt agtgattcag gaacagaaga tacaaggaat    2340
caaggtattg gattaatagt tggatctgcc cccaaaaagg ttttaaatga tggggatacc    2400
gttgttttac acatgggtgc agcccataag aaccaaaaat atcgtgcctt gatgctaact    2460
actgaaaatg gaattcaaaa ttataattca gatgataatg caccagttgc tgaaacagat    2520
gataatggtg atttagtttt cagtaacaaa gatattaatg gtcaagctaa cactgcaatt    2580
aaacaagttg ccaatccaga ggtgaatggt tatctagcgg catgggttcc ggttggggct    2640
tccgatgacc aagattcaag aacagcacca tccactagtc aaaataatga tggtaatgtt    2700
ttgcacgaaa acgacgcact agattcaaat cttattttg aaggattttc taacttccaa    2760
ccaactccaa caaatcatga tgaatatgca acgttgtaa ttgctaagaa tgcgtcacta    2820
tttaaggatt ggggtgtaac aagtttcgaa atggcaccac aatacagatc tagtcaagat    2880
catacattcg ttgattctac aatcgataac ggttacgcct tttcagatag atatgacttg    2940
ggatttggta caccaactaa atatggaaca gatgaagact taagaaatgc aataaaatct    3000
cttcatgata atggtatgca agtaatggct gatgtagtat acaaccaatt atataatttg    3060
ccaggacaag aagttgtatc tgcaaccaga gcaggtgtta ctggtaatac aaatgcatta    3120
cctttggta ctcaattgta tgtagttaat acaatcggtg gtggagatta tcaaaagaaa    3180
tatggtggag cattcttaaa tgaactgcaa gaacaatatc catcattatt caaatctcaa    3240
aagtacaagt attactacaa aaattatgct aataatggtg ctggaccagg ttatttaaca    3300
gttaatgatg cagaacgttc ggatattcca tataatcaac caatcactga atggtcagct    3360
aagtatatga atggaactaa tattcttgga cgtggtatgg gttatgtatt aaaggactgg    3420
aatacaggtg attatttcaa gttaagcggg agcgattcaa cactaccaag tagtttaact    3480
tacaagagcg gttgggttga aaatcctgat agtacttggt catactatga aaagaataat    3540
attgacaaat taactggatc tcaagttatt aatgaggaaa gagtttctt tgataacaac    3600
ggtattcaag ttaaggagg atgggtaaaa aattcaaatg gtacctattc ttactatgac    3660
aagaatagtg gaaacatcct aactggtgat caattaatcg acggtgaaca tttcttctttt    3720
gataacaatg gtgttcaagt aaaaggaaaa tggataaaga atagtgatgg gtctaagtca    3780
tattacgatt ctcacttagg aaaacttata aagacggata aaaaagtatc ttctaatgct    3840
cgaaaaaaga aatctaagga agaattattg tatgagaatg ccttaaaagt tttaagaaaa    3900
gataagaaac gtctcgataa aaataagaca aaggcaaata tcagaaaata taataaatct    3960
ctaaaaaaat atcgtaaagc aaagaagaaa cttttagcga ttactaagaa tagagttgct    4020
aatgctagaa aagcgattaa aattgctaaa aaagttcttt ctaagagaaa aaatattaat    4080
aatgaaaaaa gatattataa agctctaaaa gaatatttatg tagcggaaaa atcatatttg    4140
aaaattactg gaaattacaa taagaagtat tattacgaat ttgataaact tactccaaaa    4200
gtcaaagtgg ttaagaacat ttattcctat aagagtagac atttttactaa aaagaataga    4260
gttaaaaaga ttaaaaaagg tactcttgtt agagttaaaa gtatagttcg aagtggtaaa    4320
gtcgctcgaa ttaatatcgg aaatggtcat tttataactt catctaaaga ttttattaag    4380
atgtttaaat aa                                                        4392
```

<210> SEQ ID NO 25
<211> LENGTH: 8475
<212> TYPE: DNA
<213> ORGANISM: Leuconostoc carnosum

<400> SEQUENCE: 25

| | | | | | |
|---|---|---|---|---|---|
| gtgacagcag | gaattttctc | tacggttgtg | tttggtatgg | ccgtatctga | cgttagtgct | 60 |
| aatgacactg | acaacactgt | gttaacttcg | aacagtggat | ttttagataa | agtagtagat | 120 |
| acgacaagta | cggataaggc | agccacacca | gataaagtag | tagatacgac | aagtacggat | 180 |
| aaggcagtca | caccagataa | agtagcagat | acgacaagta | cggataaggc | agtcacacca | 240 |
| gataaagtag | cagatacgac | aagtacggat | aaggcagcca | caccggataa | agtagtagat | 300 |
| acgacaagta | cggataaggc | agccacaccg | gataaagtag | tagatacgac | aagtacggat | 360 |
| aaggcagcca | caccggataa | agtagtagat | acgacaagta | cggataaggc | agccacacca | 420 |
| gataaagtag | tagatacgac | gagtacggat | aaggcagcca | caccggataa | agtagcagat | 480 |
| acaacgagta | cggataaggc | agccacacca | gataaagtag | tagatacgac | gagtacagat | 540 |
| aaggcagcca | caccagataa | agtagtagat | acgacgagta | cagataaggc | agccacacca | 600 |
| gataaagtag | tagatacgac | aagtacagat | aaggcagcca | caccggataa | agtggtagat | 660 |
| acgacaagta | cggataaggc | agcagataga | accattagta | tttctggtaa | aacagttaaa | 720 |
| aatattgagg | aaattggtgg | gaaaacttat | tttgtagggg | atgatggcaa | agtcaaaaaa | 780 |
| aacttcacgg | ttattgttga | tgggcaagta | atgtattttg | acaaagagtc | tggagcattg | 840 |
| acttcgaacc | ataagcaata | taagaaggt | ctttcagata | taacaaatga | acataatgct | 900 |
| gcctattcat | tagaaaacga | caactttaca | caaattgata | gttacttaac | tgccaatagt | 960 |
| tggtaccgtc | caaaagatat | attaaaaagt | ggcacaacat | ggacagcctc | aaccgataaa | 1020 |
| gactctcgcc | cattacttat | gtcatggtgg | ccagatcaac | aaacagaact | atcttattta | 1080 |
| aagtatatgc | aatcagcagg | tttcttagca | gaggatgtta | atttatcaga | aaataatagc | 1140 |
| attgatgatc | taacagctgc | agcaatggat | gttcagaaaa | atgttgaagc | aaagattagc | 1200 |
| ctatcaggta | atacagattg | gttgaaagaa | gatatgaatc | agtttgttga | ttcacagtca | 1260 |
| aattggaata | tcagcagtga | gtcaaaaggc | actgatcatc | ttcagggcgg | cgctttattg | 1320 |
| tatggtaaca | gtgatatgac | accagatgct | aattctgatt | atcggttact | gaatcgcaca | 1380 |
| ccaaaaaacc | aaaccggaca | aatcagtgct | acgaatgatc | agggtggtta | tgagatgtta | 1440 |
| ttggctaatg | atgtcgataa | ttctaatcca | attgttcaag | ccgaacaatt | aaattggtta | 1500 |
| cactacatga | tgaacattgg | tagtattaca | aaaaatgatt | caacggctaa | ttttgatggt | 1560 |
| tatagagttg | atgcggtaga | taacgtgaac | gctgatttgt | tacaaattgc | tggtgactac | 1620 |
| ttcaaggccg | cttatgggac | ggacaaaagt | gatgcaaatg | ctaataatca | tatttctatt | 1680 |
| cttgaagatt | gggataatag | tgatcctgac | tacgtcaaaa | agcacgggaa | tgaacaatta | 1740 |
| actatggatt | ttccgatgca | tttggcatta | aaatatgctt | taaatatgcc | tattgatatg | 1800 |
| cgtagtgggc | ttgaaccggc | aattaagaca | agtctggtga | accgatcaca | agatgcaaca | 1860 |
| gaaaatgagg | cacagccaaa | ctactcgttt | atacgtgccc | atgatagtga | agtacagact | 1920 |
| gttattgctc | aaattattaa | agataaaatt | aatccaaagt | cagatggttt | gacagttaca | 1980 |
| cctgatgaaa | ttgcgaaagc | ttttgaaatc | tataatgcag | atgaactaaa | agctgataag | 2040 |
| gcatacacag | cttttaatat | cccgtcatct | tatgcacttt | tgttgactaa | taaagatacg | 2100 |

```
gtgcctcgtg tttactatgg cgatttattt acagatgatg acaatatat gtctgatcat    2160 tcaccatatt atgatgctat tacgacttta ttagcgtcac gtattaaata tgcggctggt    2220
ggtcaaagca tgggtatgac gtatttacac gataatcaag aagttttgac atctgtacgt    2280
tatggtaaag gggctctgac agcagatgat ttgggtaatg ttgacacacg tacacaaggt    2340
attggacttg ttatcagtaa taaaacggat ttgagtttaa agagtgatga gagcgttgtg    2400
ctgaatatgg gtgtcgcaca taaaaatcaa gcatatcgcc cggcaatgtt gactactaag    2460
tcaggattaa aaatttacga tactgatgat ggtgcaccaa ttgtttatac aaataattta    2520
ggacagctaa tttttaacgc agatacagtc tatggtgtga gtgatccaca agtttcaggg    2580
taccttgctg cgtgggttcc tgttggcgca actgaagatc aagatgctag aactaaaggc    2640
agtcatgatg gaacaactga tgggaatgtc tatcattcca acgctgcatt agattctcag    2700
gtcatatatg aaggtttctc taatttccag gcaatgccaa cgaccactga tgaatatact    2760
aacgtaaaga ttgcacaaaa tgcacagtgg tttaaaaaat taggactgac aagttttgaa    2820
ctggcaccgc aatatcgttc tagcacagat agtagctttt tagactctgt tattcaaaat    2880
ggatacgctt ttactgatcg atatgatgtg ggttataata caccaacaaa atatggtaca    2940
gtcgatcaat tattagatgc attgagagca ttacattcac aagatatcca agcaattaat    3000
gattgggtac ctgatcaaat ttataactta cccggggagc aaattgtaac agcgagtcgt    3060
accaatggat ccgaaaaata cgatgatgat tcagtgatta gtaatacttt tatgattca    3120 cgtactatcg gtggtggaga atatcaagcg atgtatggcg gggctttctt agatcaattg    3180
aagcaagcat atcctggttt gtttgaaaca aaacagcttt ctactggtgt tgcaatggat    3240
cctgatgtaa aaataaaaga atggtctgct aagtatttta atggttctaa cattcaaggg    3300
cgtggtgctt ggtatgtact aaaagactgg gcaactaata agtacttcag tgtctcgagt    3360
aataatacat ttttacctaa gcaattattg ggtgaaaaag ctagtacagg atttattacg    3420
aacgatggaa aaacagaatt ttattcaaca agtggctacc aggcaaagaa tacatttatt    3480
gaagacaacg gtaactggta ttacttcgat aatgatggtt atagcgtagt tggaaagcaa    3540
gtgattgata taaacacta ctatttcttg cctaatggtg tcgaattgca agatgcctat    3600
ttatcagatg gggataagca atattattat aaaaaaactg gtcgacaaat agtaaatcag    3660
tattatagag atgagcaagg tgattggagg tatttctttg cagatgggca tatggctctt    3720
gggttaactg acattgtttc aaatgatgga actcatgcga cacagtattt tgataacaat    3780
ggtgttcaag tgaaaggaac atcagaacga gataaagatg gtaatattca ctattttgat    3840
ggtacatctg gtaatttagt tgttagttca tggggacaat tgtcggacgg atcatggctt    3900
tacctgaatg ataaaggcat tgctgttacg ggtgctcaac aaattgatgg tcaatcacta    3960
tactttaatg aagatggtaa agaagtaaag ggtgatgcgg taacagataa tcaagggaat    4020
atacgttatt ttgatggtga atctggtcac atggtggtta attcatgggg taaattacct    4080
gatggttcat ggatgtattt gaatgataag ggtattgctg ttaccgggca acaaaaaatc    4140
aacaatgaag tcttatattt caatgctgat ggtaagcaaa tcaaaagtgc atttaaagaa    4200
ctagtggacg gatcatggct ttacctgaat gataaaggca ttgctgttac gggtgctcaa    4260
caaattgatg gtcaatcact atactttaat gaagatggta agaagtaaa gggtgatgcg    4320 gtaacagata tcaagggaa tatacgttat tttgatggtg aatctggtca catggtggtt    4380
aattcatggg gtaaattacc cgatggttca tggatgtatt tgaatgataa gggtattgct    4440
gttaccgggc aacaaaaaat caacaatgaa atcttatatt ttgatgctga tggtaagcag    4500
```

```
ttaaagaata cactgaaaac attatccgat ggttcacgta tttatttgga tggtaaaggt    4560
gtttctgcaa caggtgttca aaaaattaat ggtaaagtgt catactttga tgttaatggc    4620
aaacaagtta gcaatcatat tcaagaactc cctgatggtt catggatgta cctagataat    4680
gatggattag ctctaattgg taatcaagac gttgatggca acaacttta ctttgatgtt     4740 gatggtaagc aaataaaaaa tgacaaagtc aaaaatagtg atggaacaat taattattac    4800
acgggtactg ttggtgaaaa actaaagcat gattttggtc agttatccga tggttcgtgg    4860
atgtatttag atgaaaatgg taatgctgtt actggtgaac aaaatattaa tgggcaacat    4920
ttatacttta aagatgatgg acagcaagtt aaaggagatg tttttgagga tgacttaggc    4980
cgtatgcgtt attatagtgc taactcaggt gagatggttg tcaatcaatt tgaacaaatt    5040
tctgatggtg cctgggctta ctttggtgat gatggtgtgg cggtaactgg tgaacaacat    5100
atcaatggac aagatctttt ctttgatgcg acaggtcaac aggttaaagg tgaaagtcga    5160
accattaatg gtattcctta tacctttgaa aaggagagtg gtgagaaacg gtctgttaat    5220
atagcaccat tactagccat gggaaattat gttacaaata tggtacaga ttggcaatat     5280 gaagtgcaag gcaatcctgt taaagggtta tatagcactt ctgataataa gttgcgttat    5340
tttgatctga caacaggtgt acagattaaa ggcaactttg ttactattgg acataacaca    5400
tactatttca atccagctaa tggagacggt gaattattgc cagatgtttc tgatggccat    5460
tatggtacga tccaagttaa agatgcgaat acaaatgaaa agacagtttg ggtttaccgt    5520
aatcaaagta atactatttt gaaaggtatt caaaatattc atggtaatat acaatacttt    5580
gacttatcaa ctggggagca aataaagggt ggtattgcaa actatgatgg caatgattat    5640
tactttgaat cagcaaaggg taacctcaca agtaaaatta gcaagtcta tacagatggt     5700 caatatgtaa ctaaagatgg aaaaagcatt tatgaagacg cacaacaaca aagtgtcagt    5760
gggttagtgt ctattaatgg tcagttacaa tacttcaatc cacaagatgg cgtacaagtt    5820
aaaaatcaac aaattattgt tgatggcgtt acttactact ttgatgaaaa tggcaatggt    5880
cagtatttgt ttacgaatac aacggtcatg ccaatggatg atttttacaaa gcacaataca   5940 gtttatagtg ataacgacaa caactttaaa aataatgttg atgggttctt aactgctgat    6000
acatggtatc gtccaaagga aatcttaaaa gcaggaacaa cttggacaac aacatcggaa    6060
agtgacatga gaccactgat cacgacatgg tggccaaata aaaatgtgca agttaactat    6120
ctaaacttta tgaaacaaaa taatctattg cacacaaatg tggagtatag cttgctatct    6180
gaccaatatg atttgaatat tgcagctcaa gcagtacaaa cagctattga aaagcgaatt    6240
gctcaagaaa atagcactga ttggttgcaa aatcttctat tcacagctca agacgatcaa    6300
ccatcttttg ttaagcaaca gtttatttgg aataaagatt ctgaatacca aggaaaaggt    6360
gatgcttggt ccagggtgg ttacctgaaa tacgggaaca ataaattgac acctaatacc     6420
aactcaaatt atcgtaaaac tgacaacgcg tttgaatttt tgttagcaaa tgatatcgat    6480
aattcgaatc cggtcgttca agctgaaaat cttaattggt tagaatatct gatgaatttt    6540
ggtactataa ctggtaagga tgacgatgca aactttgata gtattcgtgt tgatgctgtt    6600
gattttatta gtaatgatac aattcaacga acatatgatt atttacgtga tgcctatcaa    6660
gtagatcaga gtgaagccaa ggctaatcaa catatttcat tagtagaggc tggattagat    6720
gcaggaacat caacagttaa aaatgatgcg cttattgaat ctaatttgcg tgaagcggct    6780
acgttatctt tggccaatgc atctggtaaa aatagtgcgt taaccaatat gttgcaagat    6840
```

-continued

```
gttgatggtg aacattgat tgcagatcat acccataatt caaccgaaaa tgaagccaca    6900
ccaaattatt caattattca tgctcatgac aaaggtattc aagagaaagt gggggctgca    6960
atttccgatg ctactggggc cgactggact aattttacag atacacaatt aaaatctggt    7020
ttggatcttt attataagga tcaacgtgct acggataaga aatataatat ttataacttg    7080
ccaagtattt atgcattaat gctcaccaat aaagacaccg taccacgtgt ttattatggt    7140
gatatgtatc aagataatgg tcagtatatg gcagagaaaa gtatctatta taatgctta    7200 gaatcattaa tgtcagcacg taaaagctat gtaagtggtg acaaactat ggatgttgat    7260 agccacggtt tgctaaaaag tgttcgtttt ggtaagggg ctatgactgc tgacacggta    7320
ggtaatgaag aaacaagaac tgaaggtatc ggtgtgttag ttggtaacga tgcttcattg    7380
aaactcaatg attcagatac agtgaccta gatatgggcg cagcacacaa aaatcaaaag    7440
tatcgtgcag caattttgac tactaataat ggtctatcaa cgttcgattc tgataaagat    7500
gcaccgattg cttggactaa tgataagggg atactaacat tttcaaataa aaatgttagt    7560
ggacaagata atactaatgt ccatggtgtt gctaatccac aggtatctgg ttatttggca    7620
gtatgggttc cagttggtgc taaagatgat caaaatgctg gacaagcgc atctacagta    7680 gtcaacacag atggtaaagt attacactct aatgcatcat tagattccaa cttaatttt    7740 gaaggattct ctaacttcca acctagagcg acaacaaatg acgaattaac caatgtcgtt    7800
atagctaaaa atgccgattt attccagaaa tggggtatta ctagctttga aatggcaccg    7860
caatatcgct caagtcagga ccacacattt ttagattcaa ccattgataa cggttatgcc    7920
ttcacagatc gttatgactt aggatttaac acaccaacga aatatggaac agatagtgat    7980
ttgcgattgg caatcaaatc attacataaa gctggcatgc aagtaatggc tgatgttgtt    8040
gataatcaag tctataactt accagaccaa gaagttgttt ctgcttcacg cgcaggtgta    8100
tatggtaatg atgtcgcgac cggatttgat acacaattgt atgctgttaa ttctgttggc    8160
ggcggtaaat atcaagcaca gtatggtgga cagtatttga gtgagttaaa gaataagtat    8220
ccagatttgt ttgaagctaa agcttatgat tattggacaa aaattatgc taatgatgga    8280 tcaaacccgt actacacatt atcacaacag actcgagatg atataccatc agacgagaaa    8340
attaagcaat ggtcagcgaa atatatgaac gggaccaatg ttttgggaca tggtatgggt    8400
tacgtactta aggattggaa tacgggtcaa tattttaaga ttaataaaga tggcgattcc    8460
aacttaccag tttaa    8475
```

<210> SEQ ID NO 26
<211> LENGTH: 8436
<212> TYPE: DNA
<213> ORGANISM: Leuconostoc mesenteroides

<400> SEQUENCE: 26

```
atgagagaca aaagaataat atgcgatcgt aaaaaattgt ataaatctgg gaaactgtta     60
gtgacagccg gtatttttc tgctgtgata tttggcgttt ccacaactaa cgtaagcgct    120
gatagcacta acaacactgg tgttacggtg tcacaagcaa cagataaagt agcagacacg    180
acggctacaa cggacaaagt agcggacaca acagctacaa cagataaagt ggccgacaca    240
gcagctacaa cggacaaagt agcggacaca acagctacaa cagataaagt ggccgacaca    300
gcagctacaa cggacaaagt agcggacaca acagctacaa cagataaagt ggccgacacg    360
acggctacaa cggacaaagt agcggacaca acagctacaa cagataaagt ggccgacaca    420
gcagctgcaa cagataaagc agccgataca gcggctacaa cggataaagt ggccgacaca    480
```

```
gcagctgcaa cggataaagt agcggacaca gtagctgcaa cggacaaagt agcggacaca      540
acagctacaa cagataaagc agccgataca gcggctacaa cggataaagt aaccgacaca      600
acagctgcaa cggataaagc agcggacacg acggctacaa cagataaagt ggccgacaca      660
acagccacaa catcagaaaa atcaaaaagt attaaacaaa ttgatggtaa aacttatttc      720
attggtaatg atggtcagcc taagaaaaat tttacagcca ttgttgacgg tcaagtatta      780
tatttcgaca aagatactgg tgctttgaca tcaaatagta gtcaatatac cgatggttta      840
gccaatatag gaaatgagca taatgcggct tattcattgt cttcggatag ttttacacaa      900
gttgatggct atctaacggc taacagttgg taccgaccta aagatatatt aaaaaatggt      960
acaacttgga cggctgcaac agcaaacgat tttcgaccat tgttaatgtc ttggtggcca     1020
gataaagata cccaagtttc atacttaaaa tatatgcaat ctgcgggatt attatcagat     1080
gacgttgcat tatcaaacaa tgatagtatg aacagtttga cggatacggc tatgactgtt     1140
caaaaaaaaa ttgaagaaaa aattggctta ttgggcagta ctgactggct taaggccgat     1200
atgaaccaaa tggttgattc acaatcgaat tggaacatta gtagtgagtc taaaggaaca     1260
gatcatttgc aaggtggtgc gctcctatac gttaatagtg atttaacacc aaatgccaat     1320
tctgattatc gtttattaaa tcgaacgcca actaaccaaa aaggtcaaat tacaacaaat     1380
ggtaatcaag gtggctatga gatgctgttg gccaacgatg ttgataattc taacccaatt     1440
gttcaagctg aacaattaaa ttggttatac tacatgatga atatcggtag catcgcccaa     1500
aatgatccaa cagcaaattt tgacggttac agagttgatg ctgttgataa cgtgaatgct     1560
gacttgttgc aaaattgctg agattatttt aaagcagcat atggaacaaa tcaaagtgac     1620
gctaatgcaa acaatcacat ttccatctta gaagactggg acaataatga tccagcgtat     1680
gtaaaagcac aggggaacaa ccaattaacc atggattttc caatgcattt ggcattgaag     1740
tattcattga atatgccaag tagtgctcgt agcggtttgg aaccagcaat ttcaacaagc     1800
ctagtaaatc gtgcagcaga cgccacagaa aatgaagccc aaccgaacta ttcatttatt     1860
cgtgcacatg atagtgaagt acaaacggtt attgctcaaa ttattaaaga taaaattaat     1920
cctagttccg atggattgac tgtctcaaca gatgaaattg ccaaagcatt cgaaatatat     1980
aatgctgacg aattaaaggc tgataaagag tataccgcat ataatatacc ctcatcatat     2040
gcattgatgt taactaacaa agatacaatt cctcgtgtgt attatggtga tttgtttacg     2100
gatgatggac aatatatgtc tgcaaaatca ccatattatg atgcacttac ttcattgctt     2160
caatcgcgag taaaatatgt ttcaggtggt caatctatga atatgactta ccttcataat     2220
aatcaaggcc ttttgacgtc agtccgctat ggaaaagacg ccatgacagc taacgacact     2280
ggtacaagtg aaacgcgcac acaaggtatt ggattaattg tcggcaacaa aactgattta     2340
aacctgaata tgatgagca aattgtactt aacatggggg ccgcacacaa aaatcaagct     2400
taccgtgcat taatgttaag tactaaagat ggcttgaaaa tttataataa tgatgacgag     2460
gcaccggtat cgtatacaga tgaccaaggc cgtttgattt ttaaatctga tgtggtttat     2520
ggtgtgagtg atgctcaggt ttctggttat ttagcagctt gggtgccagt cggtgcaaac     2580
gatagccaag atgctagaac agaaagtagt acaacagcgt caacagatgg taataccctat    2640 cattcaaata gtgccttaga ttctcaactt atatatgaag ctttttcaaa cttccaagcc     2700
atgccaacac aggccgatga gtataccaat atcaagattg ccgaaaatgc acaattattc     2760
aagagccttg ggataacaag ctttgaattg gcacctcaat accgttcaag tacggataac     2820
```

```
agtttcttag attcagttat tcaaaatggc tatgccttca cggatcgcta cgacattggt    2880
tataatacgc ctacaaagta cggtacagtt gaccaactat tagatgcttt aagagcattg    2940
catgctcaag gcattcaggc tatcaatgat tgggtcccag accaaattta taatttgcct    3000
ggggaagaaa tagtgacagc cagtcgaaca aacggttcgg gaaaggtgaa tgaaagttca    3060
gttattaata atacgctata tgattctcgt actgttggtg gcggagagta tcaagcaata    3120
tatggaggtg ctttcttaga taagttaaaa caagattatc ctgagttatt tgaaacaaaa    3180
caaatttcaa caggtgaagc aatgaaccct gatgtcaaaa tcacagaatg gtcagctaag    3240
tattttaatg gctcaaacat tcaaggacgt ggtgcatggt atgttctcaa ggattggtca    3300
acaaatcaat actttaatgt ttcaagtggt agtgaatttt tacctaagca actgttaggc    3360
gaaaaaacaa gtacagggtt taccaacgtg gacaatggca agactgagtt ttattctacg    3420
agtggctacc aagcaaagaa tacatttatt caagataatg acaattggta ttattttgat    3480
aatgatggct atatggttgt tggcggtcaa gaaattaatg gtaaaaaata ttatttccta    3540
ccaaatggtg tagagttaca agatgcttat ttgtctgatg ggactagtga gtattactac    3600
agtagtgatg gtcgtcaaat ttctaatcaa tattatcaag gatcagacaa caactggcgt    3660
tatttctttg cagatggtca tatggctgta gggttagcaa caattactac agaaaatggt    3720
acaacaaatc aacaatattt cgatgcaaat ggtgtgcaac ttaagggcgt agctataaag    3780
gatactgatg gcaatgtgca ctattttgat ggcaagacag gaaacatggt tataaattcc    3840
tggggtaaaa taagcgatgg ttcatggtta tacttaaatg atagcggtgt agcggtcaca    3900
ggaccgcaaa atattaacgg ccaaaatctt tacttcaacg aagacggtat tcaagtaaag    3960
ggtgaagcca ttactgataa tagtggaaac atacattatt atgatcgcag cacaggaaat    4020
atggttgtga actcatgggg tgaaacgaat aatggttcat ggctatactt gaacgacaag    4080
ggtgatgccg ttacaggaga acaagttatt gacggtcaaa aactatattt cagtagtaat    4140
ggaatccaac ttaaaaatac attcaagaag ctatccgatg gttcatggct atatttgaac    4200
gataaaggtc ttccagtgac aggagcacag gtcattgatg gacaaaactt gtatttcgac    4260
caagatggga agcaagtcaa gggtgacgtt gctacagatg gacaaggtaa cactcattat    4320
tatgatggca acacaggaaa tatggttact aattcatggg cagagttacc ggacggttca    4380
tggatgtatc tagacaatga tggcaatcct ttaacaggac agcaaaagat tgatggccag    4440
tcactctact ttaatgatgc tggtaagcaa atcaaaaacg cattggttaa actagatgat    4500
gggtcaacaa tttacctcga tgataaaggt gtttcatcaa ctggtattca agaattgat    4560 gataagatat attattttga tcctgatggt aaacaagtag tatgtcgttt tgaagaatta    4620
ccagatggtt catggatgta tctagatgat gacggtgttg ctgctacggg cgctcaaaaa    4680
attaatggcc aggaattata tttcgacaat agcgggaaac aagtcaagaa cgacaaagta    4740
attaatgacg atggaacaat aaactattac acaggtatga gcggtgaaaa actaaaaaat    4800
gattttggtg aattaccaga cggttcatgg atgtacttgg ataatcaagg taatgctgta    4860
ataggtgccc aaaaaattaa tggccagaat ctttacttca agacagacgg acgacaggtt    4920
aagggtgaag caaatgttga ttcatcaggt gaaatgcact tctatgatcc tgattctggc    4980
gagctaatta caaatagatt tgaacaagtt gctagtggtg tatgggctta ctttgatgcc    5040
aaaggtgttg ctgtaactgg tgagcaacga attggtaagc aaaatttatt ttttgatcca    5100
actggttatc aagttaaagg cgacaaacga acaattgacg gcgttctcta tacctttgat    5160
aaagaaagtg gtgagagaaa gggtttagat tctatatcgg tattacccac caatggacaa    5220
```

```
tacacaaccg ataaggccca aaattggtat taccaagtcg atggtgaaaa tgtaaaaggg    5280
ctatatacaa ataatgatgg tcaattacgt tacttcgatt tgacaactgg cgtgcagact    5340
aaaggtaatt ttgtgacaat tggcaatgat acctactatt tcaccaagga acaaggggat    5400
ggacagatag tttctgaggt tgtgtcagga cactatggta ctgtccagtt gagtgacaat    5460
tcgtctgcat gggtttatcg cggtgcaaat gatcaaattt tgaaaggcct acagaatata    5520
aacggtcgtc tgcaatattt tgatctaacc accggtgcgc aattaaaagg cggtgctgca    5580
aactatgatg gcaaccttta ttattttgaa tcatcagatg gtaacctagt cagtaaaatt    5640
cagcaatctt attctactgg gaattatgtg accgatggtg ataaagtaac atatgctgat    5700
gagcaaaaca accaagtcac gggattagcg ttgattgatg atcaactaca atacttcgat    5760
ccaagtgacg gtcgtcaagt caagaatgag caggttatcg ttgatggcgt cacatactac    5820
tttgataaaa atggtaatgg acaatacttg tttacaaata ctgcaacgat gtcaactaat    5880
gaatttgcca acatagtgc tgcttatagc aatgatagtt ctagcttcaa gaatacgata    5940
gatggtttct tgacggccga tacctggtat cgccctaaag atatcttgga aaacggacaa    6000
acgtgggtag tttcttcaac aaatgacgtg cgaccactga taacagtttg gtggctaaat    6060
aaagatgttc aagttaatta ttcaaatttt atgaagcaaa atggtttgct agatacaagt    6120
agtcaattta atctacaatc tgatcaatat gacttgaatg tcgccgcgca aaagttcaa    6180 gtggctattg aaaaacgcat ttcgaaagaa aagagtacag attggttgaa agatctttg    6240 tttgaagctc atgaagatac gccttcattt gtgaaacaac aatttattg gaataaagat    6300 tctgaatatc aaggtcaagg ggatgcgtgg ttccaaggtg gttatctgaa atatggtaac    6360
aatgaattaa ccccaacaac gaactcagat tatcgtgaat ccggtaatac attagacttc    6420
ttgcttgcta atgatgtcga caattctaac ccagcggttc aagctgaaaa tttgaattgg    6480
ttacattatt taatgaactt tggcacgatt acagctaatg atgatgatgc taattttgac    6540
agtattcgta ttgatgccgt tgactttatt gataatgatg ccattcagag aacctacgat    6600
tacatgcgtg atgcttataa agttgatgca agtgaagaca acgctaataa gcatatttca    6660
ctagtggaag ctggattaga tgctggtacc tctacaatta gagtgatgc tttagttgaa    6720 tctaacttta gagaggcagc tacactatcg ctagcaaatc aatcagggga aaatagttcc    6780
ttgactaata tgttgcaaga cattgatggt ggccagatta tagctgatca cgccaacaat    6840
gcaacagaaa atgaatcaac gccaaattat tcaattattc atgctcatga taggggatt    6900 caagaaaagg ttggtgcagc aattaccgac gttactggtg cagactggac gaatttcacc    6960
gatgaccaat taaagaagg attagcagct tattatcaag atcaacgttc aacgaataaa    7020
aagtataaca tctataactt acctagtatc tatgctttaa tgttgaccaa taaggacaca    7080
gttcctcgtg tttattacgg tgatatgtat caagatgatg ccagtatat ggaaaagcaa    7140 agtatttatt atgatgccat tgtttccttg atgaacacta gaaagagtta tgtgagtggt    7200
gggcaaacta tggatgtaga tgaacatggt ttgttgaaga gtgttcgttt tggtaaagac    7260
gcaatgacag ctagtgacct tggtacgaat gaaacacgca ctgaaggtgt tggtgtgctg    7320
gtcggcaatg attcttcact aaaactaaat gattcagata cagttacttt agagatgggg    7380
gcggctcata aaaccaaaa gtaccgagct gcattgttga caactagtga tggtattgtt    7440
acgtatgatg ctgataatga tgcaccaaca atctggacag atgaccgtgg tacattgacg    7500
ttctcaaata aggagattgc tggtcaagat tatactagtg tgcaaggatt cgctaattca    7560
```

```
caagtatcag gttacttagc agtttgggtg cccgtaggag ctagtgacga tcaagatgtc    7620
cgaacagcag cattaacaga tgcaaatctt gatgacaaag tactgcattc taatgctgca    7680
ttagattcga acttgattta cgaaggcttt tctaactttc aacctaaagc aaccaccaat    7740
gatgaattga ctaacgtagt aattgctaaa aatgctaatt tatttgaaaa gtggggaatc    7800
acaagttttg agatggcacc acaatatcgt tcaagtgggg accacacgtt cttagattca    7860
acgattgata tggttatgc atttactgac cgatacgatt tgggatttga aacaccaact    7920
aagtacggta ctgataagga tttgcgtact gcaattaaag cattgcacca atcaaatatg    7980
caggttatgg ctgatgtagt tgataaccaa gtttataatt tatctggaca ggaggtcgta    8040
tcagcttcac gtgccggtgt ttacggcaat gatgtgtcaa ctggatttgg gacacaactc    8100
tatgcggtta atagtgttgg tggtggtaaa tatcaagccc aatacggtgg tgaatatttg    8160
aatgaattga agcaacaata cccagatttg ttcgaagcta agacgtatga ctattgggtt    8220
aaaaattatt caaatgacgg atcggatccg tattacacac tgtcgcaaaa cacacgaaaa    8280
gatatgccaa gtagtgaggt cattaaacaa tggtcagcta aatatatgaa tggtactaat    8340
gtattaggaa acggtatggg atatgttttg aaagattgga atacaggtga gtatttcaaa    8400
attggagaaa agaatgctga ttttataaca aattaa                              8436
```

<210> SEQ ID NO 27
<211> LENGTH: 1107
<212> TYPE: PRT
<213> ORGANISM: Leuconostoc mesenteroides

<400> SEQUENCE: 27

```
Val Lys Gly Asp Lys Arg Thr Ile Asp Gly Val Leu Tyr Thr Phe Asp
1               5                   10                  15

Lys Glu Ser Gly Glu Arg Lys Gly Leu Asp Ser Ile Ser Val Leu Pro
            20                  25                  30

Thr Asn Gly Gln Tyr Thr Thr Asp Lys Ala Gln Asn Trp Tyr Tyr Gln
        35                  40                  45

Val Asp Gly Glu Asn Val Lys Gly Leu Tyr Thr Asn Asp Gly Gln
    50                  55                  60

Leu Arg Tyr Phe Asp Leu Thr Thr Gly Val Gln Thr Lys Gly Asn Phe
65                  70                  75                  80

Val Thr Ile Gly Asn Asp Thr Tyr Tyr Phe Thr Lys Glu Gln Gly Asp
                85                  90                  95

Gly Gln Ile Val Ser Glu Val Val Ser Gly His Tyr Gly Thr Val Gln
            100                 105                 110

Leu Ser Asp Asn Ser Ser Ala Trp Val Tyr Arg Gly Ala Asn Asp Gln
        115                 120                 125

Ile Leu Lys Gly Leu Gln Asn Ile Asn Gly Arg Leu Gln Tyr Phe Asp
    130                 135                 140

Leu Thr Thr Gly Ala Gln Leu Lys Gly Gly Ala Ala Asn Tyr Asp Gly
145                 150                 155                 160

Asn Leu Tyr Tyr Phe Glu Ser Ser Asp Gly Asn Leu Val Ser Lys Ile
                165                 170                 175

Gln Gln Ser Tyr Ser Thr Gly Asn Tyr Val Thr Asp Gly Asp Lys Val
            180                 185                 190

Thr Tyr Ala Asp Glu Gln Asn Asn Gln Val Thr Gly Leu Ala Leu Ile
        195                 200                 205

Asp Asp Gln Leu Gln Tyr Phe Asp Pro Ser Asp Gly Arg Gln Val Lys
    210                 215                 220
```

```
Asn Glu Gln Val Ile Val Asp Gly Val Thr Tyr Tyr Phe Asp Lys Asn
225                 230                 235                 240

Gly Asn Gly Gln Tyr Leu Phe Thr Asn Thr Ala Thr Met Ser Thr Asn
                245                 250                 255

Glu Phe Ala Lys His Ser Ala Ala Tyr Ser Asn Asp Ser Ser Ser Phe
            260                 265                 270

Lys Asn Thr Ile Asp Gly Phe Leu Thr Ala Asp Thr Trp Tyr Arg Pro
        275                 280                 285

Lys Asp Ile Leu Glu Asn Gly Gln Thr Trp Val Val Ser Ser Thr Asn
    290                 295                 300

Asp Val Arg Pro Leu Ile Thr Val Trp Trp Leu Asn Lys Asp Val Gln
305                 310                 315                 320

Val Asn Tyr Ser Asn Phe Met Lys Gln Asn Gly Leu Leu Asp Thr Ser
                325                 330                 335

Ser Gln Phe Asn Leu Gln Ser Asp Gln Tyr Asp Leu Asn Val Ala Ala
            340                 345                 350

Gln Lys Val Gln Val Ala Ile Glu Lys Arg Ile Ser Lys Glu Lys Ser
        355                 360                 365

Thr Asp Trp Leu Lys Asp Leu Leu Phe Glu Ala His Glu Asp Thr Pro
370                 375                 380

Ser Phe Val Lys Gln Gln Phe Ile Trp Asn Lys Asp Ser Glu Tyr Gln
385                 390                 395                 400

Gly Gln Gly Asp Ala Trp Phe Gln Gly Gly Tyr Leu Lys Tyr Gly Asn
                405                 410                 415

Asn Glu Leu Thr Pro Thr Thr Asn Ser Asp Tyr Arg Glu Ser Gly Asn
            420                 425                 430

Thr Leu Asp Phe Leu Leu Ala Asn Asp Val Asp Asn Ser Asn Pro Ala
        435                 440                 445

Val Gln Ala Glu Asn Leu Asn Trp Leu His Tyr Leu Met Asn Phe Gly
450                 455                 460

Thr Ile Thr Ala Asn Asp Asp Ala Asn Phe Asp Ser Ile Arg Ile
465                 470                 475                 480

Asp Ala Val Asp Phe Ile Asp Asn Asp Ala Ile Gln Arg Thr Tyr Asp
                485                 490                 495

Tyr Met Arg Asp Ala Tyr Lys Val Asp Ala Ser Glu Asp Asn Ala Asn
            500                 505                 510

Lys His Ile Ser Leu Val Glu Ala Gly Leu Asp Ala Gly Thr Ser Thr
        515                 520                 525

Ile Lys Ser Asp Ala Leu Val Glu Ser Asn Phe Arg Glu Ala Ala Thr
530                 535                 540

Leu Ser Leu Ala Asn Gln Ser Gly Glu Asn Ser Ser Leu Thr Asn Met
545                 550                 555                 560

Leu Gln Asp Ile Asp Gly Gly Gln Ile Ile Ala Asp His Ala Asn Asn
            565                 570                 575

Ala Thr Glu Asn Glu Ser Thr Pro Asn Tyr Ser Ile Ile His Ala His
        580                 585                 590

Asp Lys Gly Ile Gln Glu Lys Val Gly Ala Ala Ile Thr Asp Val Thr
        595                 600                 605

Gly Ala Asp Trp Thr Asn Phe Thr Asp Asp Gln Leu Lys Glu Gly Leu
    610                 615                 620

Ala Ala Tyr Tyr Gln Asp Gln Arg Ser Thr Asn Lys Lys Tyr Asn Ile
625                 630                 635                 640
```

-continued

```
Tyr Asn Leu Pro Ser Ile Tyr Ala Leu Met Leu Thr Asn Lys Asp Thr
            645                 650                 655

Val Pro Arg Val Tyr Tyr Gly Asp Met Tyr Gln Asp Asp Gly Gln Tyr
        660                 665                 670

Met Glu Lys Gln Ser Ile Tyr Tyr Asp Ala Ile Val Ser Leu Met Asn
            675                 680                 685

Thr Arg Lys Ser Tyr Val Ser Gly Gln Thr Met Asp Val Asp Glu
    690                 695                 700

His Gly Leu Leu Lys Ser Val Arg Phe Gly Lys Asp Ala Met Thr Ala
705                 710                 715                 720

Ser Asp Leu Gly Thr Asn Glu Thr Arg Thr Glu Gly Val Gly Val Leu
                725                 730                 735

Val Gly Asn Asp Ser Ser Leu Lys Leu Asn Asp Ser Asp Thr Val Thr
            740                 745                 750

Leu Glu Met Gly Ala Ala His Lys Asn Gln Lys Tyr Arg Ala Ala Leu
        755                 760                 765

Leu Thr Thr Ser Asp Gly Ile Val Thr Tyr Asp Ala Asp Asn Asp Ala
    770                 775                 780

Pro Thr Ile Trp Thr Asp Asp Arg Gly Thr Leu Thr Phe Ser Asn Lys
785                 790                 795                 800

Glu Ile Ala Gly Gln Asp Tyr Thr Ser Val Gln Gly Phe Ala Asn Ser
                805                 810                 815

Gln Val Ser Gly Tyr Leu Ala Val Trp Val Pro Val Gly Ala Ser Asp
            820                 825                 830

Asp Gln Asp Val Arg Thr Ala Ala Leu Thr Ala Asn Leu Asp Asp
        835                 840                 845

Lys Val Leu His Ser Asn Ala Ala Leu Asp Ser Asn Leu Ile Tyr Glu
    850                 855                 860

Gly Phe Ser Asn Phe Gln Pro Lys Ala Thr Thr Asn Asp Glu Leu Thr
865                 870                 875                 880

Asn Val Val Ile Ala Lys Asn Ala Asn Leu Phe Glu Lys Trp Gly Ile
                885                 890                 895

Thr Ser Phe Glu Met Ala Pro Gln Tyr Arg Ser Ser Gly Asp His Thr
            900                 905                 910

Phe Leu Asp Ser Thr Ile Asp Asn Gly Tyr Ala Phe Thr Asp Arg Tyr
        915                 920                 925

Asp Leu Gly Phe Glu Thr Pro Thr Lys Tyr Gly Thr Asp Lys Asp Leu
    930                 935                 940

Arg Thr Ala Ile Lys Ala Leu His Gln Ser Asn Met Gln Val Met Ala
945                 950                 955                 960

Asp Val Val Asp Asn Gln Val Tyr Asn Leu Ser Gly Gln Glu Val Val
                965                 970                 975

Ser Ala Ser Arg Ala Gly Val Tyr Gly Asn Asp Val Ser Thr Gly Phe
            980                 985                 990

Gly Thr Gln Leu Tyr Ala Val Asn Ser Val Gly Gly Gly Lys Tyr Gln
        995                 1000                1005

Ala Gln Tyr Gly Gly Glu Tyr Leu Asn Glu Leu Lys Gln Gln Tyr
        1010                1015                1020

Pro Asp Leu Phe Glu Ala Lys Thr Tyr Asp Tyr Trp Val Lys Asn
        1025                1030                1035

Tyr Ser Asn Asp Gly Ser Asp Pro Tyr Tyr Thr Leu Ser Gln Asn
        1040                1045                1050

Thr Arg Lys Asp Met Pro Ser Ser Glu Val Ile Lys Gln Trp Ser
```

```
          1055                1060                1065

Ala Lys Tyr Met Asn Gly Thr Asn Val Leu Gly Asn Gly Met Gly
        1070                1075                1080

Tyr Val Leu Lys Asp Trp Asn Thr Gly Glu Tyr Phe Lys Ile Gly
        1085                1090                1095

Glu Lys Asn Ala Asp Phe Ile Thr Asn
        1100                1105

<210> SEQ ID NO 28
<211> LENGTH: 856
<212> TYPE: PRT
<213> ORGANISM: Leuconostoc mesenteroides

<400> SEQUENCE: 28

Thr Met Ser Thr Asn Glu Phe Ala Lys His Ser Ala Tyr Ser Asn
1               5                   10                  15

Asp Ser Ser Ser Phe Lys Asn Thr Ile Asp Gly Phe Leu Thr Ala Asp
                20                  25                  30

Thr Trp Tyr Arg Pro Lys Asp Ile Leu Glu Asn Gly Gln Thr Trp Val
            35                  40                  45

Val Ser Ser Thr Asn Asp Val Arg Pro Leu Ile Thr Val Trp Trp Leu
50                  55                  60

Asn Lys Asp Val Gln Val Asn Tyr Ser Asn Phe Met Lys Gln Asn Gly
65                  70                  75                  80

Leu Leu Asp Thr Ser Ser Gln Phe Asn Leu Gln Ser Asp Gln Tyr Asp
                85                  90                  95

Leu Asn Val Ala Ala Gln Lys Val Gln Val Ala Ile Glu Lys Arg Ile
                100                 105                 110

Ser Lys Glu Lys Ser Thr Asp Trp Leu Lys Asp Leu Leu Phe Glu Ala
            115                 120                 125

His Glu Asp Thr Pro Ser Phe Val Lys Gln Gln Phe Ile Trp Asn Lys
            130                 135                 140

Asp Ser Glu Tyr Gln Gly Gln Gly Asp Ala Trp Phe Gln Gly Gly Tyr
145                 150                 155                 160

Leu Lys Tyr Gly Asn Asn Glu Leu Thr Pro Thr Thr Asn Ser Asp Tyr
                165                 170                 175

Arg Glu Ser Gly Asn Thr Leu Asp Phe Leu Leu Ala Asn Asp Val Asp
            180                 185                 190

Asn Ser Asn Pro Ala Val Gln Ala Glu Asn Leu Asn Trp Leu His Tyr
            195                 200                 205

Leu Met Asn Phe Gly Thr Ile Thr Ala Asn Asp Asp Ala Asn Phe
            210                 215                 220

Asp Ser Ile Arg Ile Asp Ala Val Asp Phe Ile Asp Asn Asp Ala Ile
225                 230                 235                 240

Gln Arg Thr Tyr Asp Tyr Met Arg Asp Ala Tyr Lys Val Asp Ala Ser
                245                 250                 255

Glu Asp Asn Ala Asn Lys His Ile Ser Leu Val Glu Ala Gly Leu Asp
            260                 265                 270

Ala Gly Thr Ser Thr Ile Lys Ser Asp Ala Leu Val Glu Ser Asn Phe
            275                 280                 285

Arg Glu Ala Ala Thr Leu Ser Leu Ala Asn Gln Ser Gly Glu Asn Ser
        290                 295                 300

Ser Leu Thr Asn Met Leu Gln Asp Ile Asp Gly Gly Gln Ile Ile Ala
305                 310                 315                 320
```

Asp His Ala Asn Asn Ala Thr Glu Asn Glu Ser Thr Pro Asn Tyr Ser
                325                 330                 335

Ile Ile His Ala His Asp Lys Gly Ile Gln Glu Lys Val Gly Ala Ala
                340                 345                 350

Ile Thr Asp Val Thr Gly Ala Asp Trp Thr Asn Phe Thr Asp Asp Gln
                355                 360                 365

Leu Lys Glu Gly Leu Ala Ala Tyr Tyr Gln Asp Gln Arg Ser Thr Asn
        370                 375                 380

Lys Lys Tyr Asn Ile Tyr Asn Leu Pro Ser Ile Tyr Ala Leu Met Leu
385                 390                 395                 400

Thr Asn Lys Asp Thr Val Pro Arg Val Tyr Tyr Gly Asp Met Tyr Gln
                405                 410                 415

Asp Asp Gly Gln Tyr Met Glu Lys Gln Ser Ile Tyr Tyr Asp Ala Ile
                420                 425                 430

Val Ser Leu Met Asn Thr Arg Lys Ser Tyr Val Ser Gly Gly Gln Thr
                435                 440                 445

Met Asp Val Asp Glu His Gly Leu Leu Lys Ser Val Arg Phe Gly Lys
        450                 455                 460

Asp Ala Met Thr Ala Ser Asp Leu Gly Thr Asn Glu Thr Arg Thr Glu
465                 470                 475                 480

Gly Val Gly Val Leu Val Gly Asn Asp Ser Ser Leu Lys Leu Asn Asp
                485                 490                 495

Ser Asp Thr Val Thr Leu Glu Met Gly Ala Ala His Lys Asn Gln Lys
                500                 505                 510

Tyr Arg Ala Ala Leu Leu Thr Thr Ser Asp Gly Ile Val Thr Tyr Asp
        515                 520                 525

Ala Asp Asn Asp Ala Pro Thr Ile Trp Thr Asp Asp Arg Gly Thr Leu
530                 535                 540

Thr Phe Ser Asn Lys Glu Ile Ala Gly Gln Asp Tyr Thr Ser Val Gln
545                 550                 555                 560

Gly Phe Ala Asn Ser Gln Val Ser Gly Tyr Leu Ala Val Trp Val Pro
                565                 570                 575

Val Gly Ala Ser Asp Asp Gln Asp Val Arg Thr Ala Ala Leu Thr Asp
        580                 585                 590

Ala Asn Leu Asp Asp Lys Val Leu His Ser Asn Ala Ala Leu Asp Ser
        595                 600                 605

Asn Leu Ile Tyr Glu Gly Phe Ser Asn Phe Gln Pro Lys Ala Thr Thr
        610                 615                 620

Asn Asp Glu Leu Thr Asn Val Val Ile Ala Lys Asn Ala Asn Leu Phe
625                 630                 635                 640

Glu Lys Trp Gly Ile Thr Ser Phe Glu Met Ala Pro Gln Tyr Arg Ser
                645                 650                 655

Ser Gly Asp His Thr Phe Leu Asp Ser Thr Ile Asp Asn Gly Tyr Ala
                660                 665                 670

Phe Thr Asp Arg Tyr Asp Leu Gly Phe Glu Thr Pro Thr Lys Tyr Gly
        675                 680                 685

Thr Asp Lys Asp Leu Arg Thr Ala Ile Lys Ala Leu His Gln Ser Asn
        690                 695                 700

Met Gln Val Met Ala Asp Val Val Asp Asn Gln Val Tyr Asn Leu Ser
705                 710                 715                 720

Gly Gln Glu Val Val Ser Ala Ser Arg Ala Gly Val Tyr Gly Asn Asp
                725                 730                 735

Val Ser Thr Gly Phe Gly Thr Gln Leu Tyr Ala Val Asn Ser Val Gly

-continued

```
            740                 745                 750
Gly Gly Lys Tyr Gln Ala Gln Tyr Gly Gly Glu Tyr Leu Asn Glu Leu
            755                 760                 765

Lys Gln Gln Tyr Pro Asp Leu Phe Glu Ala Lys Thr Tyr Asp Tyr Trp
        770                 775                 780

Val Lys Asn Tyr Ser Asn Asp Gly Ser Asp Pro Tyr Tyr Thr Leu Ser
785                 790                 795                 800

Gln Asn Thr Arg Lys Asp Met Pro Ser Ser Glu Val Ile Lys Gln Trp
                805                 810                 815

Ser Ala Lys Tyr Met Asn Gly Thr Asn Val Leu Gly Asn Gly Met Gly
                820                 825                 830

Tyr Val Leu Lys Asp Trp Asn Thr Gly Glu Tyr Phe Lys Ile Gly Glu
            835                 840                 845

Lys Asn Ala Asp Phe Ile Thr Asn
    850                 855
```

POLYPEPTIDES CAPABLE OF PRODUCING GLUCANS HAVING ALPHA (1-->2) LINKAGES AND USE OF THE SAME

This application a continuation of U.S. application Ser. No. 15/767,689 (filed Apr. 12, 2018, now U.S. patent Ser. No. 10/822,383), which is the National Stage application of International Application No. PCT/US16/63233 (filed Nov. 22, 2016), which claims the benefit of International Application Nos. PCT/CN2015/095687 (filed Nov. 26, 2015) and PCT/CN2016/085547 (filed Jun. 13, 2016), both of which all of which prior applications are incorporated herein by reference in their entireties.

FIELD OF INVENTION

The disclosure relates to, for example, proteins that are capable of forming glucan having alpha-1,2 linkages, reactions and methods for producing such glucan, compositions comprising this glucan, and various applications of using this glucan.

REFERENCE TO SEQUENCE LISTING SUBMITTED ELECTRONICALLY

The official copy of the sequence listing is submitted electronically via EFS-Web as an ASCII formatted sequence listing with a file named 20161122_CL6550WOPCT3_SequenceListing.txt created on Nov. 21, 2016 and having a size of 413 kilobytes and is filed concurrently with the specification. The sequence listing contained in this ASCII-formatted document is part of the specification and is herein incorporated by reference in its entirety.

BACKGROUND

The enzymatic addition of alpha-1,2 branching to dextrans has been reported. A glucosyltransferase (DsrE) from *Leuconostoc mesenteroides* NRRL B-1299 has a second catalytic domain ("CD2") capable of adding alpha-1,2 branching to dextrans (U.S. Pat. Nos. 7,439,049 and 5,141,858; U.S. Patent Appl. Publ. No. 2009-0123448; Bozonnet et al., J. Bacteria 184:5753-5761, 2002). U.S. Patent Appl. Pub. No. 2010-0284972 describes methods and compositions for improving the health of a subject by administering compositions comprising alpha-1,2-branched alpha-1,6 dextrans. Sarbini et al. (Appl. Environ. Microbiol. 77:5307-5315, 2011) describes in vitro fermentation of dextran and alpha-1,2-branched dextrans by human fecal microbiota. Brison et al. (J. Biol. Chem. 287:7915-7924, 2012) describes a truncated form of the DsrE glucosyltransferase from *Leuconostoc mesenteroides* NRRL B-1299 (a glucan binding domain [GBD] coupled to the second catalytic domain, CD2 [i.e., GBD-CD2]) that is capable of adding alpha-1,2 branching to dextrans. Despite these reports, there remains a need to identify further enzymes that are capable of producing glucans having alpha-1,2 linkages.

SUMMARY

In one aspect, the present disclosure regards a reaction composition comprising at least water, sucrose, an alpha-glucan substrate, and a polypeptide that is capable of forming at least one alpha-1,2 branch from the alpha-glucan substrate, wherein the polypeptide comprises an amino acid sequence that is at least 90% identical to:
(i) the mature form of a sequence selected from the group consisting of SEQ ID NOs:4, 1, 7, 3, 5, 6, 7, 8, 9, 10, 11, 12 and 13;
(ii) SEQ ID NO:2.7 or a sub-sequence within any one of SEQ ID NOs:4, 2, 3, 5, 6, 7, 8, 9, 10, 11, 12, or 13 that aligns with SEQ ID NO:27, and/or
(iii) a sequence selected from the group consisting of SEQ ID NOs:4, 1, 2, 3, 5, 9, 10, 11, 12, and 13.

The present disclosure also concerns a method of producing a glucan composition that comprises alpha-1,2 linkages, the method comprising:
(a) providing at least the following reaction components: water, sucrose, an alpha-glucan substrate, and a polypeptide that is capable of forming at least one alpha-1,2 branch from the alpha-glucan substrate, wherein the polypeptide comprises an amino acid sequence that is at least 90% identical to:
 (i) the mature form of a sequence selected from the group consisting of SEQ ID NOs:4, 1, 2, 3, 5, 6, 7, 8, 9, 10, 11, 12, and 13;
 (ii) SEQ ID NO:27 or a sub-sequence within any one of SEQ ID NOs:4, 2, 3, 5, 6, 7, 8, 9, 10, 11, 12, or 13 that aligns with SEQ ID NO:27; and/or
 (iii) a sequence selected from the group consisting of SEQ ID NOs:4, 1, 2, 3, 5, 6, 7, 8, 9, 10, 11, 12, and 13;
(b) combining the reaction components under suitable conditions whereby the polypeptide catalyzes the synthesis of at least one alpha-1,2 branch from the alpha-glucan substrate, thereby forming a glucan composition comprising alpha-1,2 linkages; and
(c) optionally isolating the glucan composition comprising alpha-1,2 linkages.

The present disclosure also concerns a composition that comprises a glucan composition comprising one or more alpha-1,2 linkages produced by a method or reaction as described herein, preferably wherein the composition is in the form of a food product, pharmaceutical product, personal care product, household care product, or industrial product, optionally wherein the composition comprises about 0.01 to 99 wt % (dry solids basis) of the glucan composition.

The present disclosure also concerns a method comprising enterally administering a substance to a mammal, wherein the substance comprises a glucan composition comprising alpha-1,2 linkages, wherein the administering results in less or slower blood glucose elevation in the mammal as compared to a mammal that is enterally administered a substance that lacks the glucan composition but instead contains a same amount of a readily digestible glucose-containing carbohydrate, wherein the glucan composition is produced by a method or reaction as described herein, optionally wherein the mammal is a human, and optionally wherein the readily digestible glucose-containing carbohydrate is sucrose, free glucose, or starch.

The present disclosure also concerns a method of producing a food or beverage, the method comprising incorporating a glucan composition comprising alpha-1,2 linkages into the food or beverage, wherein the glycemic index of the resulting food or beverage is not increased, or only marginally increased, compared to a food or beverage that lacks the glucan composition, and wherein the glucan composition is produced by a method or reaction as described herein.

BRIEF DESCRIPTION OF THE BIOLOGICAL SEQUENCES

The identification (gi) and accession numbers provided below are from GENEBANK (available at National Center for Biotechnology Information [NCBI] website).

SEQ ID NO:1 is the amino acid sequence of full length GTFJ18 (old gi: 356644413, new gi: 504090610, Acc. No. WP_014324604.1, *Leuconostoc mesenteroides*). The predicted mature secreted form of GTFJ18 is believed to correspond to positions 21-2771 of SEQ ID NO:1. SEQ ID NOs:1 and 13 are identical.

SEQ ID NO:2 is the amino acid sequence from gi: 116096814 (GENBANK Acc. No. ABJ61965.1, *Leuconostoc mesenteroides*; also referred to herein as GTF6814). The predicted mature secreted form of GTF6814 is believed to correspond to positions 21-2821 of SEQ ID NO:2.

SEQ ID NO:3 is the amino acid sequence from gi: 916260333 (GENBANK Acc. No. WP_050995379.1, *Leuconostoc carnosum*; also referred to herein as GTF0333). The predicted secreted mature form of GTF0333 is believed to correspond to positions 41-2844 of SEQ ID NO:3.

SEQ ID NO:4 is the amino acid sequence from gi: 902949905 (GENBANK Acc. No. GAP05007.1, *Fructobacillus tropaeoli*; also referred to herein as GTF9905 or FtrGtfl). The predicted expressed form (contemplated to be a secreted, mature form) of GTF9905 is believed to correspond to positions 36-1672 of SEQ ID NO:4.

SEQ ID NO:5 is the amino acid sequence from gi: 938153845 (GENBANK Acc. No. WP_054608463.1, *Lactobacillus kunkeei*; also referred to herein as GTF3845). The predicted mature secreted form of GTF3845 is believed to correspond to positions 51-1632 of SEQ ID NO:5.

SEQ ID NO:6 is the amino acid sequence from gi: 938153846 (GENBANK Acc. No. WP_054608464.1, *Lactobacillus kunkeei*; also referred to herein as GTF3846). The predicted mature secreted form of GTF3846 is believed to correspond to positions 51-1318 of SEQ ID NO:6.

SEQ ID NO:7 is the amino acid sequence from gi: 927068954 (GENBANK Acc. No. KOY70706.1, *Lactobacillus kunkeei*; also referred to herein as GTF8954). The predicted mature secreted form of GTF8954 is believed to correspond to positions 51-1139 of SEQ ID NO:7.

SEQ ID NO:8 is the amino acid sequence from gi: 927268464 (GENBANK Acc. No. WP_053795842.1, *Lactobacillus kunkeei*; also referred to herein as GTF8464). The predicted mature secreted form of GTF8464 is believed to correspond to positions 51-1463 of SEQ ID NO:8.

SEQ ID NO:9 is the amino acid sequence from gi: 908395133 (GENBANK Acc. No. WP_049752804.1, *Leuconostoc mesenteroides*; also referred to herein as GTF5133). The predicted mature secreted form of GTF5133 is believed to correspond to positions 41-2841 of SEQ ID NO:9.

SEQ ID NO:10 is the amino acid sequence from gi: 935566432 (GENBANK Acc. No. WP_054450649.1, *Lactobacillus kunkeei*; also referred to herein as GTF6432). The predicted mature secreted form of GTF6432 is believed to correspond to positions 46-2580 of SEQ ID NO:10.

SEQ ID NO:11 is the amino acid sequence from gi: 916985575 (GENBANK Acc. No. WP_051592287.1, *Lactobacillus kunkeei*; also referred to herein as GTF5575). The predicted mature secreted form of GTF5575 is believed to correspond to positions 51-1463 of SEQ ID NO:11.

SEQ ID NO:12 is the amino acid sequence from gi: 407242790 (GENBANK Acc. No. AFT82440.1, *Leuconostoc carnosum* JB16; also referred to herein as GTF2790). The predicted mature secreted form of GTF2790 is believed to correspond to positions 21-2824 of SEQ ID NO:12.

SEQ ID NO:13 is the amino acid sequence from gi: 504090610 (GENBANK Acc. No. WP_014324604.1, *Leuconostoc mesenteroides*; also referred to herein as GTF0610). The predicted mature secreted form of GTF0610 is believed to correspond to positions 21-2771 of SEQ ID NO:13.

SEQ ID NO:14 is the DNA sequence encoding full length GTFJ18 (SEQ ID NO:1).

SEQ ID NO:15 is the DNA sequence of nucleotides 846926-855391 from gb: CP000414.1, and encodes GTF6814 (SEQ ID NO:2).

SEQ ID NO:16 is the DNA sequence of the complementary sequence to nucleotides 1620046-1611512 from gb: CP003851.1, and encodes GTF0333 (SEQ ID NO:3).

SEQ ID NO:17 is the DNA sequence of nucleotides 237-5252 from gi: 850934366, and encodes GTF9905 (SEQ ID NO:4). SEQ ID NO:34 is a codon-optimized sequence encoding the expressed form of GTF9905 (SEQ ID NO:4).

SEQ ID NO:18 is the DNA sequence of the complementary sequence to nucleotides 13658-8760 from gb: JXDF01000026.1, and encodes GTF3845 (SEQ ID NO:5).

SEQ ID NO:19 is the DNA sequence of the complementary sequence of nucleotides 17742-13786 from gb: JXDF01000026.1, and encodes GTF3846 (SEQ ID NO:6).

SEQ ID NO:20 is the DNA sequence of the complementary sequence to nucleotides 99099-95680 from gb: JXCW01000006.1, and encodes GTF8954 (SEQ ID NO:7).

SEQ ID NO:21 is the DNA sequence of the complementary sequence to nucleotides 23080-18689 from gb: JXCU01000040.1, and encodes GTF8464 (SEQ ID NO:8).

SEQ ID NO:22 is the DNA sequence of nucleotides 846866-855391 from gb: CP000414.1, and encodes GTF5133 (SEQ ID NO:9).

SEQ ID NO:23 is the DNA sequence of the complementary sequence to nucleotides 7742-3 from gb: JXDB01000011.1, and encodes GTF6432 (SEQ ID NO:10).

SEQ ID NO:24 is the DNA sequence of the complementary sequence to nucleotides 4456-65 from gb: AZBY01000038.1, and encodes GTF5575 (SEQ ID NO:11).

SEQ ID NO:25 is the DNA sequence of the complementary sequence to nucleotides 1619986-1611512 from gb: CP003851.1, and encodes GTF2790 (SEQ ID NO:12).

SEQ ID NO:26 is the DNA sequence of nucleotides 845078-853513 from gb: CP003101.3, and encodes GTF0610 (SEQ ID NO:13).

SEQ ID NO:27 is the amino acid sequence of GTFJ18T1, which is represents an N-terminal-truncated (first 1664 residues removed) form of GTFJ18 (SEQ ID NO:1).

SEQ ID NO:28 is the amino acid sequence of the GTFJ18 CD2.

SEQ ID NO:29 is a codon-optimized nucleotide sequence encoding mature GTF8117 (SEQ ID NO:30) (with an added start-methionine) of the *Lactobacillus animalis* KCTC 3501 protein of GENBANK Acc. No. KRM57462.1.

SEQ ID NO:31 is a nucleotide sequence encoding mature GTF6831 (SEQ ID NO:32) of the *Streptococcus salivarius* M18 protein of GENBANK Acc. No. WP_004182667.1.

SEQ ID NO:33 is the amino acid sequence of GTF5604, which is derived from *Streptococcus criceti* HS-6 (GENBANK® Acc. No. WP_004226213.1, old gi: 357235604; also referred to as SG1018 glucosyltransferase or GtfHS6). The mature form of GTF5604 is predicted to begin at amino acid position 37.

SEQ ID NO:34 is a codon-optimized sequence encoding the expressed form of GTF9905 (SEQ ID NO:4).

DETAILED DESCRIPTION

The disclosures of all cited patent and non-patent literature are incorporated herein by reference in their entirety.

The articles "a", "an", and "the" preceding an element or component are intended to be nonrestrictive regarding the number of instances (i.e., occurrences) of the element or component. Therefore "a", "an", and "the" should be read to include one or at least one, and the singular word form of the element or component also includes the plural unless the number is obviously meant to be singular.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

The terms "alpha-glucan", "alpha-glucan polymer" and the like are used interchangeably herein. An alpha-glucan is a polymer comprising glucose monomeric units linked together by alpha-glycosidic linkages (can also be referred to as alpha-glucosidic linkages).

The terms "linkage", "glycosidic linkages", "glycosidic bonds" and the like refer to the covalent bonds connecting the sugar monomers within a saccharide compound (oligosaccharides and/or polysaccharides). Examples of glycosidic linkages include alpha-linked glucose oligomers with 1,6-alpha-D-glycosidic linkages (herein also referred to as "alpha-1,6" linkages); 1,3-alpha-D-glycosidic linkages (herein also referred to as "alpha-1,3" linkages); 1,4-alpha-D-glycosidic linkages (herein also referred to as "alpha-1,4" linkages); 1,2-alpha-D-glycosidic linkages (herein also referred to as "alpha-1,2" linkages); and combinations of such linkages typically associated with branched saccharide oligomers.

The terms "glucosyltransferase", "glucosyltransferase enzyme", "GTF", "glucansucrase" and the like are used interchangeably herein. The activity of a glucosyltransferase herein catalyzes the reaction of the substrate sucrose to make the products alpha-glucan and fructose. Some byproducts of a glucosyltransferase reaction may include glucose and/or leucrose, for example. Wild type forms of glucosyltransferase enzymes generally contain (in the N-terminal to C-terminal direction) a signal peptide, a variable domain, a catalytic domain, and a glucan-binding domain. An example of a glucosyltransferase herein is a 1,2-branching enzyme.

The terms "reaction composition", "enzymatic reaction", "glucosyltransferase reaction", "glucan synthesis reaction", and the like are used interchangeably herein and generally refer to a reaction that initially comprises water, sucrose, at least one active glucosyltransferase enzyme, and optionally other components. For a 1,2-branching reaction composition herein, another component that is included is an alpha-glucan substrate. Components that can be further present in a glucosyltransferase reaction typically after it has commenced include the products fructose and alpha-glucan, and optionally byproducts such as glucose and leucrose. It would be understood that in embodiments in which a glucosyltransferase has 1,2-branching activity, the alpha-glucan product can represent the 1,2-branch material synthesized by the enzyme, and/or the entire alpha-glucan product itself (i.e., alpha-glucan substrate plus added 1,2-branches). The term "under suitable conditions" as used herein refers to reaction conditions that support conversion of sucrose to products fructose and alpha-glucan via glucosyltransferase enzyme activity.

The term "polypeptide that is capable of forming at least one alpha-1,2 branch from an alpha-glucan substrate" refers to a catalytically active glucosyltransferase (or active fragment thereof) capable of introducing one or more alpha-1,2 glycosidic linkages (using sucrose as an additional substrate) to an alpha-glucan substrate (or "alpha-glucan backbone") via one or more branches (can also be referred to herein as a "1,2-branching enzyme" or with other like terms). The polypeptide is believed to add one glucose group per branch. In certain embodiments, such a polypeptide is a truncated glucosyltransferase that includes a catalytic domain capable of performing alpha-1,2 branching from an alpha-glucan substrate. It would be recognized by one of skill in the art that truncations can encompass the deletion of amino acids in either or both N and C-terminal directions relative to the catalytic domain capable of adding alpha-1,2 branching that are present in a wild-type sequence. For example, N-terminal truncations may be produced from genes which encode a glucosyltransferase starting from a delayed start codon and C-terminal truncations may be produced from genes which encode a glucosyltransferase ending at a premature stop codon. In certain embodiments, a polypeptide includes at least one glucan binding domain in addition to the catalytic domain. In certain embodiments, a polypeptide is a truncated glucosyltransferase that includes a catalytic domain capable of adding alpha-1,2 branching to an alpha-glucan substrate backbone alone or in combination with a glucan binding domain and that does not include a domain capable of synthesizing linkages other than alpha-1,2 glycosidic linkages.

An "alpha-glucan substrate" or "alpha-glucan backbone" (and like terms) as referred to herein can comprise (i) alpha-1,6 or (ii) alpha-1,6 and alpha-1,3 glycosidic linkages, for example, and typically has a degree of polymerization (DP) of at least 3 and is typically water-soluble. In typical embodiments, an alpha-glucan substrate is capable of being modified (i.e., the addition of at least one alpha-1,2 glycosidic linkage) under aqueous reaction conditions by a polypeptide having alpha-1,2 branching activity in the presence of sucrose. "Beta-glucan" is typically excluded as being part of an alpha-glucan substrate herein.

An "alpha-1,2 branch" (and like terms) as referred to herein can be from an alpha-glucan substrate backbone herein, for example. Where an alpha-1,2 branch stems from a 1,6-linked glucose of a backbone, such 1,2-linkage can also be referred to as alpha-1,2,6. A branch that is alpha-1,2-linked to an alpha-glucan backbone herein typically has one glucose group (can optionally be referred to as a pendant glucose). The percent of 1,2-branching in a glucan herein refers to that percentage of all the linkages in the glucan that represent 1,2-branch points (e.g., 1,2,6).

Herein, "alpha-1,3,6" refers to a branch point in which the branch glucose is alpha-1,3-linked to a 1,6-linked glucose monomer of a backbone.

A glucan product of a 1,2-branching reaction herein (e.g., "glucan composition comprising alpha-1,2 linkages", "alpha-1,2-branched glucan composition", "a glucan herein" and like terms) can be characterized, for example, in terms of (i) any alpha-glucan substrate herein plus (ii) any added 1,2-branching herein.

The terms "mature", "secreted", "mature secreted" and the like are used interchangeably herein. A mature protein is one that can pass through the cellular membrane of a cell, particularly a bacterial cell. A mature protein in some aspects results from post-translational removal (cleavage away) of a "signal sequence" (or "signal peptide") from the N-terminus of the protein's immature (preprocessed) form. A signal sequence typically directs an immature protein to the cell membrane, and is removed from the protein during transit thereof through the membrane (i.e., during the protein secretion process). Heterologous expression herein of a mature protein can employ a signal sequence, in which case the likely goal is secretion of the protein to the surrounding media. Alternatively, heterologous expression can employ expressing a protein designed to already lack its signal sequence (a start methionine is typically added to the N-terminus in such embodiments); such mature protein expression typically entails lysing cells to release the protein, since it is not secreted. A signal sequence herein can either be native or heterologous with respect to the protein with which it is optionally employed.

The term "dextran" herein refers to a water-soluble alpha-glucan comprising at least 50% alpha-1,6 glycosidic linkages (typically with up to 49% alpha-1,3 glycosidic linkages, some of which may occur at branching points). Dextrans often have an average molecular weight above 1000 kDa. Enzymes capable of synthesizing dextran from sucrose may be described as "dextransucrases" (EC 2.4.1.5). A dextran is an example of a suitable alpha-glucan substrate herein.

The terms "alpha-glucanohydrolase", "glucanohydrolase" and the like as used herein refer to an enzyme capable of endo- or exo-hydrolyzing an alpha-glucan oligomer. A glucanohydrolase may be defined by its hydrolysis activity towards certain alpha-glycosidic linkages. Examples may include, but are not limited to, dextranases (EC 3.2.1.1; capable of endohydrolyzing alpha-1,6-linked glycosidic bonds), mutanases (EC 3.2.1.59; capable of endohydrolyzing alpha-1,3-linked glycosidic bonds), and alternanases (EC 3.2.1.-; capable of endohydrolytically cleaving alternan). Various factors including, but not limited to, the level of branching, type of branching, and relative branch length within certain alpha-glucans may adversely impact the ability of an alpha-glucanohydrolase to hydrolyze some glycosidic linkages.

The molecular weight of a glucan herein (e.g., alpha-glucan substrate or glucan composition comprising alpha-1,2 linkages) can be represented as degree of polymerization (DP), Daltons, or as grams/mole. DP refers to the number of glucoses comprised within a glucan (e.g., a glucan of DP 10 means that the glucan contains 10 glucoses). Various means are known in the art for calculating molecular weight measurements such as with high-pressure liquid chromatography (HPLC), size exclusion chromatography (SEC), or gel permeation chromatography (GPC).

The term "water-soluble" as used herein characterizes a glucan that has the capability of dissolving in water and/or an aqueous solution herein, where the entire glucan molecule is dissolvable. Typically, the conditions for such solubility include a water/solution temperature range of about 1 to 85° C., which includes temperatures suitable for various uses, such as in beverages and/or household care applications.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

A "mammal" herein can be a human, pet (e.g., feline, canine), domesticated/raised mammal (e.g., bovine, porcine, equine, ovine or rodent or other small mammal (e.g., mouse, rat, rabbit) for example.

The term "enteral administration" and like terms refer to feeding or drug administration via the gastrointestinal ((ii) tract. This contrasts with parenteral administration, which occurs from routes outside the GI tract (e.g., intravenous).

While most instances herein of enteral administration are performed by ingestion (i.e., by mouth; orally), some instances can be via direct delivery to the esophagus or stomach (e.g., using a feeding tube).

The term "glycemic index" as used herein refers to a number associated with a particular type of food that indicates the food's effect on a mammal's blood glucose (blood sugar) level. A value of 100 represents the standard, which is an equivalent amount of pure glucose. A low glycemic index is typically about 55 or less, a medium glycemic index is typically about 56 to 69, and a high glycemic index is typically about 70 or above, The term "glycern.ic response" herein refers to the change in blood glucose levels after consuming a particular food or combination of foods. A "marginal increase" in glycemic index of a food product herein refers to an increase in glycemic index of less than about 1%. 2%, 3%, 4%, 5%, 6%, 7%, 8%, 9%, or 10%, for example.

A "readily digestible glucose-containing carbohydrate" herein refers to a carbohydrate that, upon ingestion by a mammal, quickly raises blood glucose levels in the mammal as compared to ingestion of a "slow glucose release glucan composition" herein. Examples of a readily digestible glucose-containing carbohydrate include sucrose, free glucose, and starch. "Free glucose" herein refers to glucose in free form that is not in glycosidic linkage with another sugar.

The terms "dietary fiber", "glucan fiber" and like terms herein refer to a glucan herein that is indigestible and/or that does not increase blood-glucose levels when enterally administered to a mammal. In general, a dietary fiber herein is not significantly hydrolyzed by endogenous enzymes in the upper gastrointestinal tract of mammals such as humans.

The terms "aqueous conditions", "aqueous reaction conditions", "aqueous setting", "aqueous system" and the like are used interchangeably herein. Aqueous conditions herein refer to a solution or mixture in which the solvent is at least about 60 wt % water, for example. A branching reaction herein typically is performed under aqueous conditions.

An "aqueous composition" herein has a liquid component that comprises at least about 10 wt % water, for example. Examples of aqueous compositions include mixtures, solutions, dispersions (e.g., colloidal dispersions), suspensions and emulsions, for example. An "aqueous solution" herein refers to a solution in which the solvent comprises water. An aqueous solution can serve as a dispersant in certain aspects herein. An alpha-1,2-branched glucan in certain embodiments can be dissolved within an aqueous solution in certain aspects.

The term "household care product" and like terms refer to products, goods and services relating to the treatment, cleaning, caring and/or conditioning of the home and its contents. The foregoing include, for example, chemicals, compositions, products, or combinations thereof having application in such care.

The terms "fabric", "textile", "cloth" and the like are used interchangeably herein to refer to a woven material having a network of natural and/or artificial fibers. Such fibers can be in the form of thread or yarn, for example.

A "fabric care composition" and like terms refer to any composition suitable for treating fabric in some manner. Examples of such a composition include laundry detergents and fabric softeners, which are examples of laundry care compositions.

The terms "heavy duty detergent", "all-purpose detergent" and the like are used interchangeably herein to refer to a detergent useful for regular washing of white and colored textiles at any temperature. The terms "low duty detergent", "fine fabric detergent" and the like are used interchangeably herein to refer to a detergent useful for the care of delicate fabrics such as viscose, wool, silk, microfiber or other fabric requiring special care. "Special care" can include conditions of using excess water, low agitation, and/or no bleach, for example.

A "detergent composition" herein typically comprises at least a surfactant (detergent compound) and/or a builder. A "surfactant" herein refers to a substance that tends to reduce the surface tension of a liquid in which the substance is dissolved. A surfactant may act as a detergent, wetting agent, emulsifier, foaming agent, and/or dispersant, for example.

The term "personal care product" and like terms refer to products, goods and services relating to the treatment, cleaning, cleansing, caring or conditioning of the person. The foregoing include, for example, chemicals, compositions, products, or combinations thereof having application in such care.

An "oral care composition" herein is any composition suitable for treating a soft or hard surface in the oral cavity such as dental (teeth) and/or gum surfaces.

The terms "polynucleotide", "polynucleotide sequence", "nucleic acid molecule" and the like are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof.

The term "gene" as used herein refers to a DNA polynucleotide sequence that expresses an RNA (RNA is transcribed from the DNA polynucleotide sequence) from a coding region, which RNA can be a messenger RNA (encoding a protein) or a non-protein-coding RNA. A gene may refer to the coding region alone, or may include regulatory sequences upstream and/or downstream to the coding region (e.g., promoters, 5'-untranslated regions, 3'-transcription terminator regions). A coding region encoding a protein can alternatively be referred to herein as an "open reading frame" (ORF). A gene that is "native" or "endogenous" refers to a gene as found in nature with its own regulatory sequences; such a gene is located in its natural location in the genome of a host cell. A "chimeric" gene refers to any gene that is not a native gene, comprising regulatory and coding sequences that are not found together in nature (i.e., the regulatory and coding regions are heterologous with each other). Accordingly, a chimeric gene may comprise regulatory sequences and coding sequences that are derived from different sources, or regulatory sequences and coding sequences derived from the same source, but arranged in a manner different than that found in nature. A "foreign" or "heterologous" gene can refer to a gene that is introduced into the host organism by gene transfer. Foreign/heterologous genes can comprise native genes inserted into a non-native organism, native genes introduced into a new location within the native host, or chimeric genes. The polynucleotide sequences in certain embodiments disclosed herein are heterologous. A "transgene" is a gene that has been introduced into the genome by a gene delivery procedure (e.g., transformation). A "codon-optimized" open reading frame has its frequency of codon usage designed to mimic the frequency of preferred codon usage of the host cell.

The term "heterologous" means not naturally found in the location of interest. For example, a heterologous gene can be one that is not naturally found in a host organism, but that is introduced into the host organism by gene transfer. As another example, a nucleic acid molecule that is present in a chimeric gene can be characterized as being heterologous, as such a nucleic acid molecule is not naturally associated with the other segments of the chimeric gene (e.g., a promoter can be heterologous to a coding sequence).

A "non-native" amino acid sequence or polynucleotide sequence comprised in a cell or organism herein does not occur in a native (natural) counterpart of such cell or organism. Such an amino acid sequence or polynucleotide sequence can also be referred to as being heterologous to the cell or organism.

"Regulatory sequences" as used herein refer to nucleotide sequences located upstream of a gene's transcription start site (e.g., promoter), 5' untranslated regions, introns, and 3' non-coding regions, and which may influence the transcription, processing or stability, and/or translation of an RNA transcribed from the gene. Regulatory sequences herein may include promoters, enhancers, silencers, 5' untranslated leader sequences, introns, polyadenylation recognition sequences, RNA processing sites, effector binding sites, stem-loop structures, and other elements involved in regulation of gene expression. One or more regulatory elements herein may be heterologous to a coding region herein.

A "promoter" as used herein refers to a DNA sequence capable of controlling the transcription of RNA from a gene. In general, a promoter sequence is upstream of the transcription start site of a gene. Promoters may be derived in their entirety from a native gene, or be composed of different elements derived from different promoters found in nature, or even comprise synthetic DNA segments. Promoters that cause a gene to be expressed in a cell at most times under all circumstances are commonly referred to as "constitutive promoters". One or more promoters herein may be heterologous to a coding region herein.

A "strong promoter" as used herein refers to a promoter that can direct a relatively large number of productive initiations per unit time, and/or is a promoter driving a higher level of gene transcription than the average transcription level of the genes in a cell.

The terms "3' non-coding sequence", "transcription terminator" and "terminator" as used herein refer to DNA sequences located downstream of a coding sequence. This includes polyadenylation recognition sequences and other sequences encoding regulatory signals capable of affecting mRNA processing or gene expression.

The terms "upstream" and "downstream" as used herein with respect to polynucleotides refer to "5' of" and "3' of", respectively.

The term "expression" as used herein refers to (i) transcription of RNA (e.g., mRNA or a non-protein-coding RNA) from a coding region, and/or (ii) translation of a polypeptide from mRNA. Expression of a coding region of a polynucleotide sequence can be up-regulated or down-regulated in certain embodiments.

The term "operably linked" as used herein refers to the association of two or more nucleic acid sequences such that the function of one is affected by the other. For example, a promoter is operably linked with a coding sequence when it is capable of affecting the expression of that coding sequence. That is, the coding sequence is under the transcriptional control of the promoter. A coding sequence can be operably linked to one (e.g., promoter) or more (e.g., promoter and terminator) regulatory sequences, for example.

The term "recombinant" when used herein to characterize a DNA sequence such as a plasmid, vector, or construct refers to an artificial combination of two otherwise separated segments of sequence, e.g., by chemical synthesis and/or by manipulation of isolated segments of nucleic acids by genetic engineering techniques.

The term "transformation" as used herein refers to the transfer of a nucleic acid molecule into a host organism or host cell by any method. A nucleic acid molecule that has been transformed into an organism/cell may be one that replicates autonomously in the organism/cell, or that integrates into the genome of the organism/cell, or that exists transiently in the cell without replicating or integrating. Non-limiting examples of nucleic acid molecules suitable for transformation are disclosed herein, such as plasmids and linear DNA molecules. Host organisms/cells herein containing a transforming nucleic acid sequence can be referred to as "transgenic", "recombinant", "transformed", "engineered", as a "transformant", and/or as being "modified for exogenous gene expression", for example.

The terms "sequence identity", "identity" and the like as used herein with respect to polynucleotide or polypeptide sequences refer to the nucleic acid residues or amino acid residues in two sequences that are the same when aligned for maximum correspondence over a specified comparison window. Thus, "percentage of sequence identity", "percent identity" and the like refer to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining "percent complementarity" of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

Percent identity can be readily determined by any known method, including but not limited to those described in: 1) Computational Molecular Biology (Lesk, A.M., Ed.) Oxford University: NY (1988); 2) Biocomputing: Informatics and Genome Projects (Smith, D.W., Ed.) Academic: NY (1993); 3) Computer Analysis of Sequence Data, Part I (Griffin, A. M., and Griffin, H. G., Eds.) Humana: NJ (1994); 4) Sequence Analysis in Molecular Biology (von Heinje, G., Ed.) Academic (1987); and 5) Sequence Analysis Primer (Gribskov, M. and Devereux, J., Eds.) Stockton: NY (1991), all of which are incorporated herein by reference.

Preferred methods for determining percent identity are designed to give the best match between the sequences tested. Methods of determining identity and similarity are codified in publicly available computer programs, for example. Sequence alignments and percent identity calculations can be performed using the MEGALIGN program of the LASERGENE bioinformatics computing suite (DNASTAR Inc., Madison, WI), for example. Multiple alignment of sequences can be performed, for example, using the Clustal method of alignment which encompasses several varieties of the algorithm including the Clustal V method of alignment (described by Higgins and Sharp, CABIOS. 5:151-153 (1989); Higgins, D. G. et al., Comput. Appl. Biosci., 8:189-191 (1992)) and found in the MEGALIGN v8.0 program of the LASERGENE bioinformatics computing suite (DNASTAR Inc.). For multiple alignments, the default values can correspond to GAP PENALTY=10 and GAP LENGTH PENALTY=10. Default parameters for pairwise alignments and calculation of percent identity of protein sequences using the Clustal method can be KTUPLE=1, GAP PENALTY=3, WINDOW=5 and DIAGONALS SAVED=5. For nucleic acids, these parameters can be KTUPLE=2, GAP PENALTY=5, WINDOW=4 and DIAGONALS SAVED=4. Additionally the Clustal W method of alignment can be used (described by Higgins and Sharp, CABIOS. 5:151-153 (1989); Higgins, D. G. et al., Comput. Appl. Biosci. 8:189-191(1992); Thompson, J. D. et al, Nucleic Acids Research, 22 (22): 4673-4680, 1994) and found in the MEGALIGN v8.0 program of the LASERGENE bioinformatics computing suite (DNASTAR Inc.). Default parameters for multiple alignment (protein/nucleic acid) can be: GAP PENALTY=10/15, GAP LENGTH PENALTY=0.2/6.66, Delay Divergen Seqs(%)=30/30, DNA Transition Weight=0.5, Protein Weight Matrix=Gonnet Series, DNA Weight Matrix=IUB. Various polypeptide amino acid sequences and polynucleotide sequences are disclosed herein as features of certain embodiments. Variants of these sequences that are at least about 70-85%, 85-90%, or 90%-95% identical to the sequences disclosed herein can be used or referenced. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence.

All the amino acid residues at each amino acid position of the proteins disclosed herein are examples. Given that certain amino acids share similar structural and/or charge features with each other (i.e., conserved), the amino acid at each position of a protein herein can be as provided in the disclosed sequences or substituted with a conserved amino acid residue ("conservative amino acid substitution") as follows:

1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other: His (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

The terms "aligns with", "corresponds with", and the like can be used interchangeably herein. Some embodiments herein relate to a sub-sequence within any one of SEQ ID NOs:4, 2, 3 and 5-13 that aligns with SEQ ID NO:27. A "sub-sequence" herein simply is a portion of any one of SEQ ID NOs:4, 2, 3 and 5-13. A sub-sequence can be characterized to align with SEQ ID NO:27 if it is at least about 50% identical with SEQ ID NO:27, or at least about 65% similar (percent total of both identical sites and conserved sites) with SEQ ID NO:27. In general, one can align the amino acid sequence of a sub-sequence with SEQ ID NO:27 using an alignment algorithm and/or software described herein (e.g., BLASTP, ClustalW, ClustalV, EMBOSS) to determine percent identity and/or similarity.

The term "isolated" means a substance in a form or environment that does not occur in nature. Non-limiting examples of isolated substances include (1) any non-naturally occurring substance, (2) any substance including, but not limited to, any host cell, enzyme, variant, nucleic acid, protein, peptide, cofactor, or carbohydrate/saccharide that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated. It is believed that the embodiments (e.g., reaction compositions and products thereof) disclosed herein are synthetic/man-made, and/or have properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein. These terms can be used to characterize the "over-expression" or "up-regulation" of a polynucleotide encoding a protein, for example.

Some aspects of the present disclosure regard a reaction composition comprising at least water, sucrose, an alpha-glucan substrate, and a polypeptide that is capable of forming at least one alpha-1,2 branch from the alpha-glucan substrate, wherein the polypeptide comprises an amino acid sequence that is at least 90% identical to:
 (i) the mature form of a sequence selected from the group consisting of SEQ Ill NOs:4, 1, 2, 3, 5, 6, 7, 8, 9, 10, 11, 12 and 13;
 (ii) SEQ ID NO:2.7 or a sub-sequence within any one of SEQ ID NOs:4, 2, 3, 5, 6, 7, 8, 9, 10, 11, 12, or 13 that aligns with SEQ NO:27; and/or
 (iii) a sequence selected from the group consisting of SEQ 1D NOs:4, 1, 2, 3, 5, 6, 7, 8, 9, 10, 11, 12, and 13.
A reaction as described immediately above can optionally be characterized herein as an alpha-1,2 branching reaction. A product of such a reaction can be referred to as a glucan composition (or glucan product) comprising alpha-1,2 linkages, for example.

A polypeptide capable of forming at least one alpha-1,2 branch from an alpha-glucan substrate in some aspects of the present disclosure can comprise, or consist of, an amino acid sequence that is 100% identical to, or at least about 90%, 91%, 92%, 93%, 94%, 95%, 96%, 97%, 98%, or 99% identical to, the predicted mature form of a sequence selected from the group consisting of SEQ ID NOs:4, 1, 2, 3 and 5-13. The following sequences are believed to be examples of mature forms (expressed forms) of these polypeptides, respectively: positions 36 to 1672 of SEQ m N0:4, positions 21 to 2771 of SEQ ID NO:1, positions 21 to 2821 of SEQ ID N0:2, positions 41 to 2844 of SEQ ID NO:3, positions 51 to 1632 of SEQ ID NO:5, positions 51 to 1318 of SEQ ID NO:6, positions 51 to 1139 of SEQ ID NO:7, positions 51 to 1463 of SEQ ID NO:8, positions 41 to 2841 of SEQ ID NO:9, positions 46 to 2580 of SEQ ID NO:10, positions 51 to 1463 of SEQ ID NO:11, positions 21 to 2824 of SEQ ID NO:12, positions 21 to 2771 of SEQ ID NO:13. Any of these sequences may optionally further comprise an added N-terminal methionine residue.

In sonic aspects, a polypeptide capable of forming at least one alpha-1,2 branch from an alpha-glucan substrate comprises, or consists of, an amino acid sequence that is 100% identical to, or at least about 90%, 91%, 92%, 93%, 94%, 95%, 96%, 97%, 98%, or 99% identical to, a sequence selected from the group consisting of SEQ ID NOs:4, 1, 2, 3 and 5-13.

SEQ NO:27 (GTFJ18T 1), which is an N-terminally shortened version of SEQ ID NO:1, is shown in the Examples below to be capable of forming at least one alpha-1,2 branch from an alpha-glucan substrate. Further, SEQ NO:4 (MT9905), which contains a sub-sequence that is relatively similar to SEQ ID NO:27, also is shown herein to be capable of forming at least one alpha-1,2 branch from an alpha-glucan substrate. Based on this information, it is believed that a. suitable polypeptide in certain embodiments can comprise an amino acid sequence that is 100% identical to, or at least about 90%, 91%, 92%, 93%, 94%, 95%, 96%, 97%, 98%, or 99% identical to, SEQ ill NO:27 or a sub-sequence within any one of SEQ ID NOs:4, 2, 3 and 5-13 that aligns with SEQ ID NO:27, In some aspects, a suitable sub-sequence that aligns with SEQ m NO:27 is as listed in the following table:

| Sub-sequence | % Identity$^a$ w/ SEQ ID NO: 27 | % Similarity$^a$ w/ SEQ ID NO: 27 |
| --- | --- | --- |
| positions 36 to 1115 of SEQ ID NO: 4 | 60.6 | 74.8 |
| positions 1715 to 2821 of SEQ ID NO: 2 | 98.1 | 98.9 |
| positions 1735 to 2834 of SEQ ID NO: 3 | 73.7 | 85.3 |
| positions 51 to 1167 of SEQ ID NO: 5 | 56.8 | 71.0 |
| positions 93 to 1178 of SEQ ID NO: 6 | 56.4 | 71.3 |
| positions 51 to 1130 of SEQ ID NO: 7 | 56.2 | 69.9 |
| positions 51 to 1158 of SEQ ID NO: 8 | 57.7 | 72.8 |
| positions 1735 to 2841 of SEQ ID NO: 9 | 98.1 | 98.9 |
| positions 1274 to 2413 of SEQ ID NO: 10 | 54.6 | 67.6 |
| positions 51 to 1158 of SEQ ID NO: 11 | 57.6 | 72.7 |
| positions 1715 to 2821 of SEQ ID NO: 12 | 73.7 | 85.4 |
| positions 1665 to 2771 of SEQ ID NO: 13 | 100.0 | 100.0 |

$^a$Percent identity and similarity values per EMBOSS alignment.

It should be apparent from some of the above embodiments that a polypeptide capable of forming at least one alpha-1,2 branch from an alpha-glucan substrate can include an amino acid sequence that is truncated relative to any of SEQ Ill N0s:1-13. In certain embodiments, a truncated amino acid sequence includes a domain from any of SEQ ILS NOs:1-13 that catalyzes the synthesis of glucan having alpha-1,2 linkages. Such a truncated amino acid sequence can optionally include one or more glucan binding domain. In certain embodiments, a truncated amino acid sequence does not include a domain that catalyzes synthesis of a glucan having linkages other than alpha-I linkages.

Some embodiments disclosed herein concern a polynucleotide comprising a nucleotide sequence that encodes any 1,2-branching enzyme (e.g., parts i, ii, or iii above as related to any of SEQ ID NOs:4, 1, 2, 3, 5-13 and 27) or other glucosyltransferase as presently disclosed. Optionally, one or more regulatory sequences are operably linked to the nucleotide sequence, and preferably a promoter sequence is included as a regulatory sequence.

A polynucleotide comprising a nucleotide sequence encoding an enzyme herein can be a vector or construct useful for transferring a nucleotide sequence into a cell, for example (e.g., expression vector). Examples of a suitable vector/construct can be selected from a plasmid, yeast artificial chromosome (YAC), cosmid, phagemid, bacterial artificial chromosome (BAC), virus, or linear DNA (e.g., linear PCR product). A polynucleotide sequence in some aspects can be capable of existing transiently (i.e., not integrated into the genome) or stably (i.e., integrated into the genome) in a cell. A polynucleotide sequence in some aspects can comprise, or lack, one or more suitable marker sequences (e.g., selection or phenotype marker).

A polynucleotide sequence in certain embodiments can comprise one or more regulatory sequences operably linked to the nucleotide sequence encoding an enzyme. For example, a nucleotide sequence encoding an enzyme may be in operable linkage with a promoter sequence (e.g., a heterologous promoter). A promoter sequence can be suitable for expression in a cell (e.g., bacterial cell such as *E. coli*; eukaryotic cell such as a fungus, yeast, insect, or mammalian cell) or in an in vitro protein expression system, for example. Examples of other suitable regulatory sequences are disclosed herein (e.g., transcription terminator sequences).

In some embodiments, a polynucleotide sequence does not comprise a regulatory sequence operably linked to a nucleotide encoding a glucosyltransferase. Such a polynucleotide could be a cloning vector (e.g., cloning plasmid), for example, used simply for sub-cloning or gene shuttling purposes.

Possible initiation control regions or promoters that can be included in an expression vector herein are numerous and familiar to those skilled in the art. Virtually any promoter capable of driving these genes is suitable, including but not limited to, CYC1, HIS3, GAL1, GAL10, ADH1, PGK, PHOS, GAPDH, ADC1, TRP 1, URA3, LEU2, ENO, TPI (useful for expression in *Saccharomyces*); AOX1 (useful for expression in *Pichia*); and lac, araB, tet, trp, $IP_L$, $IP_R$, T7, tac, and trc (useful for expression in *Escherichia coli*) as well as the amy, apr, npr promoters and various phage promoters useful for expression in *Bacillus*.

DNA fragments which control transcriptional termination may also be derived from various genes native to a preferred host cell. In certain embodiments, the inclusion of a termination control region is optional. In certain embodiments, the expression vector includes a termination control region derived from the preferred host cell.

In certain embodiments, any polypeptide disclosed herein is in the form of a fusion protein. For example, a polypeptide may include one or more tag sequences that can aide in purification of the polypeptide. Exemplary tag sequences include: GST (glutathione-S-transferase), intein-CBD (chitin-binding domain), MBD (maltose binding domain), and histidine tags.

In certain embodiments, an expression vector is included in a host cell, particularly a microbial host cell. In some embodiments, a microbial host cell can be found within the fungal or bacterial families, and/or grow over a wide range of temperature, pH values, and solvent tolerances. For example, it is contemplated that any of bacteria, yeast, and filamentous fungi may suitably host the expression vector. Inclusion of an expression vector in a host cell may be used for intracellular and/or extracellular expression of a polypeptide as disclosed herein. Transcription, translation and the protein biosynthetic apparatus can remain invariant relative to the cellular feedstock used to generate cellular biomass; functional genes typically can be expressed regardless. Examples of host cells include, but are not limited to, bacterial, fungal or yeast species such as *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus*. In certain embodiments, a fungal host cell is *Trichoderma*, such as a strain of *Trichoderma reesei*. In certain embodiments, bacterial host strains include *Escherichia, Bacillus, Kluyveromyces*, and *Pseudomonas*. In some embodiments, the bacterial host cell is *Bacillus subtilis* or *Escherichia coli*.

In certain embodiments, (i) a host cell includes more than one expression vector, and/or (ii) multiple polypeptides are expressed in the host cell. For example, in certain embodiments, a host cell includes an expression vector for the expression of an alpha-glucanohydrolase. It would be recognized that the expression vector for expressing an alpha-glucanohydrolase can be the same or different than the expression vector for expressing a polypeptide capable of forming at least one alpha-1,2 branch from an alpha-glucan substrate.

An alpha-glucan substrate/backbone in certain embodiments of the present disclosure has a degree of polymerization (DP) of at least 3, comprises at least (i) alpha-1,6 glycosidic linkages or (ii) alpha-1,3 and alpha-1,6 glycosidic linkages, and typically is water-soluble.

In some aspects, an alpha-glucan substrate can have a DP of about, or at least about, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 100, 105, 110 150, 200, 250, 300, 400, 500, 600, 700, 800, 900, 1000, 1100, 1200, 1300, 1400, 1500, 1600, 1700, 1800, 1900, or 2000. The DP of an alpha-glucan substrate can optionally be expressed as a range between any two of these values. Merely as examples, the DP can be about 8-20, 8-30, 8-100, or 8-500 (which happen to be examples of DP8+alpha-glucan substrates), 3-4, 3-5, 3-6, 3-7, 3-8, 4-5, 4-6, 4-7, 4-8, 5-6, 5-7, 5-8, 6-7, 6-8, or 7-8. Merely as other examples, the DP can be 90-120, 95-120, 100-120, 105-120, 110-120, 115-120, 90-115, 95-115, 100-115, 105-115, 110-115, 90-110, 95-110, 100-110, 105-110, 90-105, 95-105, 100-105, 90-100, 95-100, or 90-95.

An alpha-glucan substrate in certain embodiments comprises at least (i) alpha-4,6 glycosidic linkages or (ii) alpha- 1,3 and alpha-1,6 glycosidic linkages. For example, the percentage of alpha-1,6 linkages can be at least about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. The linkage profile of an alpha-glucan substrate can optionally be expressed as having a range between any two of these values. The other substrate linkages in any of these embodiments can be alpha-1,3 (e.g., up to 80%), and/or not include any alpha-1,4 or alpha-1,2 linkages, for example. In some aspects, an alpha-glucan substrate comprises at least 50% alpha-1,6 glycosidic linkages. In some other embodiments, an alpha-glucan substrate comprises 1 to 50% alpha-1,3 glycosidic linkages.

In certain embodiments, an alpha-glucan substrate is prepared using an enzyme selected from glucosyltransferases (typically from the GH70 family of glycoside hydrolases), dextrin dextranases, 4,6-alpha-glucosyltransferases ("Gtf-B type" from family GH70), or combinations thereof. Optionally, at least one alpha-glucosidase is further included, such as a dextranase and/or mutanase. In some embodiments, an alpha-glucan substrate is a product of a glucosyltransferase comprising, or consisting of, an amino acid sequence that is 100% identical to, or at least about 90%, 91%, 92%, 93%. 94%. 95%. 96%, 97%, 98%, or 99% identical to, SEQ ID NO:30 (GTF8117) 32 (GTF683 I), or 33 (GTF5604). An alpha-glucan substrate herein can be prepared by an appropriate glucosyltransferase reaction composition (e.g., comprising at least water and sucrose, in addition to at least one GTF enzyme).

An alpha-glucan substrate can be synthesized (and optionally isolated) before enzymatically introducing alpha-1,2 branching, or may be concomitantly synthesized in the presence of an alpha-1,2 branching enzyme (i.e., glucan substrate backbone synthesis can be conducted in the same reaction mixture with the polypeptide having alpha-1,2 branching activity in the presence of an effective amount of sucrose). An alpha-glucan substrate may be produced in a variety of ways including, but not limited to, (1) synthesis from at least one glucosyltransferase (using a polypeptide that is different from the polypeptide having alpha-1,2 branching activity) in the presence of sucrose, (2) synthesis from maltodextrin obtainable from starch or sucrose (e.g., maltodextrin substrate synthesized from sucrose using an amylosucrase) using a polypeptide having dextrin dextranase activity, a Gtf-B type GH70 glucosyltransferase, or a combination thereof, (3) synthesis using method (1) and/or (2) in the presence of at least one alpha-glucanohydrolase (e.g., dextranase, mutanase, or a combination thereof), and (4) any combination of (1), (2), or (3) so long as the alpha-glucan substrate is capable of being acted upon by the polypeptide having alpha-1,2 branching activity. In a further embodiment, an alpha-glucan substrate may be synthesized prior to an alpha-1,2 branching step or may be synthesized concomitant with alpha-1,2 branching (i.e., the polypeptide having alpha-1,2 branching activity and an effective amount of sucrose is present in the aqueous reaction mixture). In the context of synthesizing an alpha-glucan substrate using any of the above embodiments, reactants for synthesis may include sucrose and/or maltodextrin, and optionally be in the presence of one or more additional acceptors. In another embodiment, the reactants may further comprise one or more acceptors, such as maltose, isomaltose, isomaltotriose, and methyl-alpha-D-glucan, to name a few.

In certain embodiments, the alpha-glucan substrate is synthesized using a combination of at least one glucosyltransferase capable of forming glucose oligomers with at least one alpha-glucanohydrolase in the same reaction mixture (i.e., they are concomitantly present and active in the reaction composition). As such, the reactants for the alpha-glucanohydrolase are represented by the glucose oligomers concomitantly being synthesized in the reaction system by the glucosyltransferase from sucrose.

A glucan product of a 1,2-branching reaction herein (e.g., "glucan composition comprising alpha-1,2 linkages") (such a product can be that of a reaction composition herein and/or a product of a method herein of producing a glucan composition) can be characterized in terms of (i) any alpha-glucan substrate herein plus (ii) any added 1,2-branching as disclosed herein, for example. The percent 1,2-branching of a glucan composition comprising alpha-1,2 linkages can be about, at least about, or less than about, 1%. 2%. 3%. 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, ..54%, or 55%. for example. This 1,2-branching profile can optionally be expressed as having a range between any two of these values. Merely as examples, the percentage of 1.2-branches in a glucan composition can be 15-50%, 15-45%, 15-40%, 15-35%, 15-30%, 15-25%, 15-20%, 20-50%, 20-45%, 20-40%, 20-35%, 20-30%, 20-25%, 25-50%, 25-45%, 25-40%, 25-35%, 25-30%, 30-50%, 30-45%, 30-40%, 30-35%, 35-50%, 35-45%, 35-40%, 40-50%, or 40-45% (some or all of such 1,2-branching profiles optionally are associated with glucan compositions herein that do not increase blood-glucose levels when enterally administered to a mammal [can optionally be referred to as a dietary glucan fiber]). Merely as additional examples, the percentage of 1,2-branches in a glucan composition can be less than about 10%, 9%, 8%, 7%, 6%, 5%, or 4%, or range from 2-10%, 4-10%, 6-10%, 2-8%, 4-8%, 6-8%, 2-6%, 4-6%, 4.5-6%, 5-6%, 4-7%, 4.5-7%, or 5-7% (such 1,2-branching profiles optionally are associated with glucan compositions herein that slowly increase blood-glucose levels when enterally administered to a mammal [can optionally be referred to as low glycemic index glucan). In some aspects, a glucan composition comprising alpha-1,2 linkages comprises only 1,6-linkages and 1,2-branches (1,2,6) (e.g., a 1,6-linked backbone decorated with 1,2-linked pendant glucoses), with no other linkage types present. In other embodiments, a glucan composition comprising alpha-1,2 linkages comprises any alpha-glucan substrate backbone as disclosed herein decorated with:1,2-linked branches. The percentage of 1,2-branch points (as well as other linkages types) herein can be determined using an $^1$H NMR or GC/MS method, for example, such as disclosed in the below Examples.

In some aspects, a glucan composition comprising alpha-1,2 linkages can have a DP of about, or at least about, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 105, 110, 120, 130, 140, 150, 160, 170, 180, 190, 200, 210, 220, 230, 240, 250, 300, 400, 500, 600, 700, 800, 900, 1000, 1100, 1200, 1300, 1400, 1500, 1600, 1700, 1800, 1900, or 2000. The DP of a glucan composition comprising alpha-1,2 linkages can optionally be expressed as a range between any two of these values. Merely as examples, the DP can be about 120-160, 125-160, 130-160, 135-160, 140-160, 145-160, 150-160, 155-160, 120-155, 125-155, 130-155, 135-155, 140-155, 145-155, 150-155, 120-150, 125-150, 130-150, 135-150, 140-150, 145-150, 120-145, 125-145, 130-145, 135-145, 140-145, 120-140, 125-140, 130-140, 135-140, 120-135, 125-135, 130-135, 120-130, 125-130, or 120-125 (such DP profiles optionally are associated with glucan compositions herein that do not increase blood-glucose levels when enterally administered to a mammal), or about 100-110. Merely as additional examples, the DP can be 100-120, 105-120, 110-120, 115-120, 100-115, 105-115, 110-115, 100-110, 105-110, or 100-105 (such DP profiles optionally are associated with glucan compositions herein that slowly increase blood-glucose levels when enterally administered to a mammal).

In some aspects, a glucan composition comprising alpha-1,2 linkages (e.g., one that is water-soluble) slowly releases glucose when fed (enteral administration) to a mammal such as a human; this type of glucan composition can be characterized as a "slow glucose release glucan composition" (or like terms). Such slow glucose release corresponds with a slow increase in Hood glucose levels (low glycemic response. In some other aspects, a glucan composition comprising alpha-1,2 linkages does not release glucose when fed to a mammal, and thereby does not result in any increase in blood glucose levels (no glycemic response). Such effects on Wood glucose levels (slow effect or no effect) are believed to be specific to the glucan composition comprising alpha-1,2 linkages, and thus independent of the effects on blood glucose levels that may result from a blood glucose-increasing ingredient (e.g., sucrose, free glucose, starch) potentially included in a substance being fed to the mammal. In other words, if a blood glucose-increasing ingredient(s) is included in a food/beverage that contains a glucan composition comprising alpha-1,2 linkages herein, any significant or fast increase in blood glucose levels in a mammal fed the food/beverage are believed to be attributable to such other blood glucose-increasing ingredient(s).

Slow glucose release herein is believed to primarily occur in the gut of a mammal following enteral administration (ingestion) of certain glucan compositions herein comprising alpha-1,2 linkages (e.g., less than about 10% alpha-1,2 branches). Slow glucose release typically does not result in a blood glucose spike. The benefit of a slow glucose release glucan herein, in comparison with sucrose and other forms of readily digestible glucose-containing carbohydrates (e.g., free glucose), is that it is digested slowly and steadily by mammals. Although a slow glucose release glucan herein is a calorically available carbohydrate—meaning that it is digestible and absorbable (e.g., refer to Table 35, which shows that sample 105-3 [an example of a slow glucose release glucan herein] ingestion resulted in an AUC value fairly equal to the AUC value resulting from free glucose ingestion)—its digestion results in a slow and sustained release of glucose as compared to the digestion of free glucose (e.g., refer to Table 35, which shows that sample 105-3 ingestion results in a maximum blood glucose concentration of 334 mg/dL at 1 h, whereas free glucose ingestion results in a maximum of 401 mg/dL just after 20 min). Thus, a slow glucose release glucan herein, following ingestion in a mammal, typically results in the same or similar total glucose release as that resulting from a readily digestible glucose-containing carbohydrate (e.g., total glucose released over 2-2.5 hours post-ingestion) (e.g., when the same amount of slow glucose release glucan or readily digestible glucose-containing carbohydrate are ingested). However, a slow glucose release glucan herein, following ingestion in a mammal (e.g., as measured within 0.25-2.5 hours post-ingestion), results in: (i) a blood glucose peak that is lower (e.g., at least about 10%, 12.5%, 15%, 17.5%, 20%, 22.5%, 25%, 10-25%, 10-20%, 10-15%, 15-25%, or 15-20% lower) than the peak induced by a readily digestible glucose-containing carbohydrate, and/or (ii) a blood glucose curve that is stretched compared to that of a readily digestible glucose-containing carbohydrate. The results of (i) and/or (ii) can be observed, for example, When the same or similar amount of slow glucose release glucan or readily digestible glucose-containing carbohydrate are ingested. Levels of glucose release in a mammal can be determined, for example, by measuring blood glucose levels.

Slow digestion and absorption of glucose from a slow glucose release glucan herein contributes to the low blood glucose response (low glycemic response) following its ingestion. It is believed that such low glycemic response in turn leads to a. low release of insulin. A low glycemic response has been considered a physiologically beneficial effect by the European Food Safety Authority. In the long-term, a diet including carbohydrates that reduce undesirably high concentrations of glucose in blood and thus a lower demand for insulin (possibly such as a slow glucose release glucan herein), is supportive for the prevention and management of diabetes mellitus, cardiovascular disease, and possibly obesity. In addition, slow release carbohydrates are of interest in physical endurance activity where an optimum use of limited carbohydrate sources might be advantageous. Carbohydrates and their supply of glucose to the brain play a central role in cognitive performance and mood. Hence a steady and sustained glucose supply may play a role in memory performance and mood.

Thus, further disclosed herein is a method comprising enterally administering (e.g., ingesting) a substance (e.g., food, beverage, supplement, or pharmaceutical) to a mammal, wherein the substance comprises a glucan composition comprising alpha-1.2 linkages, wherein the administering results in less or slower blood glucose elevation in the mammal as compared to a mammal that is enterally administered a substance that lacks the glucan composition but instead contains a same amount of a readily digestible glucose-containing carbohydrate (e.g., if 1 g of the glucan composition was used, then comparison is with 1 g of the readily digestible glucose-containing carbohydrate), wherein the glucan composition is produced by any branching method or reaction herein. Enteral administration can, for example, be via self-administration (e.g., any form of ingestion such as eating, drinking, taking medicine) or non-self-administration (e.g., oral gavage, feeding apparatus such as feeding tube).

Thus, further disclosed herein is a method of producing an ingestible product (e.g., food or beverage), the method comprising incorporating a glucan composition comprising alpha-1,2 linkages into the ingestible product, wherein the glycemic index of the resulting ingestible product is not increased, or only marginally increased, compared to an ingestible product that lacks the glucan composition, and wherein the glucan composition is produced by any branching method or reaction herein.

Compositions Comprising Alpha-1,2-branched Glucan Compositions Produced Herein

A composition comprising an alpha-1,2-branched glucan as presently disclosed can be an aqueous composition in certain embodiments.

It is believed that an aqueous composition comprising an alpha-1,2-branched glucan can, in some aspects, have a viscosity of about, or at least about, 3, 4, 5, 10, 15, 20, 25, 30, 35, 40, 45, or 50 cPs (centipoise). Viscosity can be measured with an aqueous composition herein at any temperature between about 3° C. to about 110° C. (or any integer between 3 and 110° C.), for example. Viscosity can be measured at atmospheric pressure (about 760 torr) or any suitable higher or lower pressure.

The pH of an aqueous composition herein can be between about 2.0 to about 12.0, for example. Alternatively, pH can be about 2.0, 3.0, 4.0, 5.0, 6.0, 7.0, 8.0, 9.0, 10.0, 11.0, 12.0; or between 5.0 to about 12.0; or between about 4.0 and 8.0; or between about 5.0 and 8.0, for example.

An aqueous composition herein can comprise a solvent having at least about 10 wt % water. In other embodiments, a solvent is at least about 20, 30, 40, 50, 60, 70, 80, 90, or 100 wt % water (or any integer value between 10 and 100 wt %), for example.

An alpha-1,2-branched glucan herein can be present in an aqueous composition at a wt % of about, or at least about, 0.01, 0.05, 0.1, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 wt %, for example.

An aqueous composition herein can generally comprises other components in addition to an alpha-1,2-branched glucan. For example, an aqueous composition can comprise one or more salts such as a sodium salt (e.g., NaCl). Other non-limiting examples of salts include those having (i) an aluminum, ammonium, barium, calcium, chromium (II or III), copper (I or II), iron (II or III), hydrogen, lead (II), lithium, magnesium, manganese (II or III), mercury (I or II), potassium, silver, sodium strontium, tin (II or IV), or zinc cation, and (ii) an acetate, borate, bromate, bromide, carbonate, chlorate, chloride, chlorite, chromate, cyanamide, cyanide, dichromate, dihydrogen phosphate, ferricyanide, ferrocyanide, fluoride, hydrogen carbonate, hydrogen phosphate, hydrogen sulfate, hydrogen sulfide, hydrogen sulfite, hydride, hydroxide, hypochlorite, iodate, iodide, nitrate, nitride, nitrite, oxalate, oxide, perchlorate, permanganate, peroxide, phosphate, phosphide, phosphite, silicate, stannate, stannite, sulfate, sulfide, sulfite, tartrate, or thiocyanate anion. Thus, any salt having a cation from (i) above and an anion from (ii) above can be in an aqueous composition, for example. A salt can be present in an aqueous composition herein at a wt % of about 0.01 to about 10.00 (or any hundredth increment between 0.01 and 10.00), for example.

A composition comprising an alpha-1,2-branched glucan herein can be non-aqueous (e.g., a dry composition) in some aspects. Examples of such embodiments include powders, granules, microcapsules, flakes, or any other form of particulate matter. Other examples include larger compositions such as pellets, bars, kernels, beads, tablets, sticks, or other agglomerates. A non-aqueous or dry composition herein typically has less than 3, 2, 1, 0.5, or 0.1 wt % water comprised therein. The amount of alpha-1,2-branched glucan herein in a non-aqueous or dry composition can be about, or at least about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, or 99.9 wt %, for example.

A composition comprising an alpha-1,2-branched glucan herein may optionally contain one or more active enzymes. Non-limiting examples of suitable enzymes include proteases, cellulases, hemicellulases, peroxidases, lipolytic enzymes (e.g., metallolipolytic enzymes), xylanases, lipases, phospholipases, esterases (e.g., arylesterase, polyesterase), perhydrolases, cutinases, pectinases, pectate lyases, mannanases, keratinases, reductases, oxidases (e.g., choline oxidase), phenoloxidases, lipoxygenases, ligninases, pullulanases, tannases, pentosanases, malanases, beta-glucanases, arabinosidases, hyaluronidases, chondroitinases, laccases, metalloproteinases, amadoriases, glucoamylases, arabinofuranosidases, phytases, isomerases, transferases and amylases. If an enzyme(s) is included, it may be comprised in a composition herein at about 0.0001-0.1 wt % (e.g., 0.01-0.03 wt %) active enzyme (e.g., calculated as pure enzyme protein), for example.

At least one, two, or more cellulases may be included in a composition herein. A cellulase herein can have endocellulase activity (EC 3.2.1.4), exocellulase activity (EC 3.2.1.91), or cellobiase activity (EC 3.2.1.21). A cellulase herein is an "active cellulase" having activity under suitable conditions for maintaining cellulase activity; it is within the skill of the art to determine such suitable conditions.

A cellulase herein may be derived from any microbial source, such as a bacteria or fungus. Chemically-modified cellulases or protein-engineered mutant cellulases are included. Suitable cellulases include, but are not limited to, cellulases from the genera *Bacillus, Pseudomonas, Streptomyces, Trichoderma, Humicola, Fusarium, Thielavia* and *Acremonium*. As other examples, a cellulase may be derived from *Humicola insolens, Myceliophthora thermophila* or *Fusarium oxysporum*; these and other cellulases are disclosed in U.S. Pat. Nos. 4,435,307, 5,648,263, 5,691,178, 5,776,757 and 7,604,974, which are all incorporated herein by reference. Exemplary *Trichoderma reesei* cellulases are disclosed in U.S. Pat. Nos. 4,689,297, 5,814,501, 5,324,649, and International Patent Appl. Publ. Nos. WO92/06221 and WO92/06165, all of which are incorporated herein by reference. Exemplary *Bacillus* cellulases are disclosed in U.S. Pat. No. 6,562,612, which is incorporated herein by reference. A cellulase, such as any of the foregoing, preferably is in a mature form lacking an N-terminal signal peptide. Commercially available cellulases useful herein include CELLUZYME® and CAREZYME® (Novozymes A/S); CLAZINASE® and PURADAX® HA (DuPont Industrial Biosciences), and KAC-500(B)® (Kao Corporation).

One or more cellulases can be directly added as an ingredient when preparing a composition disclosed herein. Alternatively, one or more cellulases can be indirectly (inadvertently) provided in the disclosed composition. For example, cellulase can be provided in a composition herein by virtue of being present in a non-cellulase enzyme preparation used for preparing a composition. Cellulase in compositions in which cellulase is indirectly provided thereto can be present at about 0.1-10 ppb (e.g., less than 1 ppm), for example.

A cellulase in certain embodiments can be thermostable. Cellulase thermostability refers to the ability of the enzyme to retain activity after exposure to an elevated temperature (e.g. about 60-70° C.) for a period of time (e.g., about 30-60 minutes). The thermostability of a cellulase can be measured by its half-life (t1/2) given in minutes, hours, or days, during which time period half the cellulase activity is lost under defined conditions.

A cellulase in certain embodiments can be stable to a wide range of pH values (e.g. neutral or alkaline pH such as pH of ~7.0 to ~11.0). Such enzymes can remain stable for a predetermined period of time (e.g., at least about 15 min., 30 min., or 1 hour) under such pH conditions.

The effective concentration of cellulase in an aqueous composition in which a fabric is treated can be readily determined by a skilled artisan. In fabric care processes, cellulase can be present in an aqueous composition (e.g., wash liquor) in which a fabric is treated in a concentration that is minimally about 0.01-0.1 ppm total cellulase protein, or about 0.1-10 ppb total cellulase protein (e.g., less than 1 ppm), to maximally about 100, 200, 500, 1000, 2000, 3000, 4000, or 5000 ppm total cellulase protein, for example.

A composition comprising an alpha-1,2-branched glucan herein can be in the form of, and/or comprised in, a household care product, personal care product, industrial product, pharmaceutical product, or food product, for example, such as any of those products described below. Any of these compositions can be aqueous compositions, for example.

Personal care products herein are not particularly limited and include, for example, skin care compositions, cosmetic compositions, antifungal compositions, and antibacterial compositions. Personal care products herein may be in the form of, for example, lotions, creams, pastes, balms, ointments, pomades, gels, liquids, combinations of these and the like. The personal care products disclosed herein can include at least one active ingredient, if desired. An active ingredient is generally recognized as an ingredient that causes an intended pharmacological effect. A personal care product herein can be used in personal care cleaning applications in certain embodiments.

A skin care product typically may include at least one active ingredient for the treatment or prevention of skin ailments, providing a cosmetic effect, or for providing a moisturizing benefit to skin, such as zinc oxide, petrolatum, white petrolatum, mineral oil, cod liver oil, lanolin, dimethicone, hard fat, vitamin A, allantoin, calamine, kaolin, glycerin, or colloidal oatmeal, and combinations of these. A skin care product may include one or more natural moisturizing factors such as ceramides, hyaluronic acid, glycerin, squalane, amino acids, cholesterol, fatty acids, triglycerides, phospholipids, glycosphingolipids, urea, linoleic acid, glycosaminoglycans, mucopolysaccharide, sodium lactate, or sodium pyrrolidone carboxylate, for example. Other ingredients that may be included in a skin care product include, without limitation, glycerides, apricot kernel oil, canola oil, squalane, squalene, coconut oil, corn oil, jojoba oil, jojoba wax, lecithin, olive oil, safflower oil, sesame oil, shea butter, soybean oil, sweet almond oil, sunflower oil, tea tree oil, shea butter, palm oil, cholesterol, cholesterol esters, wax esters, fatty acids, and orange oil.

A personal care product herein can also be in the form of makeup, lipstick, mascara, rouge, foundation, blush, eyeliner, lip liner, lip gloss, other cosmetics, sunscreen, sun block, nail polish, nail conditioner, bath gel, shower gel, body wash, face wash, lip balm, skin conditioner, cold cream, moisturizer, body spray, soap, body scrub, exfoliant, astringent, scruffing lotion, depilatory, permanent waving solution, antidandruff formulation, antiperspirant composition, deodorant, shaving product, pre-shaving product, after-shaving product, cleanser, skin gel, rinse, dentifrice composition, toothpaste, or mouthwash, for example.

A personal care product in some aspects can be a hair care product. Examples of hair care products herein include shampoo, hair conditioner (leave-in or rinse-out), cream rinse, hair dye, hair coloring product, hair shine product, hair serum, hair anti-frizz product, hair split-end repair product, mousse, hair spray, and styling gel. A hair care product can be in the form of a liquid, paste, gel, solid, or powder in some embodiments. A hair care product as presently disclosed typically comprises one or more of the following ingredients, which are generally used to formulate hair care products: anionic surfactants such as polyoxyethylenelauryl ether sodium sulfate; cationic surfactants such as stearyltrimethylammonium chloride and/or distearyltrimethylammonium chloride; nonionic surfactants such as glyceryl monostearate, sorbitan monopalmitate and/or polyoxyethylenecetyl ether; wetting agents such as propylene glycol, 1,3-butylene glycol, glycerin, sorbitol, pyroglutamic acid salts, amino acids and/or trimethylglycine; hydrocarbons such as liquid paraffins, petrolatum, solid paraffins, squalane and/or olefin oligomers; higher alcohols such as stearyl alcohol and/or cetyl alcohol; superfatting agents; antidandruff agents; disinfectants; anti-inflammatory agents; crude drugs; water-soluble polymers such as methylcellulose, hydroxycellulose and/or partially deacetylated chitin; antiseptics such as paraben; ultra-violet light absorbers; pearling agents; pH adjustors; perfumes; and pigments.

A pharmaceutical product herein can be in the form of an emulsion, liquid, elixir, gel, suspension, solution, cream, or ointment, for example. Also, a pharmaceutical product herein can be in the form of any of the personal care products disclosed herein, such as an antibacterial or antifungal composition. A pharmaceutical product can further comprise one or more pharmaceutically acceptable carriers, diluents, and/or pharmaceutically acceptable salts. An alpha-1,2-branched glucan disclosed herein can also be used in capsules, encapsulants, tablet coatings, and excipients for medicaments and drugs.

A household care and/or industrial product herein can be in the form of drywall tape-joint compounds; mortars; grouts; cement plasters; spray plasters; cement stucco; adhesives; pastes; wall/ceiling texturizers; binders and processing aids for tape casting, extrusion forming, injection molding and ceramics; spray adherents and suspending/dispersing aids for pesticides, herbicides, and fertilizers; fabric care products such as fabric softeners and laundry detergents; dishwashing detergents; hard surface cleaners; air fresheners; polymer emulsions; gels such as water-based gels; surfactant solutions; paints such as water-based paints; protective coatings; adhesives; sealants and caulks; inks such as water-based ink; metal-working fluids; or emulsion-based metal cleaning fluids used in electroplating, phosphatizing, galvanizing and/or general metal cleaning operations, for example. A household care product or industrial product herein can be used in cleaning applications in certain embodiments, and as such can be comprised in detergent compositions, for example.

Alpha-1,2-branched glucans disclosed herein are believed to be useful for providing one or more of the following physical properties to a personal care product, pharmaceutical product, household care product, industrial product, or food product: glycemic index modification, dietary fiber, thickening, freeze/thaw stability, lubricity, moisture retention and release, texture, consistency, shape retention, emulsification, binding, suspension, dispersion, gelation, reduced mineral hardness, for example. Examples of a concentration or amount of an alpha-1,2-branched glucan in a product can be any of the weight percentages provided above, for example.

An alpha-1,2-branched glucan as presently disclosed may be formulated (e.g., blended, mixed, incorporated into, etc.) with one or more other materials suitable for use in a food product and/or other ingestible products herein (e.g., nutritional supplements, pharmaceuticals). Optionally, an alpha- 1,2-branched glucan herein can be provided in a syrup for use in preparing and/or modifying any food or other ingestible product as presently disclosed.

In some embodiments, an alpha-1,2-branched glucan herein may be included in a product with at least one of the following: monosaccharides, disaccharides, glucose, sucrose, fructose, leucrose, corn syrup, high fructose corn syrup, isomerized sugar, maltose, trehalose, panose, raffinose, cellobiose, isomaltose, honey, maple sugar, fruit-derived sweeteners, sorbitol, maltitol, isomaltitol, lactose, nigerose, kojibiose, xylitol, erythritol, dihydrochalcone, stevioside, alpha-glycosyl stevioside, acesulfame potassium, alitame, neotame, glycyrrhizin, thaumantin, sucralose, L-aspartyl-L-phenylalanine methyl ester, saccharine, maltodextrin, starch, potato starch, tapioca starch, dextran, soluble corn fiber, resistant maltodextrins, branched maltodextrins, inulin, polydextrose, fructo-oligosaccharides, galacto-oligosaccharides, xylo-oligosaccharides, arabinoxylo-oligosaccharides, nigero-oligosaccharides, gentio-oligosaccharides, hemicellulose, fructose oligomer syrup, isomalto-oligosaccharides, fillers, excipients, and binders.

In certain embodiments, an ingestible product comprises 0.01 to 99 wt %, 0.1 to 90 wt %, 1 to 90 wt %, or 5 to 80 wt % of alpha-1,2-branched glucan herein on a dry solids basis.

The term "food" is intended to encompass food for human consumption as well as for animal (e.g., mammal) consumption. By "functional food" it is meant any fresh or processed food claimed to have a health-promoting and/or disease-preventing and/or disease-(risk)-reducing property beyond the basic nutritional function of supplying nutrients. Functional food may include, for example, processed food or foods fortified with health-promoting additives. Examples of functional food are foods fortified with vitamins, or fermented foods with live cultures.

Other ingredients that can be included in an ingestible product herein are water or other aqueous solutions, fats, sugars, starch, binders, thickeners, colorants, flavorants, odorants, acidulants (such as lactic acid or malic acid, among others), stabilizers, high intensity sweeteners, and/or minerals, among others.

One or more alpha-1,2-branched glucan products herein may be provided in any of the food embodiments presently disclosed. Depending on the desired effect(s), (i) an alpha-1,2-branched glucan with dietary fiber qualities and/or (ii) an alpha-1,2-branched glucan that has a low glycemic index may be used as appropriate.

Examples of suitable food products include bread, breakfast cereals, biscuits, cakes, cookies, crackers, yogurt, kefir, miso, natto, tempeh, kimchee, sauerkraut, water, milk, fruit juice, vegetable juice, carbonated soft drinks, non-carbonated soft drinks, coffee, tea, beer, wine, liquor, alcoholic drink, snacks, soups, frozen desserts, fried foods, pizza, pasta products, potato products, rice products, corn products, wheat products, dairy products, hard candies, nutritional bars, cereals, dough, processed meats and cheeses, yoghurts, ice cream confections, milk-based drinks, salad dressings, sauces, toppings, desserts, confectionery products, cereal-based snack bars, prepared dishes, and the like.

In certain embodiments, an ingestible product herein can comprise at least one dietary fiber source. In those aspects in which an alpha-1,2-branched glucan herein is a dietary fiber itself (e.g., glucan having about 15-45% 1,2-branches in some cases), such glucan can be the sole fiber source or in addition to one or more other fiber sources. Suitable dietary fibers herein include oligo- or polysaccharides such as resistant/branched maltodextrins/fiber dextrins (e.g., NTJTRIOSE® from Roquette Freres, Lestrem, France; FIBERSOL-2 ® from ADM-Matsutani LLC, Decatur, Illinois), polydextrose (e.g., LITESSE® or LITESSE® ULTRA from Danisco-DuPont Nutrition & Health, Wilmington, DE), soluble corn fiber (e.g., PROMITOR® from Tate & Lyle, London, UK), isomalto-oligosaccharides (IMOs), alternan and/or malto-alternan oligosaccharides (MAOs) (e.g., FIBERMALT™ from Aevotis GmbH, Potsdam, Germany; SUCROMALT™ from Cargill Inc., Minneapolis, MN), pullulan, resistant starch, inulin, fructo-oligosaccharides (FOS), galacto-oligosaccharides (GOS), xylo-oligosaccharides, arabinoxylo-oligosaccharides, nigero-oligosaccharides, gentio-oligosaccharides, hemicellulose and fructose oligomer syrup.

An alpha-1,2-branched glucan herein can be added to foods as a replacement or supplement for conventional carbohydrates, for example.

In certain embodiments, an ingestible product herein can comprise at least one artificial sweetener including, but not limited to, stevia, aspartame, sucralose, neotame, acesulfame potassium, saccharin, and any combination thereof. An ingestible product herein can comprise at least one sugar substitute, for example, such as brazzein, curculin, erythritol, glycerol, glycyrrhizin, hydrogenated starch hydrolysates, inulin, isomalt, lactitol, mabinlin, maltitol, malto-oligosaccharide, malto-alternan oligosaccharides (such as XTEND® SUCROMALT™, available from Cargill Inc., Minneapolis, MN), mannitol, miraculin, a mogroside mix, monatin, monellin, osladin, pentadin, sorbitol, stevia, tagatose, thaumatin, xylitol, and any combination thereof.

In certain embodiments, a food product containing an alpha-1,2-branched glucan herein will have a lower (e.g., at least about 5%, 10%, 15%, 20%, or 25% lower) glycemic response, glycemic index, and/or glycemic load than a similar food product in which a conventional carbohydrate (e.g., a readily digestible glucose-containing carbohydrate) is used (e.g., when used at same or similar amount). Further, because an alpha-1,2-branched glucan in some aspects is characterized to have low or no digestibility in the human stomach and/or small intestine, the caloric content of the food product is reduced (following the above comparison). An alpha-1,2-branched glucan can be used in food products alone or in combination with bulking agents, such as sugar alcohols or maltodextrins, to reduce caloric content, to enhance the food's nutritional profile, and/or as a partial replacement for fat.

It is contemplated that an alpha-1,2-branched glucan herein may be used in food products as a tenderizer or texturizer, to increase crispness or snap, to improve eye appeal, and/or to improve the rheology of dough, batter, or other food compositions. It is also contemplated that the glucan be used in food products as a humectant, to increase product shelf life, to produce a softer, moister texture, to reduce water activity, and/or to immobilize and manage water. Additional uses of the glucan may include: replacement of an egg wash and/or to enhance the surface sheen of a food product, to alter flour starch gelatinization temperature, to modify the texture of the product, and to enhance browning of the product.

An alpha-1,2-branched glucan can be used in a variety of types of food products. One type of food product in which the present glucan can be useful is bakery products (baked foods), such as cakes, brownies, cookies, cookie crisps, muffins, breads, and sweet doughs. There are two main categories of bakery products: yeast-raised and chemically-leavened. In yeast-raised products, like donuts, sweet doughs, and breads, a glucan herein can be used to replace sugars, but a small amount of sugar may still be desired due to the need for a fermentation substrate for the yeast or for crust browning. Alpha-1,2-branched glucan in a syrup, for example, can be added with other liquids as a direct replacement for non-fiber containing syrups or liquid sweeteners. The dough would then be processed under conditions commonly used in the baking industry including being mixed, fermented, divided, formed or extruded into loaves or shapes, proofed, and baked or fried. The product can be baked or fried using conditions similar to traditional products. Breads are commonly baked at temperatures ranging from 420° F. to 520° F. (216-271° C.)°. for 20 to 23 minutes and doughnuts can be fried at temperatures ranging from 400-415° F. (204-213° C.), although other temperatures and times could also be used.

Chemically leavened products typically have more sugar and may contain have a higher level of the carbohydrate compositions and/or edible syrups comprising alpha-glucan herein. A finished cookie can contain 30% sugar, which could be replaced, entirely or partially, with carbohydrate compositions and/or syrups comprising the present glucan composition. These products could have a pH of 4-9.5, for example. The moisture content can be between 2-40%, for example.

Glucan compositions herein (e.g., in a syrup) can be readily incorporated and may be added to the fat at the beginning of mixing during a creaming step or in any method similar to the syrup or dry sweetener that it is being used to replace. The product would be mixed and then formed, for example by being sheeted, rotary cut, wire cut, or through another forming process. The products would then be baked under typical baking conditions, for example at 200-450° F. (93-232° C.).

Another type of food product in which a glucan herein (e.g., in a syrup) can be used is breakfast cereal. For example, glucan-containing syrups could be used to replace all or part of the sugar in extruded cereal pieces and/or in the coating on the outside of those pieces. The coating is typically 30-60% of the total weight of the finished cereal piece. The syrup can be applied in a spray or drizzled on, for example.

Another type of food product in which an alpha-1,2-branched glucan herein can be used is dairy products. Examples of suitable dairy products include yogurt, yogurt drinks, milk drinks, flavored milks, smoothies, ice cream, shakes, cottage cheese, cottage cheese dressing, and dairy desserts, such as quarg and the whipped mousse-type products. This would include dairy products that are intended to be consumed directly (such as packaged smoothies) as well as those that are intended to be blended with other ingredients (such as blended smoothies). It can be used in pasteurized dairy products, such as ones that are pasteurized at a temperature from 160° F. to 285° F. (71-141° C.).

Another type of food product in which an alpha-1,2-branched glucan herein can be used is confections. Examples of suitable confections include hard candies, fondants, nougats and marshmallows, gelatin jelly candies or gummies, jellies, chocolate, licorice, chewing gum, caramels and toffees, chews, mints, tableted confections, and fruit snacks. In fruit snacks, a composition comprising a glucan herein could be used in combination with fruit juice. The fruit juice would provide the majority of the sweetness, and the composition comprising the glucan would reduce the total sugar content and possibly add fiber. Compositions comprising the alpha-glucan herein can be added to the initial candy slurry and heated to the finished solids content. The slurry could be heated from 200-305° F. (93-152° C.) to achieve the finished solids content. Acid could be added before or after heating to give a finished pH of 2-7. The composition comprising the glucan could be used as a replacement for 0-100% of the sugar and 1-100% of the corn syrup or other sweeteners present.

Another type of food product in which an alpha-1,2-branched glucan herein can be used is jams and jellies. Jams and jellies are made from fruit; jam contains fruit pieces, while jelly is made from fruit juice. The composition comprising the present glucan can be used in place of sugar or other sweeteners as follows: weigh fruit and juice into a tank; premix sugar, the alpha-glucan-containing composition and pectin; add the dry composition to the liquid and cook to a temperature of 214-220° F. (101-104° C.); hot fill into jars and retort for 5-30 minutes.

Another type of food product in which an alpha-1,2-branched glucan herein can be used are beverages. Examples of suitable beverages include carbonated beverages, fruit juices, concentrated juice mixes (e.g., margarita mix), clear waters, and beverage dry mixes. The use of an alpha-1,2-branched glucan dietary fiber herein may overcome clarity problems that result when other types of fiber are added to beverages. A complete replacement of sugars may be possible (which could be, for example, being up to 12% or more of the total formula).

Another suitable type of food product is high solids fillings. Examples of high solids fillings include fillings in snack bars, toaster pastries, donuts, and cookies. A high solids filling could be an acid/fruit filling or a savory filling, for example. An alpha-1,2-branched glucan herein could be added to products that would be consumed as is, or products that would undergo further processing, by a food processor (additional baking) or by a consumer (bake stable filling). In certain embodiments, the high solids fillings would have a solids concentration between 67-90%. The solids could be entirely replaced with a composition comprising the alpha-glucan or it could be used for a partial replacement of the other sweetener solids present (e.g., replacement of current solids from 5-100%). Typically fruit fillings would have a pH of 2-6, while savory fillings would be between 4-8 pH. Fillings could be prepared cold or heated at up to 250° F. (121° C.) to evaporate to the desired finished solids content.

Another suitable type of food product that can comprise glucan herein is represented by extruded and sheeted snacks. Examples of extruded and sheeted include puffed snacks, crackers, tortilla chips, and corn chips. In preparing an extruded piece, a composition comprising the present glucan would be added directly with the dry products. A small amount of water would be added in the extruder, and then it would pass through various zones ranging from 100° F. to 300° F. (38-149° C.). The dried product could be added at levels from 0-50% of the dry products mixture. A syrup comprising the glucan could also be added at one of the liquid ports along the extruder. The product would come out at either a low moisture content (5%) and then baked to remove the excess moisture, or at a slightly higher moisture content (10%) and then fried to remove moisture and cook out the product. Baking could be at temperatures up to 500° F. (260° C.). for 20 minutes. Baking would more typically be at 350° F. (177° C.) for 10 minutes. Frying would typically be at 350° F. (177° C.) for 2-5 minutes. In a sheeted snack, the glucan could be used as a partial replacement of the other dry ingredients (for example, flour). The glucan could be from 0-50% of the dry weight. The product would be dry mixed, and then water added to form cohesive dough. The product mix could have a pH from 5 to 8. The dough would then be sheeted and cut and then baked or fried. Baking could be at temperatures up to 500° F. (260° C.) for 20 minutes. Frying would typically be at 350° F. (177° C.) for 2-5 minutes. Another potential benefit from the use of a composition comprising the glucan is a reduction of the fat content of fried snacks by as much as 15% when it is added as an internal ingredient or as a coating on the outside of a fried food.

Another type of food product in which a glucan herein can be used is gelatin desserts. The ingredients for gelatin desserts are often sold as a dry mix with gelatin as a gelling agent. The sugar solids could be replaced partially or entirely with a composition comprising the present glucan in the dry mix. The dry mix can then be mixed with water and heated to 212° F. (100° C.). to dissolve the gelatin and then more water and/or fruit can be added to complete the gelatin dessert. The gelatin is then allowed to cool and set. Gelatin can also be sold in shelf stable packs. In that case the stabilizer is usually carrageenan-based. As stated above, a composition comprising the alpha-glucan could be used to replace up to 100% of the other sweetener solids. The dry ingredients are mixed into the liquids and then pasteurized and put into cups and allowed to cool and set.

Another type of food product in which a composition comprising glucan herein can be used is snack bars. Examples of snack bars in which it can be used include breakfast and meal replacement bars, nutrition bars, granola bars, protein bars, and cereal bars. It could be used in any part of the snack bars, such as in the high solids filling, the binding syrup or the particulate portion. A complete or partial replacement of sugar in the binding syrup may be possible. The binding syrup is typically from 50-90% solids and applied at a ratio ranging from 10% binding syrup to 90% particulates, to 70% binding syrup to 30% particulates. The binding syrup is made by heating a solution of sweeteners, bulking agents and other binders (like starch) to 160-230° F. (71-110° C.) (depending on the finished solids needed in the syrup). The syrup is then mixed with the particulates to coat the particulates, providing a coating throughout the matrix. A composition comprising the glucan could also be used in the particulates themselves. This could be an extruded piece, directly expanded or gun puffed. It could be used in combination with another grain ingredient, corn meal, rice flour or other similar ingredient.

Another type of food product in which a composition comprising a glucan herein can be used is cheese, cheese sauces, and other cheese products. Examples of cheese, cheese sauces, and other cheese products in which it can be used include lower milk solids cheese, lower fat cheese, and calorie reduced cheese. In block cheese, it can help to improve the melting characteristics, or to decrease the effect of the melt limitation added by other ingredients such as starch. It could also be used in cheese sauces, for example as a bulking agent, to replace fat, milk solids, or other typical bulking agents.

Another type of food product in which a glucan herein can be used is films that are edible and/or water soluble. Examples of films in which it can be used include films that are used to enclose dry mixes for a variety of foods and beverages that are intended to be dissolved in water, or films that are used to deliver color or flavors such as a spice film that is added to a food after cooking while still hot. Other film applications include, but are not limited to, fruit and vegetable leathers, and other flexible films.

In another embodiment, compositions comprising a glucan herein can be used is soups, syrups, sauces, and dressings. A typical dressing could be from 0-50% oil, with a pH range of 2-7. It could be cold processed or heat processed. It would be mixed, and then stabilizer would be added. The composition comprising the glucan could easily be added in liquid or dry form with the other ingredients as needed. The dressing composition may need to be heated to activate the stabilizer. Typical heating conditions would be from 170-200° F. (77-93° C.) for 1-30 minutes. After cooling, the oil is added to make a pre-emulsion. The product is then emulsified using a homogenizer, colloid mill, or other high shear process. Sauces can have from 0-10% oil and from 10-50% total solids, and can have a pH from 2-8. Sauces can be cold processed or heat processed. The ingredients are mixed and then heat processed. A glucan herein could easily be added in liquid or dry form with the other ingredients as needed. Typical heating would be from 170-200° F. (77-93° C.) for 1-30 minutes. Soups are more typically 20-50% solids and in a more neutral pH range (4-8). They can be a dry mix, to which a dry composition comprising glucan herein could be added, or a liquid soup which is canned and then retorted. In soups, resistant corn syrup could be used up to 50% solids, though a more typical usage would be to deliver 5 g of fiber/serving.

Another type of food product in which a glucan herein can be used is coffee creamers. Examples of coffee creamers in which it can be used include both liquid and dry creamers. A dry blended coffee creamer can be blended with commercial creamer powders of the following fat types: soybean, coconut, palm, sunflower, or canola oil, or butterfat. These fats can be non-hydrogenated or hydrogenated. The composition comprising the glucan can be added as a fiber source, optionally together with fructo-oligosaccharides, polydextrose, inulin, maltodextrin, resistant starch, sucrose, and/or conventional corn syrup solids. The composition can also contain high intensity sweeteners, such as sucralose, acesulfame potassium, aspartame, or combinations thereof. These ingredients can be dry blended to produce the desired composition. A spray dried creamer powder is a combination of fat, protein and carbohydrates, emulsifiers, emulsifying salts, sweeteners, and anti-caking agents. The fat source can be one or more of soybean, coconut, palm, sunflower, or canola oil, or butterfat. The protein can be sodium or calcium caseinates, milk proteins, whey proteins, wheat proteins, or soy proteins. The carbohydrate could be a composition comprising the glucan alone or in combination with fructo-oligosaccharides, polydextrose, inulin, resistant starch, maltodextrin, sucrose, corn syrup or any combination thereof. The emulsifiers can be mono- and diglycerides, acetylated mono- and diglycerides, or propylene glycol monoesters. The salts can be trisodium citrate, monosodium phosphate, disodium phosphate, trisodium phosphate, tetrasodium pyrophosphate, monopotassium phosphate, and/or dipotassium phosphate. The composition can also contain high intensity sweeteners, such as those describe above. Suitable anti-caking agents include sodium silico-aluminates or silica dioxides. The products are combined in slurry, optionally homogenized, and spray dried in either a granular or agglomerated form. Liquid coffee creamers are simply a homogenized and pasteurized emulsion of fat (either dairy fat or hydrogenated vegetable oil), some milk solids or caseinates, corn syrup, and vanilla or other flavors, as well as a stabilizing blend. The product is usually pasteurized via HTST (high temperature short time) at 185° F. (85° C.) for 30 seconds, or UHT (ultra-high temperature), at 285° F. (141° C.) for 4 seconds, and homogenized in a two stage homogenizer at 500-3000 psi (3.45-20.7 MPa) first stage, and 200-1000 psi (1.38-6.89 MPa) second stage. The coffee creamer is usually stabilized so that it does not break down when added to coffee.

Another type of food product in which a glucan herein can be used (e.g., as a syrup) is food coatings such as icings, frostings, and glazes. In icings and frostings, the glucan can be used as a sweetener replacement (complete or partial) to lower caloric content and increase fiber content. Glazes are typically about 70-90% sugar, with most of the rest being water, and the glucan can be used to entirely or partially replace the sugar. Frosting typically contains about 2-40% of a liquid/solid fat combination, about 20-75% sweetener solids, color, flavor, and water. The glucan can be used to replace all or part of the sweetener solids, or as a bulking agent in lower fat systems.

Another type of food product in which a glucan herein can be used is pet food, such as dry or moist dog food. Pet foods are made in a variety of ways, such as extrusion, forming, and formulating as gravies. The glucan could be used at levels of 0-50% in each of these types.

Another type of food product in which a glucan herein can be used is fish and meat. Conventional corn syrup is already used in some meats, so a glucan-containing syrup herein can be used as a partial or complete substitute. For example, the glucan syrup could be added to brine before it is vacuum tumbled or injected into the meat. It could be added with salt and phosphates, and optionally with water binding ingredients such as starch, carrageenan, or soy proteins.

Beneficial Physiological Properties

Gas Production

A rapid rate of gas production in the lower gastrointestinal tract gives rise to gastrointestinal discomfort such as flatulence and bloating, whereas if gas production is gradual and low, the body can more easily cope. For example, it is possible that inulin gives a boost of gas production that is rapid and high when compared to the disclosed glucan at an equivalent dosage, whereas, in some embodiments, the disclosed glucan has a rate of gas release that is lower than that of inulin at an equivalent dosage.

In one embodiment, consumption of food products containing the disclosed glucan might result in a rate of gas production that is well tolerated for food applications. In one embodiment, the relative rate of gas production is no more than the rate observed for inulin under similar conditions, such as the same or less than inulin, or less than inulin, or much less than inulin at an equivalent dosage. In another embodiment, the relative rate of gas formation is measured over 3 hours or 24 hours using the methods described herein. In some embodiments, the rate of gas formation is at least 1%, 2%, 3%, 4%, 5%, 6%, 7%, 8%, 9%, 10%, 15%, 20%, 25%, or 30% less than the rate observed for inulin under the same reaction conditions.

Short Chain Fatty Acid Production

Use of a glucan herein may facilitate the production of energy yielding metabolites through colonic fermentation. Use of a glucan herein may facilitate the production of short chain fatty acids (SCFAs), such as propionate and/or butyrate. SCFAs are known to lower cholesterol. Consequently, a glucan herein may lower the risk of developing high cholesterol. As the production of SCFAs or the increased ratio of SCFA to acetate is beneficial for the control of cholesterol levels in a mammal in need thereof, the disclosed glucan composition may be of particular interest to nutritionists and consumers for the prevention and/or treatment of cardiovascular risks. Thus, in another aspect, the disclosure provides a method for improving the health of a subject comprising administering a composition comprising the disclosed glucan composition to a subject in an amount effective to exert a beneficial effect on the health of said subject, such as for treating cholesterol-related diseases. In addition, it is generally known that SCFAs lower the pH in the gut and this helps calcium absorption. Thus, compounds according to the present disclosure may also affect mineral absorption. This means that they may also improve bone health, or prevent or treat osteoporosis by lowering the pH due to SCFA increases in the gut. The production of SCFA may increase viscosity in small intestine which reduces the re-absorption of bile acids; increasing the synthesis of bile acids from cholesterol and reduces circulating low density lipoprotein (LDL) cholesterol.

An "effective amount" of a compound or composition as defined herein refers to an amount effective, at dosages and for periods of time necessary, to achieve a desired beneficial physiological effect, such as lowering of blood cholesterol, increasing SCFA production or preventing or treating a gastrointestinal disorder. For instance, the amount of a composition administered to a subject will vary depending upon factors such as the subject's condition, the subject's body weight, the age of the subject, and whether a composition is the sole source of nutrition. The effective amount may be readily set by a medical practitioner or dietician. In general, a sufficient amount of the composition is administered to provide the subject with up to about 50 g per day; or, for example, about 25 g to about 35 g per day. In some embodiments, the amount of the disclosed glucan composition that a subject receives is in the range of about 0.1 g to about 50 g per day, or in the range of 0.5 g to 20 g per day, or 1 g to 10 g per day. A compound or composition as defined herein may be taken in multiple doses, for example 1 to 5 times, spread out over the day or acutely, or may be taken in a single dose. A compound or composition as defined herein may also be fed continuously over a desired period. In certain embodiments, the desired period is at least one week or at least two weeks or at least three weeks or at least one month or at least six months.

In some embodiments, this disclosure provides a method for decreasing blood triglyceride levels in a subject in need thereof by administering a compound or a composition as defined herein to a subject in need thereof. In another embodiment, this disclosure provides a method for decreasing low density lipoprotein levels in a subject in need thereof by administering a compound or a composition as defined herein to a subject in need thereof. In another embodiment, the disclosure provides a method for increasing high density lipoprotein levels in a subject in need thereof by administering a compound or a composition as defined herein to a subject in need thereof.

Attenuation of Postprandial Blood Glucose Concentrations/Glycemic Response

The presence of bonds other than alpha-1,4 backbone linkages in the disclosed glucan composition provides improved digestion resistance as enzymes of the human digestion track may have difficultly hydrolyzing such bonds and/or branched linkages. The presence of branches provides partial or complete indigestibility to the glucan in some embodiments, and therefore virtually no or a slower absorption of glucose into the body, which results in a lower glycemic response. Accordingly, the disclosure provides a glucan composition for the manufacture of food and drink compositions resulting in a lower glycemic response. For example, these compounds can be used to replace sugar or other rapidly digestible carbohydrates, and thereby lower the glycemic load of foods, reduce calories, and/or lower the energy density of foods. Also, the stability of the disclosed glucan composition possessing these types of bonds allows them to be easily passed through into the large intestine where they may serve as a substrate specific for the colonic microbial flora.

Improvement of Gut Health

In a further embodiment, compounds as disclosed herein may be used for the treatment and/or improvement of gut health. In some embodiments, the glucan composition is slowly fermented in the gut by the gut microflora. In some embodiments, the present compounds exhibit (in an in vitro gut model) a tolerance no worse than inulin or other commercially available fibers such as PROMITOR® (soluble corn fiber, Tate & Lyle), NUTRIOSE® (soluble corn fiber or dextrin, Roquette), or FIBERSOL®-2 (digestion-resistant maltodextrin, Archer Daniels Midland Company & Matsutani Chemical) (i.e., similar level of gas production), and in particular, provide for an improved tolerance over one or more of the commercially available fibers, i.e. the fermentation of the present glucan results in less gas production than inulin in 3 hours or 24 hours, thereby lowering discomfort, such as flatulence and bloating, due to gas formation. In one aspect, the disclosure also relates to a method for moderating gas formation in the gastrointestinal tract of a subject by administering a compound or a composition as disclosed herein to a subject in need thereof, so as to decrease gut pain or gut discomfort due to flatulence and bloating. In further embodiments, compositions as disclosed herein provide subjects with improved tolerance to food fermentation, and may be combined with fibers, such as inulin or FOS, GOS, or lactulose to improve tolerance by lowering gas production. In another embodiment, compounds as disclosed herein may be administered to improve laxation or improve regularity by increasing stool bulk.

Prebiotics and Probiotics

A glucan herein may be useful as a prebiotic, or as a "synbiotic" when used in combination with a probiotic, as discussed below. By "prebiotic" it is meant a food ingredient that beneficially affects a subject by selectively stimulating the growth and/or activity of one or a limited number of bacteria in the gastrointestinal tract, particularly the colon, and thus improves the health of the subject. Examples of prebiotics include fructo-oligosaccharides, inulin, polydextrose, resistant starch, soluble corn fiber, gluco-oligosaccharides, galacto-oligosaccharides, arabinoxylan-oligosaccharides, lactitol, and lactulose.

In another embodiment, compositions comprising a glucan herein can further comprise at least one probiotic organism. By "probiotic organism", it is meant living microbiological dietary supplements that provide beneficial effects to a subject through their function in the digestive tract. In order to be effective, a probiotic micro-organisms must be able to survive the digestive conditions, and must be able to colonize the gastrointestinal tract at least temporarily without any harm to the subject. Only certain strains of microorganisms have these properties. In some embodiments, the probiotic microorganism is selected from the group comprising *Lactobacillus* spp., *Bifidobacterium* spp., *Bacillus* spp., *Enterococcus* spp., *Escherichia* spp., *Streptococcus* spp., and *Saccharomyces* spp. Specific microorganisms include, but are not limited to *Bacillus subtilis, Bacillus cereus, Bifidobacterium animalis, Bifidobacterium bificum, Bifidobacterium breve, Bifidobacterium infantis, Bifidobacterium lactis, Bifidobacterium longum, Bifidobacterium thermophilum, Enterococcus faecium, Enterococcus faecium, Lactobacillus acidophilus, Lactobacillus bulgaricus, Lactobacillus casei, Lactobacillus lactis, Lactobacillus plantarum, Lactobacillus reuteri, Lactobacillus rhamnosus, Streptococcus faecium, Streptococcus mutans, Streptococcus thermophilus, Saccharomyces boulardii*, Torulopsia, *Aspergillus oryzae*, and *Streptomyces* among others, including their vegetative spores, non-vegetative spores (*Bacillus*) and synthetic derivatives. In some embodiments, probiotic microorganisms include, but are not limited to, members of three bacterial genera: *Lactobacillus, Bifidobacterium* and *Saccharomyces*.

In some embodiments, the composition comprises a probiotic organism in an amount sufficient to delivery at least 1 to 200 billion, 1 to 100 billion, or 1 to 50 billion viable probiotic organisms. The amount of probiotic organisms delivered as described above may be per dosage and/or per day, where multiple dosages per day may be suitable for some applications. Two or more probiotic organisms may be used in a composition, for example.

Compositions disclosed herein can be in the form of a fabric care composition. A fabric care composition herein can be used for hand wash, machine wash and/or other purposes such as soaking and/or pretreatment of fabrics, for example. A fabric care composition may take the form of, for example, a laundry detergent; fabric conditioner; any wash-, rinse-, or dryer-added product; unit dose or spray. Fabric care compositions in a liquid form may be in the form of an aqueous composition as disclosed herein. In other aspects, a fabric care composition can be in a dry form such as a granular detergent or dryer-added fabric softener sheet. Other non-limiting examples of fabric care compositions herein include: granular or powder-form all-purpose or heavy-duty washing agents; liquid, gel or paste-form all-purpose or heavy-duty washing agents; liquid or dry fine-fabric (e.g., delicates) detergents; cleaning auxiliaries such as bleach additives, "stain-stick", or pre-treatments; substrate-laden products such as dry and wetted wipes, pads, or sponges; sprays and mists.

A detergent composition herein may be in any useful form, e.g., as powders, granules, pastes, bars, unit dose, or liquid. A liquid detergent may be aqueous, typically containing up to about 70 wt % of water and 0 wt % to about 30 wt % of organic solvent. It may also be in the form of a compact gel type containing only about 30 wt % water.

A detergent composition herein typically comprises one or more surfactants, wherein the surfactant is selected from nonionic surfactants, anionic surfactants, cationic surfactants, ampholytic surfactants, zwitterionic surfactants, semipolar nonionic surfactants and mixtures thereof. In some embodiments, the surfactant is present at a level of from about 0.1% to about 60%, while in alternative embodiments the level is from about 1% to about 50%, while in still further embodiments the level is from about 5% to about 40%, by weight of the detergent composition. A detergent will usually contain 0 wt % to about 50 wt % of an anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. In addition, a detergent composition may optionally contain 0 wt % to about 40 wt % of a nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO92/06154, which is incorporated herein by reference).

A detergent composition herein typically comprises one or more detergent builders or builder systems. In some embodiments incorporating at least one builder, the cleaning compositions comprise at least about 1%, from about 3% to about 60%, or even from about 5% to about 40%, builder by weight of the composition. Builders include, but are not limited to, alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present disclosure. Additional examples of a detergent builder or complexing agent include zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst).

In some embodiments, builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present disclosure, including those known in the art (See, e.g., EP2100949).

In some embodiments, suitable builders can include phosphate builders and non-phosphate builders. In some embodiments, a builder is a phosphate builder. In some embodiments, a builder is a non-phosphate builder. A builder can be used in a level of from 0.1% to 80%, or from 5% to 60%, or from 10% to 50%, by weight of the composition. In some embodiments, the product comprises a mixture of phosphate and non-phosphate builders. Suitable phosphate builders include mono-phosphates, di-phosphates, tri-polyphosphates or oligomeric-polyphosphates, including the alkali metal salts of these compounds, including the sodium salts. In some embodiments, a builder can be sodium tripolyphosphate (STPP). Additionally, the composition can comprise carbonate and/or citrate, preferably citrate that helps to achieve a neutral pH composition. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include ammonium and/or alkali metal salts, i.e., lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

A detergent composition herein can comprise at least one chelating agent. Suitable chelating agents include, but are not limited to, copper, iron and/or manganese chelating agents and mixtures thereof. In embodiments in which at least one chelating agent is used, the composition comprises from about 0.1% to about 15%, or even from about 3.0% to about 10%, chelating agent by weight of the composition.

A detergent composition herein can comprise at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

A detergent composition herein can comprise one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. Additional dye transfer inhibiting agents include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethyl ethylenediaminetriacetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof, which can be used alone or in combination with any of the above. In embodiments in which at least one dye transfer inhibiting agent is used, a composition herein may comprise from about 0.0001% to about 10%, from about 0.01% to about 5%, or even from about 0.1% to about 3%, by weight of the composition.

A detergent composition herein can comprise silicates. In some of these embodiments, sodium silicates (e.g., sodium disilicate, sodium metasilicate, and/or crystalline phyllosilicates) find use. In some embodiments, silicates are present at a level of from about 1% to about 20% by weight of the composition. In some embodiments, silicates are present at a level of from about 5% to about 15% by weight of the composition.

A detergent composition herein can comprise dispersants. Suitable water-soluble organic materials include, but are not limited to the homo- or co-polymeric acids or their salts, in which the polycarboxylic acid comprises at least two carboxyl radicals separated from each other by not more than two carbon atoms.

A detergent composition herein may additionally comprise one or more enzymes as delineated above.

In some embodiments, a detergent composition can comprise one or more enzymes (e.g., any disclosed herein), each at a level from about 0.00001% to about 10% by weight of the composition and the balance of cleaning adjunct materials by weight of composition. In some other embodiments, a detergent composition can also comprise each enzyme at a level of about 0.0001% to about 10%, about 0.001% to about 5%, about 0.001% to about 2%, or about 0.005% to about 0.5%, by weight of the composition.

Enzymes that may be comprised in a detergent composition herein may be stabilized using conventional stabilizing agents, e.g., a polyol such as propylene glycol or glycerol; a sugar or sugar alcohol; lactic acid; boric acid or a boric acid derivative (e.g., an aromatic borate ester).

A detergent composition in certain embodiments may comprise one or more polymers. Examples of suitable polymers include carboxymethyl cellulose (CMC), poly(vinylpyrrolidone) (PVP), polyethylene glycol (PEG), poly(vinyl alcohol) (PVA), polycarboxylates such as polyacrylates, maleic/acrylic acid copolymers and lauryl methacrylate/acrylic acid copolymers.

A detergent composition herein may contain a bleaching system. For example, a bleaching system can comprise an $H_2O_2$ source such as perborate or percarbonate, which may be combined with a peracid-forming bleach activator such as tetraacetylethylenediamine (TAED) or nonanoyloxybenzenesulfonate (NOBS). Alternatively, a bleaching system may comprise peroxyacids (e.g., amide, imide, or sulfone type peroxyacids). Alternatively still, a bleaching system can be an enzymatic bleaching system comprising perhydrolase, for example, such as the system described in WO2005/056783.

A detergent composition herein may also contain conventional detergent ingredients such as fabric conditioners, clays, foam boosters, suds suppressors, anti-corrosion agents, soil-suspending agents, anti-soil redeposition agents, dyes, bactericides, tarnish inhibitors, optical brighteners, or perfumes. The pH of a detergent composition herein (measured in aqueous solution at use concentration) is usually neutral or alkaline (e.g., pH of about 7.0 to about 11.0).

A detergent composition herein may also contain at least one anti-redeposition agent and/or clay soil removal agent (such agents can optionally be characterized as whiteness maintenance agents in certain aspects). Examples of suitable anti-redeposition and/or clay soil removal agents herein include polyethoxy zwitterionic surfactants, water-soluble copolymers of acrylic or methacrylic acid with acrylic or methacrylic acid-ethylene oxide condensates (e.g., U.S. Pat. No. 3,719,647), cellulose derivatives such as carboxymethylcellulose and hydroxypropylcellulose (e.g., U.S. Pat. Nos. 3,597,416 and 3,523,088), and mixtures comprising non-ionic alkyl polyethoxy surfactant, polyethoxy alkyl quaternary cationic surfactant and fatty amide surfactant (e.g., U.S. Pat. No. 4,228,044). Non-limiting examples of other suitable anti-redeposition and clay soil removal agents are disclosed in U.S. Pat. Nos. 4,597,898 and 4,891,160, and Int. Pat. Appl. Publ. No. WO95/32272, all of which are incorporated herein by reference.

Particular forms of detergent compositions that can be adapted for purposes disclosed herein are disclosed in, for example, US20090209445A1, US20100081598A1, U.S. Pat. No. 7,001,878B2, EP1504994B1, WO2001085888A2, WO2003089562A1, WO2009098659A1, WO2009098660A1, WO2009112992A1, WO2009124160A1, WO2009152031A1, WO2010059483A1, WO2010088112A1, WO2010090915A1, WO2010135238A1, WO2011094687A1, WO2011094690A1, WO2011127102A1, WO2011163428A1, WO2008000567A1, WO2006045391A1, WO2006007911A1, WO2012027404A1, EP1740690B1, WO2012059336A1, U.S. Pat. No. 6,730,646B1, WO2008087426A1, WO2010116139A1, and WO2012104613A1, all of which are incorporated herein by reference.

Laundry detergent compositions herein can optionally be heavy duty (all purpose) laundry detergent compositions. Exemplary heavy duty laundry detergent compositions comprise a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, e.g., C8-C18 alkyl ethoxylated alcohols and/or C6-C12 alkyl phenol alkoxylates), where the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quaternary ammonium compounds, alkyl quaternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic surfactants and mixtures thereof.

A detergent herein such as a heavy duty laundry detergent composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated C1-C6 carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof.

A detergent herein such as a heavy duty laundry detergent composition may optionally include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example REPEL-O-TEX SF, SF-2 AND SRP6, TEXCARE SRA100, SRA300, SRN100, SRN170, SRN240, SRN300 AND SRN325, MARLOQUEST SL), anti-redeposition agent(s) herein (0.1 wt % to 10 wt %), include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); and polymeric carboxylate (such as maleate/acrylate random copolymer or polyacrylate homopolymer).

A detergent herein such as a heavy duty laundry detergent composition may optionally further include saturated or unsaturated fatty acids, preferably saturated or unsaturated C12-C24 fatty acids (0 wt % to 10 wt %); deposition aids disclosed herein (examples for which include polysaccharides, cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic starch, cationic polyacylamides, and mixtures thereof).

A detergent herein such as a heavy duty laundry detergent composition may optionally further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetracetic acid (PDTA), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetriacetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

A detergent herein such as a heavy duty laundry detergent composition may optionally include silicone or fatty-acid based suds suppressors; hueing dyes, calcium and magnesium cations, visual signaling ingredients, anti-foam (0.001 wt % to about 4.0 wt %), and/or a structurant/thickener (0.01 wt % to 5 wt %) selected from the group consisting of diglycerides and triglycerides, ethylene glycol distearate, microcrystalline cellulose, microfiber cellulose, biopolymers, xanthan gum, gellan gum, and mixtures thereof). A structurant can also be referred to as a structural agent.

A detergent herein can be in the form of a heavy duty dry/solid laundry detergent composition, for example. Such a detergent may include: (i) a detersive surfactant, such as any anionic detersive surfactant disclosed herein, any non-ionic detersive surfactant disclosed herein, any cationic detersive surfactant disclosed herein, any zwitterionic and/or amphoteric detersive surfactant disclosed herein, any ampholytic surfactant, any semi-polar non-ionic surfactant, and mixtures thereof; (ii) a builder, such as any phosphate-free builder (e.g., zeolite builders in the range of 0 wt % to less than 10 wt %), any phosphate builder (e.g., sodium tri-polyphosphate in the range of 0 wt % to less than 10 wt %), citric acid, citrate salts and nitrilotriacetic acid, any silicate salt (e.g., sodium or potassium silicate or sodium meta-silicate in the range of 0 wt % to less than 10 wt %); any carbonate salt (e.g., sodium carbonate and/or sodium bicarbonate in the range of 0 wt % to less than 80 wt %), and mixtures thereof; (iii) a bleaching agent, such as any photobleach (e.g., sulfonated zinc phthalocyanines, sulfonated aluminum phthalocyanines, xanthenes dyes, and mixtures thereof), any hydrophobic or hydrophilic bleach activator (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, nonanoyloxybenzene sulfonate-NOBS, nitrile quats, and mixtures thereof), any source of hydrogen peroxide (e.g., inorganic perhydrate salts, examples of which include mono or tetra hydrate sodium salt of perborate, percarbonate, persulfate, perphosphate, or persilicate), any preformed hydrophilic and/or hydrophobic peracids (e.g., percarboxylic acids and salts, percarbonic acids and salts, perimidic acids and salts, peroxymonosulfuric acids and salts, and mixtures thereof); and/or (iv) any other components such as a bleach catalyst (e.g., imine bleach boosters examples of which include iminium cations and polyions, iminium zwitterions, modified amines, modified amine oxides, N-sulphonyl imines, N-phosphonyl imines, N-acyl imines, thiadiazole dioxides, perfluoroimines, cyclic sugar ketones, and mixtures thereof), and a metal-containing bleach catalyst (e.g., copper, iron, titanium, ruthenium, tungsten, molybdenum, or manganese cations along with an auxiliary metal cations such as zinc or aluminum and a sequestrate such as EDTA, ethylenediaminetetra(methylenephosphonic acid).

Compositions disclosed herein can be in the form of a dishwashing detergent composition. Examples of dishwashing detergents include automatic dishwashing detergents (typically used in dishwasher machines) and hand-washing dish detergents. A dishwashing detergent composition can be in any dry or liquid/aqueous form as disclosed herein, for example. Components that may be included in certain embodiments of a dishwashing detergent composition include, for example, one or more of a phosphate; oxygen- or chlorine-based bleaching agent; non-ionic surfactant; alkaline salt (e.g., metasilicates, alkali metal hydroxides, sodium carbonate); any active enzyme disclosed herein; anti-corrosion agent (e.g., sodium silicate); anti-foaming agent; additives to slow down the removal of glaze and patterns from ceramics; perfume; anti-caking agent (in granular detergent); starch (in tablet-based detergents); gelling agent (in liquid/gel based detergents); and/or sand (powdered detergents).

Dishwashing detergents such as an automatic dishwasher detergent or liquid dishwashing detergent can comprise (i) a non-ionic surfactant, including any ethoxylated non-ionic surfactant, alcohol alkoxylated surfactant, epoxy-capped poly(oxyalkylated) alcohol, or amine oxide surfactant present in an amount from 0 to 10 wt %; (ii) a builder, in the range of about 5-60 wt %, including any phosphate builder (e.g., mono-phosphates, di-phosphates, tri-polyphosphates, other oligomeric-polyphosphates, sodium tripolyphosphate-STPP), any phosphate-free builder (e.g., amino acid-based compounds including methyl-glycine-diacetic acid [MGDA] and salts or derivatives thereof, glutamic-N,N-diacetic acid [GLDA] and salts or derivatives thereof, iminodisuccinic acid (IDS) and salts or derivatives thereof, carboxy methyl inulin and salts or derivatives thereof, nitrilotriacetic acid [NTA], diethylene triamine penta acetic acid [DTPA], B-alaninediacetic acid [B-ADA] and salts thereof), homopolymers and copolymers of poly-carboxylic acids and partially or completely neutralized salts thereof, monomeric polycarboxylic acids and hydroxycarboxylic acids and salts thereof in the range of 0.5 wt % to 50 wt %, or sulfonated/carboxylated polymers in the range of about 0.1 wt % to about 50 wt %; (iii) a drying aid in the range of about 0.1 wt % to about 10 wt % (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds thereof, particularly of the reactive cyclic carbonate and urea type); (iv) a silicate in the range from about 1 wt % to about 20 wt % (e.g., sodium or potassium silicates such as sodium disilicate, sodium meta-silicate and crystalline phyllosilicates); (v) an inorganic bleach (e.g., perhydrate salts such as perborate, percarbonate, perphosphate, persulfate and persilicate salts) and/or an organic bleach (e.g., organic peroxyacids such as diacyl- and tetraacylperoxides, especially diperoxydodecanedioic acid, diperoxytetradecanedioic acid, and diperoxyhexadecanedioic acid); (vi) a bleach activator (e.g., organic peracid precursors in the range from about 0.1 wt % to about 10 wt %) and/or bleach catalyst (e.g., manganese triazacyclononane and related complexes; Co, Cu, Mn, and Fe bispyridylamine and related complexes; and pentamine acetate cobalt(III) and related complexes); (vii) a metal care agent in the range from about 0.1 wt % to 5 wt % (e.g., benzatriazoles, metal salts and complexes, and/or silicates); and/or (viii) any active enzyme disclosed herein in the range from about 0.01 to 5.0 mg of active enzyme per gram of automatic dishwashing detergent composition, and an enzyme stabilizer component (e.g., oligosaccharides, polysaccharides, and inorganic divalent metal salts).

It is believed that numerous commercially available detergent formulations can be adapted to include an alpha-1,2-branched glucan as disclosed herein. Examples include PUREX® ULTRAPACKS (Henkel), FINISH® QUANTUM (Reckitt Benckiser), CLOROX™ 2 PACKS (Clorox), OXICLEAN MAX FORCE POWER PAKS (Church & Dwight), TIDE® STAIN RELEASE, CASCADE® ACTIONPACS, and TIDE® PODS™ (Procter & Gamble).

Compositions disclosed herein can be in the form of an oral care composition, for example. Examples of oral care compositions include dentifrices, toothpaste, mouth wash, mouth rinse, chewing gum, edible strips, and tooth cream/gel that provide some form of oral care (e.g., treatment or prevention of cavities [dental caries], gingivitis, plaque, tartar, and/or periodontal disease). An oral care composition can also be for treating an "oral surface", which encompasses any soft or hard surface within the oral cavity including surfaces of the tongue, hard and soft palate, buccal mucosa, gums and dental surfaces. A "dental surface" herein is a surface of a natural tooth or a hard surface of artificial dentition including a crown, cap, filling, bridge, denture, or dental implant, for example.

An oral care composition herein can comprise about 0.01-15.0 wt % (e.g., ~0.1-10 wt % or ~0.1-5.0 wt %, ~0.1-2.0 wt %) of one or more alpha-1,2-branched glucans as disclosed herein, for example. One or more other thickening or dispersion agents can also be provided in an oral care composition herein, such as a carboxyvinyl polymer, carrageenan (e.g., L-carrageenan), natural gum (e.g., karaya, xanthan, gum arabic, tragacanth), colloidal magnesium aluminum silicate, or colloidal silica, for example.

An oral care composition herein may be a toothpaste or other dentifrice, for example. Such compositions, as well as any other oral care composition herein, can additionally comprise, without limitation, one or more of an anticaries agent, antimicrobial or antibacterial agent, anticalculus or tartar control agent, surfactant, abrasive, pH-modifying agent, foam modulator, humectant, flavorant, sweetener, pigment/colorant, whitening agent, and/or other suitable components. Examples of oral care compositions to which one or more alpha-1,2-branched glucans herein can be added are disclosed in U.S. Patent Appl. Publ. Nos. 2006/0134025, 2002/0022006 and 2008/0057007, which are incorporated herein by reference.

An anticaries agent herein can be an orally acceptable source of fluoride ions. Suitable sources of fluoride ions include fluoride, monofluorophosphate and fluorosilicate salts as well as amine fluorides, including olaflur (N'-octadecyltrimethylendiamine-N,N,N'-tris(2-ethanol)-dihydrofluoride), for example. An anticaries agent can be present in an amount providing a total of about 100-20000 ppm, about 200-5000 ppm, or about 500-2500 ppm, fluoride ions to the composition, for example. In oral care compositions in which sodium fluoride is the sole source of fluoride ions, an amount of about 0.01-5.0 wt %, about 0.05-1.0 wt %, or about 0.1-0.5 wt %, sodium fluoride can be present in the composition, for example.

An antimicrobial or antibacterial agent suitable for use in an oral care composition herein includes, for example, phenolic compounds (e.g., 4-allylcatechol; p-hydroxybenzoic acid esters such as benzylparaben, butylparaben, ethylparaben, methylparaben and propylparaben; 2-benzylphenol; butylated hydroxyanisole; butylated hydroxytoluene; capsaicin; carvacrol; creosol; eugenol; guaiacol; halogenated bisphenolics such as hexachlorophene and bromochlorophene; 4-hexylresorcinol; 8-hydroxyquinoline and salts thereof; salicylic acid esters such as menthyl salicylate, methyl salicylate and phenyl salicylate; phenol; pyrocatechol; salicylanilide; thymol; halogenated diphenylether compounds such as triclosan and triclosan monophosphate), copper (II) compounds (e.g., copper (II) chloride, fluoride, sulfate and hydroxide), zinc ion sources (e.g., zinc acetate, citrate, gluconate, glycinate, oxide, and sulfate), phthalic acid and salts thereof (e.g., magnesium monopotassium phthalate), hexetidine, octenidine, sanguinarine, benzalkonium chloride, domiphen bromide, alkylpyridinium chlorides (e.g. cetylpyridinium chloride, tetradecylpyridinium chloride, N-tetradecyl-4-ethylpyridinium chloride), iodine, sulfonamides, bisbiguanides (e.g., alexidine, chlorhexidine, chlorhexidine digluconate), piperidino derivatives (e.g., delmopinol, octapinol), *magnolia* extract, grapeseed extract, rosemary extract, menthol, geraniol, citral, eucalyptol, antibiotics (e.g., augmentin, amoxicillin, tetracycline, doxycycline, minocycline, metronidazole, neomycin, kanamycin, clindamycin), and/or any antibacterial agents disclosed in U.S. Pat. No. 5,776,435, which is incorporated herein by reference. One or more antimicrobial agents can optionally be present at about 0.01-10 wt % (e.g., 0.1-3 wt %), for example, in the disclosed oral care composition.

An anticalculus or tartar control agent suitable for use in an oral care composition herein includes, for example, phosphates and polyphosphates (e.g., pyrophosphates), polyaminopropanesulfonic acid (AMPS), zinc citrate trihydrate, polypeptides (e.g., polyaspartic and polyglutamic acids), polyolefin sulfonates, polyolefin phosphates, diphosphonates (e.g.,azacycloalkane-2,2-diphosphonates such as azacycloheptane-2,2-diphosphonic acid), N-methyl azacyclopentane-2,3-diphosphonic acid, ethane-1-hydroxy-1,1-diphosphonic acid (EHDP), ethane-1-amino-1,1-diphosphonate, and/or phosphonoalkane carboxylic acids and salts thereof (e.g., their alkali metal and ammonium salts). Useful inorganic phosphate and polyphosphate salts include, for example, monobasic, dibasic and tribasic sodium phosphates, sodium tripolyphosphate, tetrapolyphosphate, mono-, di-, tri- and tetra-sodium pyrophosphates, disodium dihydrogen pyrophosphate, sodium trimetaphosphate, sodium hexametaphosphate, or any of these in which sodium is replaced by potassium or ammonium. Other useful anticalculus agents in certain embodiments include anionic polycarboxylate polymers (e.g., polymers or copolymers of acrylic acid, methacrylic, and maleic anhydride such as polyvinyl methyl ether/maleic anhydride copolymers). Still other useful anticalculus agents include sequestering agents such as hydroxycarboxylic acids (e.g., citric, fumaric, malic, glutaric and oxalic acids and salts thereof) and aminopolycarboxylic acids (e.g., EDTA). One or more anticalculus or tartar control agents can optionally be present at about 0.01-50 wt % (e.g., about 0.05-25 wt % or about 0.1-15 wt %), for example, in the disclosed oral care composition.

A surfactant suitable for use in an oral care composition herein may be anionic, non-ionic, or amphoteric, for example. Suitable anionic surfactants include, without limitation, water-soluble salts of C8-20 alkyl sulfates, sulfonated monoglycerides of C8-20 fatty acids, sarcosinates, and taurates. Examples of anionic surfactants include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable non-ionic surfactants include, without limitation, poloxamers, polyoxyethylene sorbitan esters, fatty alcohol ethoxylates, alkylphenol ethoxylates, tertiary amine oxides, tertiary phosphine oxides, and dialkyl sulfoxides. Suitable amphoteric surfactants include, without limitation, derivatives of C8-20 aliphatic secondary and tertiary amines having an anionic group such as a carboxylate, sulfate, sulfonate, phosphate or phosphonate. An example of a suitable amphoteric surfactant is cocoamidopropyl betaine. One or more surfactants are optionally present in a total amount of about 0.01-10 wt % (e.g., about 0.05-5.0 wt % or about 0.1-2.0 wt %), for example, in the disclosed oral care composition.

An abrasive suitable for use in an oral care composition herein may include, for example, silica (e.g., silica gel, hydrated silica, precipitated silica), alumina, insoluble phosphates, calcium carbonate, and resinous abrasives (e.g., a urea-formaldehyde condensation product). Examples of insoluble phosphates useful as abrasives herein are orthophosphates, polymetaphosphates and pyrophosphates, and include dicalcium orthophosphate dihydrate, calcium pyrophosphate, beta-calcium pyrophosphate, tricalcium phosphate, calcium polymetaphosphate and insoluble sodium polymetaphosphate. One or more abrasives are optionally present in a total amount of about 5-70 wt % (e.g., about 10-56 wt % or about 15-30 wt %), for example, in the disclosed oral care composition. The average particle size of an abrasive in certain embodiments is about 0.1-30 microns (e.g., about 1-20 microns or about 5-15 microns).

An oral care composition in certain embodiments may comprise at least one pH-modifying agent. Such agents may be selected to acidify, make more basic, or buffer the pH of a composition to a pH range of about 2-10 (e.g., pH ranging from about 2-8, 3-9, 4-8, 5-7, 6-10, or 7-9). Examples of pH-modifying agents useful herein include, without limitation, carboxylic, phosphoric and sulfonic acids; acid salts (e.g., monosodium citrate, disodium citrate, monosodium malate); alkali metal hydroxides (e.g. sodium hydroxide, carbonates such as sodium carbonate, bicarbonates, sesquicarbonates); borates; silicates; phosphates (e.g., monosodium phosphate, trisodium phosphate, pyrophosphate salts); and imidazole.

A foam modulator suitable for use in an oral care composition herein may be a polyethylene glycol (PEG), for example. High molecular weight PEGS are suitable, including those having an average molecular weight of about 200000-7000000 (e.g., about 500000-5000000 or about 1000000-2500000), for example. One or more PEGS are optionally present in a total amount of about 0.1-10 wt % (e.g. about 0.2-5.0 wt % or about 0.25-2.0 wt %), for example, in the disclosed oral care composition.

An oral care composition in certain embodiments may comprise at least one humectant. A humectant in certain embodiments may be a polyhydric alcohol such as glycerin, sorbitol, xylitol, or a low molecular weight PEG. Most suitable humectants also may function as a sweetener herein. One or more humectants are optionally present in a total amount of about 1.0-70 wt % (e.g., about 1.0-50 wt %, about 2-25 wt %, or about 5-15 wt %), for example, in the disclosed oral care composition.

A natural or artificial sweetener may optionally be comprised in an oral care composition herein. Examples of suitable sweeteners include dextrose, sucrose, maltose, dextrin, invert sugar, mannose, xylose, ribose, fructose, levulose, galactose, corn syrup (e.g., high fructose corn syrup or corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, and cyclamates. One or more sweeteners are optionally present in a total amount of about 0.005-5.0 wt %, for example, in the disclosed oral care composition.

A natural or artificial flavorant may optionally be comprised in an oral care composition herein. Examples of suitable flavorants include vanillin; sage; marjoram; parsley oil; spearmint oil; cinnamon oil; oil of wintergreen (methylsalicylate); peppermint oil; clove oil; bay oil; anise oil; *eucalyptus* oil; citrus oils; fruit oils; essences such as those derived from lemon, orange, lime, grapefruit, apricot, banana, grape, apple, strawberry, cherry, or pineapple; bean- and nut-derived flavors such as coffee, cocoa, cola, peanut, or almond; and adsorbed and encapsulated flavorants. Also encompassed within flavorants herein are ingredients that provide fragrance and/or other sensory effect in the mouth, including cooling or warming effects. Such ingredients include, without limitation, menthol, menthyl acetate, menthyl lactate, camphor, *eucalyptus* oil, eucalyptol, anethole, eugenol, *cassia*, oxanone, Irisone®, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), and menthone glycerol acetal (MGA). One or more flavorants are optionally present in a total amount of about 0.01-5.0 wt % (e.g., about 0.1-2.5 wt %), for example, in the disclosed oral care composition.

An oral care composition in certain embodiments may comprise at least one bicarbonate salt. Any orally acceptable bicarbonate can be used, including alkali metal bicarbonates such as sodium or potassium bicarbonate, and ammonium bicarbonate, for example. One or more bicarbonate salts are optionally present in a total amount of about 0.1-50 wt % (e.g., about 1-20 wt %), for example, in the disclosed oral care composition.

An oral care composition in certain embodiments may comprise at least one whitening agent and/or colorant. A suitable whitening agent is a peroxide compound such as any of those disclosed in U.S. Pat. No. 8,540,971, which is incorporated herein by reference. Suitable colorants herein include pigments, dyes, lakes and agents imparting a particular luster or reflectivity such as pearling agents, for example. Specific examples of colorants useful herein include talc; mica; magnesium carbonate; calcium carbonate; magnesium silicate; magnesium aluminum silicate; silica; titanium dioxide; zinc oxide; red, yellow, brown and black iron oxides; ferric ammonium ferrocyanide; manganese violet; ultramarine; titaniated mica; and bismuth oxychloride. One or more colorants are optionally present in a total amount of about 0.001-20 wt % (e.g., about 0.01-10 wt % or about 0.1-5.0 wt %), for example, in the disclosed oral care composition.

Additional components that can optionally be included in an oral composition herein include one or more enzymes (above), vitamins, and anti-adhesion agents, for example. Examples of vitamins useful herein include vitamin C, vitamin E, vitamin B5, and folic acid. Examples of suitable anti-adhesion agents include solbrol, ficin, and quorum-sensing inhibitors.

A composition comprising an alpha-1,2-branched glucan herein can be an ether derivative of the glucan in some embodiments (i.e., an alpha-1,2-branched glucan herein can be derivatized to be ether-linked to one or more different organic groups). The degree of substitution (DoS) of an alpha-1,2-branched glucan with one or more etherified organic groups can be about 0.0025 to about 3.0, for example. Alternatively, the DoS can be about, or at least about, 0.0025, 0.005, 0.01, 0.025, 0.05, 0.075, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0, for example (can optionally be expressed as a range between any two of these values).

An organic group etherified to an alpha-1,2-branched glucan herein can be an alkyl group such as a methyl, ethyl, propyl, butyl, pentyl, hexyl, heptyl, octyl, nonyl, or decyl group, for example. In some aspects, an organic group etherified to an alpha-1,2-branched glucan can be a substituted alkyl group in which there is a substitution on one or more carbons of the alkyl group. The substitution(s) may be one or more hydroxyl, aldehyde, ketone, and/or carboxyl groups. For example, a substituted alkyl group may be a hydroxy alkyl group, dihydroxy alkyl group, or carboxy alkyl group. Examples of suitable hydroxy alkyl groups are hydroxymethyl, hydroxyethyl, hydroxypropyl, hydroxybutyl and hydroxypentyl groups. Other examples include dihydroxy alkyl groups (diols) such as dihydroxymethyl, dihydroxyethyl, dihydroxypropyl, dihydroxybutyl and dihydroxypentyl groups. Examples of suitable carboxy alkyl groups are carboxymethyl (—CH$_2$COOH), carboxyethyl, carboxypropyl, carboxybutyl and carboxypentyl groups.

An organic group etherified to an alpha-1,2-branched glucan can be a positively charged organic group in some aspects. A positively charged group herein can be a substituted ammonium group, for example. Examples of substituted ammonium groups are primary, secondary, tertiary and quaternary ammonium groups. Further examples of suitable positively charged groups are disclosed in U.S. Pat. Appl. Publ. No. 2016/0311935, which is incorporated herein by reference.

An alpha-1,2-branched glucan ether compound in certain embodiments can contain one type of organic group. A specific non-limiting example of such a compound is carboxymethyl alpha-1,2-branched glucan. Alternatively, an alpha-1,2-branched glucan ether compound can contain two or more different types of organic groups. In some aspects, a glucan ether compound herein can comprise at least one nonionic organic group and at least one anionic group as ether groups. In some aspects, a glucan ether compound herein can comprise at least one nonionic organic group and at least one positively charged organic group as ether groups.

The percentage of the monosaccharide units of an alpha-1,2-branched glucan ether compound herein that are ether-linked to an organic group (i.e., where one or more hydroxyl groups of a monosaccharide monomeric unit have been etherified) can vary depending on the degree to which an alpha-1,2-branched glucan is etherified in an etherification reaction. This percentage can be at least about 30%, 40%, 50%, 60%, 70%, 80%, 90%, or 100% (or any integer value between 30% and 100%), for example.

Any alpha-1,2-branched glucan as presently disclosed can be used to prepare a corresponding ether compound. Any suitable process for ether-derivatizing oligosaccharides and/or polysaccharides can be employed, such as disclosed in U.S. Pat. Nos. 2,961,439, 2,344,179, 2,203,703, 2,203,704, 2,380,879, and 2,974,134, U.S. Pat. Appl. Publ. Nos. 2014/0179913, 2016/0304629, 2016/0311935, 2015/0232785, and 20150239995, and Int. Pat. Appl. Publ. No. WO16/160738, all of which are incorporated herein by reference.

Solely as an example, an ether compound herein can be prepared by (i) adding about 35-45% (e.g., 40%) alpha-1,2 branches to a glucan backbone with at least 95% (e.g., 100%) alpha-1,6 linkages and a molecular weight of about 15-20 kD (e.g. kD), and (ii) etherifying the alpha-1,2-branched glucan product with any organic group disclosed above (e.g., carboxymethyl group).

Another aspect of the present disclosure regards a method of producing a glucan composition that comprises alpha-1,2 linkages. Such a method can comprise the steps of:

(a) providing at least the following reaction components: water, sucrose, an alpha-glucan substrate, and a polypeptide that is capable of forming at least one alpha-1,2 branch from the alpha-glucan substrate, wherein the polypeptide comprises an amino acid sequence that is at least 90% identical to:
  (i) the mature form of a sequence selected from 1F e group consisting of SEQ ID NOs:4, 1, 2, 3, 5, 6, 7, 8, 9, 10, 11, 12, and 13;
  (ii) SEQ ID NO:27 or a sub-sequence within any one of SEQ ID NOs:4, 2, 3, 5, 6, 7, 8, 9, 10, 11, 12, or 13 that aligns with SEQ ID NO:27; and/or
  (iii) a sequence selected from the group consisting of SEQ ID NOs:4, I, L, 3, 5, 6, 7, 8, 9, 10, 11, 12, and 13;

(b) combining the reaction components under suitable conditions whereby the polypeptide catalyzes the synthesis of at least one alpha-1,2 branch from the alpha-glucan substrate, thereby forming a glucan composition comprising one or more alpha-1,2 linkages; and (c) optionally isolating the glucan composition comprising one or more alpha-1,2 linkages.

Any of the features disclosed herein (e.g., above and in the below Examples) regarding a reaction composition (1,2-branching reaction) can characterize appropriate aspects of such a glucan production method, and vice versa.

The production of a glucan composition comprising alpha-1,2 linkages can be carried out by combining the reaction components under any suitable reaction conditions, such as those disclosed herein. A reaction may be carried out in an aqueous solution, and/or in certain embodiments, it can be carried out in situ within a product (e.g., a food, pharmaceutical, personal care, household care, or industrial product) following any known methodology. In certain embodiments, 1,2-branching enzyme(s) is added to a sucrose-containing liquid food product. The enzyme can reduce the amount of sucrose in the liquid food product while increasing the amount of fructose and alpha-1,2-branched glucan. Suitable methodology for in situ production of glucan within a food product can be found in WO2013/182686, for example, which is incorporated herein by reference.

The concentration of a 1,2-branching enzyme herein can depend on its specific catalytic activity, and typically is chosen to obtain the desired overall rate of reaction. The enzyme concentration typically ranges from 0.0001 mg to 20 mg per mL of total reaction volume, or from 0.001 mg to 10 mg per mL. The 1,2-branching enzyme may also be immobilized on a soluble or insoluble support using known methods; see for example, Immobilization of Enzymes and Cells; Gordon F. Bickerstaff, Editor; Humana Press, Totowa, NJ, USA; 1997. 1,2-branching enzyme may be provided in whole microbial cells, as microbial cell surface-displayed enzyme, permeabilized microbial cells, microbial cell extracts, partially purified form or purified form, or any mixture thereof.

In certain embodiments, a method to produce an alpha-1,2-branched glucan composition further includes step (d) of concentrating the glucan composition.

In certain embodiments, the alpha-glucan substrate concentration at the initiation of alpha-1,2 branching is at least about 10 g/L, or 50 g/L to 500 g/L, or 100 g/L to 500 g/L, or 150 g/L to 450 g/L, or 250 g/L to 450 g/L, or 250 g/L to 600 g/L.

The sucrose concentration used during the reaction may vary. In certain embodiments, the sucrose concentration initially present when the reaction components are combined is at least about 50 g/L, or 50 g/L to 600 g/L, or 100 g/L to 500 g/L, or 100 g/L to 200 g/L, or 150 g/L to 450 g/L, or 200 g/L to 450 g/L, or 250 g/L to 600 g/L. In particular embodiments, the sucrose concentration is about 200 g/L or 100 g/L. Higher concentrations of sucrose may be used if the reaction occurs concomitantly with an alpha-glucan substrate preparation reaction.

The weight ratio of sucrose to alpha-glucan substrate backbone during a 1,2 branching reaction herein may vary. In one embodiment, the weight ratio of sucrose to alpha-glucan substrate backbone may range from 0.01:1.0 to 1.0:0.01, inclusive. In certain embodiments, the method is carried out at a pH between 3 and 8, or between 4 and 8, or between 5 and 8, or between 5.5 and 7.5, or between 5.5 to about 6.5. In certain embodiments, the set of reaction components includes a suitable buffer including, but not limited to, phosphate, pyrophosphate, bicarbonate, acetate, or citrate. The concentration of buffer, when employed, is typically from 0.1 mM to 1.0 M, or from 1 mM to 300 mM, or from 10 mM to 100 mM. The method may optionally utilize pH control to maintain an optimum pH over the course of the reaction, by incremental or continuous addition of a suitable acid or base to maintain pH in the desired range for optimal enzyme activity.

The duration of a 1,2-branching reaction herein may vary and can often be determined by the amount of time it takes to use all of the available sucrose substrate. In certain embodiments, the reaction is conducted until at least 90%, or at least 95%, or at least 99% of the sucrose initially present in the reaction mixture is consumed. In certain embodiments, the reaction time is about 1 hour to 168 hours, 1 hour to 72 hours, 1 hour to 24 hours, or 1 hour to 2 hours.

The temperature of a 1,2-branching reaction herein may be chosen to control both the reaction rate and the stability of the enzymes(s) used, as desired. The temperature of the reaction may range from just above the freezing point of the reaction formulation (approximately 0° C.) to about 60° C., or from 5° C. to about 47° C., or a range of about 20° C. to about 37° C., for example.

In certain embodiments, the set of reaction components can further include an alpha-glucanohydrolase (exo- and/or endo-glucanohydrolase). In certain embodiments, the alpha-glucanohydrolase is a dextranase or mutanase, such as an endomutanase or endodextranase. In certain embodiments, the alpha-glucanohydrolase is a dextranase (EC 2.1.1.11), mutanase (EC 3.1.1.59) or combination thereof. In certain embodiments, the dextranase is a food grade dextranase from *Chaetomium erraticum*. In certain embodiments, the dextranase from *Chaetomium erraticum* is DEXTRA-NASE® PLUS L, available from Novozymes A/S, Denmark.

In certain embodiments, isolating a 1,2-branched glucan product composition includes at least one of centrifugation, filtration, fractionation, chromatographic separation, dialysis, evaporation, and dilution.

Any of the foregoing conditions herein for synthesizing a glucan composition with alpha-1,2 branches, such as the foregoing or those described in the below Examples, can be applied to practicing a reaction composition as presently disclosed.

Non-limiting examples of compositions and methods disclosed herein include:

1. A reaction composition comprising at least water, sucrose, an alpha-glucan substrate, and a polypeptide that is capable of forming at least one alpha-1,2 branch from the alpha-glucan substrate, wherein the polypeptide comprises an amino acid sequence that is at least 90% identical to: (i) the mature form of a sequence selected from the group consisting of SEQ ID NOs:4, 1, 2, 3, 5, 6, 7, 8, 9, 10, 11, 12, and 13; (ii) SEQ ID NO:27 or a sub-sequence within any one of SEQ ID NOs:4, 2, 3, 5, 6, 7, 8, 9, 10, 11, 12, or 13 that aligns with SEQ ID NO:27; and/or (iii) a sequence selected from the group consisting of SEQ ID NOs:4, 1, 2, 3, 5, 6, 7, 8, 9, 10, 11, 12, and 13.

2. The reaction composition of embodiment 1, wherein the sequence of (i) comprises: positions 36 to 1672 of SEQ NO:4, positions 21 to 2771 of SEQ ID NO:1, positions 21 to 2821 of SEQ ID NO:2, positions 41 to 2844 of SEQ ID NO:3, positions 51 to 1632 of SEQ ID NO:5, positions 51 to 1318 of SEQ ID NO:6, positions 51 to 1139 of SEQ ID NO:7, positions 51 to 1463 of SEQ ID NO:8, positions 41 to 2841 of SEQ ID NO:9, positions 46 to 2580 of SEQ ID NO:10, positions 51 to 1463 of SEQ ID NO:11, positions 21 to 282.4 of SEQ ID NO:12, or positions 21 to 2771 of SEQ ID NO:13.

3. The reaction composition of embodiment 1, wherein the sequence of (ii) comprises: positions 36 to 1115 of SEQ ID NO:4, positions 1715 to 2821 of SEQ ID NO:2, positions 1735 to 2834 of SEQ ID NO:3, positions 51 to 1167 of SEQ ID NO:5, positions 93 to 1178 of SEQ ID NO:6, positions 51 to 1130 of SEQ ID NO:7, positions 51 to 1158 of SEQ NO:8, positions 1735 to 2841 of SEQ Ill NO:9, positions 1274 to 2413 of SEQ ID NO:10, positions 51 to 1158 of SEQ ID NO:11, positions 1715 to 2821 of SEQ ID NO:12, or positions 1665 to 2771 of SEQ ID NO:13.

4. The reaction composition of any of embodiments 1-3, wherein the alpha-glucan substrate has a degree of polymerization of at least 3, and comprises at least (i) alpha-1,6 glycosidic linkages or (ii) alpha-1,6 and alpha-1,3 glycosidic linkages.

5. A method of producing a glucan composition that comprises alpha-1,2 linkages, the method comprising: (a) providing at least the following reaction components: water, sucrose, an alpha-glucan substrate, and a polypeptide that is capable of forming at least one alpha-1,2 branch from the alpha-glucan substrate, wherein the polypeptide comprises an amino acid sequence that is at least 90% identical to: (i) the mature form of a sequence selected from the group consisting of SEQ ID NOs:4, 1, 2, 3, 5, 6, 7, 8, 9, 10, 11, 12, and 13: (ii) SEQ ID NO:27 or a sub-sequence within any one of SEQ ID NOs:4, 2, 3, 5, 6, 7, 8, 9, 10, 11, 12, or 13 that aligns with SEQ ID NO:27; and/or (iii) a. sequence selected from the group consisting of SEQ ID NOs:4, 1, 2, 3, 5, 6, 7, 8, 9, 10, 11, 12, and 13; (b) combining the reaction components under suitable conditions whereby the polypeptide catalyzes the synthesis of at least one alpha-1,2 branch from the alpha-glucan substrate, thereby forming a glucan composition comprising one or more alpha-1,2 linkages; and (c) optionally isolating the glucan composition comprising one or more alpha-1,2 linkages.

6. The method of embodiment 5, wherein the alpha-glucan substrate (i) has a degree of polymerization of at least 3, and comprises at least (i) alpha-1,6 glycosidic linkages or (ii) alpha-1,6 and alpha-1,3 glycosidic linkages.

7. The method of any of embodiments 5-6, wherein the alpha-glucan substrate and sucrose are present in (b) in a ratio between 0.01:1 and 1:0.01, inclusive.

8. The method of any of embodiments 5-7, wherein the reaction components further comprise an alpha-glucanohydrolase.

9. A composition that comprises a glucan composition comprising one or more alpha-4,2 linkages produced by the method of any of embodiments 5-8 or as produced by the reaction composition of any of embodiments 1-4, preferably wherein the composition is in the form of a food product, pharmaceutical product, personal care product, household care product, or industrial product, optionally wherein the composition comprises about 0.01 to 99 wt % (dry solids basis) of the glucan composition.

10. The composition of embodiment 9, wherein the glucan composition comprising alpha-1,2 linkages is water-soluble and slowly releases glucose when fed to a mammal, wherein the mammal is preferably a human.

11. The composition of any of embodiments 9-10, wherein the glucan composition comprising alpha-1,2 linkages has 10% or less of alpha-1,2 branching.

12. The composition of embodiment 9, wherein the glucan composition comprising alpha-1,2 linkages is water-soluble and acts as a dietary fiber when fed to a mammal, wherein said mammal is preferably a human.

13. The composition of any of embodiments 9 or 12, wherein the glucan composition comprising alpha-1,2 linkages has at least about 15% alpha-1,2 branching.

14. The composition of any of embodiments 9-13, further comprising at least one ingredient selected from the group consisting of: synbiotics, peptides, peptide hydrolysates, proteins, protein hydrolysates, soy proteins, dairy proteins, amino acids, polyols, polyphenols, vitamins, minerals, herbals, herbal extracts, fatty acids, polyunsaturated fatty acids (PUFAs), phytosteroids, betaine, carotenoids, digestive enzymes, and probiotic organisms; preferably wherein the composition is in the form of a food product or pharmaceutical product.

15. The composition of any of embodiments 9-14, wherein the composition is in the form of a food product or pharmaceutical product, and further comprising at least one ingredient selected from the group consisting of: monosaccharides, disaccharides, glucose, sucrose, fructose, leucrose, corn syrup, high fructose corn syrup, isomerized sugar, maltose, trehalose, panose, raffinose, cellobiose, isomaltose, honey, maple sugar, fruit-derived sweeteners, sorbitol, maltitol, iso- maltitol, lactose, nigerose, kojibiose, xylitol, erythritol, dihydrochalcone, stevioside, alpha-glycosyl stevioside, acesulfame potassium, alitame, neotame, glycyrrhizin, thaumantin, sucralose, L-aspartyl-L-phenylalanine methyl ester, saccharine, maltodextrin, starch, potato starch, tapioca starch, dextran, soluble corn fiber, resistant maltodextrins, branched maltodextrins, inulin, polydextrose, fructo-oligosaccharides, galacto-oligosaccharides, xylo-oligosaccharides, arabinoxylo-oligosaccharides, nigero-oligosaccharides, gentio-oligosaccharides, hemicellulose, fructose oligomer syrup, isomalto-oligosaccharides, fillers, excipients, and binders.

16. The composition of embodiment 9, wherein the composition is a detergent composition, and wherein the composition is preferably a household product.

17. A method comprising enterally administering a substance to a mammal, wherein the substance comprises a glucan composition comprising alpha-1,2 linkages, wherein the administering results in less or slower blood glucose elevation in the mammal as compared to a mammal that is enterally administered a substance that lacks the glucan composition but instead contains a same amount of a readily digestible glucose-containing carbohydrate, wherein the glucan composition is produced by the method of any of embodiments 5-8 or as produced by the reaction composition of any of embodiments 1-4, optionally wherein the mammal is a human, and optionally wherein the readily digestible glucose-containing carbohydrate is sucrose, free glucose, or starch.

18. A method of producing an ingestible product, the method comprising incorporating a glucan composition comprising alpha-1,2 linkages into the ingestible product, wherein the glycemic index of the resulting ingestible product is not increased, or only marginally increased, compared to an ingestible product that lacks the glucan composition (but is otherwise the same), and wherein the glucan composition is produced by the method of any of embodiments 5-8 or as produced by the reaction composition of any of embodiments 1-4.

EXAMPLES

The disclosure is further defined in the following Examples. It should be understood that the Examples, while indicating certain embodiments, is given by way of illustration only. From the above discussion and the Examples, one skilled in the art can ascertain essential characteristics of this disclosure, and without departing from the spirit and scope thereof, can make various changes and modifications to adapt to various uses and conditions.

The meaning of abbreviations is as follows: "sec" or "s" means second(s), "ms" mean milliseconds, "min" means minute(s), "h" or "hr" means hour(s), "pt" means microliter(s), "mL" means milliliter(s), "L" means liter(s); "mL/min" is milliliters per minute; "µg/mL" is microgram(s) per milliliter(s); "LB" is Luria broth; "µm" is micrometers, "nm" is nanometers; "OD" is optical density; "IPTG" is isopropyl-O-D-thio-galactoside; "g" is gravitational force; "mM" is millimolar; "SDS-PAGE" is sodium dodecyl sulfate polyacrylamide; "mg/mL" is milligrams per milliliters; "N" is normal; "w/v" is weight for volume; "DTT" is dithiothreitol; "BCA" is bicinchoninic acid; "DMAc" is N, N'-dimethyl acetamide; "LiCl" is Lithium chloride' "NMR" is nuclear magnetic resonance; "DMSO" is dimethylsulfoxide; "SEC" is size exclusion chromatography; "GI" or "gi" means GenInfo Identifier, a system used by GENBANK® and other sequence databases to uniquely identify polynucleotide and/or polypeptide sequences within the respective databases; "DPx" means glucan degree of polymerization having "x" units in length; "ATCC" means American Type Culture Collection (Manassas, VA), "DSMZ" and "DSM" refer to Leibniz Institute DSMZ-German Collection of Microorganisms and Cell Cultures, (Braunschweig, Germany); "EELA" is the Finish Food Safety Authority (Helsinki, Finland;) "CCUG" refer to the Culture Collection, University of Goteborg, Sweden; "Suc." means sucrose; "Gluc." means glucose; "Fruc." means fructose; "Leuc." means leucrose; and "Rxn" means reaction.

General Methods

All reagents, restriction enzymes and bacterial culture materials were obtained from BD Diagnostic Systems (Sparks, MD), Invitrogen/Life Technologies Corp. (Carlsbad, CA), Life Technologies (Rockville, MD), QIAGEN (Valencia, CA), Sigma-Aldrich Chemical Company (St. Louis, MO), or Pierce Chemical Co. (a division of Thermo Fisher Scientific Inc., Rockford, IL) unless otherwise specified. IPTG, (cat #I6758), triphenyltetrazolium chloride, and BCA protein assay reagents were obtained from the Sigma Co., (St. Louis, MO). BELLCO spin flasks were obtained from the Bellco Co., (Vineland, NJ). LB medium was obtained from Becton, Dickinson and Company (Franklin Lakes, New Jersey).

Reducing sugars were determined using the PAHBAH assay (Lever, Anal. Biochem. 47, 273-279, 1972).

Example 1

Identification of Polypeptides Capable of Forming Glucans Having Alpha (1,2) Linkages The GTF-J18 sequence (from *Leuconostoc mesenteroides* subsp. *mesenteroides* J18) (SEQ ID NO:1) contains three distinct regions: catalytic domain 1 ("CD1"), a glucan binding domain, and CD2. CD1 and CD2 are GH70 domains, responsible for different catalytic activity.

We have shown that an N-terminally truncated version of GTFJ18, designated GTFJ18T1 (SEQ ID NO:27), can produce alpha-1,2-branching when an alpha-1,6-linked polysaccharide is provided in the reaction (see Example 1 of International Pat. Appl. Publ. No. WO2015/183714, which is incorporated herein by reference) (also refer to Example 6 below). GTF-J18T1 (SEQ ID NO:27) only includes a portion of the glucan binding domain and CD2. This suggests that CD2 from GTF-J18 ("GTF-J18-CD2") can catalyze alpha-1,2-branching on an alpha-1,6-linked polysaccharide substrate.

The GTF-J18-CD2 sequence (SEQ ID NO:28) was used as a query to BLAST against the non-redundant version of the GENBANK Protein database. Forty sequences were reported by BLAST as more than 50% identical to the GTF-J18-CD2 sequence (SEQ ID NO:28) in the BLAST High Scoring Segment. The forty sequences were aligned using the TARGET2K program from the SAM suite from UCSC (SAM: Package of HMNI tools released by the Karplus group at UC Santa Cruz; the algorithms in SAM are described in Karplus et al., Bioinformatics 14:846-856, 1998). Thirteen sequences (SEQ ID NOs:1-13) that were at least 60% identical to the GTF-J18-CD2 sequence (SEQ ID NO:28) in the aligned region were selected as polypeptides possibly capable of forming glucans having alpha (1,2) linkages and are disclosed herein.

Example 2

Expression of *Lactobacillus animalis* KCTC 3501 glucosyltransferase GTF8117

A putative glucosyltransferase gene, LanGtfl, with GI no. 335358117 (old) (new GI no. 948839227; GENBANK Acc. No. KRM57462.1) was identified from *Lactobacillus animalis KCTC* 3501 ("GTF8117" herein). GTF8117 protein has a 37 amino acid signal peptide predicted by SignalP4.0 (Petersen et al., Nature Methods 8:785-786, 2011). This indicates that GTF8117 is a secreted protein. The gene sequence encoding the mature protein of GTF8117 was codon-optimized for expression in *Bacillus subtilis*. The gene was synthesized by Generay (Shanghai, China), and inserted into the p2JM103BBI plasmid (Vogtentanz, Protein Expr. Punf. 55:40-52, 2007), resulting in the pZZH561 plasmid. pZZHB561 contains (in 5' to 3' direction) an aprE promoter, a sequence encoding an aprE signal sequence used to direct protein secretion in *Bacillus subtilis*, an oligonucleotide that encodes Ala-Gly-Lys to facilitate secretion of the target protein, and the synthetic gene encoding the target protein.

Another expression plasmid, pDCQ1004, was constructed for expressing GTF8117 without a signal peptide. Plasmid pZZHB561 was used as the template for PCR amplification of the GTF8117 coding sequence together with the Tlat terminator. The PCR product was cloned into the SpeI and BamEII sites of the *B. subtilis* integrative expression plasmid, p4JH, having an aprE promoter, but no signal sequence-coding region. The resulting pDCQ1004 plasmid contains SEQ ID NO:29, which encodes mature GTF8117 with an added N-terminal methionine (SEQ ID NO:30). pDCQ1004 was used to transform *B. subtilis* BG6006 cells to express GTF8117 (SEQ ID NO:30). The *B. subtilis* host BG6006 strain contains nine protease deletions (amyE:: xylRPxylAcomK-ermC, degUHy32, oppA, AspoHE3501, AaprE, AaprE, Aepr, AispA, Abpr, Avpr, AwprA, Ampr-ybg, AnprB). The transformed cells were spread on LB plates supplemented with 5 μg/mL chloramphenicol. The colonies grown on these plates were streaked several times onto LB plates with 25 μg/mL chloramphenicol. The resulting amplified colonies were grown in LB containing 25 μg/mL chloramphenicol for 6-8 hours, and then subcultured into Grant's II medium and grown at 30° C. for 2-3 days. The cultures were spun at 15,000 g for 30 min at 4° C. and the collected supernatants, which were expected to contain soluble intracellular proteins due to cell autolysis, were filtered through 0.22-μm filters. The filtered supernatants were aliquoted and frozen at −80° C., and were used later in a p-hydroxybenzoic acid hydrazine (PAHBAH) assay to determine enzyme activity. The clone with supernatant with the highest activity in the PAHBAH assay (named as strain SG1024) was used to make seed vials for fermentation.

Further production of GTF8117 (SEQ ID NO:30) was conducted in Example 4.

Example 3

Expression of *Streptococcus salivarius* M18 glucosyltransferase GTF6831

A putative glucosyltransferase (old GI no. 345526831, new GI no. 490287001; GENBANK Acc. No. WP_004182667.1) was identified from *Streptococcus sali-*

*varius* M18. This enzyme is herein referred to as "GTF6831" and has 1600 amino acid residues with the first 42 residues predicted to be the native signal peptide by the SignalP4.1 program. The gene nucleotide sequence (SEQ ID NO:31) encoding the mature protein of GTF6831 (SEQ ID NO:32) was synthesized by GenScript USA Inc. (Piscataway, NJ). The synthesized sequence (SEQ ID NO:31) was cloned into the NheI and HindIII sites of the *Bacillus subtilis* integrative expression plasmid p4JH under the aprE promoter and sequence encoding a *B. subtilis* AprE signal peptide. The construct was first transformed into *E. coli* DH10B and selected on LB with ampicillin (100 µg/mL) plates. The confirmed construct, pDCQ990-5, allowed expression of mature GTF6831 glucosyltransferase (SEQ ID NO:32). pDCQ990-5 was then transformed into *B. subtilis* BG6006, which contains nine protease deletions (amyE:: xylRPxylAcomK-ennC, degUHy32, oppA, AspoHE3501, AaprE, AnprE, Aepr, AispA, Abpr, Avpr, AwprA, Ampr-ybg, AnprB), and selected on LB plates with chloramphenicol (5 µg/mL). The colonies grown on these plates were streaked several times onto LB plates with 25 µg/mL chloramphenicol. The multiple colonies of the resulting *B. subtilis* expression strain, SG1190, were grown in LB medium with 25 µg/mL chloramphenicol for 6-8 hours first, and then subcultured into Grant's II medium and grown at 30° C. for 2-3 days. The cultures were spun at 15,000 g for 30 min at 4° C. and the supernatants were filtered through 0.22-lam filters. The filtered supernatants were aliquoted and frozen at −80° C., and later used in a PAHBAH assay to determine enzyme activity. The clone with the highest PAHBAH activity was chosen to make the seed vial for fermentation.

Further production of GTF6831 (SEQ ID NO:32) was conducted in Example 5.

Example 4

Production of GTF8117 glucosyltransferase in *B. subtilis*

The GTF8117 glucosyltransferase (SEQ ID NO:30) was produced using the SG1204 strain, which is a nine protease-knockout *B. subtilis*, comK strain, containing the pDCQ1004 plasmid. Initially, a frozen vial of SG1204 was grown into 40 mL seed medium containing 10 g/L soytone, 5 g/L yeast extract, 10 g/L NaCl, 10 g/L glucose and 10 mg/L chloramphenicol antibiotic. The growth temperature was 30° C. and an initial pH of 7.2. A 250-mL seed flask containing 40 mL of seed medium was placed in a shaker-incubator at 30° C. and mixed at 300 rpm for 2.83 hours. After that time the inoculum grew to an OD (600 nm) value of 0.33 units. 30 mL of the grown seed medium was used to inoculate a production vessel containing 7 liters of fermentation medium.

The fermentation medium contained 5 g/L corn steep solids, 8 g/L sodium phosphate monobasic monohydrate, 8 g/L potassium phosphate monohydrate, 4.2 g/L magnesium sulfate heptahydrate, 0.3 g/L ferrous sulfate heptahydrate, 0.2 g/L manganese chloride tetrahydrate, 0.1 g/L calcium chloride dehydrate and 2.06 mL/L of the antifoam agent, FOAM BLAST 882.

The following operating conditions were set: 30° C., pH 7.2, and 25% dissolved oxygen. The fermentation ran initially in batch mode, starting with a residual glucose concentration of 10 g/L. As the residual glucose was almost depleted at 15.3 hours of elapsed fermentation time, we commenced continuous glucose feeding by initiating a fed-batch mode. The pH was controlled using a 69% v/v NH$_4$OH solution (20% NH$_3$ content). Glucose was fed until 40.6 hours of elapsed fermentation time, delivering approximately 1593 grams at 650 g/L glucose concentration. At 40.6 hours, the glucose feed stopped while maintaining the other operating conditions for approximately one-half hour in order to allow complete consumption of the remaining residual glucose. Then, at 41.1 hours of elapsed fermentation time, the lysis portion of the run was initiated by complementing the glucose cessation with an increase of the operating fermentation temperature to 33° C., a complete stop of the air flow, reduction of the agitation speed to 200 rpm, and a lift of the pH control conditions, resulting in complete, in situ cell lysis within the ensuing 8-hour period. The fermentation run ended 49.1 hours after onset.

The supernatant of the end-of-run broth was collected and analyzed by HPLC for the presence of GTF8117 (SEQ ID NO:30) by measuring the consumption rate of the sucrose and the corresponding production rate of fructose. This biochemical assay measured 4.64 mg GTF8117/mL (472 U/mL, based on sucrose consumption) and 4.25 mg GTF8117/mL (based on fructose production). The supernatant was stored at −80° C.

GTF8117 (SEQ ID NO:30) produced in this Example was used in one or more of the following Examples to synthesize glucan to serve as a substrate for an alpha-1,2-branching enzyme.

Example 5

Production of GTF6831 glucosyltransferase in *B. subtilis*

The GTF6831 glucosyltransferase (SEQ ID NO:32) was produced using the SG1190 strain, which is a nine protease-knockout *B. subtilis*, comK strain, containing the pDCQ990-5 plasmid. The seed flask medium, fermentation medium, and all operating conditions were the same as outlined in Example 4. The fermentation run lasted 53 hours. Cell lysis was initiated at 41 hours elapsed fermentation time and lasted 12 hours. The total amount of glucose feed delivered was 2147 grams of 50% w/w solution.

After lysis, the supernatant was collected and analyzed by HPLC for the presence of enzyme GTF6831 (SEQ ID NO:32) by measuring the consumption rate of the residual sucrose and the corresponding production rate of fructose. This biochemical assay measured 108.7 U/mL supernatant. Centrifugation of the lysate produced a supernatant having 114.5 U/mL of activity; the supernatant was stored at −80° C.

GTF6831 (SEQ ID NO:32) produced in this Example was used in one or more of the following Examples to synthesize glucan to serve as a substrate for an alpha-1,2-branching enzyme.

Example 6

Expression of the truncated glucosyltransferase, GTFJ18T1, and testing its alpha-1,2 branching activity The following example describes expression of a full length glucosyltransferase and a truncated version of this enzyme in *E. coli*, and testing their respective alpha-1,2 branching activity on a glucan backbone. The full length glucosyltransferase produced glucan with little alpha-1,2 branching, whereas the truncated version of the glucosyltransferase produced glucan with a significant amount of alpha-1,2 branching.

The putative glucosyltransferase (old GENBANK® gi: 356644413, new gi: 504090610, Acc. No. WP_014324604.1) from *Leuconostoc mesenteroides* subsp. *mesenteroides* J18 (designated as GTFJ18) has 2771 amino acids (SEQ ID NO:1). It was identified as a glycosyl hydrolase from complete genome sequencing of the J18 strain isolated from Kimchi (Jung et al., J. Bacteriol. 194: 730, 2012). The full length sequence of GTFJ18 has 68.6% amino acid identity to the DsrE protein (2835 amino acids in length) from *Leuconostoc mesenteroides* NRRL B-1299 (GENBANK® gi: 23320943, Acc. No. CAD22883.1). The DsrE protein was shown to be a bifunctional protein with two catalytic domains (Bozonnet et al., J. Bacteriol. 184: 5763,2002). The first catalytic domain "CD1" catalyzes the synthesis of alpha-1,6 linkages and the second catalytic domain "CD2" catalyzes the synthesis of alpha-1,2 linkages. The CD1 and CD2 domains are separated by a glucan binding domain "GBD" (Fabre et al., J. Bacteria 187:296, 2005). The CD1 domains of the DsrE and GTFJ18 proteins share 79.3% amino acid identity and the CD2 domains of the two proteins share 76.6% amino acid identity.

The N-terminal 20 amino acids of GTFJ18 (SEQ ID NO:1) was deduced as the signal peptide by the SignalP 4.0 program (Petersen et al., ibid.). To construct the full length GTFJ18 expression plasmid, DNA encoding the mature protein without the signal peptide was synthesized by GenScript USA Inc.. The synthesized gene was subcloned into the NheI and HindIII sites of the pET23D+vector (NOVAGEN®; Merck KGaA, Darmstadt, Germany). A polynucleotide encoding a truncated version of GTFJ18, termed GTF18T1 (SEQ ID NO:27), containing the C-terminal CD2 domain and part of a GBD domain (in total containing amino acid residues 1665-2771 of SEQ ID NO:1) was also subcloned into the pET23D+vector. The plasmids carrying gene sequences encoding either the full length (SEQ ID NO:1) or truncated (SEQ ID NO:27) GTFJ18 protein were transformed into *E. coli* BL21 DE3 host cells resulting in strains EC0059 and EC0059T1, respectively. Cells of EC0059 and EC0059T1 were grown to OD ~0.5 and induced with 1 mM IPTG at 37° C. for 3 hours or alternatively they were induced at 23° C. overnight. The cells were collected by centrifugation at 4000×g for 10 min and resuspended in PBS buffer pH 6.8. The cells were broken by passing through a French Press at 14,000 psig (— 96.53 MPa) twice and the cell debris was pelleted by centrifugation at 15,000×g for 20 min. The supernatant of each crude enzyme extract was aliquoted and frozen at −80° C.

The alpha-1,2 branching activities of each enzyme (GTFJ18 or GTFJ18T1) were individually tested on the glucan product of the glucosyltransferase, GTF5604, which is derived from *Streptococcus criceti* HS-6 (GENBANK® Acc. No. WP_004226213.1, old gi: 357235604) and disclosed in International Pat. Appl. Publ. No. WO2015/183714 (also referred to therein as SG1018 glucosyltransferase or GtfHS6). GTF5604 (SEQ ID NO:33) has 1338 amino acids with the N-terminal 36 amino acids deduced as its signal peptide by the SignalP 4.0 program. The native nucleotide sequence (positions 1289627-1293643 of GENBANK Acc. No. NZ AEUV02000002.1) encoding full length GTF5604 (SEQ ID NO:33) including its native signal peptide was synthesized by GenScript and cloned into the SpeI and HindIII sites of the replicative *Bacillus* expression plasmid pHYT (Takara Bio Inc., Otsu, Japan) under the *B. subtilis* aprE promoter. The construct was first transformed into *E. coli* DH10B and selected on ampicillin (100 µg/mL) plates. The confirmed clone, pDCQ918, was then transformed into *Bacillus subtilis* strain BG6006 (amyE::xylRPxylAcomK-ermC, degUHy32, oppA, AspoHE3501, AaprE, AnprE, Aepr, AispA, Abpr, Avpr, AwprA, Ampr-ybg, AnprB) and selected on tetracycline (12.5 µg/mL) plates, afterwhich the transformed strain, termed as SG1018, was grown in LB containing 10 µg/mL tetracycline first, followed by subculturing into Grant's II medium containing 12.5 Ng/mL tetracycline and growth at 37° C. for 2-3 days. The cultures were spun at 15,000×g for 30 min at 4° C. and the supernatant was filtered through 0.22-µm filters. A glucan synthesis reaction was set up containing 10% (v/v) of the 5G1018 supernatant with 100 g/L sucrose, 10 mM sodium citrate pH 5 and 1 mM $CaCl_2$). All sucrose was consumed in the reaction after 6 hours at 37° C.; the glucan product had a molecular weight of about 3000 and consisted of almost 100% alpha-1,6 linkages. The glucan synthesis reaction was subjected to heat inactivation at 95° C. for 30 min.

A branching reaction was set up with 70% (v/v) of the heat-inactivated glucan synthesis reaction. The enzyme being tested for branching activity off of the above glucan product, GTFJ18 or GTFJ18T1, was provided as 10% (v/v) of the above-prepared crude cell extract from EC0059 or EC0059T1, respectively, with 40 g/L sucrose. Each branching reaction was incubated at 37° C. or 30° C. for 22 hours and the products were analyzed by HPLC for sucrose consumption and NMR for linkage profile.

NMR data were acquired on an Agilent DD2 spectrometer (Agilent Technologies, Inc., Santa Clara, CA) operating at 500 MHz for 41 using a 5-mm cryogenic triple-resonance pulsed-field gradient probe. Water suppression was obtained by carefully placing the observe transmitter frequency on resonance for the residual water signal in a "presat" experiment, and then using the first slice of a NOESY experiment with a full phase cycle (multiple of 32) and a mix time of 10 ms. One-dimensional 41 spectra were acquired with a spectral width of 6410 Hz, acquisition time of 5.1 s, 65536 data points, 4 s pre-saturation and a 90-degree observe pulse. Signal averaging typically involved accumulation of 64 scans. Sample temperature was maintained at 25° C.

Liquid samples were prepared by adding either 50 or 100 µL of completed branching reactions to a 5-mm NMR tube along with 60 µL of D20 containing 12.4 mM 4,4-dimethyl-4-silapentane-1-sulfonic acid sodium salt (DSS) as an internal chemical shift reference, and the balance (450 or 400 µL) of D20 for a total volume of 560 µL. The DSS methyl resonance was set to 0 ppm.

Chemical shift assignments for different anomeric linkages were taken from Goffin et al. (Bull Korean Chem. Soc. 30:2535, 2009). Assignments specific to alpha-1,2 branching on an alpha-1,6 backbone were taken from Maina et al. (Carb. Res. 343:1446,2008). Alpha-1,2 substitution on the 1,6 backbone (i.e., alpha 1-2,6 linkage) leads to a characteristic chemical shift (5.18 ppm) for the anomeric H adjacent the substitution site. The anomeric H of the 1,2-linked sugar (5.10 ppm) is obscured by leucrose in reaction mixtures but is directly observed in purified samples.

The product of the branching reaction comprising GTFJ18 contained 97% alpha-1,6 linkages and only 0.6% alpha-1,2 linkages. The product of the branching reaction comprising GTFJ18T1 (SEQ ID NO:27) contained 82% alpha-1,6 linkages and 18% alpha-1,2 linkages. Thus, the truncated enzyme, GTFJ18T1 (SEQ ID NO:27) showed much higher alpha-1,2 branching activity compared to its full length counterpart, GTFJ18. Although not intending to be bound by any theory herein, this result may be due to that the CD1 domain in full length GTFJ18 was very active and competed with the CD2 branching domain for the sucrose substrate.

Thus, GTFJ18T1 (SEQ ID NO:27) has significant alpha-1,2 branching activity and can be used to modify the structure of a glucan substrate. Further production of this enzyme was conducted in Example 7.

Example 7

Production of the GTFJ18T1 1,2-branching enzyme using E. coli

The GTFJ18T1 1,2-branching enzyme (SEQ ID NO:27) disclosed in Example 6 was produced using the EC0059T1 strain, which is a BL21 DE3 E. coli strain containing the targeted enzyme genetic information in a plasmid. Initially, a frozen vial of EC0059T1 was grown into 260 mL seed medium containing 10 g/L yeast extract, 16 g/L tryptone, 5 g/L NaCl, no glucose, and 100 mg/L ampicillin antibiotic. The growth temperature was 30° C. and the initial pH was 6.8. A 1-L seed flask containing 260 mL of seed medium for inoculating two fermentation vessels was placed in a shaker-incubator and mixed at 250 rpm for 3.7 hours. After that time the inoculum grew to an OD (600 nm) value of 4.0 units. 125 mL of the grown seed medium was used to inoculate each of the production vessels containing 7 liters of fermentation medium.

The fermentation medium contained 5 g/L yeast extract, 5 g/L potassium phosphate monobasic, 1.9 g/L NaCl, 1.0 g/L TWEEN-80 and 0.1 mL/L BIOSPUMEX 153K antifoam agent. These components were added prior to vessel/broth sterilization. After the sterilization cycle was completed and the operating temperature leveled and its set value, we added via sterile technique the following compounds: 2/4 g/L magnesium sulfate heptahydrate, 50 mg/L ferrous sulfate heptahydrate, 100 mg/L calcium chloride dehydrate, 10 mL/L NIT trace elements cocktail, 100 mg/L ampicillin antibiotic and 10 g/L glucose. The MT trace elements cocktail solution contained: 10 g/L citric acid monohydrate, 2 g/L manganese sulfate monohydrate, 2 g/L sodium chloride, 0.5 g/L ferrous sulfate heptahydrate, 0.2 g/L zinc sulfate heptahydrate, 20 mg/L copper sulfate pentahydrate, 20 mg/L sodium molybdate dehydrate and 2.94 mg/L calcium chloride dihydrate.

The fermentation run was controlled at 30° C., pH 6.8, and 25% dissolved oxygen. Initially, for the first 5 hours the fermentation ran in a batch mode, starting with a residual glucose concentration of 10 g/L. After 5 hours of elapsed fermentation time, we commenced with continuous glucose feeding and initiated a fed-batch mode. Glucose was carefully fed aiming to maintain a very low, residual glucose concentration (<0.1 g/L). At 17 hours of elapsed fermentation time, we induced production of GTFJ18T1 protein (SEQ ID NO:27) by adding IPTG to the broth, achieving a residual concentration of 0.5 mM. Induction lasted 7 hours in one experiment and 16 hours in the other. During this time we continued the feed of glucose while maintaining a very low residual concentration (<0.1 g/L).

At the end of the two fermentations (24 and 33 hours, respectively) the cell pellet was recovered from approximately 9 kg of fermentation broth in an RC-12 centrifuge using 2-liter bottles. A set of two plastic bags was placed within the bottles for easy recovery of the cell paste. The centrifugation was done at 6728 RCF for 20 minutes. After the liquid was decanted from the bags, the cell pellet was frozen at −80° C.; a total of 1943 grams of frozen paste was recovered. The frozen paste was subsequently added to 3.2 liters of buffer (50 mM potassium phosphate, pH 6.0), and after the paste had thawed, the resulting cell suspension was homogenized using an APV-100 homogenizer operated at a pressure of approximately 850 bar. The homogenate was cooled over ice, and then decanted into six 1-liter centrifuge bottles. The bottles were spun for over an hour in an RC-3 centrifuge at 5890 RCF. The supernatant was decanted into bottles and stored frozen at −80° C.; aliquots of the two fermentation run lysate supernatants were analyzed for the presence of the target enzyme, GTFJ18T1 (SEQ ID NO:27), by measuring the rate of conversion of sucrose to fructose. The biochemical assays measured 5.8 U/mL and 9.90 U/mL of active enzyme for the two fermentations, respectively. A second centrifugation of the 5.8 U/ml supernatant at 12,000 rpm using an SS34 rotor produced a clarified supernatant with 5.0 U/mLGTFJ18T1 activity (stored frozen at −80° C.).

GTFJ18T1 (SEQ ID NO:27) produced in this Example was used in one or more of the following Examples.

Example 8

Sequences of Fructobacillus tropaeoli F214-1 glucosyltransferase, FtrGtfl (GTF9905)

A glucosyltransferase gene, FtrGtfl, was identified from Fructobacillus tropaeoli F214-1. The nucleic acid sequence for the FtrGtfl gene (GENBANK Acc. No. DF968096.1, SEQ ID NO:17), and the amino acid sequence of the hypothetical protein encoded by the FtrGtfl gene (GENBANK Acc. No. GAP05007.1, gi 902949905, SEQ ID NO:4, "GTF9905" herein) were found in the NCBI database. A portion of SEQ ID NO:4 aligned with SEQ ID NO:28 in the analysis disclosed above in Example 1, thereby identifying GTF9905 as a putative alpha-1,2 branching enzyme. The mature, secreted form GTF9905 corresponds with positions 36-1672 of SEQ ID NO:4.

Example 9

Sequences for Expressing Mature GTF9905 (FtrGtfl)

A nucleotide sequence encoding the mature version of GTF9905 (Gtfl from Fructobacillus tropaeoli F214-1) was codon-optimized for expression in Bacillus subtilis, resulting in SEQ ID NO:34. This sequence was synthesized by Generay (Shanghai, China) and inserted into the p2JM103BBI plasmid (Vogtentanz, Protein Expr. Punf. 55:40-52, 2007), resulting in pZQ2-CRC08152-FtrGtfl plasmid. pZQ2-CRC08152-FtrGtfl contains (in 5' to 3' direction) an aprE promoter, a sequence encoding an aprE signal sequence used to direct protein secretion in Bacillus subtilis, an oligonucleotide that encodes Ala-Gly-Lys to facilitate the secretion of the target protein, and the synthetic sequence (SEQ ID NO:34) encoding the mature form of GTF9905 (i.e., positions 36-1672 of SEQ ID NO:4)

Plasmid pZQ2-CRC08152-FtrGtfl was used to transform B. subtilis cells, and the transformed cells were spread on Luria Agar plates supplemented with 5 ppm chloramphenicol. A colony with correct insertion, as confirmed by PCR and sequencing, was selected and subjected to fermentation for GTF9905 production.

Example 10

Production of GTF9905 (FtrGtfl)

The B. subtilis transformant colony with correct insertion was picked into 5 mL Luria broth medium supplemented with 5 ppm chloramphenicol and grown overnight. 30 µL of this culture was then inoculated into a 250-mL shake flask containing 30 mL Grant's II medium supplemented with 5 ppm chloramphenicol, which was then incubated at 30° C. with 250 rpm shaking for 48 hours. The resulting culture supernatant was collected by centrifugation at 24,000×g for 1 h at 4° C. and filtered with 0.22-µm filter.

The supernatant, which contained GTF9905, was first dialyzed with 50 mM K2HPO4 pH 6.8 buffer in dialysis tubing (Thermo product #68100), afterwhich the dialyzed supernatant was lyophilized using the FREEZONE 6 freeze-dry system (Labconco) and stored at −80° C. (22.5 U/mL).

GTF9905 produced in this Example was used in one or more of the following Examples.

Example 11

GTF8117 and GTF6831 Enzyme Activity Assay

Glucosyltransferase activity assays for GTF8117 and GTF6831 were performed by incubating each GTF enzyme with 200 g/L sucrose in 25 mM acetate buffer at pH 5.5 in the presence of 25 g/L dextran (MW 1500, Sigma-Aldrich, Cat. #31394) at 37° C. and 125 rpm orbital shaking. One aliquot of reaction mixture was withdrawn at 1 h, 2 h and 3 h incubation periods and heated at 90° C. for 5 min to inactivate the GTF. Insoluble material was removed by centrifugation at 13,000×g for 5 min, followed by filtration through 0.22-µm nylon membrane. The resulting filtrate was analyzed by HPLC with AMINEX HPX-87C columns series at 85° C. (Bio-Rad, Hercules, CA) to quantify sucrose concentration. The sucrose concentration at each time point was plotted against the reaction time and the initial reaction rate was determined from the slope of the linear plot. One unit of GTF activity was defined as the amount of enzyme needed to consume one micromole of sucrose in one minute under the assay conditions.

Example 12

GTF9905 and GTFJ18T1 Enzyme 1,2-Branching Activity Assay

Glucosyltransferase activity assays for 1,2-branching enzymes GTF9905 and GTFJ18T1 were performed by incubating each enzyme with 100 g/L sucrose in 50 mM acetate buffer at pH 5.5 in the presence of dextran 40K (Sigma-Aldrich Cat #D1662-100G) at 30° C. and 125 rpm orbital shaking. One aliquot of reaction mixture was withdrawn at 1 h, 2 h and 3 h incubation periods and heated at 90° C. for 5 min to inactivate the enzyme. Insoluble material was removed by centrifugation at 13,000×g for 5 min, followed by filtration through 0.2-µm nylon membrane. The resulting filtrate was analyzed by HPLC with AMINEX HPX-87C columns series at 85° C. (Bio-Rad, Hercules, CA) to quantify sucrose concentration. The sucrose concentration at each time point was plotted against the reaction time and the initial reaction rate was determined from the slope of the linear plot. One unit of GTF 1,2-branching enzyme activity was defined as the amount of enzyme needed to consume one micromole of sucrose in one minute under the assay conditions.

Example 13

Production of soluble alpha-1,2-branched polysaccharides by stepwise combination of glucosyltransferase GTF8117 and alpha-1,2 branching enzyme GTF9905

First, a reaction was performed to prepare glucan that was used in the second part of this Example as a substrate for 1,2-branching enzyme. A reaction mixture (20 mL) comprised of sucrose (488 g/L) and GTF8117 (Example 4, 9.4 U/mL) was adjusted to pH 5.5 with 6.0 N hydrochloric acid and stirred at 47° C. Aliquots were withdrawn at predetermined times and quenched by heating at 90° C. for 20 min. The resulting heat-treated aliquots were centrifuged and the supernatants analyzed by HPLC to determine the concentration of sucrose, glucose, fructose, leucrose, oligosaccharides and polysaccharides. After 6 h, the reaction mixture was heated to 90° C. for 30 minutes, and an aliquot of the heat-treated reaction mixture was centrifuged and the resulting supernatant analyzed for soluble monosaccharides, oligosaccharides and polysaccharides (DP8+) (Table 1). The DP8+polysaccharides appeared to contain about 100% alpha-1,6 linkages.

TABLE 1

HPLC analysis of soluble monosaccharides, oligosaccharides and polysaccharides produced by glucosyltransferase GTF8117.

| DP8 + g/L | DP7 g/L | DP6 g/L | DP5 g/L | DP4 g/L | DP3 g/L | DP2 g/L | Sucrose g/L | Leucrose g/L | Glucose g/L | Fructose g/L |
|---|---|---|---|---|---|---|---|---|---|---|
| 241 | 0.0 | 0.0 | 0.0 | 0.0 | 0.0 | 5.5 | 0.1 | 20.1 | 3.4 | 240 |

A second reaction was then performed to conduct alpha-1,2 branching from the products of the first reaction. The second reaction mixture was prepared by mixing 5.84 mL of the heat-treated first reaction mixture prepared above with 2.92 mL of sucrose solution (600 g/L sucrose in deionized water; final sucrose concentration 175 g/L), 0.67 mL of 0.75 M sodium acetate buffer (pH 5.5, 50 mM final concentration), 0.070 mL deionized water and 0.50 mL of a centrifuged cell lysate containing alpha-1,2-branching enzyme GTF9905 (Example 10; final GTF9905 concentration 1.13 U/mL), followed by stirring at 30° C. Aliquots were withdrawn at predetermined times and quenched by heating at 90° C. for 20 min. The resulting heat-treated aliquots were centrifuged and the supernatants analyzed by HPLC to determine the concentration of sucrose, glucose, fructose, leucrose, oligosaccharides and polysaccharides. After 76.2 h, the reaction mixture was heated to 90° C. for 20 minutes, and an aliquot of the heat-treated reaction mixture was centrifuged. The resulting supernatant was analyzed for soluble monosaccharides, oligosaccharides and polysaccharides (Table 2), and analyzed by $^1$H NMR spectroscopy to determine the anomeric linkages of the oligosaccharides and polysaccharides (Table 3).

TABLE 2

HPLC analysis of soluble monosaccharides, oligosaccharides and polysaccharides produced by an alpha-1,2 branching reaction.

| DP8 + g/L | DP7 g/L | DP6 g/L | DP5 g/L | DP4 g/L | DP3 g/L | DP2 g/L | Sucrose g/L | Leucrose g/L | Glucose g/L | Fructose g/L |
|---|---|---|---|---|---|---|---|---|---|---|
| 239 | 0.0 | 0.0 | 0.0 | 0.0 | 0 | 5.4 | 12 | 33 | 15 | 209 |

TABLE 3

Anomeric linkage analysis of soluble oligosaccharides and polysaccharides by $^1$H NMR spectroscopy.

| % alpha-1,4 | % alpha-1,3 | % alpha-1,3,6 | % alpha-1,2,6 | % alpha-1,6 | % alpha-1,2 branching |
|---|---|---|---|---|---|
| 0 | 0 | 0 | 51.7 | 48.3 | 51.7 |

Thus, GTF9905 has significant alpha-1,2 branching activity and can be used to modify the structure of a glucan substrate.

Example 14

Production of soluble alpha-1,2-branched polysaccharides by stepwise combination of glucosyltransferase GTF6831 and alpha-1,2 branching enzyme GTF9905

First, a reaction was performed to prepare glucan that was used in the second part of this Example as a substrate for 1,2-branching enzyme. A reaction mixture (20 mL) comprised of sucrose (488 g/L) and GTF6831 (Example 5, 4.6 U/mL) was adjusted to pH 5.5 with 6.0 N hydrochloric acid and stirred at 47° C. Aliquots were withdrawn at predetermined times and quenched by heating at 90° C. for 20 min. The resulting heat-treated aliquots were centrifuged and the supernatants analyzed by HPLC to determine the concentration of sucrose, glucose, fructose, leucrose, oligosaccharides and polysaccharides. After 24.5 h, the reaction mixture was heated to 90° C. for 30 minutes, and an aliquot of the heat-treated reaction mixture was centrifuged and the resulting supernatant analyzed for soluble monosaccharides, oligosaccharides and polysaccharides (DP8+) (Table 4).

TABLE 4

HPLC analysis of soluble monosaccharides, oligosaccharides and polysaccharides produced by glucosyltransferase GTF6831.

| DP8 + g/L | DP7 g/L | DP6 g/L | DP5 g/L | DP4 g/L | DP3 g/L | DP2 g/L | Sucrose g/L | Leucrose g/L | Glucose g/L | Fructose g/L |
|---|---|---|---|---|---|---|---|---|---|---|
| 263 | 0.1 | 1.5 | 1.3 | 0.0 | 0.0 | 4.8 | 2.8 | 36 | 4.3 | 221 |

A second reaction was then performed to conduct alpha-1,2 branching from the products of the first reaction. The second reaction mixture was prepared by mixing 5.84 mL of the heat-treated first reaction mixture prepared above with 2.92 mL of sucrose solution (600 g/L sucrose in deionized water; final sucrose concentration 175 g/L), 0.67 mL of 0.75 M sodium acetate buffer (pH 5.5, 50 mM final concentration), 0.070 mL deionized water and 0.50 mL of a centrifuged cell lysate containing alpha-1,2-branching enzyme GTF9905 (Example 10, final GTF9905 concentration 1.13 U/mL), followed by stirring at 30° C. Aliquots were withdrawn at predetermined times and quenched by heating at 90° C. for 20 min. The resulting heat-treated aliquots were centrifuged and the supernatants analyzed by HPLC to determine the concentration of sucrose, glucose, fructose, leucrose, oligosaccharides and polysaccharides. After 76.2 h, the reaction mixture was heated to 90° C. for 20 minutes, and an aliquot of the heat-treated reaction mixture was centrifuged. The resulting supernatant was analyzed for soluble monosaccharides, oligosaccharides and polysaccharides (Table 5), and analyzed by $^1$H NMR spectroscopy to determine the anomeric linkages of the oligosaccharides and polysaccharides (Table 6).

TABLE 5

HPLC analysis of soluble monosaccharides, oligosaccharides and polysaccharides produced by an alpha-1,2 branching reaction.

| DP8 + g/L | DP7 g/L | DP6 g/L | DP5 g/L | DP4 g/L | DP3 g/L | DP2 g/L | Sucrose g/L | Leucrose g/L | Glucose g/L | Fructose g/L |
|---|---|---|---|---|---|---|---|---|---|---|
| 231 | 0.0 | 0.0 | 0.0 | 0.0 | 0 | 5.0 | 23 | 38 | 16 | 196 |

TABLE 6

Anomeric linkage analysis of soluble oligosaccharides and polysaccharides by $^1$H NMR spectroscopy.

| % alpha-1,4 | % alpha-1,3 | % alpha-1,3,6 | % alpha-1,2,6 | % alpha-1,6 | % alpha-1,2 branching |
|---|---|---|---|---|---|
| 0 | 0 | 0 | 50.8 | 49.2 | 50.8 |

Thus, it was further shown that GTF9905 has significant alpha-1,2 branching activity and can be used to modify the structure of a glucan substrate.

Example 15

Production of soluble alpha-1,2-branched polysaccharides by stepwise combination of glucosyltransferase GTF6831 and alpha-1,2 branching enzyme GTFJ18T1 First, a reaction was performed to prepare glucan that was used in the second part of this Example as a substrate for 1,2-branching enzyme. A reaction mixture (20 mL) comprised of sucrose (488 g/L) and GTF6831 (Example 5, 4.6 U/mL) was adjusted to pH 5.5 with 6.0 N hydrochloric acid and stirred at 47° C. Aliquots were withdrawn at predetermined times and quenched by heating at 90° C. for 20 min. The resulting heat-treated aliquots were centrifuged and the supernatants analyzed by HPLC to determine the concentration of sucrose, glucose, fructose, leucrose, oligosaccharides and polysaccharides. After 22.5 h, the reaction mixture was heated to 90° C. for 30 minutes, and an aliquot of the heat-treated reaction mixture was centrifuged and the resulting supernatant analyzed for soluble monosaccharides, oligosaccharides and polysaccharides (DP8+) (Table 7).

TABLE 7

HPLC analysis of soluble monosaccharides, oligosaccharides and polysaccharides produced by glucosyltransferase GTF6831.

| DP8 + g/L | DP7 g/L | DP6 g/L | DP5 g/L | DP4 g/L | DP3 g/L | DP2 g/L | Sucrose g/L | Leucrose g/L | Glucose g/L | Fructose g/L |
|---|---|---|---|---|---|---|---|---|---|---|
| 273 | 0.0 | 1.0 | 1.0 | 0.7 | 0.0 | 5.5 | 2.6 | 33.4 | 3.7 | 212 |

A second reaction was then performed to conduct alpha-1,2 branching from the products of the first reaction. The second reaction mixture was prepared by mixing 5.84 mL of the heat-treated first reaction mixture prepared above with 2.09 mL of sucrose solution (600 g/L sucrose in deionized water; final sucrose concentration 125 g/L), 0.67 mL of 0.75 M sodium acetate buffer (pH 5.5, 50 mM final concentration) and 1.40 mL of a centrifuged cell lysate containing alpha-1,2-branching enzyme GTFJ18T1 (Example 7, final GTFJ18T1 concentration 0.70 U/mL), followed by stirring at 30° C. Aliquots were withdrawn at predetermined times and quenched by heating at 90° C. for 20 min. The resulting heat-treated aliquots were centrifuged and the supernatants analyzed by HPLC to determine the concentration of sucrose, glucose, fructose, leucrose, oligosaccharides and polysaccharides. After 51.5 h, the reaction mixture was heated to 90° C. for 30 minutes, and an aliquot of the heat-treated reaction mixture was centrifuged. The resulting supernatant was analyzed for soluble monosaccharides, oligosaccharides and polysaccharides (Table 8), and analyzed by $^1$H NMR spectroscopy to determine the anomeric linkages of the oligosaccharides and polysaccharides (Table 9).

TABLE 8

HPLC analysis of soluble monosaccharides, oligosaccharides and polysaccharides produced by an alpha-1,2 branching reaction.

| DP8+ g/L | DP7 g/L | DP6 g/L | DP5 g/L | DP4 g/L | DP3 g/L | DP2 g/L | Sucrose g/L | Leucrose g/L | Glucose g/L | Fructose g/L |
|---|---|---|---|---|---|---|---|---|---|---|
| 204 | 0.0 | 0.0 | 0.0 | 0.0 | 0 | 3.2 | 17.1 | 38.6 | 7.2 | 173 |

TABLE 9

Anomeric linkage analysis of soluble oligosaccharides and polysaccharides by $^1$H NMR spectroscopy.

| % alpha-1,4 | % alpha-1,3 | % alpha-1,3,6 | % alpha-1,2,6 | % alpha-1,6 | % alpha-1,2 branching |
|---|---|---|---|---|---|
| 0 | 0 | 0 | 37.1 | 62.9 | 37.1 |

Thus, it was further shown that GTFJ18T1 has significant alpha-1,2 branching activity and can be used to modify the structure of a glucan substrate.

Example 16

Production of soluble alpha-1,2-branched polysaccharides by simultaneous combination of glucosyltransferase GTF8117 and alpha-1,2 branching enzyme GTF9905 (1)

A reaction mixture comprising sucrose (450 g/L), GTF8117 (Example 4, 0.944 U/mL;), and alpha-1,2-branching enzyme GTF9905 (Example 10, 1.06 U/mL) in 54 mM acetate buffer, pH 5.5 was stirred at 30° C. Aliquots were withdrawn at predetermined times and quenched by heating at 90° C. for 20 min. Heat-treated aliquots were centrifuged and the supernatants were analyzed by HPLC to determine the concentration of sucrose, glucose, fructose, leucrose, oligosaccharides and polysaccharides. After 74 h, the reaction mixture was heated to 90° C. for 20 minutes and centrifuged. The resulting supernatant was analyzed for soluble monosaccharides, oligosaccharides and polysaccharides (DP8+) (Table 10), and analyzed by $^1$H NMR spectroscopy to determine the anomeric linkages of the oligosaccharides and polysaccharides (Table 11).

TABLE 10

HPLC analysis of soluble monosaccharides, oligosaccharides and polysaccharides produced by simultaneous glucan synthesis and alpha-1,2 branching reactions.

| DP8+ g/L | DP7 g/L | DP6 g/L | DP5 g/L | DP4 g/L | DP3 g/L | DP2 g/L | Sucrose g/L | Leucrose g/L | Glucose g/L | Fructose g/L |
|---|---|---|---|---|---|---|---|---|---|---|
| 192 | 0.0 | 0.0 | 0.0 | 0.0 | 1.4 | 8.7 | 4.7 | 44.1 | 23.4 | 199 |

TABLE 11

Anomeric linkage analysis of soluble oligosaccharides and polysaccharides by ¹H NMR spectroscopy.

| % alpha-1,4 | % alpha-1,3 | % alpha-1,3,6 | % alpha-1,2,6 | % alpha-1,6 | % alpha-1,2 branching |
|---|---|---|---|---|---|
| 0 | 0 | 0 | 39.3 | 60.7 | 39.3 |

Thus, it was further shown that GTF9905 has significant alpha-1,2 branching activity and can be used to modify the structure of a glucan substrate.

Example 17

Production of soluble alpha-1,2-branched polysaccharides by simultaneous combination of glucosyltransferase GTF8117 and alpha-1,2 branching enzyme GTF9905 (2)

A reaction mixture comprised of sucrose (500 g/L), GTF8117 (Example 4, 2.83 U/mL), and alpha-1,2-branching enzyme GTF9905 (Example 10, 3.17 U/mL) in 54 mM acetate buffer, pH 5.5 was stirred at 30° C. Aliquots were withdrawn at predetermined times and quenched by heating at 90° C. for 20 min. Heat-treated aliquots were centrifuged and the supernatants were analyzed by HPLC to determine the concentration of sucrose, glucose, fructose, leucrose, oligosaccharides and polysaccharides. After 28.5 h, the reaction mixture was heated to 90° C. for 20 minutes and centrifuged. The resulting supernatant was analyzed for soluble monosaccharides, oligosaccharides and polysaccharides (DP8+) (Table 12), and analyzed by 41 NMR spectroscopy to determine the anomeric linkages of the oligosaccharides and polysaccharides (Table 13).

TABLE 12

HPLC analysis of soluble monosaccharides, oligosaccharides and polysaccharides produced by simultaneous glucan synthesis and alpha-1,2 branching reactions.

| DP8+ g/L | DP7 g/L | DP6 g/L | DP5 g/L | DP4 g/L | DP3 g/L | DP2 g/L | Sucrose g/L | Leucrose g/L | Glucose g/L | Fructose g/L |
|---|---|---|---|---|---|---|---|---|---|---|
| 215 | 0.0 | 0.0 | 0.0 | 0.0 | 1.4 | 8.5 | 2.2 | 46.3 | 23.8 | 234 |

TABLE 13

Anomeric linkage analysis of soluble polysaccharides by ¹H NMR spectroscopy.

| % alpha-1,4 | % alpha-1,3 | % alpha-1,3,6 | % alpha-1,2,6 | % alpha-1,6 | % alpha-1,2 branching |
|---|---|---|---|---|---|
| 0 | 0 | 0 | 34.3 | 65.7 | 34.3 |

Thus, it was further shown that GTF9905 has significant alpha-1,2 branching activity and can be used to modify the structure of a glucan substrate.

Example 18

Production of soluble alpha-1,2-branched polysaccharides by simultaneous combination of glucosyltransferase GTF8117 and alpha-1,2 branching enzyme GTFJ18T1 (1)

A reaction mixture comprised of sucrose (450 g/L), GTF8117 (Example 4, 0.944 U/mL), and alpha-1,2-branching enzyme GTFJ18T1 (Example 7, 1.06 U/mL) in 54 mM acetate buffer, pH 5.5 was stirred at 30° C. Aliquots were withdrawn at predetermined times and quenched by heating at 90° C. for 20 min. Heat-treated aliquots were centrifuged and the supernatants were analyzed by HPLC to determine the concentration of sucrose, glucose, fructose, leucrose, oligosaccharides and polysaccharides. After 71 h, the reaction mixture was heated to 90° C. for 20 minutes and centrifuged. The resulting supernatant was analyzed for soluble monosaccharides, oligosaccharides and polysaccharides (DP8+) (Table 14), and analyzed by ¹H NMR spectroscopy to determine the anomeric linkages of the oligosaccharides and polysaccharides (Table 15).

TABLE 14

HPLC analysis of soluble monosaccharides, oligosaccharides and polysaccharides produced by simultaneous glucan synthesis and alpha-1,2 branching reactions.

| DP8+ g/L | DP7 g/L | DP6 g/L | DP5 g/L | DP4 g/L | DP3 g/L | DP2 g/L | Sucrose g/L | Leucrose g/L | Glucose g/L | Fructose g/L |
|---|---|---|---|---|---|---|---|---|---|---|
| 194 | 0.0 | 0.0 | 0.0 | 0.0 | 0.0 | 8.0 | 1.3 | 70.4 | 14.3 | 201 |

TABLE 15

Anomeric linkage analysis of soluble oligosaccharide and polysaccharide by $^1$H NMR spectroscopy.

| % alpha-1,4 | % alpha-1,3 | % alpha-1,3,6 | % alpha-1,2,6 | % alpha-1,6 | % alpha 1,2 branching |
|---|---|---|---|---|---|
| 0 | 0 | 0 | 34.0 | 66.0 | 34.0 |

Thus, it was further shown that GTFJ18T1 has significant alpha-1,2 branching activity and can be used to modify the structure of a glucan substrate.

Example 19

Production of soluble alpha-1,2-branched polysaccharides by simultaneous combination of glucosyltransferase GTF8117 and alpha-1,2 branching enzyme GTFJ18T1 (2)

A reaction mixture comprised of sucrose (450 g/L), GTF8117 (Example 4, 0.472 U/mL), and alpha-1,2-branching enzyme GTFJ18T1 (Example 7, 1.06 U/mL) in 54 mM acetate buffer, pH 5.5 was stirred at 30° C. Aliquots were withdrawn at predetermined times and quenched by heating at 90° C. for 20 min. Heat-treated aliquots were centrifuged and the supernatants were analyzed by HPLC to determine the concentration of sucrose, glucose, fructose, leucrose, oligosaccharides and polysaccharides. After 131 h, the reaction mixture was heated to 90° C. for 20 minutes and centrifuged. The resulting supernatant was analyzed for soluble monosaccharides, oligosaccharides and polysaccharides (DP8+) (Table 16), and analyzed by $^1$H NMR spectroscopy to determine the anomeric linkages of the oligosaccharides and polysaccharides (Table 17).

TABLE 16

HPLC analysis of soluble monosaccharides, oligosaccharides and polysaccharides produced by simultaneous glucan synthesis and alpha-1,2 branching reactions.

| DP8+ g/L | DP7 g/L | DP6 g/L | DP5 g/L | DP4 g/L | DP3 g/L | DP2 g/L | Sucrose g/L | Leucrose g/L | Glucose g/L | Fructose g/L |
|---|---|---|---|---|---|---|---|---|---|---|
| 131 | 0.0 | 0.0 | 0.0 | 0.0 | 2.5 | 11.2 | 0.4 | 107 | 20.5 | 182 |

TABLE 17

Anomeric linkage analysis of soluble oligosaccharide and polysaccharide by $^1$H NMR spectroscopy.

| % alpha-1,4 | % alpha-1,3 | % alpha-1,3,6 | % alpha-1,2,6 | % alpha-1,6 | % alpha-1,2 branching |
|---|---|---|---|---|---|
| 0 | 0 | 0 | 39.1 | 60.9 | 39.1 |

Thus, it was further shown that GTFJ18T1 has significant alpha-1,2 branching activity and can be used to modify the structure of a glucan substrate.

Example 20

Isolation and characterization of alpha-1,2-branched polysaccharides

Four 500-mL reactions (1-4) containing 200 g/L sucrose and 9.44 U/mL of GTF8117 (Example 4) were adjusted to pH 5.5 and mixed at 47° C. on a rotary shaker for 18 h. Aliquots of each product mixture were removed at predetermined times, heated at 90° C. for 20 min, cooled to ca. 25° C., and then centrifuged; the resulting supernatants were analyzed by HPLC to determine the concentration of sucrose, glucose, fructose, and leucrose present during conversion of sucrose to a linear alpha-1,6-dextran polysaccharide (Table 18). After 18 h, the four reaction mixtures were heated at 90° C. for 20 min, cooled to ca. 25° C., and then centrifuged; the resulting supernatants were combined and stored at 5° C. prior to use in a subsequent reaction (below) that added alpha-1,2-glucosyl branching to the alpha-1,6-linked dextran polysaccharide reaction product.

TABLE 18

HPLC analysis of soluble monosaccharides and disaccharides produced by conversion of sucrose to polysaccharide using GTF8117.

| Reaction no. | Sucrose g/L | Leucrose g/L | Glucose g/L | Fructose g/L |
|---|---|---|---|---|
| 1 | 0.92 | 7.0 | 2.3 | 103 |
| 2 | 0.89 | 6.6 | 2.2 | 97.3 |
| 3 | 0.95 | 6.9 | 2.4 | 103 |
| 4 | 0.95 | 6.9 | 2.3 | 103 |

Two 250-mL jacketed resin kettles were each charged with 100 mL of the GTF8117 reaction product supernatant from above (final concentration: 80 g/L of total dissolved solids derived from sucrose), 33.3 mL of a 600 g/L sucrose stock solution (final concentration of 80 g/L sucrose), and 91.7 mL of distilled water. The mixtures were heated in situ at 80° C. for 30 minutes, then cooled to 30° C., afterwhich 25 mL of GTFJ18T1 enzyme solution (Example 7, 0.5 U/mL final GTFJ18T1 concentration) was added and the pH immediately adjusted to 5.5 with 0.5% sodium hydroxide (these two reactions are referred to below as Reactions 1 and 2). The reaction pH was continuously controlled at 5.5 using a pH electrode connected to a peristaltic pump that fed 0.5% sodium hydroxide into the reaction mixture as needed. Aliquots were withdrawn at predetermined times and quenched by heating at 90° C. for 20 min. The resulting heat-treated aliquots were centrifuged and the supernatants analyzed by HPLC to determine the concentration of sucrose, glucose, fructose, leucrose, oligosaccharides and polysaccharides. After 44 h, each reaction mixture (Reactions 1 and 2) was heated to 90° C. for 20 minutes and centrifuged. The resulting supernatants were analyzed by HPLC for soluble monosaccharides, oligosaccharides and polysaccharides (Table 19); by $^1$H NMR spectroscopy to determine the anomeric linkages of the oligosaccharides and polysaccharides (Table 20); and by size-exclusion chromatography for molecular weight (Table 21).

TABLE 19

HPLC analysis of soluble monosaccharides and disaccharides produced in Reactions 1 and 2.

| Reaction no. | Sucrose g/L | Leucrose g/L | Glucose g/L | Fructose g/L |
|---|---|---|---|---|
| 1 | 27.1 | 7.4 | 0 | 50.0 |
| 2 | 34.4 | 5.8 | 0 | 46.9 |

TABLE 20

Anomeric linkage analysis of soluble alpha-1,2-branched polysaccharides produced in Reactions 1 and 1.

| Reaction no. | % alpha-1,4 | % alpha-1,3 | % alpha-1,3,6 | % alpha-1,2,6 | % alpha-1,6 | % alpha-1,2 branching |
|---|---|---|---|---|---|---|
| 1 | 0 | 0 | 0 | 46.7 | 53.3 | 46.7 |
| 2 | 0 | 0 | 0 | 41.4 | 58.6 | 41.4 |

TABLE 21

Molecular weight analysis of alpha-1,2-branched polysaccharides produced in Reactions 1 and 2.

| Reaction no. | Mn | Mp | Mw | Mz | PDI |
|---|---|---|---|---|---|
| 1 | 11348 | 29189 | 25460 | 35600 | 2.244 |
| 2 | 11023 | 27148 | 23868 | 33166 | 2.165 |

Thus, it was further shown that GTFJ18T1 has significant alpha-1,2 branching activity and can be used to modify the structure of a glucan substrate.

The supernatants from Reactions 1 and 2 were combined, and the alpha-1,2-branched polysaccharides therein were purified and isolated by ultrafiltration (UF) using a 5-kDa molecular weight cutoff (MWCO) polyethersulfone (PES) membrane (Pall Centramate™ LV). HPLC analysis of the UF retentate indicated no detectable monosaccharides, disaccharides or DP2-DP8 oligosaccharides. The UF retentate was adjusted to ca. 5 wt % dissolved solids and the resulting solution lyophilized to produce the soluble alpha-1,2-branched polysaccharides as a dry solid. The solid polysaccharide product was analyzed by 41 NMR spectroscopy (Table 22) and by GC/MS to determine the anomeric linkages of the polysaccharides (Table 23).

TABLE 22

Anomeric linkage analysis ($^1$H NMR) of soluble alpha-1,2-branched polysaccharides produced in Reactions 1 and 2 (combined).

| sample no. | % alpha-1,4 | % alpha-1,3 | % alpha-1,3,6 | % alpha-1,2 | % alpha-1,2,6 | % alpha-1,6 | % alpha-1,2 branching |
|---|---|---|---|---|---|---|---|
| 105-1 | 0 | 0 | 0 | 31.1 | 31.1 | 37.8 | 45.2 |

TABLE 23

Anomeric linkage analysis (GC/MS) of soluble alpha-1,2-branched polysaccharides produced using GTFJ18Tl in Reactions 1 and 2 (combined).

| sample no. | % alpha-1,3 | % alpha-1,2 | % alpha-1,6 | % alpha-1,4 | % alpha-1,3,6 | % alpha-1,2,6 |
|---|---|---|---|---|---|---|
| 105-1 | 0.3 | 0.8 | 57.5 | 0.2 | 0.5 | 40.7 |

Example 21

Isolation and characterization of alpha-1,2-branched polysaccharides

Two 250-mL jacketed resin kettles were each charged with 100 mL of the GTF8117 reaction product supernatant produced in the first part of Example 20 above (final concentration: 80 g/L of total dissolved solids derived from sucrose), 33.3 mL of a 600 g/L sucrose stock solution (final concentration of 80 g/L sucrose), and 91.7 mL of distilled water. The mixtures were heated in situ at 80° C. for 30 minutes, then cooled to 30° C., afterwhich 25 mL of GTFJ18T1 enzyme solution (Example 7, 0.5 U/mL final GTFJ18T1 concentration) was added and the pH immediately adjusted to 5.5 with 0.5% sodium hydroxide (these two reactions are referred to below as Reactions 3 and 4). The reaction pH was continuously controlled at 5.5 using a pH electrode connected to a peristaltic pump that fed 0.5% sodium hydroxide into the reaction mixture as needed. Aliquots were withdrawn at predetermined times and quenched by heating at 90° C. for 20 min. The resulting heat-treated aliquots were centrifuged and the supernatants analyzed by HPLC to determine the concentration of sucrose, glucose, fructose, leucrose, oligosaccharides and polysaccharides. After 4 h, each reaction mixture (Reactions 3 and 4) was heated to 90° C. for 20 minutes and centrifuged. The resulting supernatants were analyzed by HPLC for soluble monosaccharides, oligosaccharides and polysaccharides (Table 24), by 41 NMR spectroscopy to determine the anomeric linkages of the oligosaccharides and polysaccharides (Table 25), and by size-exclusion chromatography for molecular weight (Table 26).

TABLE 24

HPLC analysis of soluble monosaccharides and disaccharides produced in Reactions 3 and 4.

| Reaction no. | Sucrose g/L | Leucrose g/L | Glucose g/L | Fructose g/L |
|---|---|---|---|---|
| 3 | 64.7 | 3.9 | 1.6 | 47.0 |
| 4 | 65.9 | 4.0 | 1.3 | 46.4 |

TABLE 25

Anomeric linkage analysis of soluble alpha-1,2-branched polysaccharides produced in Reactions 3 and 4.

| Reaction no. | % alpha-1,4 | % alpha-1,3 | % alpha-1,3,6 | % alpha-1,2,6 | % alpha-1,6 | % alpha-1,2 branching |
|---|---|---|---|---|---|---|
| 3 | 0 | 0 | 0 | 21.4 | 78.6 | 21.4 |
| 4 | 0 | 0 | 0 | 20.5 | 79.5 | 20.5 |

TABLE 26

Molecular weight analysis of alpha-1,2-branched polysaccharides produced in Reactions 3 and 4.

| Reaction no. | Mn | Mp | Mw | Mz | PDI |
|---|---|---|---|---|---|
| 3 | 10395 | 23593 | 20458 | 28218 | 1.968 |
| 4 | 10282 | 23121 | 20092 | 27639 | 1.954 |

Thus, it was further shown that GTFJ18T1 has significant alpha-1,2 branching activity and can be used to modify the structure of a glucan substrate.

The supernatants from Reactions 3 and 4 were combined, and the alpha-1,2-branched polysaccharides therein were purified and isolated by ultrafiltration (UF) using a 5-kDa molecular weight cutoff (MWCO) polyethersulfone (PES) membrane (Pall Centramate™ LV). HPLC analysis of the UF retentate indicated no detectable monosaccharides, disaccharides or DP2-DP8 oligosaccharides. The UF retentate was adjusted to ca. 5 wt % dissolved solids and the resulting solution lyophilized to produce the soluble alpha-1,2-branched polysaccharides as a dry solid. The solid polysaccharide product was analyzed by $^1$H NMR spectroscopy (Table 27) and by GC/MS to determine the anomeric linkages of the polysaccharides (Table 28).

TABLE 27

Anomeric linkage analysis ($^1$H NMR) of soluble alpha-1,2-branched polysaccharides produced in Reactions 3 and 4 (combined).

| sample no. | % alpha-1,4 | % alpha-1,3 | % alpha-1,3,6 | % alpha-1,2 | % alpha-1,2,6 | % alpha-1,6 | % alpha-1,2 branching |
|---|---|---|---|---|---|---|---|
| 105-2 | 0 | 0 | 0 | 17.7 | 17.3 | 65 | 21.0 |

TABLE 28

Anomeric linkage analysis (GC/MS) of soluble alpha-1,2-branched polysaccharides produced using GTFJ18T1 in Reactions 3 and 4 (combined).

| sample no. | % alpha-1,3 | % alpha-1,2 | % alpha-1,6 | % alpha-1,4 | % alpha-1,3,6 | % alpha-1,2,6 |
|---|---|---|---|---|---|---|
| 105-2 | 0.2 | 0.4 | 78.1 | 0.1 | 0.4 | 20.8 |

Example 22

Isolation and characterization of alpha-1,2-branched polysaccharides

Two 250-mL jacketed resin kettles were each charged with 175 mL of the GTF8117 reaction product supernatant produced in the first part of Example 20 above (final concentration: 140 g/L of total dissolved solids derived from sucrose), 4.2 mL of a 600 g/L sucrose stock solution (final concentration of 10 g/L sucrose), and 45.8 mL of distilled water. The mixtures were heated in situ at 80° C. for 30 minutes, then cooled to 30° C., afterwhich 25 mL of GTFJ18T1 enzyme solution (Example 7, 0.5 U/mL final GTFJ18T1 concentration) was added and the pH immediately adjusted to 5.5 with 0.5% sodium hydroxide (these two reactions are referred to below as Reactions 5 and 6). The reaction pH was continuously controlled at 5.5 using a pH electrode connected to a peristaltic pump that fed 0.5% sodium hydroxide into the reaction mixture as needed. Aliquots were withdrawn at predetermined times and quenched by heating at 90° C. for 20 min. The resulting heat-treated aliquots were centrifuged and the supernatants analyzed by HPLC to determine the concentration of sucrose, glucose, fructose, leucrose, oligosaccharides and polysaccharides. After 20 h, each reaction mixture (Reactions 5 and 6) was heated to 90° C. for 20 minutes and centrifuged. The resulting supernatants were analyzed by HPLC for soluble monosaccharides, oligosaccharides and polysaccharides (Table 29), by $^1$H NMR spectroscopy to determine the anomeric linkages of the oligosaccharides and polysaccharides (Table 30), and by size-exclusion chromatography for molecular weight (Table 31).

TABLE 29

HPLC analysis of soluble monosaccharides and disaccharides produced in Reactions 5 and 6.

| Reaction no. | Sucrose g/L | Leucrose g/L | Glucose g/L | Fructose g/L |
|---|---|---|---|---|
| 5 | 4.2 | 4.2 | 0 | 58.5 |
| 6 | 0.4 | 3.7 | 0 | 53.8 |

TABLE 30

Anomeric linkage analysis of soluble alpha-1,2-branched polysaccharides produced in Reactions 5 and 6.

| Reaction no. | % alpha-1,4 | % alpha-1,3 | % alpha-1,3,6 | % alpha-1,2,6 | % alpha 1,6 | % alpha-1,2 branching |
|---|---|---|---|---|---|---|
| 5 | 0 | 0 | 0 | 4.6 | 95.4 | 4.6 |
| 6 | 0 | 0 | 0 | 5.8 | 94.2 | 5.8 |

TABLE 31

Molecular weight analysis of alpha-1,2-branched polysaccharides produced in Reactions 5 and 6.

| Reaction no. | Mn | MP | Mw | Mz | PDI |
|---|---|---|---|---|---|
| 5 | 9032 | 20263 | 17725 | 24229 | 1.962 |
| 6 | 9492 | 20425 | 17851 | 24297 | 1.881 |

Thus, it was further shown that GTFJ18T1 has significant alpha-1,2 branching activity and can be used to modify the structure of a glucan substrate.

The supernatants from Reactions 5 and 6 were combined, and the alpha-1,2-branched polysaccharides therein were purified and isolated by ultrafiltration (UF) using a 5-kDa molecular weight cutoff (MWCO) polyethersulfone (PES) membrane (Pall Centramate™ LV). HPLC analysis of the UF retentate indicated no detectable monosaccharides, disaccharides or DP2-DP8 oligosaccharides. The UF retentate was adjusted to ca. 5 wt % dissolved solids and the resulting solution lyophilized to produce the soluble alpha- 1,2-branched polysaccharides as a dry solid. The solid polysaccharide product was analyzed by $^1$H NMR spectroscopy (Table 32) and by GC/MS to determine the anomeric linkages of the polysaccharides (Table 33).

TABLE 32

Anomeric linkage analysis of soluble alpha-1,2-branched polysaccharides produced in Reactions 5 and 6.

| sample no. | % alpha-1,4 | % alpha-1,3 | % alpha-1,3,6 | % alpha-1,2 | % alpha-1,2,6 | % alpha-1,6 | % alpha-1,2 branching |
|---|---|---|---|---|---|---|---|
| 105-3 | 0 | 0 | 0 | 5.1 | 5.1 | 89.8 | 5.4 |

TABLE 33

Anomeric linkage analysis of soluble alpha-1,2-branched polysaccharides produced in Reactions 5 and 6.

| sample no. | % alpha-1,3 | % alpha-1,2 | % alpha-1,6 | % alpha-1,4 | % alpha-1,3,6 | % alpha-1,2,6 |
|---|---|---|---|---|---|---|
| 105-3 | 0.2 | 0.5 | 90.1 | 0.4 | 0.5 | 8.3 |

Example 23

Glycemic Response in Mice

The objective of the screening study was to assess the digestibility of sample 105-1 (Example 20), sample 105-2 (Example 21), and sample 105-3 (Example 22) that were each produced using GTF8117 and GTFJ18T1, by evaluating the glycemic response of male mice following a single dose. Seven groups of male C57B 1/6 mice each received a single dose of one of the three test substances (sample 105-1, -2, or -3), positive or negative control substances, or a vehicle control. Blood was obtained via the tail vein in order to measure glucose levels using a glucometer. Multiple readings were obtained on the day of test substance exposure.

The oral route of administration was selected because it is the intended route of human exposure and the most efficient way to deliver an accurate dose. Groups of 12 young adult male C57B 1/6 J mice were dosed by oral gavage with one of the following treatments: a test substance (sample 105-1, sample 105-2, or sample 105-3), a positive control substance (glucose [data shown], or an alpha-1,3-linked glucan having no alpha-1,2 branches [data not shown]), a negative control substance (Litesse® Ultra), or a vehicle control (deionized water). The dose level was 2000 mg/kg for all treatments except for the water control, which was administered at the same dose volume (10 mL/kg) as the other treatments (Table 34).

The experiment was conducted after habituating the animals to the testing procedure, including daily gavage with water and multiple baseline glucometer readings prior to dosing. Three baseline glucometer readings were performed within approximately 1 hour prior to dosing (pre-dose measurements 1-3), with approximately 20 minutes between each of the three readings and between the third reading and dosing. Post-dose glucometer readings were performed after approximately 20, 40, 60, and 120 minutes. The ALPHA TRAK 2 glucometer was used to measure the glucose in at least 0.3 microliter of blood obtained by pricking the tail vein with a sterile needle. The area under the curve (AUC) was calculated for 0 to 2 hours. The AUC was calculated by adding together a series of trapezoids rather than a prediction model of a smooth curve. The final baseline value was designated as "0 minutes post-dosing" for the purpose of the calculation.

Under the conditions of the study, administration of sample 105-1 or sample 105-2 at 2000 mg/kg by oral gavage did not result in any increase in blood glucose; the glycemic response was similar to that of the Litesse® Ultra dietary fiber or deionized water (Table 35). Administration of sample 105-3 at 2000 mg/kg by oral gavage resulted in a glycemic response with a slower onset and lower peak magnitude than that induced by free glucose (a positive control) (the alpha-1,3-linked glucan having no alpha-1,2 branches induced a glycemic response very similar to that induced by glucose [data not shown]). A glycemic response (i.e., a statistically significant increase in blood glucose levels) was considered to be a potential indicator of the digestibility of these test substances at a maximal dose of 2000 mg/kg.

TABLE 34

Study design.

| Group | Number and Sex | Treatment | Description | Dose Level[a] |
|---|---|---|---|---|
| 1 | 12 male | Water | Vehicle Control | n/a |
| 2 | 12 male | Litesse ® Ultra | Negative Control | 2000 mg/kg |
| 3 | 12 male | Sample 105-1 | Test Substance | 2000 mg/kg |
| 4 | 12 male | Sample 105-2 | Test Substance | 2000 mg/kg |
| 5 | 12 male | Sample 105-3 | Test Substance | 2000 mg/kg |
| 6 | 12 male | Glucose | Positive Control | 2000 mg/kg |

[a]Weight of test substance/kg animal body weight.

TABLE 35

| | Pre-Dose Measurements | | | Post-Dose Measurements | | | | |
|---|---|---|---|---|---|---|---|---|
| | 1 | 2 | 3 | 20 min | 40 min | 1 hr | 2 hr | AUC, 0-2 hr[a] |
| Water | 194 (24) | 250 (53) | 266 (51) | 264 (29) | 292 (56) | 263 (59) | 249 (39) | 31780 (3875) |
| Litesse ® Ultra | 186 (27) | 208 (28) | 273 (45) | 288 (70) | 268 (34) | 299 (47) | 247 (38) | 33233 (3917) |
| 105-1 | 195 (29) | 218 (25) | 265 (39) | 275 (62) | 306 (63) | 276 (40) | 231 (40) | 32229 (3494) |
| 105-2 | 192 (25) | 215 (29) | 243 (34) | 294 (42) | 290 (63) | 280 (43) | 250 (55) | 32793 (2331) |
| 105-3 | 200 (31) | 212 (18) | 289 (40) | 301 (41) | 331 (61) | 334 (42)[#] | 273 (62) | 37072 (3611)[#] |
| Glucose | 204 (35) | 206 (27) | 274 (50) | 401 (77)[#] | 374 (73)[#] | 308 (44) | 245 (53) | 37876 (3974)[#] |

*Data (each measurement reading) are presented as "mean (SD)".
[#]Statistically significant at p < 0.05 by One Way ANOVA followed by Dunnett's test, compared with the water control.
[a]The final baseline value was designated as "0 minutes post-dosing" for the purpose of the AUC calculation.

Thus, sample 105-3 can be characterized as a slow glucose release glucan composition herein, and samples 105-1 and 105-2 can be characterized as having dietary fiber qualities. It is noteworthy that sample 105-3 has less than 10% alpha-1,2 branching (Example 22), whereas samples 105-1 and 105-2 each have greater than 15% alpha-1,2 branching (Examples 20-21).

Example 24

Preparation of a Yogurt/Drinkable Smoothie

The following example describes the preparation of a yogurt/drinkable smoothie containing the present alpha-1,2-branched glucan.

TABLE 36

| Ingredients | wt % |
|---|---|
| Distilled Water | 49.00 |
| SUPRO XT40 Soy Protein Isolate | 6.50 |
| Fructose | 1.00 |
| GRINDSTED ASD525, Danisco | 0.30 |
| Apple Juice Concentrate (70 Brix) | 14.79 |
| Strawberry Puree, Single Strength | 4.00 |
| Banana Puree, Single Strength | 6.00 |
| Plain Lowfat Yogurt-Greek Style, Cabot | 9.00 |
| 1% Red 40 Solution | 0.17 |
| Strawberry Flavor (DD-148-459-6) | 0.65 |
| Banana Flavor (#29513) | 0.20 |
| 75/25 Malic/Citric Blend | 0.40 |
| Alpha-1,2-branched glucan (presently disclosed) | 8.00 |
| TOTAL | 100.00 |

Step No. Procedure
Pectin Solution Formation
1 Heat 50% of the formula water to 160° F. (~71.1° C.).
2 Disperse the pectin with high shear; mix for 10 minutes.
3 Add the juice concentrates and yogurt; mix for 5-10 minutes until the yogurt is dispersed.
Protein Slurry
1 Into 50% of the batch water at 140° F. (60° C.), add the SUPRO XT40 and mix well.
2 Heat to 170° F. (~76.7° C.) and hold for 15 minutes.
3 Add the pectin/juice/yogurt slurry to the protein solution; mix for 5 minutes.
4 Add the fructose, glucan, flavors and colors; mix for 3 minutes.
5 Adjust the pH using phosphoric acid to the desired range (pH range 4.0-4.1).
6 Ultra High Temperature (UHT) processing at 224° F. (106.7° C.) for 7 seconds with UHT homogenization after heating at 2500/500 psig (17.24/3.45 MPa) using an indirect steam (IDS) unit.
7 Collect product in bottles and cool in ice bath.
8 Store product in refrigerated conditions.

Example 25

Preparation of a Water Preparation Comprising Alpha-1,2-Branched Glucan

The following example describes the preparation of an enhanced water composition.

TABLE 37

| Ingredient | wt % |
|---|---|
| Water, deionized | 86.41 |
| Pistachio Green #06509 | 0.00 |
| Alpha-1,2-branched glucan (presently disclosed herein) | 8.00 |
| Sucrose | 5.28 |
| Citric Acid | 0.08 |
| Flavor (M748699M) | 0.20 |
| Vitamin C, ascorbic acid | 0.02 |
| TOTAL | 100.00 |

Step No. Procedure
1 Add dry ingredients and mix for 15 minutes.
2 Add remaining dry ingredients; mix for 3 minutes.
3 Adjust pH to 3.0+/−0.05 using citric acid as shown in formulation.
4 Ultra High Temperature (UHT) processing at 224° F. (106.7° C.) for 7 seconds with homogenization at 2500/500 psig (17.24/3.45 MPa).
5 Collect product in bottles and cool in ice bath.
6 Store product in refrigerated conditions.

Example 26

Preparation of a Spoonable Yogurt Formulation

The following example describes the preparation of a spoonable yogurt containing alpha-1,2-branched glucan.

TABLE 38

| Ingredient | wt % |
| --- | --- |
| Skim Milk | 84.00 |
| Sugar | 5.00 |
| Yogurt (6051) | 3.00 |
| Cultures (add to pH break point) | |
| Alpha-1,2-branched glucan (presently disclosed herein) | 8.00 |
| TOTAL | 100.00 |

Step No. Procedure
1 Add dry ingredients to base milk liquid; mix for 5 min.
2 Pasteurize at 195° F. (~90.6° C.) for 30 seconds, homogenize at 2500 psig (17.24 MPa), and cool to 105-110° F. (~40.6-43.3° C.).
3 Inoculate with culture; mix gently and add to water batch or hot box at 108° F. (~42.2° C.) until pH reaches 4.5-4.6.

Fruit Prep Procedure
1 Add water to batch tank; heat to 140° F. (~60° C.).
2 Pre-blend carbohydrates and stabilizers. Add to batch tank and mix well.
3 Add acid to reduce the pH to the desired range (target pH 3.5-4.0).
4 Add flavor.
5 Cool and refrigerate.

Example 27

Preparation of a Model Snack Bar Formulation

The following example describes the preparation of a model snack bar containing alpha-1,2-branched glucan as presently disclosed.

TABLE 39

| Ingredients | wt % |
| --- | --- |
| Corn Syrup 63 DE | 15.30 |
| Alpha-1,2-branched glucan (presently disclosed herein) solution (70 Brix) | 16.60 |
| Sunflower Oil | 1.00 |
| Coconut Oil | 1.00 |
| Vanilla Flavor | 0.40 |
| Chocolate Chips | 7.55 |
| SUPRO ® Nugget 309 | 22.10 |
| Rolled Oats | 18.00 |
| Arabic Gum | 2.55 |
| Alkalized Cocoa Powder | 1.00 |
| Milk Chocolate Coating Compound | 14.50 |
| TOTAL | 100.00 |

Step No. Procedure
1 Combine corn syrup with liquid glucan solution. Warm syrup in microwave for 10 seconds.
2 Combine syrup with oils and liquid flavor in mixing bowl. Mix for 1 minute at speed 2.
3 Add all dry ingredients in bowl and mix for 45 seconds at speed 1.
4 Scrape and mix for another 30 seconds or until dough is mixed.
5 Melt chocolate coating.
6 Fully coat the bar with chocolate coating.

Example 28

Preparation of a Wafer

The following example describes the preparation of a wafer containing alpha-1,2-branched glucan as presently disclosed.

TABLE 40

| Ingredients | wt % |
| --- | --- |
| Flour, white plain | 38.17 |
| Alpha-1,2-branched glucan (presently disclosed herein) | 2.67 |
| Oil, vegetable | 0.84 |
| GRINSTED ® CITREM 2-in-1 (Danisco) citric acid ester made from sunflower or palm oil (emulsifier) | 0.61 |
| Salt | 0.27 |
| Sodium bicarbonate | 0.11 |
| Water | 57.33 |

Step No. Procedure
1. High shear the water, oil and CITREM for 20 seconds.
2. Add dry ingredients slowly, high shear for 2-4 minutes.
3. Rest batter for 60 minutes.
4. Deposit batter onto hot plate set at 200° C. top and bottom, bake for 1 minute 30 seconds.
5. Allow cooling pack as soon as possible.

Example 29

Preparation of a soft chocolate chip cookie

The following example describes the preparation of a soft chocolate chip cookie containing alpha-1,2-branched glucan as presently disclosed.

TABLE 41

| Ingredients | wt % |
| --- | --- |
| Stage 1 | |
| Lactitol, C | 16.00 |
| Cake margarine | 17.70 |
| Salt | 0.30 |
| Baking powder | 0.80 |
| Eggs, dried whole | 0.80 |
| Bicarbonate of soda | 0.20 |
| Vanilla flavor | 0.26 |
| Caramel flavor | 0.03 |
| Sucralose powder | 0.01 |
| Stage 2 | |
| Alpha-1,2-branched glucan (presently disclosed herein) Solution (70 brix) | 9.50 |
| Water | 4.30 |

TABLE 41-continued

| Ingredients | wt % |
|---|---|
| Stage 3 | |
| Flour, pastry | 21.30 |
| Flour, high ratio cake | 13.70 |
| Stage 4 | |
| Chocolate chips, 100% lactitol, sugar-free | 15.10 |

Step No. Procedure
1. Cream together Stage 1 ingredients under fast speed for 1 minute.
2. Blend with Stage 2 under slow speed for 2 minutes.
3. Add Stage 3 under slow speed for 20 seconds.
4. Scrape down bowl; add Stage 4 under slow speed for 20 seconds.
5. Divide into 30 g pieces, flatten, and place onto silicone-lined baking trays.
6. Bake at 190° C. for 10 minutes approximately.

Example 30

Preparation of a Reduced Fat Short-Crust Pastry Dough

The following example describes the preparation of a reduced fat short-crust pastry dough containing alpha-1,2-branched glucan as presently disclosed.

TABLE 42

| Ingredients | wt % |
|---|---|
| Flour, plain white | 56.6 |
| Water | 15.1 |
| Margarine | 11.0 |
| Shortening | 11.0 |
| alpha-1,2-branched glucan (presently disclosed herein) | 6.0 |
| Salt | 0.3 |

Step No. Procedure
1. Dry blend the flour, salt and glucan (dry).
2. Gently rub in the fat until the mixture resembles fine breadcrumbs.
3. Add enough water to make a smooth dough.

Example 31

Preparation of a low sugar cereal cluster

The following example describes the preparation of a low sugar cereal cluster containing alpha-1,2-branched glucan as presently disclosed.

TABLE 43

| Ingredients | wt % |
|---|---|
| Syrup Binder<br>Lactitol, MC 50%<br>Alpha-1,2-branched glucan (presently disclosed herein) Solution (70 brix) 25%<br>Water 25% | 30.0 |
| Cereal Mix<br>Rolled Oats 70%<br>Flaked Oats 10%<br>Crisp Rice 10%<br>Rolled Oats 10% | 60.0 |
| Vegetable oil | 10.0 |

Step No. Procedure
1. Chop the fines.
2. Weigh the cereal mix and add fines.
3. Add vegetable oil on the cereals and mix well.
4. Prepare the syrup by dissolving the ingredients.
5. Allow the syrup to cool down.
6. Add the desired amount of syrup to the cereal mix.
7. Blend well to ensure even coating of the cereals.
8. Spread onto a tray.
9. Place in a dryer/oven and allow to dry out.
10. Leave to cool down completely before breaking into clusters.

Example 32

Preparation of a Pectin Jelly

The following example describes the preparation of a pectin jelly containing alpha-1,2-branched glucan as presently disclosed.

TABLE 44

| Ingredients | wt % |
|---|---|
| Component A | |
| Xylitol | 4.4 |
| Pectin | 1.3 |
| Component B | |
| Water | 13.75 |
| Sodium citrate | 0.3 |
| Citric Acid, anhydrous | 0.3 |
| Component C | |
| Alpha-1,2-branched glucan (presently disclosed herein) Solution (70 brix) | 58.1 |
| Xylitol | 21.5 |
| Component D | |
| Citric acid | 0.35 |
| Flavor, Color | q.s. |

Step No. Procedure 1. Dry blend the pectin with the xylitol (Component A). 2. Heat Component B until solution starts to boil. 3. Add Component A gradually, and then boil until completely dissolved.
4. Add Component C gradually to avoid excessive cooling of the batch. 5. Boil to 113° C. 6. Allow to cool to <100° C. and then add color, flavor and acid (Component D).
Deposit immediately into starch molds. 7. Leave until firm, then de-starch.

Example 33

Preparation of a Chewy Candy

The following example describes the preparation of a chewy candy containing alpha-1,2-branched glucan as presently disclosed.

TABLE 45

| Ingredients | wt % |
| --- | --- |
| Alpha-1,2-branched glucan (presently disclosed herein) | 35 |
| Xylitol | 35 |
| Water | 10 |
| Vegetable fat | 4.0 |
| Glycerol Monostearate (GMS) | 0.5 |
| Lecithin | 0.5 |
| Gelatin 180 bloom (40% solution) | 4.0 |
| Xylitol, CM50 | 10.0 |
| Flavor, color & acid | q.s. |

Step No. Procedure
1. Mix the glucan, xylitol, water, fat, GMS and lecithin together, and then cook gently to 158° C.
2. Cool the mass to below 90° C. and then add the gelatin solution, flavor, color and acid.
3. Cool further and then add the xylitol CMS°. Pull the mass immediately for 5 minutes.
4. Allow the mass to cool again before processing (cut and wrap or drop rolling).

Example 34

Preparation of a Coffee—Cherry Ice Cream

The following example describes the preparation of a coffee-cherry ice cream containing alpha-1,2-branched glucan as presently disclosed.

TABLE 46

| Ingredients | wt % |
| --- | --- |
| Fructose, C | 8.00 |
| Alpha-1,2-branched glucan (presently disclosed herein) | 10.00 |
| Skimmed milk powder | 9.40 |
| Anhydrous Milk Fat (AMF) | 4.00 |
| CREMODAN ® SE 709 Emulsifier & Stabilizer System (Danisco) | 0.65 |
| Cherry Flavoring U35814 (Danisco) | 0.15 |
| Instant coffee | 0.50 |
| Tri-sodium citrate | 0.20 |
| Water | 67.10 |

Step No. Procedure
1. Add the dry ingredients to the water while agitating vigorously.
2. Melt the fat.
3. Add the fat to the mix at 40° C.
4. Homogenize at 200 bar/70-75° C.
5. Pasteurize at 80-85° C./20-40 seconds.
6. Cool to ageing temperature (5° C.).
7. Age for minimum 4 hours.
8. Add flavor to the mix.
9. Freeze in continuous freezer to desired overrun (100% is recommended).
10. Harden and store at −25° C.

What is claimed:

1. A composition comprising an ether derivative of an alpha-glucan, wherein the alpha-glucan comprises (i) a backbone and (ii) one or more alpha-1,2 linkages that branch from the backbone,
   wherein the backbone has a degree of polymerization of 3 to 2000, and 100% of the glycosidic linkages of the backbone are alpha-1,6 linkages,
   and wherein the alpha-glucan does not contain any glycosidic linkages aside from alpha-1,6 and alpha-1,2 glycosidic linkages.

2. The composition of claim 1, wherein the degree of polymerization is 10 to 2000.

3. The composition of claim 1, wherein the degree of polymerization is 10 to 1300.

4. The composition of claim 1, wherein the degree of polymerization is 1100 to 1400.

5. The composition of claim 1, wherein the degree of polymerization is 1200 to 1300.

6. The composition of claim 1, wherein the degree of polymerization is 10 to 150.

7. The composition of claim 1, wherein the alpha-glucan has about 1% to 45% alpha-1,2 branching.

8. The composition of claim 1, wherein the alpha-glucan has about 3% to 40% alpha-1,2 branching.

9. The composition of claim 1, wherein the alpha-glucan has about 3% to 20% alpha-1,2 branching.

10. The composition of claim 1, wherein the alpha-glucan has about 1% to 10% alpha-1,2 branching.

11. The composition of claim 1, wherein the alpha-glucan has about 3% to 7% alpha-1,2 branching.

12. The composition of claim 1, wherein the alpha-glucan has about 5% alpha-1,2 branching.

13. The composition of claim 1, wherein the alpha-glucan has a degree of substitution of about 0.0025 to about 3.0 with at least one organic group in ether linkage to the alpha-glucan.

14. The composition of claim 13, wherein the degree of substitution is about 0.05 to about 0.4.

15. The composition of claim 13, wherein the degree of substitution is about 0.05 to about 0.1.

16. The composition of claim 13, wherein the organic group is carboxy alkyl, hydroxy alkyl, or alkyl.

17. The composition of claim 13, wherein the organic group is carboxymethyl.

18. The composition of claim 13, wherein the organic group is hydroxypropyl, dihydroxypropyl, hydroxyethyl, methyl, or ethyl.

19. The composition of claim 13, wherein the organic group is a positively charged organic group.

20. The composition of claim 19, wherein the positively charged organic group is a substituted ammonium group.

21. The composition of claim 20, wherein the substituted ammonium group is a quaternary ammonium group.

22. The composition of claim 1, further comprising at least one enzyme selected from a protease, cellulase, polyesterase, amylase, cutinase, lipase, pectate lyase, perhydrolase, xylanase, peroxidase, mannanase, or laccase.

23. The composition of claim 1, further comprising at least one surfactant selected from an anionic surfactant, nonionic surfactant, cationic surfactant, ampholytic surfactant, or zwitterionic surfactant.

24. The composition of claim 1, wherein the composition is a lotion, cream, paste, balm, ointment, pomade, gel, or liquid.

25. The composition of claim 1, wherein the composition is a powder, granule, microcapsule, or flake.

26. The composition of claim 1, wherein the composition is a pellet, bar, kernel, bead, tablet, or stick.

27. The composition of claim 1, wherein the composition is a spray or mist.

28. The composition of claim 1, wherein the composition is a wipe.

29. The composition of claim 1, wherein the composition is a pad or sponge.

* * * * *